US011945882B2

(12) United States Patent
Yamaguchi et al.

(10) Patent No.: US 11,945,882 B2
(45) Date of Patent: Apr. 2, 2024

(54) METHOD FOR PRODUCING ANTIBODY-DRUG CONJUGATE

(71) Applicant: DAIICHI SANKYO COMPANY, LIMITED, Tokyo (JP)

(72) Inventors: Tatsuya Yamaguchi, Tokyo (JP); Takashi Kouko, Tokyo (JP); Shigeru Noguchi, Tokyo (JP); Yohei Yamane, Tokyo (JP); Fumikatsu Kondo, Tokyo (JP); Takahiro Aoki, Tokyo (JP); Tadahiro Takeda, Tokyo (JP); Kohei Sakanishi, Tokyo (JP); Hitoshi Sato, Tokyo (JP); Tsuyoshi Ueda, Tokyo (JP); Shinji Matuura, Tokyo (JP); Kei Kurahashi, Tokyo (JP); Yutaka Kitagawa, Tokyo (JP); Tatsuya Nakamura, Tokyo (JP)

(73) Assignee: DAIICHI SANKYO COMPANY, LIMITED, Tokyo (JP)

( * ) Notice: Subject to any disclaimer, the term of this patent is extended or adjusted under 35 U.S.C. 154(b) by 0 days.

(21) Appl. No.: 16/642,245

(22) PCT Filed: Aug. 30, 2018

(86) PCT No.: PCT/JP2018/032056
§ 371 (c)(1),
(2) Date: Feb. 26, 2020

(87) PCT Pub. No.: WO2019/044947
PCT Pub. Date: Mar. 7, 2019

(65) Prior Publication Data
US 2020/0385422 A1 Dec. 10, 2020

(30) Foreign Application Priority Data

Aug. 31, 2017 (JP) .................................. 2017-167691

(51) Int. Cl.
*C07K 1/30* (2006.01)
*C07K 5/10* (2006.01)

(52) U.S. Cl.
CPC ............ *C07K 5/10* (2013.01); *C07B 2200/13* (2013.01)

(58) Field of Classification Search
None
See application file for complete search history.

(56) References Cited

U.S. PATENT DOCUMENTS

| 5,480,968 | A  | 1/1996  | Kraus et al. |
| 5,677,171 | A  | 10/1997 | Hudziak et al. |
| 5,821,337 | A  | 10/1998 | Carter et al. |
| 5,834,476 | A  | 11/1998 | Terasawa et al. |
| 5,837,673 | A  | 11/1998 | Tsujihara et al. |
| 5,892,043 | A  | 4/1999  | Tsujihara et al. |
| 5,968,511 | A  | 10/1999 | Akita et al. |
| 6,071,719 | A  | 6/2000  | Halsey et al. |
| 6,096,868 | A  | 8/2000  | Halsey et al. |
| 6,214,345 | B1 | 4/2001  | Firestone et al. |
| 6,291,671 | B1 | 9/2001  | Inoue et al. |
| 6,835,807 | B1 | 12/2004 | Susaki et al. |
| 7,041,818 | B2 | 5/2006  | Susaki et al. |
| 7,449,184 | B2 | 11/2008 | Allison et al. |
| 7,585,491 | B2 | 9/2009  | Govindan |
| 7,833,979 | B2 | 11/2010 | Sullivan et al. |
| 7,837,980 | B2 | 11/2010 | Alley et al. |
| 7,999,083 | B2 | 8/2011  | Govindan et al. |
| 8,226,945 | B2 | 7/2012  | Ebens et al. |
| 8,268,319 | B2 | 9/2012  | Govindan |
| 8,394,607 | B2 | 3/2013  | Ebens et al. |
| 8,425,912 | B2 | 4/2013  | Govindan |
| 8,524,865 | B2 | 9/2013  | Ebens et al. |
| 8,741,291 | B2 | 6/2014  | Bhat et al. |
| 8,802,820 | B2 | 8/2014  | Chamberlain et al. |
| 8,907,071 | B2 | 12/2014 | Sullivan et al. |
| 8,968,741 | B2 | 3/2015  | Ebens et al. |

(Continued)

FOREIGN PATENT DOCUMENTS

| CA | 2927832 A1 | 11/2011 |
| CA | 2815154 A1 | 2/2012 |

(Continued)

OTHER PUBLICATIONS

Lowe, Derek; "The big and the little." Blog "In the pipeline" Dec. 3, 2007.*

(Continued)

*Primary Examiner* — Fred H Reynolds

(74) *Attorney, Agent, or Firm* — Foley & Lardner LLP

(57) ABSTRACT

Crystals of the compound represented by formula (1), a method for the production thereof, and a method for producing an antibody-drug conjugate using the crystals.

63 Claims, 6 Drawing Sheets

Specification includes a Sequence Listing.

(56) References Cited

U.S. PATENT DOCUMENTS

| | | | |
|---|---|---|---|
| 9,808,537 B2 | 11/2017 | Masuda et al. | |
| 9,850,312 B2 | 12/2017 | Agatsuma et al. | |
| 9,872,924 B2 | 1/2018 | Naito et al. | |
| 10,195,288 B2 * | 2/2019 | Masuda | A61K 31/4745 |
| 10,227,417 B2 | 3/2019 | Agatsuma et al. | |
| 10,383,878 B2 | 8/2019 | Hettmann et al. | |
| 2003/0018989 A1 | 1/2003 | Brennan et al. | |
| 2003/0148931 A1 | 8/2003 | Takahashi et al. | |
| 2003/0166513 A1 | 9/2003 | Imura et al. | |
| 2004/0185053 A1 | 9/2004 | Govindan | |
| 2005/0123536 A1 | 6/2005 | Law et al. | |
| 2005/0228007 A1 | 10/2005 | Jagtap et al. | |
| 2005/0271671 A1 | 12/2005 | Griffiths | |
| 2005/0276812 A1 | 12/2005 | Ebens, Jr. et al. | |
| 2006/0018899 A1 | 1/2006 | Kao et al. | |
| 2006/0134109 A1 | 6/2006 | Gaitanaris et al. | |
| 2006/0135546 A1 * | 6/2006 | Basavaraja | C07D 491/22 514/283 |
| 2006/0193865 A1 | 8/2006 | Govindan | |
| 2007/0031402 A1 | 2/2007 | Zhang et al. | |
| 2007/0071764 A1 | 3/2007 | Sullivan et al. | |
| 2008/0050310 A1 | 2/2008 | Ebens et al. | |
| 2008/0131363 A1 | 6/2008 | Govindan et al. | |
| 2008/0161245 A1 | 7/2008 | Kratz et al. | |
| 2008/0248047 A1 | 10/2008 | Das et al. | |
| 2008/0260744 A1 | 10/2008 | Gaitanaris et al. | |
| 2008/0305044 A1 | 12/2008 | McDonagh et al. | |
| 2009/0178153 A1 | 7/2009 | Gaitanaris et al. | |
| 2009/0274713 A1 | 11/2009 | Chari et al. | |
| 2009/0286258 A1 | 11/2009 | Kaur et al. | |
| 2009/0291093 A1 | 11/2009 | Govindan | |
| 2010/0068181 A1 | 3/2010 | Paliwal et al. | |
| 2010/0105627 A1 | 4/2010 | Salama et al. | |
| 2010/0120816 A1 | 5/2010 | Fontana et al. | |
| 2010/0303802 A1 | 12/2010 | Zoffmann Jensen et al. | |
| 2011/0045587 A1 | 2/2011 | Sullivan et al. | |
| 2011/0059076 A1 | 3/2011 | McDonagh et al. | |
| 2011/0070248 A1 | 3/2011 | Ichikawa et al. | |
| 2011/0185439 A1 | 7/2011 | Gaitanaris et al. | |
| 2011/0229406 A1 | 9/2011 | Hettmann et al. | |
| 2011/0293513 A1 | 12/2011 | Govindan et al. | |
| 2012/0121615 A1 | 5/2012 | Flygare et al. | |
| 2012/0171201 A1 | 7/2012 | Sapra | |
| 2012/0201809 A1 | 8/2012 | Bhat et al. | |
| 2012/0328634 A1 | 12/2012 | Govindan | |
| 2013/0089872 A1 | 4/2013 | Nakamura et al. | |
| 2013/0123178 A1 | 5/2013 | Dimarchi et al. | |
| 2013/0216561 A1 | 8/2013 | Govindan | |
| 2013/0247233 A1 | 9/2013 | Gaitanaris et al. | |
| 2014/0004078 A1 | 1/2014 | Govindan | |
| 2015/0297748 A1 | 10/2015 | Masuda et al. | |
| 2015/0352224 A1 | 12/2015 | Naito et al. | |
| 2016/0219845 A1 | 8/2016 | Gaitanaris et al. | |
| 2016/0279259 A1 | 9/2016 | Masuda et al. | |
| 2016/0282365 A1 | 9/2016 | Gaitanaris et al. | |
| 2016/0287722 A1 | 10/2016 | Govindan | |
| 2016/0297890 A1 | 10/2016 | Agatsuma et al. | |
| 2016/0333112 A1 | 11/2016 | Naito et al. | |
| 2017/0021031 A1 | 1/2017 | Hettmann et al. | |
| 2017/0188555 A1 | 7/2017 | Gaitanaris et al. | |
| 2018/0147292 A1 * | 5/2018 | Noguchi | A61K 31/40 |
| 2018/0215782 A1 | 8/2018 | Kono et al. | |
| 2019/0151328 A1 | 5/2019 | Hettmann et al. | |
| 2019/0225686 A1 * | 7/2019 | Iida | A61K 47/6825 |
| 2020/0384121 A1 * | 12/2020 | Nishi | C07C 231/02 |
| 2020/0385486 A1 * | 12/2020 | Naito | A61K 47/6857 |

FOREIGN PATENT DOCUMENTS

| | | | |
|---|---|---|---|
| CA | 2859255 A1 | 6/2013 | |
| CN | 1227499 A | 9/1999 | |
| CN | 1764478 A | 4/2006 | |
| CN | 101023100 A | 8/2007 | |
| CN | 101490087 A | 7/2009 | |
| CN | 102481364 A | 5/2012 | |
| CN | 102786418 A | * 11/2012 | |
| CN | 105085529 A | * 11/2015 | |
| CN | 105163763 A | 12/2015 | |
| EP | 0 495 432 A1 | 7/1992 | |
| EP | 0 737 686 A1 | 10/1996 | |
| EP | 0 916 348 A1 | 5/1999 | |
| EP | 1 155 702 A1 | 11/2001 | |
| EP | 2 594 589 A1 | 5/2013 | |
| EP | 2 799 452 A1 | 11/2014 | |
| EP | 2 910 573 A1 | 8/2015 | |
| EP | 2 968 588 B1 | 1/2019 | |
| JP | H05-59061 A | 3/1993 | |
| JP | H06-80891 A | 3/1994 | |
| JP | H06-87746 A | 3/1994 | |
| JP | H6087746 A | 3/1994 | |
| JP | H08-337584 A | 12/1996 | |
| JP | H10-095802 A | 4/1998 | |
| JP | H1171280 A | 3/1999 | |
| JP | H11-092405 A | 4/1999 | |
| JP | 2002-060351 A | 2/2002 | |
| JP | 2005-511627 A | 4/2005 | |
| JP | 2005-343837 A | 12/2005 | |
| JP | 2006-511526 A | 4/2006 | |
| JP | 2007-527872 A | 10/2007 | |
| JP | 2008-521828 A | 6/2008 | |
| JP | 2009-538629 A | 11/2009 | |
| JP | 2010-513524 A | 4/2010 | |
| JP | 2011-519864 A | 7/2011 | |
| JP | 2011-524001 A | 8/2011 | |
| JP | 2012-509259 A | 4/2012 | |
| JP | 2012-100671 A | 5/2012 | |
| JP | 2013-500253 A | 1/2013 | |
| JP | 2013-534535 A | 9/2013 | |
| JP | 2013-534906 A | 9/2013 | |
| KR | 1020010052385 A | 6/2001 | |
| KR | 1020110044808 A | 4/2011 | |
| RU | 2404810 C2 | 7/2008 | |
| RU | 2450008 C2 | 7/2010 | |
| TW | I232930 B | 5/2005 | |
| TW | 200817434 A | 4/2008 | |
| WO | WO-97/46260 A1 | 12/1997 | |
| WO | WO-00/25825 A1 | 5/2000 | |
| WO | WO-01/00244 A2 | 1/2001 | |
| WO | WO-02/00734 A1 | 1/2002 | |
| WO | WO-03/013602 A1 | 2/2003 | |
| WO | WO-03/015826 A1 | 2/2003 | |
| WO | WO-03/043583 A2 | 5/2003 | |
| WO | WO-03/074566 A2 | 9/2003 | |
| WO | WO-2005/040825 A2 | 5/2005 | |
| WO | WO-2005/112919 A2 | 12/2005 | |
| WO | WO-2006/065533 A2 | 6/2006 | |
| WO | WO-2006/092230 A2 | 9/2006 | |
| WO | WO-2007/077028 A2 | 7/2007 | |
| WO | WO-2008/100624 A2 | 8/2008 | |
| WO | WO-2008/116219 A1 | 9/2008 | |
| WO | WO-2008/144891 A1 | 12/2008 | |
| WO | WO-2011/011474 A1 | 1/2011 | |
| WO | WO-2011/021397 A1 | 2/2011 | |
| WO | WO-2011/068845 A1 | 6/2011 | |
| WO | WO-2011/145744 A1 | 11/2011 | |
| WO | WO-2011/155579 A1 | 12/2011 | |
| WO | WO-2012/019024 A2 | 2/2012 | |
| WO | WO-2012/064733 A2 | 5/2012 | |
| WO | WO-2013/068946 A2 | 5/2013 | |
| WO | WO-2013/077458 A1 | 5/2013 | |
| WO | WO-2013/163229 A1 | 10/2013 | |
| WO | WO-2013/188740 A1 | 12/2013 | |
| WO | WO-2014/057687 A1 | 4/2014 | |
| WO | WO-2014/061277 A1 | 4/2014 | |
| WO | WO-2015/098099 A1 | 7/2015 | |
| WO | WO-2015/115091 A1 | 8/2015 | |
| WO | WO-2015/142675 A2 | 9/2015 | |
| WO | WO-2015/155998 A1 | 10/2015 | |

(56) References Cited

FOREIGN PATENT DOCUMENTS

| WO | WO-2016/140232 A1 | 9/2016 |
| WO | WO-2018/135501 A1 | 7/2018 |

OTHER PUBLICATIONS

Xu, Renjie et al; "Solubility determination and thermodynamic modeling of 2, 4-dinitroaniline in nine organic solvents from t=(278.15 to 318.15)k and mixing properties of soluions." J. Chem. Thermodynamics (2016) 102 p. 178-187.*
Machine translation of Luo et al., CN 105085529.*
Machine translation of Lv et al., CN 102786418.*
The question at the Researchgate webpage about column backpressure and answers https://www.researchgate.net/post/Can_an_HPLC_column_be_clogged_and_let_some_solvents_go_through_while_others_raise_the_pressure, downloade Nov. 18, 2021.*
Cotton, M. et al; "Solid state nmr and hydrogen deuterioum exchange in a bilayer solubilized peptide: structureal and mechanistic implications." Biophys. J. (1999) 76 p. 1179-1189.*
Starratt, Alvin Neil and Brown, Brian Ellman; "Synthesis of proctolin, a pharmacologically active pentapeptide in insects." Can. J. Chem. (1977) 55 p. 4238-4244.*
McPherson, Alexander and Gavira, Jose A.; "Introduction to protein crystallization." Acta Cryst (2014) F70 p. 2-20.*
The chemical company's description of cetyl trimethyl ammonium bromide; https://thechemco.com/chemical/cetyl-trimethyl-ammonium-bromide/#:~:text=At%20standard%20temperature%20and%20pressure,not%20all%2C%20common%20organic%20solvents, available 2013.*
Saberi, Amir Hossein et al; "Crystallization kinetics of palm oil in blends with palm based diacylglycerol." Food Res. Int. (2011) 44 p. 425-435.*
Recrystallization instructions, UMass system, available online 2016.*
Ducry et al., "Antibody—Drug Conjugates: Linking Cytotoxic Payloads to Monoclonal Antibodies," Bioconjugate Chem, vol. 21, 2010, pp. 5-13.
Alley et al., "Antibody-drug conjugates: targeted drug delivery for cancer," Current Opinion in Chemical Biology, vol. 14, 2010, pp. 529-537.
Damle, Nitin K., "Tumour-targeted chemotherapy with immunoconjugates of calicheamicin," Expert Opin. Biol. Ther., vol. 4, No. 9, 2004, pp. 1445-1452.
Senter et al., "The discovery and development of brentuximab vedotin for use in relapsed Hodgkin lymphoma and systemic anaplastic large cell lymphoma," Nature Biotechnology, vol. 30, No. 7, Jul. 2012, pp. 631-637.
Burris, III et al., "Phase II Study of the Antibody Drug Conjugate Trastuzumab-DM1 for the Treatment of Human Epidermal Growth Factor Receptor 2 (HER2)—Positive Breast Cancer After Prior HER2-Directed Therapy," Journal of Clinical Oncology, vol. 29, No. 4, Feb. 1, 2011, pp. 398-405.
Ogitani et al., "DS-8201a, A Novel HER2-Targeting ADC with a Novel DNA Topoisomerase I Inhibitor, Demonstrates a Promising Antitumor Efficacy with Differentiation from T-DM1," Clinical Cancer Research, vol. 22, No. 20, Oct. 15, 2016, pp. 5097-5108.
Ogitani et al., "Bystander killing effect of DS-8201a, a novel anti-human epidermal growth factor receptor 2 antibody-drug conjugate, in tumors with human epidermal growth factor receptor 2 heterogeneity," Cancer Science, vol. 107, 2016, pp. 1039-1046.
International Searching Authority, "International Search Report," issued in connection with International Patent Application No. PCT/JP2018/032056, dated Nov. 27, 2018.
Acchione et al., "Impact of linker and conjugation chemistry on antigen binding, Fc receptor binding and thermal stability of model antibody-drug conjugates," mAbs, 2012, 4(3):362-372.
Adams et al., "Humanization of a recombinant monoclonal antibody to produce a therapeutic HER dimerization inhibitor, pertuzumab," Cancer Immunol. Immunother. 55:717-727 (2006).

Alimandi et al., "Cooperative signaling of ErbB3 and ErbB2 in neoplastic transformation and human mammary carcinomas," Oncogene 10:1813-1821 (1995)—9 Pages.
Allander et al., "Gastrointestinal Stromal Tumors with KIT Mutations Exhibit a Remarkably Homogeneous Gene Expression Profile," Cancer Research, vol. 61, pp. 8624-8628, Dec. 15, 2001.
Australian Intellectual Property Office, "Examination Report No. 2 for Standard Patent Application," Australian Patent Application No. 2014371934, dated Sep. 13, 2019.
Barginear et al., "Trastuzumab-DM1: A Review of the Novel Immuno-Conjugate for HER2-Overexpressing Breast Cancer," The Open Breast Cancer Journal 1:25-30 (2009).
Barok et al., Trastuzumab-DM1 is highly effective in preclinical models of HER2-positive gastric cancer, Cancer Letters, 2011, vol. 306, No. 2, pp. 172-179 (9 pages).
Baselga et al., "Phase II Study of Weekly Intravenous Recombinant Humanized Anti-p185HER2 Monoclonal Antibody in Patients with HER2/neu-Overexpressing Metastatic Breast Cancer," J. Clin. Oncol. 14(3):737-744 (Mar. 1996).
Basu et al., "The Epithelial/Carcinoma Antigen EGP-1 Recognized by Monoclonal Antibody RS7-3G11, is Phosphorylated on Serine 303," Int. J. Cancer 62(4):472-479 (1995).
Bauer et al., "Emerging Agents for the Treatment of Advanced, Imatinib-Resistant Gastrointestinal Stromal Tumors: Current Status and Future Directions," Drugs, vol. 75, 2015, pp. 1323-1334.
Beck, Alain, "The Next Generation of Antibody-drug Conjugates Comes of Age," Discovery Medicine 10(53):329-339 (Oct. 16, 2010)—8 Pages.
Behrens et al., "Methods for site-specific drug conjugation to antibodies," mAbs, vol. 6, No. 1, 2014, pp. 46-53.
Blok et al., "Cytoplasmic Overexpression of HER2: a Key Factor in Colorectal Cancer", Clinical Insights: Oncology, vol. 7, 2013 pp. 41-51.
Bouchard et al., "Antibody-drug conjugates—A new wave of cancer drugs," Bioorganic & Medicinal Chemistry Letters, vol. 24, 2014, pp. 5357-5363.
Burke P J et al. (2009), "Design, Synthesis, and Biological Evaluation of Antibody-Drug Conjugates Comprised of Potent Camptothecin Analogues", Bioconjugate Chemistry, vol. 20, No. 6, pp. 1242-1250—9 Pages.
Calabrese et al., "Assignment of TACSTD1 (alias TROP1, M4S1) to human chromosome 2p21 and refinement of mapping of TACSTD2 (alias TROP2, M1S1) to human chromosome 1p32 by in situ hybridization," Cytogenet Cell Genet. 92(1-2):164-165 (2001).
Canadian Examiner's Interview Summary issued in Canadian Patent Application No. 2885800 dated Mar. 28, 2017.
Canadian Office Action dated Apr. 13, 2018 in corresponding application No. 2939802.
Cardillo, T., "Humanized Anti-Trop-2 IgG-SN-38 Conjugate for Effective Treatment of Diverse Epithelial Cancers: Preclinical Studies in Human Cancer Xenograft Models and Monkeys," Clinical Cancer Research 17(10): 3157-3169 (2011).
Chi et al., "ETV1 is a lineage survival factor that cooperates with KIT in gastrointestinal stromal tumours," Nature, vol. 467, Oct. 14, 2010, pp. 849-855.
Chinese Office Action issued to corresponding App. No. 201480071134.0—dated Aug. 20, 2019 (5 pages), dated Aug. 20, 2019.
Colombian Reconsideration Petition dated Mar. 15, 2018 in corresponding application No. NC2016/0000187—36 pages.
Corless et al., "Gastrointestinal stromal tumours: origin and molecular oncology," Nature Reviews, Cancer, vol. 11, Dec. 2011, pp. 865-878.
Coussens et al., "Tyrosine Kinase Receptor with Extensive Homology to EGF Receptor Shares Chromosomal Location with neu Oncogene," Science 230(4730):1132-1139 (Dec. 1985).
D. Loo et al: "Development of an Fc-Enhanced Anti-B7-H3 Monoclonal Antibody with Potent Antitumor Activity", Clinical Cancer Research, vol. 18, No. 14, Jul. 15, 2012 (Jul. 15, 2012), pp. 3834-3845, XP055092714, ISSN: 1078-0432, DOI: 10.1158/1078-0432.CCR-12-0715.
De Jager, R., et al., "DX-8951f: summary of phase I clinical trials", Annals New York Academy of Sciences, pp. 260-273. 2000.

(56) References Cited

OTHER PUBLICATIONS

Defazio et al., "Expression of c-erbB Receptors, Heregulin and Oestrogen Receptor in Human Breast Cell Lines," Int. J. Cancer 87:487-498 (2000)—12 Pages.
Demetri et al., "NCCN Task Force Report: Update on the Management of Patients with Gastrointestinal Stromal Tumors," Journal of the National Comprehensive Cancer Network, vol. 8, Supplement 2, Apr. 2010, pp. S-1-S-41.
Di Fiore et al., "erbB-2 Is a Potent Oncogene When Overexpressed in NIH/3T3 Cells," Science 237:178-182 (Jul. 1987).
Donaghy, Heather, "Effects of antibody, drug and linker on the preclinical and clinical toxicities of antibody-drug conjugates," mAbs, vol. 8, No. 4, 2016, pp. 659-671.
Dosio et al., "Antibody-targeted leucinostatin A", Journal of Controlled Release, No. 32, (1994), pp. 37-44.
El Sewedy et al., "Cloning of the Murine Trop2 Gene: Conservation of a PIP2-Binding Sequence in the Cytoplasmic Domain of Trop-2," Int. J. Cancer 75(2):324-330 (1998).
English-language translation of International Search Report issued in International Patent Application No. PCT/JP2015/002020 dated Jul. 20, 2015—4 Pages.
Esteva et al., "A Phase II Study of Intravenous Exatecan Mesylate (DX-8951f) Administered Daily for 5 Days Every 3 Weeks to Patients with Metastatic Breast Carcinoma", American Cancer Society,2003,900-907.
European Search Report in corresponding application No. 15776810.2 dated Aug. 11, 2017.
European Search Report issued in corresponding application No. 15743738.5 dated Aug. 9, 2017.
Extended European Search Report dated Feb. 4, 2020 for corresponding Application No. 19206764.3.
Extended European Search Report dated May 13, 2016, in European Patent Application No. 13847461.4.
Extended European Search Report dated May 6, 2016, in European Patent Application No. 13845596.9.
Extended European Search Report dated Nov. 30, 2020 for corresponding European Patent Application No. 18742022.9.
Extended European Search Report issued in European Patent Application No. 14874745.4 dated May 10, 2017.
Faulk et al., "Antigens of human trophoblasts: A working hypothesis for their role in normal and abnormal pregnancies," Proc. Natl. Acad. Sci. USA 75(4):1947-1951 (1978).
Fendly et al., "Characterization of Murine Monoclonal Antibodies Reactive to Either the Human Epidermal Growth Factor Receptor or HER2/neu Gene Product," Cancer Research 50:1550-1558 (1990).
Final Office Action issued in U.S. Appl. No. 15/221,851 dated Nov. 13, 2017.
First Examination Report on Indian Application No. 202017010043 dated Jun. 13, 2021.
Fong et al., "High expression of TROP2 correlates with poor prognosis in pancreatic cancer," Br. J. Cancer 99(8):1290-1295 (2008).
Fong et al., "TROP2: a novel prognostic marker in squamous cell carcinoma of the oral cavity," Mod. Pathol. 21(2):186-191 (2008).
Fornaro et al., "Cloning of the Gene Encoding Trop-2, a Cell-Surface Glycoprotein Expressed by Human Carcinomas," Int. J. Cancer 62(5):610-618 (1995).
Fukushige et al., "Localization of a Novel v-erbB-Related Gene, c-erbB-2, on Human Chromosome 17 and Its Amplification in a Gastric Cancer Cell Line," Mol. Cell. Biol. 6(3):955-958 (1986).
Gomez-Monterrey et al., "Design, Synthesis, and Cytotoxic Evaluation of Acyl Derivatives of 3-Aminonaphtho[2,3-b]thiophene-4,9-dione, a Quinone-Based System," Journal of Medicinal Chemistry, 2011, 54(12):4077-4091, abstract.
Graus-Porta et al., "ERbB-2, the preferred heterodimerization partner of all ErbB receptors, is a mediator of lateral signaling," EMBO J. 16(7):1647-1655 (1997).
Gravalos et al., "HER2 in gastric cancer: a new prognostic factor and a novel therapeutic target," Ann. Oncol. 19:1523-1529 (2008).

Haasen Dorothea et al: "G protein-coupled receptor internalization assays in the high-content screening format", Biomembranes: Transport Theory: Cells and Model Membranes; [Methods in Enzymology, ISSN 0076-6879], Elsevier, Academic Press, NL, vol. 414, Jan. 1, 2006 (Jan. 1, 2006), pp. 121-139.
Hardwick et al., "Immunohistochemical detection of p53 and c-erbB-2 in oesophageal carcinoma; no correlation with prognosis," Eur. J. Surg. Oncol. 23:30-35 (1997).
Hinrichs et al., "Antibody Drug Conjugates: Nonclinical Safety Considerations," the AAPS Journal, vol. 17, No. 5, Sep. 2015, pp. 1055-1064.
Hirata T: "Producing monoclonal antibody of extracellular domain of metabotropic glutamate receptor 1, by hybridizing spleen cell of non-human animal immunized by olfactory tract, with myeloma cell, culturing hybridoma, screening culture supernatant", WPI/ Thomson,, vol. 2004, No. 36, Apr. 22, 2004 (Apr. 22, 2004).
Hudis, M.D., Clifford A., "Trastuzumab—Mechanism of Action and Use in Clinical Practice," N. Engl. J. Med. 357(1):39-51 (2007).
Hudziak et al., "Increased expression of the putative growth factor receptor p185HER2 causes transformation and tumorigenesis of NIH 3T3 cells," Proc. Natl. Acad. Sci. USA 84:7159-7163 (1987).
I. Sullivan, et al. "Osimertinib in the treatment of patients with epidermal growth factor receptor T790M mutation-positive metastatic non-small cell lung cancer: clinical trial evidence and experience", Therapeutic Advances in Respiratory Disease, vol. 10(6), pp. 549-565, 2016 (17 pages).
IN Office Action issued in the corresponding Indian Patent Application Ser. No. 201647013640, dated Jul. 19, 2019.
Inoue, K., et al., "CM-Dextran-Polyalcohol-Camptothecin Conjugate", Polymer Drugs in the Clinical Stage, (2003), pp. 145-153.
International Search Report and Written Opinion for correspondence Application No. PCT/JP2018/007152 dated Apr. 24, 2018.
International Search Report for corresponding Application No. PCT/JP2014/006421 dated Mar. 17, 2015.
International Search Report for PCT/JP2013/006069, dated Dec. 17, 2013.
International Search Report for PCT/JP2013/006178, dated Dec. 17, 2013.
International Search Report issued in International Patent Application No. PCT/JP2015/000355 dated Apr. 21, 2015.
International Searching Authority, "International Search Report," issued in connection with International Patent Application No. PCT/JP2018/001065, dated Apr. 17, 2018.
International Searching Authority, "Written Opinion," issued in connection with International Patent Application No. PCT/JP2018/001065, dated Apr. 17, 2018.
Janne, P., et al., "Phase 1 study of the Anti-HER3 Antibody Drug Conjugate U3-1402 in Metastic or Unresectable EGFR-mutant NSCLC.", Journal of Thoracic Oncology, vol. 12, No. 11, Supp. Supplement 2, pp. S2290, abstract No. P3.04-013, Nov. 2017 (3 pages).
Japanese Office Action dated Dec. 6, 2016 in corresponding application No. 2016-540705.
Joto et al., "DX-8951F, A Water-Soluble Camptothecin Analog, Exhibits Potent Antitumor Activity Against a Human Lung Cancer Cell Line and its SN-38-Resistant Variant," Int. J. Cancer 72:680-686 (1997)—7 Pages.
Kamath et al., "Challenges and advances in the assessment of the disposition of antibody-drug conjugates," Biopharmaceutics & Drug Disposition, 2015, 9 pages.
Kang et al, "Engineering multivalent antibodies to target heregulin-induced HER3 signaling in breast cancer cells, mAbs", Mar./Apr. 2014, vol. 6, No. 2, pp. 340-353.
Kaptain et al., "Her-2/neu and Breast Cancer," Diagn. Mol. Pathol. 10(3):139-152 (2001).
Karunagaran et al., "ErbB-2 is a common auxiliary subunit of NDF and EGF receptors: implications for breast cancer," EMBO J. 15(2):254-264 (1996).
Kawakami et al—"The anti-HER3 antibody patritumab abrogates cetuximab resistance mediated by heregulin in colorectal cancer cells", Oncotarget, vol. 5, No. 23, Dec.-May 2014, 11847-11856—10 pages.

(56) References Cited

OTHER PUBLICATIONS

Kimio Yonesaka, "Anti-HER3 Antibody Patritumab Overcomes Resistance to EGFR Inhibitor in Non-small Cell Lung Cancer", The Japan Lung Cancer Society, vol. 55, pp. 948-955, 2015 (8 pages).
Korean Office Action dated May 1, 2018 in corresponding application No. 10-2016-7015961.
Korkaya et al., "HER2 regulates the mammary stem/progenitor cell population driving tumorigenesis and invasion," Oncogene 27:6120-6130 (2008).
Kraus et al., "Demonstration of ligand-dependent signaling by the erbB-3 tyrosine kinase and its constitutive activation in human breast tumor cells," Proc. Natl. Acad. Sci. USA 90:2900-2904 (Apr. 1993)—5 Pages.
Kraus et al., "Isolation and characterization of ERBB3, a third member of the ERBB/epidermal growth factor receptor family: Evidence for overexpression in a subset of human mammary tumors," Proc. Natl. Acad. Sci. USA 86:9193-9197 (Dec. 1989)—5 pages.
Kumazawa et al., "Antitumor activity of DX-8951f: a new camptothecin derivative," Exp. Opin. Invest. Drugs 7(4):625-632 (1998)—8 Pages.
Kumazawa et al., "DE-310, a novel macromolecular carrier system for the camptothecin analog DX-8951f: Potent antitumor activities in various murine tumor models," Cancer Sci. 95(2):168-175 (Feb. 2004)—8 Pages.
Linnenbach et al., "Sequence investigation of the major gastrointestinal tumor-associated antigen gene family, GA733," Proc. Natl. Acad. Sci. 86(1):27-31 (Jan. 1989).
Lipinski et al., "Human trophoblast cell-surface antigens defined by monoclonal antibodies," Proc. Natl. Acad. Sci. 78(8):5147-5150 (Aug. 1981).
Martin et al., "Constitutive Activity among Orphan Class-A G Protein Coupled Receptors," PLOS One, Sep. 18, 2015, pp. 1-12.
Masubuchi, N., "Pharmacokinetics of DE-310, a novel macromolecular carrier system for the camptothecin analog DX-8951f, in tumor-bearing mice," Pharmazie, vol. 59, No. 5, 2004, pp. 374-377.
McDonagh et al., "Engineered antibody-drug conjugates with defined sites and stoichiometries of drug attachment," Protein Engineering, Design & Selection, 2006, 19(7):299-307.
Mitsui et al., "A New Water-soluble Camptothecin Derivative, DX-8951f, Exhibits Potent Antitumor Activity against Human Tumors in vitro and in vivo," Jpn. J. Cancer Res. 86:776-782 (Aug. 1995)—7 Pages.
Moghaddas et al., "Whether HER2-positive non-breast cancers are candidates for treatment with Ado-trastuzumab emtansine?", J. Res Parm Pract, vol. 5(4), 2016 pp. 227-233.
Momoko Hase et al: Characterization of an Orphan G Protein-coupled Receptor, GPR20, That Constitutively Activates G i Proteins:, Journal of Biological Chemistry, vol. 283, No. 19, May 9, 2008 (May 9, 2008), pp. 12747-12755.
Mühlmann et al., "TROP2 expression as prognostic marker for gastric carcinoma," J. Clin. Pathol. 62(2):152-158 (2009).
Naidu et al., "Expression of c-erbB3 protein in primary breast carcinomas," British Journal of Cancer 78(10): 1385-1390 (1998)—6 Pages.
Nakada et al., "Novel antibody drug conjugates containing exatecan derivative-based cytotoxic payloads," Bioorganic & Medical Chemistry Letters 26(6):1542-1545 (2016)—4 Pages.
Ning et al., "TROP2 expression and its correlation with tumor proliferation and angiogenesis in human gliomas," Neurol. Sci. 34(10):1745-1750 (2013).
Non-Final Office Action dated Apr. 5, 2019 in U.S. Appl. No. 15/821,697.
Non-Final Office Action issued in U.S. Appl. No. 14/435,114 dated Jul. 21, 2016.
Non-Final Office Action issued in U.S. Appl. No. 14/436,458 dated Jul. 19, 2016.
Non-Final Office Action issued in U.S. Appl. No. 15/180,203 dated Jul. 25, 2016.
Non-Final Office Action issued in U.S. Appl. No. 15/221,851 dated Jul. 7, 2017.
Non-Final Office Action issued in U.S. Appl. No. 15/821,662 dated Jan. 17, 2018.
Notice of Allowance dated Aug. 25, 2017 for corresponding U.S. Appl. No. 15/187,179.
Notice of Allowance dated May 18, 2017 for corresponding U.S. Appl. No. 15/187,179.
Notice of Allowance issued in U.S. Appl. No. 15/221,851 dated Jun. 13, 2018.
O'Dowd et al., "Cloning and chromosomal mapping of four putative novel human G-protein-coupled receptor genes," Gene. vol. 187, 1997, pp. 75-81.
Ochi et al, "A possible mechanism for the long-lasting antitumor effect of the macromolecular conjugate DE-310: mediation by cellular uptake and drug release of its active camptothecin analog DX-8951," Cancer Chemotherapy and Pharmacology 55(4): 323-332 (2004).
International Search Report and Written Opinion from PCT/2017/036215 dated Nov. 21, 2017, (19 pages).
Office Action dated Apr. 22, 2016, in Singapore Patent Application No. 11201502887W.
Office Action issued in Colombian Application No. NC2016/0000187 dated May 9, 2017. An English translation is provided.
Office Action issued in U.S. Appl. No. 15/187,179 dated Oct. 21, 2016.
Ogitani et al., "Wide application of a novel topoisomerase I inhibitor-based drug conjugation technology," Bioorganic & Medicinal Chemistry Letters, vol. 26, 2016, 5069-5072.
Oguma et al, "Validation study of a method for assaying DE-310, a macromolecular carrier conjugate containing an anti-tumor camptothecin derivative, and the free drug in tumor tissue by high performance liquid chromatography/atmospheric pressure chemical ionization tandem mass spectrometry", Biomedical Chromatography, 2005, vol. 19, No. 1, pp. 19-26—(8 pages).
Ohmachi et al., "Clinical Significance of TROP2 Expression in Colorectal Cancer," Clin. Cancer Res. 12(10):3057-3063 (May 15, 2006).
Opposition dated May 3, 2017, against corresponding Colombian Patent Application No. NC2016/0000187.
Perez et al., "Antibody-drug conjugates: current status and future directions," Drug Discovery Today, vol. 19, No. 7, Jul. 2014, pp. 869-881.
Peters et al., "Antibody-drug conjugates as novel anti-cancer chemotherapeutics," Bioscience Reports, vol. 35, 2015, pp. 1-20.
Plowman et al., "Molecular cloning and expression of an additional epidermal growth factor receptor-related gene," Proc. Natl. Acad. Sci. USA 87:4905-4909 (Jul. 1990)—5 Pages.
Polakis, Paul, "Antibody Drug Conjugates for Cancer Therapy," Pharmacological Reviews, vol. 68, pp. 3-19, Jan. 2016.
Ripani et al., "Human Trop-2 is a Tumor-Associated Calcium Signal Transducer," Int. J. Cancer 76(5):671-676 (1998).
Rowinsky, "Preclinical and Clinical Development of Exatecan(DX-8951f)", Camptothecins in Cancer Therapy, 2005, pp. 317-318 (25 pages).
Russian Office Action dated Mar. 5, 2019 in corresponding application No. 2016143351.
Russian Office Action dated Oct. 11, 2018 in corresponding application No. 2016123597—13 pages.
Scott et al., "Antibody therapy of cancer," Nature Reviews, vol. 12, Apr. 2012, pp. 278-287.
Sergina, N.V., et al. "Escape from HER-family tyrosine kinase inhibitor therapy by the kinase-inactive HER3", Nature, vol. 445, pp. 437-441, 2007 (6 pages).
Shen et al., "Conjugation site modulates the in vivo stability and therapeutic activity of antibody-drug conjugates," Nature Biotechnology, vol. 30, Jan. 22, 2012, pp. 184-189.
Shiose et al, "Systematic Research of Peptide Spacers Controlling Drug Release from Macromolecular Prodrug System, Carboxymethyldextran Polyalcohol-Peptide-Drug Conjugates," Bioconjugate Chem. 20(1):60-70(2009).
Shiose et al., "Relationship between Drug Release of DE-310, Macromolecular Prodrug of DX-8951f, and Cathepsins Activity in Several Tumors," Biol. Pharm. Bull., 2007, 30(12):2365-2370.

(56) References Cited

OTHER PUBLICATIONS

Sievers et al, Antibody-Drug Conjugates in Cancer Therapy, Annual Review of Medicine, 2013, vol. 64, No. 1, pp. 15-29.
Slamon et al., "Human Breast Cancer: Correlation of Relapse and Survival with Amplification of the HER-2/neu Oncogene," Science 235:177-182 (1987).
Slamon et al., "Studies of the HER-2/neu Proto-oncogene in Human Breast and Ovarian Cancer," Science 244:707-712 (1989).
Sliwkowski et al., "Nonclinical Studies Addressing the Mechanism of Action of Trastuzumab (Herceptin)," Semin. Oncol. 26(4) Suppl. 12: 60-70 (Aug. 1999).
Sliwkowski et al., "Coexpression of erbB2 and erbB3 Proteins Reconstitutes a High Affinity Receptor for Heregulin." J. Biol. Chem. 269(20):14661-14665 (1994).
Soepenberg et al., "Phase I and Pharmacokinetic Study of DE-310 in Patients with Advanced Solid Tumors," Clin. Cancer Res. 11:703-711 (Jan. 15, 2005)—9 Pages.
Soepenberg, "Liquid chromatographic assays for DE-310, a novel camptothecin analog, and two major enzymatic products in human matrices," Journal of Chromatography B, 799, 15-22 (2004).
Stepan et al., "Expression of Trop2 Cell Surface Glycoprotein in Normal and Tumor Tissues: Potential Implications as a Cancer Therapeutic Target," Journal of Histochemistry & Cytochemistry vol. 59, No. 7, pp. 701-710. 2011.
Takiguchi et al., "Antitumor Effect of DX-8951, a Novel Camptothecin Analog, on Human Pancreatic Tumor Cells and Their CPT-11-resistant Variants Cultured in vitro and Xeografted in Nude Mice," Jpn. J. Cancer Res. 88:760-769 (Aug. 1997)—10 Pages.
Tsuchikama et al., "Antibody-drug conjugates: recent advances in conjugation and linker chemistries," Protein & Cell, Oct. 14, 2016, 14 pages.
Velez et al., "APOE*E2 allele delays age of onset in PSEN1 E280A Alzheimer's disease," Molecular Psychiatry, 2015, pp. 1-9.
Vogel et al., "Efficacy and Safety of Trastuzumab as a Single Agent in First-Line Treatment of HER2-Overexpressing Metastatic Breast Cancer," J. Clin. Oncol. 20(3):719-726 (Feb. 2002).
Wang et al., "Identification of Trop-2 as an oncogene and an attractive therapeutic target in colon cancers," Mol. Cancer Ther. 7(2):280-285 (Feb. 2008).
Wente et al., "DE-310, a macromolecular prodrug of the topoisomerase-I-inhibitor exatecan (DX-8951), in patients with operable solid tumors," Investigational New Drugs 23:339-347 (2005)—9 Pages.
Yamaguchi, Teruhide, "Current situations and the future prospect of monoclonal antibody products," Report of the National Institute of Health, vol. 132, 2014, pp. 36-46. abstract only.
Yano et al., "Comparison of HER2 gene amplification assessed by fluorescence in situ hybridization and HER2 protein expression assessed by immunohistochemistry in gastric cancer," Oncol. Rep. 15:65-71 (2006).
Yonesaka, K., et al., "Anti-HER3 monoclonal antibody patritumab sensitizes refractory non-small cell lung cancer to the epidermal growth factor receptor inhibitor erlotinib", Oncogene vol. 35, pp. 878-886, 2016 (10 pages.
International Searching Authority, "Written Opinion," issued in connection with International Patent Application No. PCT/JP2018/032056, dated Nov. 27, 2018.
Guillory, "Generation of Polymorphs, Hydrates, Solvates, and Amorphous Solids" Chapter 5, Drugs and the pharmaceutical sciences, 95 (1999) pp. 183-226.
Office Action dated Nov. 1, 2021 issued in a corresponding Canadian Patent Application No. 3073924, (7 pages).
Search Report dated Nov. 29, 2021 in Russian Application No. 2020111448, (4 pages).
"Organic Chemistry Experiments", Laboratory Center of Chemical and Molecular Sciences Faculty of Wuhan University, pp. 53-61, Wuhan University Press, Jan. 31, 2017).
Office Action and Search Report issued in corresponding Chinese Patent Application No. 201880056466X, dated Nov. 15, 2022.
Office Action issued in related Russian Patent Application No. 2020111448, dated Apr. 8, 2022.
Harwood L M et al: "Experimental organic chemistry—Principles and practice", Jan. 1, 1989 (Jan. 1, 1989), Experimental Chemistry—Organic Chemistry and Reaction,, pp. 127-132, XP003025361.
Non-Final Office Action issued in related U.S. Appl. No. 16/640,914, dated Jun. 30, 2022.
Office Action issued in corresponding European Patent Application No. 18849765.5, dated Nov. 17, 2022.
Office Action issued in corresponding Japanese Patent Application No. 2019-539605, dated Sep. 13, 2022.
Office Action issued in corresponding Japanese Patent Application No. 2019-539605, dated Apr. 4, 2023.
B. Hancock, "Predicting the Crystallization Propensity of Drug-Like Molecules", Journal of Pharmaceutical Sciences, vol. 106 (2017) pp. 28-30.
Japanese Patent Office, "Decision to Grant a Patent," issued in connection with Japanese Patent Application No. 2016-117096, dated Jul. 4, 2017.
Allowance issued in connection with Taiwanese Patent Application No. 104103127, dated Apr. 11, 2018.
Chinese Office Action dated Nov. 8, 2019 for corresponding Application No. 201580019138.9—4 pages.
Chinese Search Report dated Jun. 24, 2020 for corresponding Application No. 108114649.
Noriaki Hirayama, Handbook of Organic Compound Crystal Production, 2008, pp. 17-23, 37-40, 45-51, 78-79.

* cited by examiner

[Figure 1]

SEQ ID NO: 1: Amino acid sequence of a heavy chain of the anti-HER2 antibody

EVQLVESGGGLVQPGGSLRLSCAASGFNIKDTYIHWVR
QAPGKGLEWVARIYPTNGYTRYADSVKGRFTISADTSK
NTAYLQMNSLRAEDTAVYYCSRWGGDGFYAMDYWGQGT
LVTVSSASTKGPSVFPLAPSSKSTSGGTAALGCLVKDY
FPEPVTVSWNSGALTSGVHTFPAVLQSSGLYSLSSVVT
VPSSSLGTQTYICNVNHKPSNTKVDKKVEPKSCDKTHT
CPPCPAPELLGGPSVFLFPPKPKDTLMISRTPEVTCVV
VDVSHEDPEVKFNWYVDGVEVHNAKTKPREEQYNSTYR
VVSVLTVLHQDWLNGKEYKCKVSNKALPAPIEKTISKA
KGQPREPQVYTLPPSREEMTKNQVSLTCLVKGFYPSDI
AVEWESNGQPENNYKTTPPVLDSDGSFFLYSKLTVDKS
RWQQGNVFSCSVMHEALHNHYTQKSLSLSPGK

[Figure 2]

SEQ ID NO: 2: Amino acid sequence of a light chain of the anti-HER2 antibody

DIQMTQSPSSLSASVGDRVTITCRASQDVNTAVAWYQQ
KPGKAPKLLIYSASFLYSGVPSRFSGSRSGTDFTLTIS
SLQPEDFATYYCQQHYTTPPTFGQGTKVEIKRTVAAPS
VFIFPPSDEQLKSGTASVVCLLNNFYPREAKVQWKVDN
ALQSGNSQESVTEQDSKDSTYSLSSTLTLSKADYEKHK
VYACEVTHQGLSSPVTKSFNRGEC

[Figure 3]
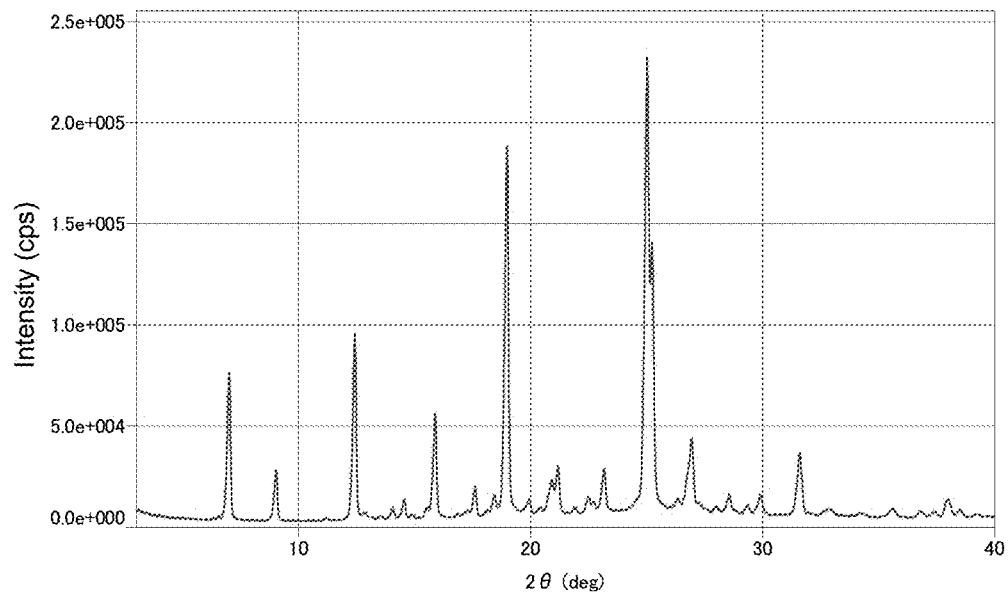
[Figure 4]
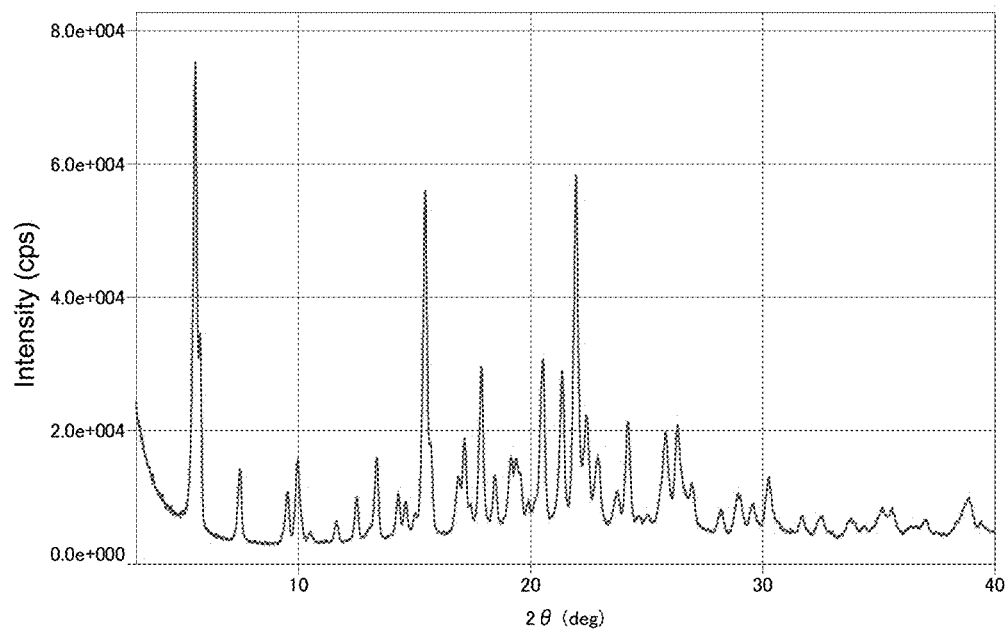

[Figure 5]

SEQ ID NO: 3: Amino acid sequence of a heavy chain of the anti-HER3 antibody

QVQLQQWGAGLLKPSETLSLTCAVYGGSFSGYYWSWIR
QPPGKGLEWIGEINHSGSTNYNPSLKSRVTISVETSKN
QFSLKLSSVTAADTAVYYCARDKWTWYFDLWGRGTLVT
VSSASTKGPSVFPLAPSSKSTSGGTAALGCLVKDYFPE
PVTVSWNSGALTSGVHTFPAVLQSSGLYSLSSVVTVPS
SSLGTQTYICNVNHKPSNTKVDKRVEPKSCDKTHTCPP
CPAPELLGGPSVFLFPPKPKDTLMISRTPEVTCVVVDV
SHEDPEVKFNWYVDGVEVHNAKTKPREEQYNSTYRVVS
VLTVLHQDWLNGKEYKCKVSNKALPAPIEKTISKAKGQ
PREPQVYTLPPSREEMTKNQVSLTCLVKGFYPSDIAVE
WESNGQPENNYKTTPPVLDSDGSFFLYSKLTVDKSRWQ
QGNVFSCSVMHEALHNHYTQKSLSLSPGK

[Figure 6]

SEQ ID NO: 4: Amino acid sequence of a light chain of the anti-HER3 antibody

DIEMTQSPDSLAVSLGERATINCRSSQSVLYSSSNRNY
LAWYQQNPGQPPKLLIYWASTRESGVPDRFSGSGSGTD
FTLTISSLQAEDVAVYYCQQYYSTPRTFGQGTKVEIKR
TVAAPSVFIFPPSDEQLKSGTASVVCLLNNFYPREAKV
QWKVDNALQSGNSQESVTEQDSKDSTYSLSSTLTLSKA
DYEKHKVYACEVTHQGLSSPVTKSFNRGEC

[Figure 7]

SEQ ID NO: 5: Amino acid sequence of a heavy chain of the anti-TROP2 antibody

MKHLWFFLLLVAAPRWVLSQVQLVQSGAEVKKPGASVK
VSCKASGYTFTTAGMQWVRQAPGQGLEWMGWINTHSGV
PKYAEDFKGRVTISADTSTSTAYLQLSSLKSEDTAVYY
CARSGFGSSYWYFDVWGQGTLVTVSSASTKGPSVFPLA
PSSKSTSGGTAALGCLVKDYFPEPVTVSWNSGALTSGV
HTFPAVLQSSGLYSLSSVVTVPSSSLGTQTYICNVNHK
PSNTKVDKRVEPKSCDKTHTCPPCPAPELLGGPSVFLF
PPKPKDTLMISRTPEVTCVVVDVSHEDPEVKFNWYVDG
VEVHNAKTKPREEQYNSTYRVVSVLTVLHQDWLNGKEY
KCKVSNKALPAPIEKTISKAKGQPREPQVYTLPPSREE
MTKNQVSLTCLVKGFYPSDIAVEWESNGQPENNYKTTP
PVLDSDGSFFLYSKLTVDKSRWQQGNVFSCSVMHEALH
NHYTQKSLSLSPGK

Signal sequence (1-19), variable region (20-140), constant region (141-470)

[Figure 8]

SEQ ID NO: 6: Amino acid sequence of a light chain of the anti-TROP2 antibody

MVLQTQVFISLLLWISGAYGDIQMTQSPSSLSASVGDR
VTITCKASQDVSTAVAWYQQKPGKAPKLLIYSASYRYT
GVPSRFSGSGSGTDFTLTISSLQPEDFAVYYCQQHYIT
PLTFGQGTKLEIKRTVAAPSVFIFPPSDEQLKSGTASV
VCLLNNFYPREAKVQWKVDNALQSGNSQESVTEQDSKD
STYSLSSTLTLSKADYEKHKVYACEVTHQGLSSPVTKS
FNRGEC

Signal sequence (1-20), variable region (21-129), constant region (130-234)

[Figure 9]

SEQ ID NO: 7: Amino acid sequence of a heavy chain of the anti-B7-H3 antibody

MKHLWFFLLLVAAPRWVLSQVQLVQSGAEVKKPGSSVK
VSCKASGYTFTNYVMHWVRQAPGQGLEWMGYINPYNDD
VKYNEKFKGRVTITADESTSTAYMELSSLRSEDTAVYY
CARWGYYGSPLYYFDYWGQGTLVTVSSASTKGPSVFPL
APSSKSTSGGTAALGCLVKDYFPEPVTVSWNSGALTSG
VHTFPAVLQSSGLYSLSSVVTVPSSSLGTQTYICNVNH
KPSNTKVDKRVEPKSCDKTHTCPPCPAPELLGGPSVFL
FPPKPKDTLMISRTPEVTCVVVDVSHEDPEVKFNWYVD
GVEVHNAKTKPREEQYNSTYRVVSVLTVLHQDWLNGKE
YKCKVSNKALPAPIEKTISKAKGQPREPQVYTLPPSRE
EMTKNQVSLTCLVKGFYPSDIAVEWESNGQPENNYKTT
PPVLDSDGSFFLYSKLTVDKSRWQQGNVFSCSVMHEAL
HNHYTQKSLSLSPGK

Signal sequence (1-19), variable region (20-141), constant region (142-471)

[Figure 10]

SEQ ID NO: 8: Amino acid sequence of a light chain of the anti-B7-H3 antibody

MVLQTQVFISLLLWISGAYGEIVLTQSPATLSLSPGER
ATLSCRASSRLIYMHWYQQKPGQAPRPLIYATSNLASG
IPARFSGSGSGTDFTLTISSLEPEDFAVYYCQQWNSNP
PTFGQGTKVEIKRTVAAPSVFIFPPSDEQLKSGTASVV
CLLNNFYPREAKVQWKVDNALQSGNSQESVTEQDSKDS
TYSLSSTLTLSKADYEKHKVYACEVTHQGLSSPVTKSF
NRGEC

Signal sequence (1-20), variable region (21-128), constant region (129-233)

[Figure 11]

SEQ ID NO: 9: Amino acid sequence of a heavy chain of the anti-GPR20 antibody

MKHLWFFLLLVAAPRWVLSEVQLVQSGAEVKKPGASVK
VSCKASGYTFTSYYISWIRQAPGQGLKYMGFINPGSGH
TNYNEKFKGRVTITADKSSTATMELSSLRSEDTAVYY
CARGAGGFLRIITKFDYWGQGTLVTVSSASTKGPSVFP
LAPSSKSTSGGTAALGCLVKDYFPEPVTVSWNSGALTS
GVHTFPAVLQSSGLYSLSSVVTVPSSSLGTQTYICNVN
HKPSNTKVDKRVEPKSCDKTHTCPPCPAPELLGGPSVF
LFPPKPKDTLMISRTPEVTCVVVDVSHEDPEVKFNWYV
DGVEVHNAKTKPREEQYNSTYRVVSVLTVLHQDWLNGK
EYKCKVSNKALPAPIEKTISKAKGQPREPQVYTLPPSR
EEMTKNQVSLTCLVKGFYPSDIAVEWESNGQPENNYKT
TPPVLDSDGSFFLYSKLTVDKSRWQQGNVFSCSVMHEA
LHNHYTQKSLSLSPGK

Signal sequence (1-19), variable region (20-142), constant region (143-472)

[Figure 12]

SEQ ID NO: 10: Amino acid sequence of a light chain of the anti-GPR20 antibody

MVLQTQVFISLLLWISGAYGDTQLTQSPSSLSASVGDR
VTITCRASKSVSTYIHWYQQKPGKQPKLLIYSAGNLES
GVPSRFSGSGSGTDFTLTISSLQPEDFANYYCQQINEL
PYTFGQGTKVEIKRTVAAPSVFIFPPSDEQLKSGTASV
VCLLNNFYPREAKVQWKVDNALQSGNSQESVTEQDSKD
STYSLSSTLTLSKADYEKHKVYACEVTHQGLSSPVTKS
FNRGEC

Signal sequence (1-20), variable region (21-129), constant region (130-234)

```
SEQUENCE LISTING

<160> NUMBER OF SEQ ID NOS: 11

<210> SEQ ID NO 1
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Heavy chain of anti-HER2 antibody

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
                100                 105                 110
```

```
Gly Thr Leu Val Thr Val Ser Ala Ser Thr Lys Gly Pro Ser Val
            115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 2
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain of anti-HER2 antibody

<400> SEQUENCE: 2
```

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 3
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Heavy chain of anti-HER3 antibody

<400> SEQUENCE: 3

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Glu Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Lys Trp Thr Trp Tyr Phe Asp Leu Trp Gly Arg Gly Thr Leu
                100                 105                 110

Val Thr Val Ser Ser Ala Ser Thr Lys Gly Pro Ser Val Phe Pro Leu
            115                 120                 125
```

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 4
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain of anti-HER3 antibody

<400> SEQUENCE: 4

Asp Ile Glu Met Thr Gln Ser Pro Asp Ser Leu Ala Val Ser Leu Gly
1               5                   10                  15

Glu Arg Ala Thr Ile Asn Cys Arg Ser Ser Gln Ser Val Leu Tyr Ser
            20                  25                  30

```
Ser Ser Asn Arg Asn Tyr Leu Ala Trp Tyr Gln Gln Asn Pro Gly Gln
         35                  40                  45

Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Tyr Tyr Ser Thr Pro Arg Thr Phe Gly Gln Gly Thr Lys Val Glu Ile
            100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
            210                 215                 220

<210> SEQ ID NO 5
<211> LENGTH: 470
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Heavy chain of anti-TROP2 antibody

<400> SEQUENCE: 5

Met Lys His Leu Trp Phe Phe Leu Leu Leu Val Ala Ala Pro Arg Trp
 1                   5                  10                  15

Val Leu Ser Gln Val Gln Leu Val Gln Ser Gly Ala Glu Val Lys Lys
             20                  25                  30

Pro Gly Ala Ser Val Lys Val Ser Cys Lys Ala Ser Gly Tyr Thr Phe
         35                  40                  45

Thr Thr Ala Gly Met Gln Trp Val Arg Gln Ala Pro Gly Gln Gly Leu
 50                  55                  60

Glu Trp Met Gly Trp Ile Asn Thr His Ser Gly Val Pro Lys Tyr Ala
 65                  70                  75                  80

Glu Asp Phe Lys Gly Arg Val Thr Ile Ser Ala Asp Thr Ser Thr Ser
                 85                  90                  95

Thr Ala Tyr Leu Gln Leu Ser Ser Leu Lys Ser Glu Asp Thr Ala Val
            100                 105                 110

Tyr Tyr Cys Ala Arg Ser Gly Phe Gly Ser Ser Tyr Trp Tyr Phe Asp
            115                 120                 125

Val Trp Gly Gln Gly Thr Leu Val Thr Val Ser Ser Ala Ser Thr Lys
130                 135                 140

Gly Pro Ser Val Phe Pro Leu Ala Pro Ser Ser Lys Ser Thr Ser Gly
145                 150                 155                 160
```

Gly Thr Ala Ala Leu Gly Cys Leu Val Lys Asp Tyr Phe Pro Glu Pro
            165                 170                 175

Val Thr Val Ser Trp Asn Ser Gly Ala Leu Thr Ser Gly Val His Thr
        180                 185                 190

Phe Pro Ala Val Leu Gln Ser Ser Gly Leu Tyr Ser Leu Ser Ser Val
    195                 200                 205

Val Thr Val Pro Ser Ser Leu Gly Thr Gln Thr Tyr Ile Cys Asn
210                 215                 220

Val Asn His Lys Pro Ser Asn Thr Lys Val Asp Lys Arg Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Glu Glu Met Thr Lys Asn
    370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

Ser Leu Ser Pro Gly Lys
465                 470

<210> SEQ ID NO 6
<211> LENGTH: 234
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain of anti-TROP2 antibody

<400> SEQUENCE: 6

Met Val Leu Gln Thr Gln Val Phe Ile Ser Leu Leu Leu Trp Ile Ser
1               5                   10                  15

Gly Ala Tyr Gly Asp Ile Gln Met Thr Gln Ser Pro Ser Ser Leu Ser
            20                  25                  30

```
Ala Ser Val Gly Asp Arg Val Thr Ile Thr Cys Lys Ala Ser Gln Asp
         35                  40                  45

Val Ser Thr Ala Val Ala Trp Tyr Gln Gln Lys Pro Gly Lys Ala Pro
 50                  55                  60

Lys Leu Leu Ile Tyr Ser Ala Ser Tyr Arg Tyr Thr Gly Val Pro Ser
 65                  70                  75                  80

Arg Phe Ser Gly Ser Gly Ser Gly Thr Asp Phe Thr Leu Thr Ile Ser
                 85                  90                  95

Ser Leu Gln Pro Glu Asp Phe Ala Val Tyr Tyr Cys Gln His Tyr
             100                 105                 110

Ile Thr Pro Leu Thr Phe Gly Gln Gly Thr Lys Leu Glu Ile Lys Arg
             115                 120                 125

Thr Val Ala Ala Pro Ser Val Phe Ile Phe Pro Pro Ser Asp Glu Gln
 130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                 165                 170                 175

Gly Asn Ser Gln Glu Ser Val Thr Glu Gln Asp Ser Lys Asp Ser Thr
             180                 185                 190

Tyr Ser Leu Ser Ser Thr Leu Thr Leu Ser Lys Ala Asp Tyr Glu Lys
             195                 200                 205

His Lys Val Tyr Ala Cys Glu Val Thr His Gln Gly Leu Ser Ser Pro
             210                 215                 220

Val Thr Lys Ser Phe Asn Arg Gly Glu Cys
225                 230

<210> SEQ ID NO 7
<211> LENGTH: 471
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Heavy chain of anti-B7-H3 antibody

<400> SEQUENCE: 7

Met Lys His Leu Trp Phe Phe Leu Leu Leu Val Ala Ala Pro Arg Trp
 1               5                  10                  15

Val Leu Ser Gln Val Gln Leu Val Gln Ser Gly Ala Glu Val Lys Lys
             20                  25                  30

Pro Gly Ser Ser Val Lys Val Ser Cys Lys Ala Ser Gly Tyr Thr Phe
             35                  40                  45

Thr Asn Tyr Val Met His Trp Val Arg Gln Ala Pro Gly Gln Gly Leu
 50                  55                  60

Glu Trp Met Gly Tyr Ile Asn Pro Tyr Asn Asp Asp Val Lys Tyr Asn
 65                  70                  75                  80

Glu Lys Phe Lys Gly Arg Val Thr Ile Thr Ala Asp Glu Ser Thr Ser
                 85                  90                  95

Thr Ala Tyr Met Glu Leu Ser Ser Leu Arg Ser Glu Asp Thr Ala Val
             100                 105                 110

Tyr Tyr Cys Ala Arg Trp Gly Tyr Tyr Gly Ser Pro Leu Tyr Tyr Phe
             115                 120                 125

Asp Tyr Trp Gly Gln Gly Thr Leu Val Thr Val Ser Ser Ala Ser Thr
 130                 135                 140
```

-continued

```
Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
                180                 185                 190

Thr Phe Pro Ala Val Leu Gln Ser Ser Gly Leu Tyr Ser Leu Ser Ser
            195                 200                 205

Val Val Thr Val Pro Ser Ser Ser Leu Gly Thr Gln Thr Tyr Ile Cys
        210                 215                 220

Asn Val Asn His Lys Pro Ser Asn Thr Lys Val Asp Lys Arg Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
                260                 265                 270

Asp Thr Leu Met Ile Ser Arg Thr Pro Glu Val Thr Cys Val Val Val
            275                 280                 285

Asp Val Ser His Glu Asp Pro Glu Val Lys Phe Asn Trp Tyr Val Asp
        290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
                340                 345                 350

Pro Ala Pro Ile Glu Lys Thr Ile Ser Lys Ala Lys Gly Gln Pro Arg
            355                 360                 365

Glu Pro Gln Val Tyr Thr Leu Pro Pro Ser Arg Glu Glu Met Thr Lys
        370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
                420                 425                 430

Lys Leu Thr Val Asp Lys Ser Arg Trp Gln Gln Gly Asn Val Phe Ser
            435                 440                 445

Cys Ser Val Met His Glu Ala Leu His Asn His Tyr Thr Gln Lys Ser
        450                 455                 460

Leu Ser Leu Ser Pro Gly Lys
465                 470

<210> SEQ ID NO 8
<211> LENGTH: 233
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain of anti-B7-H3 antibody

<400> SEQUENCE: 8

Met Val Leu Gln Thr Gln Val Phe Ile Ser Leu Leu Leu Trp Ile Ser
1               5                   10                  15
```

-continued

```
Gly Ala Tyr Gly Glu Ile Val Leu Thr Gln Ser Pro Ala Thr Leu Ser
             20                  25                  30

Leu Ser Pro Gly Glu Arg Ala Thr Leu Ser Cys Arg Ala Ser Ser Arg
         35                  40                  45

Leu Ile Tyr Met His Trp Tyr Gln Gln Lys Pro Gly Gln Ala Pro Arg
     50                  55                  60

Pro Leu Ile Tyr Ala Thr Ser Asn Leu Ala Ser Gly Ile Pro Ala Arg
 65                  70                  75                  80

Phe Ser Gly Ser Gly Ser Gly Thr Asp Phe Thr Leu Thr Ile Ser Ser
                 85                  90                  95

Leu Glu Pro Glu Asp Phe Ala Val Tyr Tyr Cys Gln Gln Trp Asn Ser
            100                 105                 110

Asn Pro Pro Thr Phe Gly Gln Gly Thr Lys Val Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230

<210> SEQ ID NO 9
<211> LENGTH: 472
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Heavy chain of anti-GPR20 antibody

<400> SEQUENCE: 9

Met Lys His Leu Trp Phe Phe Leu Leu Leu Val Ala Ala Pro Arg Trp
 1               5                  10                  15

Val Leu Ser Glu Val Gln Leu Val Gln Ser Gly Ala Glu Val Lys Lys
             20                  25                  30

Pro Gly Ala Ser Val Lys Val Ser Cys Lys Ala Ser Gly Tyr Thr Phe
         35                  40                  45

Thr Ser Tyr Tyr Ile Ser Trp Ile Arg Gln Ala Pro Gly Gln Gly Leu
     50                  55                  60

Lys Tyr Met Gly Phe Ile Asn Pro Gly Ser Gly His Thr Asn Tyr Asn
 65                  70                  75                  80

Glu Lys Phe Lys Gly Arg Val Thr Ile Thr Ala Asp Lys Ser Ser Ser
                 85                  90                  95

Thr Ala Thr Met Glu Leu Ser Ser Leu Arg Ser Glu Asp Thr Ala Val
            100                 105                 110

Tyr Tyr Cys Ala Arg Gly Ala Gly Gly Phe Leu Arg Ile Ile Thr Lys
        115                 120                 125
```

```
Phe Asp Tyr Trp Gly Gln Gly Thr Leu Val Thr Val Ser Ser Ala Ser
    130                 135                 140
Thr Lys Gly Pro Ser Val Phe Pro Leu Ala Pro Ser Ser Lys Ser Thr
145                 150                 155                 160
Ser Gly Gly Thr Ala Ala Leu Gly Cys Leu Val Lys Asp Tyr Phe Pro
                165                 170                 175
Glu Pro Val Thr Val Ser Trp Asn Ser Gly Ala Leu Thr Ser Gly Val
            180                 185                 190
His Thr Phe Pro Ala Val Leu Gln Ser Ser Gly Leu Tyr Ser Leu Ser
        195                 200                 205
Ser Val Val Thr Val Pro Ser Ser Ser Leu Gly Thr Gln Thr Tyr Ile
210                 215                 220
Cys Asn Val Asn His Lys Pro Ser Asn Thr Lys Val Asp Lys Arg Val
225                 230                 235                 240
Glu Pro Lys Ser Cys Asp Lys Thr His Thr Cys Pro Pro Cys Pro Ala
                245                 250                 255
Pro Glu Leu Leu Gly Gly Pro Ser Val Phe Leu Phe Pro Pro Lys Pro
            260                 265                 270
Lys Asp Thr Leu Met Ile Ser Arg Thr Pro Glu Val Thr Cys Val Val
        275                 280                 285
Val Asp Val Ser His Glu Asp Pro Glu Val Lys Phe Asn Trp Tyr Val
290                 295                 300
Asp Gly Val Glu Val His Asn Ala Lys Thr Lys Pro Arg Glu Glu Gln
305                 310                 315                 320
Tyr Asn Ser Thr Tyr Arg Val Val Ser Val Leu Thr Val Leu His Gln
                325                 330                 335
Asp Trp Leu Asn Gly Lys Glu Tyr Lys Cys Lys Val Ser Asn Lys Ala
            340                 345                 350
Leu Pro Ala Pro Ile Glu Lys Thr Ile Ser Lys Ala Lys Gly Gln Pro
        355                 360                 365
Arg Glu Pro Gln Val Tyr Thr Leu Pro Pro Ser Arg Glu Glu Met Thr
370                 375                 380
Lys Asn Gln Val Ser Leu Thr Cys Leu Val Lys Gly Phe Tyr Pro Ser
385                 390                 395                 400
Asp Ile Ala Val Glu Trp Glu Ser Asn Gly Gln Pro Glu Asn Asn Tyr
                405                 410                 415
Lys Thr Thr Pro Pro Val Leu Asp Ser Asp Gly Ser Phe Phe Leu Tyr
            420                 425                 430
Ser Lys Leu Thr Val Asp Lys Ser Arg Trp Gln Gln Gly Asn Val Phe
        435                 440                 445
Ser Cys Ser Val Met His Glu Ala Leu His Asn His Tyr Thr Gln Lys
450                 455                 460
Ser Leu Ser Leu Ser Pro Gly Lys
465                 470

<210> SEQ ID NO 10
<211> LENGTH: 234
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain of anti-GPR20 antibody

<400> SEQUENCE: 10
```

Met Val Leu Gln Thr Gln Val Phe Ile Ser Leu Leu Leu Trp Ile Ser
1               5                   10                  15

Gly Ala Tyr Gly Asp Thr Gln Leu Thr Gln Ser Pro Ser Ser Leu Ser
                20                  25                  30

Ala Ser Val Gly Asp Arg Val Thr Ile Thr Cys Arg Ala Ser Lys Ser
            35                  40                  45

Val Ser Thr Tyr Ile His Trp Tyr Gln Gln Lys Pro Gly Lys Gln Pro
    50                  55                  60

Lys Leu Leu Ile Tyr Ser Ala Gly Asn Leu Glu Ser Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Asn Tyr Tyr Cys Gln Gln Ile Asn
                100                 105                 110

Glu Leu Pro Tyr Thr Phe Gly Gln Gly Thr Lys Val Glu Ile Lys Arg
                115                 120                 125

Thr Val Ala Ala Pro Ser Val Phe Ile Phe Pro Pro Ser Asp Glu Gln
        130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
                180                 185                 190

Tyr Ser Leu Ser Ser Thr Leu Thr Leu Ser Lys Ala Asp Tyr Glu Lys
                195                 200                 205

His Lys Val Tyr Ala Cys Glu Val Thr His Gln Gly Leu Ser Ser Pro
            210                 215                 220

Val Thr Lys Ser Phe Asn Arg Gly Glu Cys
225                 230

<210> SEQ ID NO 11
<211> LENGTH: 4
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Peptide linker

<400> SEQUENCE: 11

Gly Gly Phe Gly
1

METHOD FOR PRODUCING ANTIBODY-DRUG CONJUGATE

CROSS-REFERENCE TO RELATED APPLICATIONS

The present application claims priority under 37 U.S.C. § 371 to International Patent Application No. PCT/JP2018/032056, filed Aug. 30, 2018, which claims priority to and the benefit of Japanese Patent Application No. 2017-167691, filed on Aug. 31, 2017. The contents of these applications are hereby incorporated by reference in their entireties.

SEQUENCE LISTING

The instant application contains a Sequence Listing which has been submitted in ASCII format via EFS-WEB and is hereby incorporated by reference in its entirety. Said ASCII copy, created on Nov. 19, 2021, is named "122622-0112_SL.txt" and is 31,880 bytes.

TECHNICAL FIELD

The present invention relates to an improved method for producing a drug-linker intermediate for an antibody-drug conjugate, and an improved method for producing an antibody-drug conjugate wherein the aforementioned method is used.

BACKGROUND ART

An antibody-drug conjugate (ADC) having a drug with cytotoxicity conjugated to an antibody, whose antigen is expressed on the surface of cancer cells and which also binds to an antigen capable of cellular internalization, and therefore can deliver the drug selectively to cancer cells, is thus expected to cause accumulation of the drug within cancer cells and to kill the cancer cells (Non-Patent Literatures 1 to 5).

As one such antibody-drug conjugate, an antibody-drug conjugate comprising an antibody and exatecan, which is a topoisomerase I inhibitor, as its components is known (Patent Literatures 1 to 5 and Non-Patent Literatures 6, 7). Since these antibody-drug conjugates exert a superior antitumor effect and safety, they are currently under clinical studies.

As methods for producing drug-linker intermediates for producing the above-described antibody-drug conjugates, methods described in Patent Literatures 1 to 4 are known.

CITATION LIST

Patent Literatures

Patent Literature 1: International Publication No. WO 2014/057687
Patent Literature 2: International Publication No. WO 2015/098099
Patent Literature 3: International Publication No. WO 2015/115091
Patent Literature 4: International Publication No. WO 2015/155998
Patent Literature 5: International Publication No. WO 2018/135501

Non-Patent Literatures

Non-Patent Literature 1: Ducry, L., et al., Bioconjugate Chem. (2010) 21, 5-13.
Non-Patent Literature 2: Alley, S. C., et al., Current Opinion in Chemical Biology (2010) 14, 529-537. Non-Patent Literature 3: Damle N. K. Expert Opin. Biol. Ther. (2004) 4, 1445-1452.
Non-Patent Literature 4: Senter P. D., et al., Nature Biotechnology (2012) 30, 631-637.
Non-Patent Literature 5: Howard A. et al., J Clin Oncol 29: 398-405.
Non-Patent Literature 6: Ogitani Y. et al., Clinical Cancer Research (2016) 22 (20), 5097-5108.
Non-Patent Literature 7: Ogitani Y. et al., Cancer Science (2016) 107, 1039-1046.

SUMMARY OF INVENTION

Technical Problem

A drug-linker intermediate for producing an antibody-drug conjugate of the present invention is the compound represented by formula (1):

[Chem. 1]

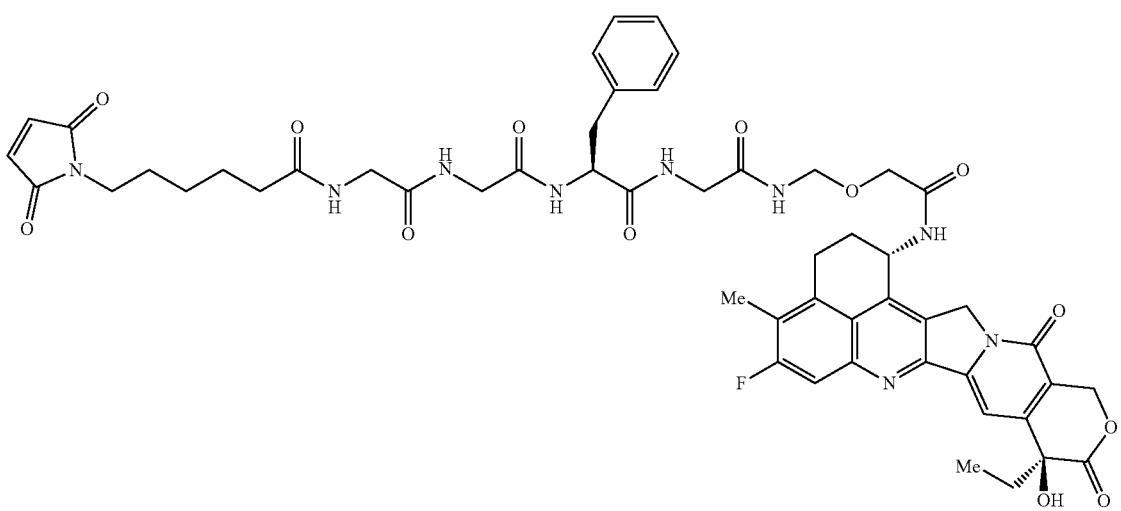

(1)

As a method for producing the compound represented by the formula (1), methods described in Patent Literatures 1 to 4 are known. However, it has not been known that the compound represented by the formula (1) can be obtained as crystals, and it is necessary to perform complicated operations such as necessary purification by chromatography. There is therefore a demand for development of an industrially better production method.

One object of the present invention is to find an improved industrially excellent method for producing a drug-linker intermediate without the need for purification by chromatography. Another object of the present invention is to construct an improved method for producing an antibody-drug conjugate wherein the aforementioned improved method for producing a drug-linker intermediate is used.

Solution to Problem

The present inventors conducted diligent studies on a method for producing a drug-linker intermediate, and consequently found that, surprisingly, the compound represented by formula (1) can be obtained as crystals. The present inventors also improved a method for producing the compound represented by the formula (1), and consequently found an industrially excellent production method without the need for purification by chromatography. The present inventors further constructed an improved method for producing an antibody-drug conjugate by using the crystals of the compound represented by the formula (1), and completed the present invention.

Specifically, the present invention relates to the following.
[1] Crystals of the compound represented by formula (1):

[Chem. 2]

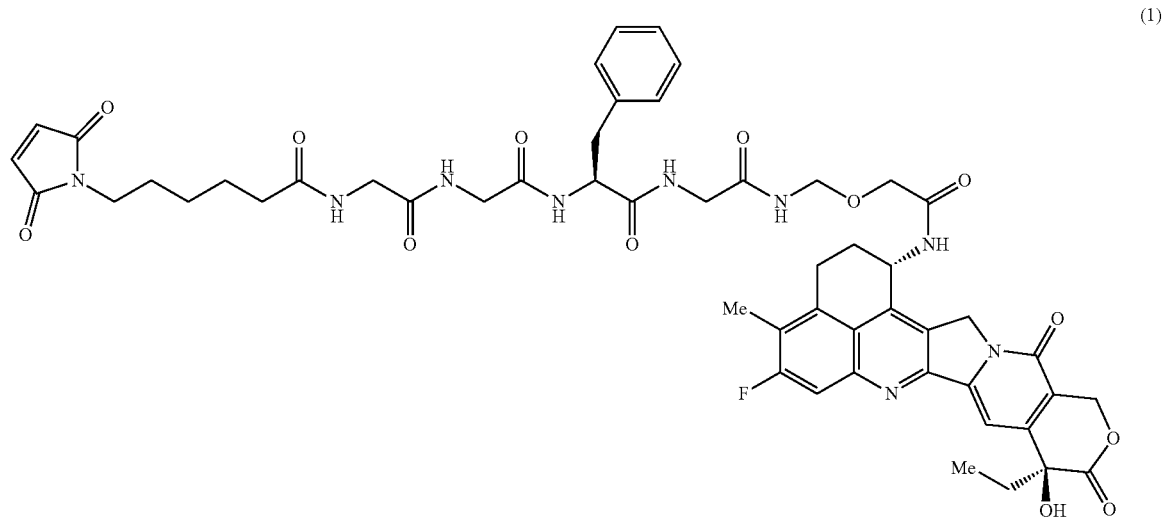 [SMILES: CC[C@@]1(O)C(=O)OCc2c1cc1n(c2=O)Cc2c-1nc1cc(F)c(C)c3c1c2[C@@H](NC(=O)COCNC(=O)CNC(=O)[C@H](Cc1ccccc1)NC(=O)CNC(=O)CNC(=O)CCCCCN1C(=O)C=CC1=O)CC3]

(1)

[2] The crystals according to [1], wherein the crystals show main peaks at diffraction angles (2θ) of 5.6±0.2°, 15.5±0.2° and 22.0±0.2° in powder X-ray diffraction obtained by irradiation with copper Kα radiation.

[3] A method for producing crystals of the compound represented by formula (1):

[Chem. 3]

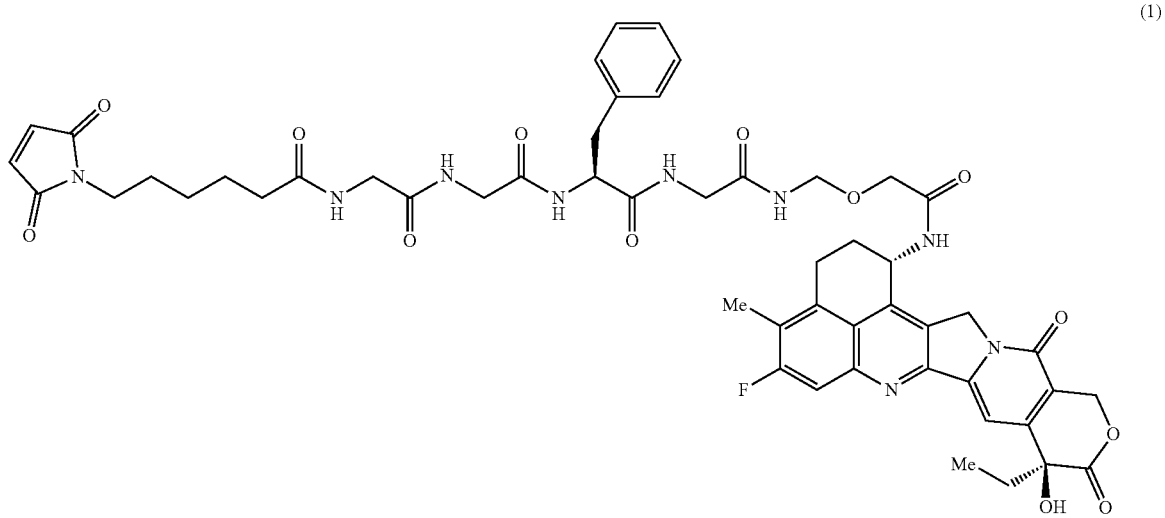

(1)

comprising the steps of: preparing a solution in which the compound represented by the formula (1) is dissolved; and then precipitating crystals of the compound represented by the formula (1) from the solution.

[4] The production method according to [3], wherein the crystals of the compound represented by the formula (1) show main peaks at diffraction angles (2θ) of 5.6±0.2°, 15.5±0.2° and 22.0±0.2° in powder X-ray diffraction obtained by irradiation with copper Kα radiation.

[5] The production method according to [3] or [4], wherein the solution in which the compound represented by the formula (1) is dissolved comprises a lower ketone and a lower alcohol as solvents.

[6] The production method according to [5], wherein the lower ketone is acetone.

[7] The production method according to [5], wherein the lower ketone is methyl ethyl ketone.

[8] The production method according to any one of [5] to [7], wherein the lower alcohol is 1-propanol.

[9] The production method according to any one of [5] to [7], wherein the lower alcohol is 2-butanol.

[10] The production method according to any one of [3] to [9], comprising a step of adding a seed crystal of the crystals of the compound represented by the formula (1).

[11] The production method according to any one of [3] to [10], wherein the compound represented by the formula (1) is produced by a production method (I),
wherein the production method (I) is a production method comprising the steps of:
deprotecting protecting groups for an amino group and a carboxy group of a compound represented by formula (B):

[Chem. 4]

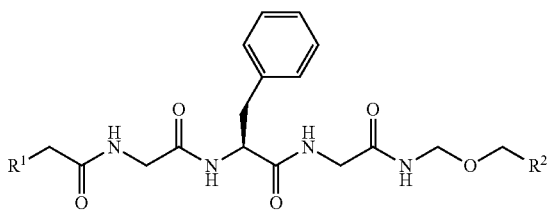

(B)

wherein $R^1$ represents an amino group protected with a protecting group, and $R^2$ represents a carboxy group protected with a protecting group, to convert it into the compound represented by formula (8):

[Chem. 5]

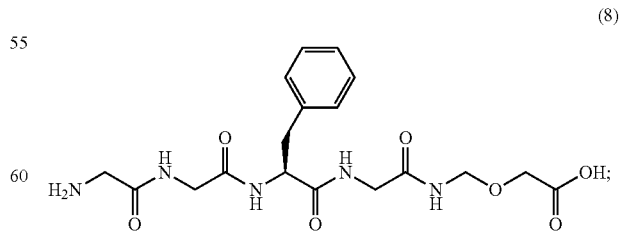

(8)

then
condensing the compound represented by the formula (8) with a compound represented by formula (C):

[Chem. 6]
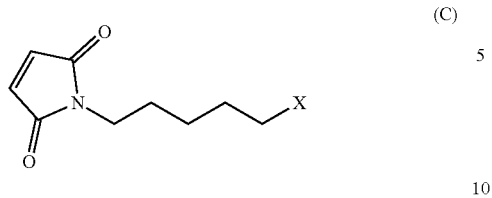
(C)
wherein X represents an active ester group or a carboxy group, to convert it into the compound represented by formula (10):
[Chem. 7]
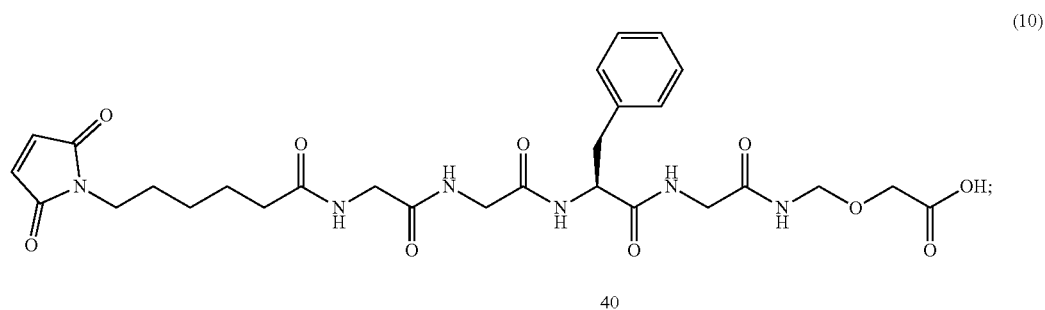
(10)
and then condensing the compound represented by the formula (10) with the compound represented by formula (11):
[Chem. 8]
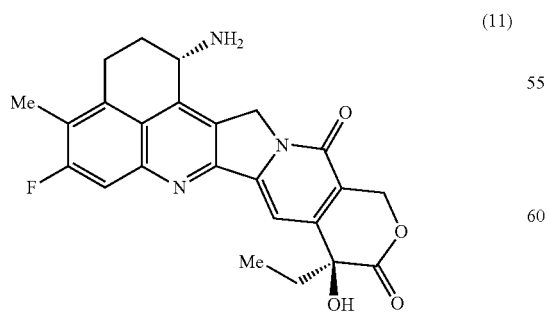
(11)
to convert it into the compound represented by the formula (1):

[Chem. 9]

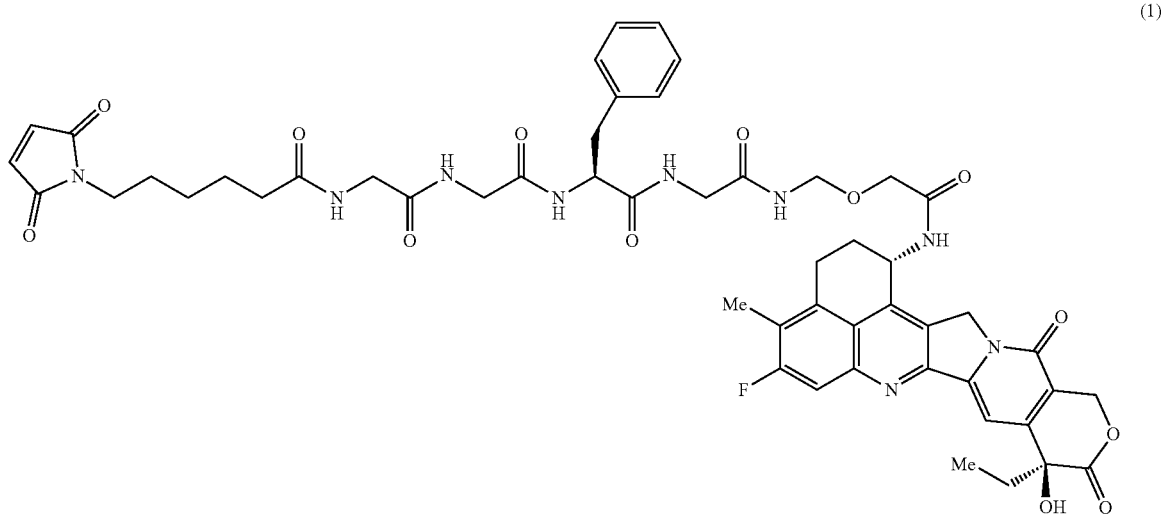

(1)

[12] The production method according to any one of [3] to [10], wherein the compound represented by the formula (1) is produced by a production method (II),
wherein the production method (II) is a production method comprising the steps of:
deprotecting a protecting group for an amino group of a compound represented by formula (B):

[Chem. 10]

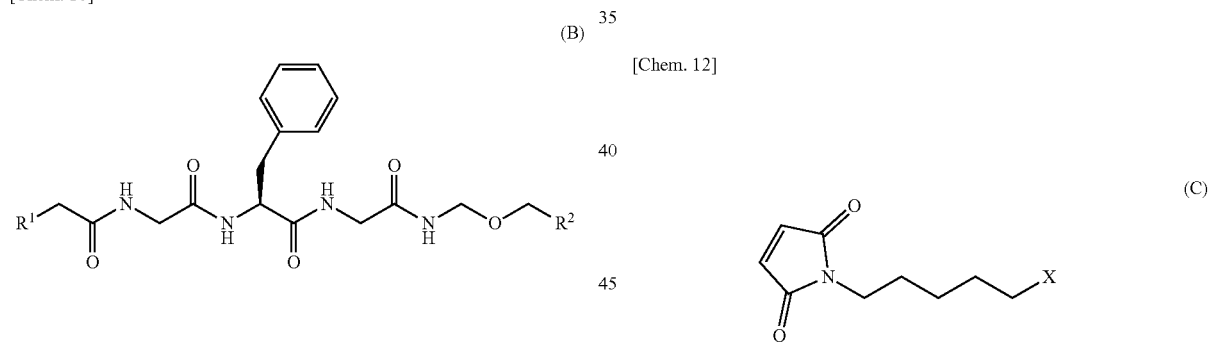

(B)

wherein R¹ represents an amino group protected with a protecting group, and R² represents a carboxy group protected with a protecting group, to convert it into a compound represented by formula (D):

[Chem. 11]

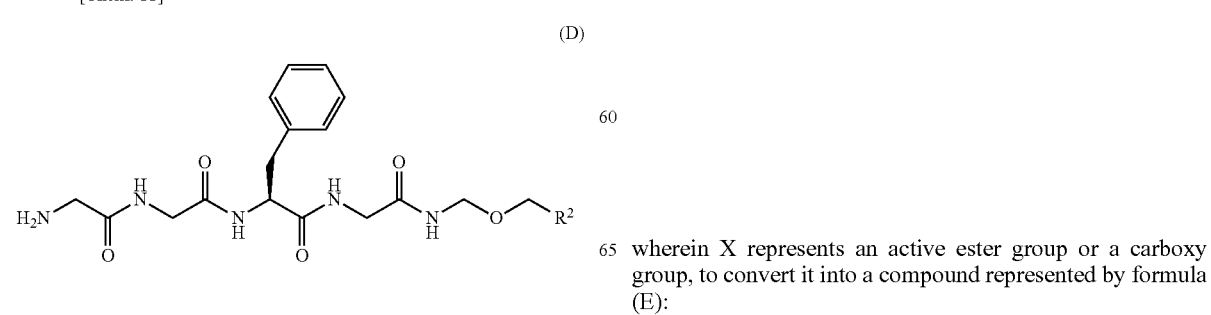

(D)

wherein $R^2$ represents the same meaning as above; then condensing the compound represented by the formula (D) with a compound represented by formula (C):

[Chem. 12]

(C)

wherein X represents an active ester group or a carboxy group, to convert it into a compound represented by formula (E):

[Chem. 13]

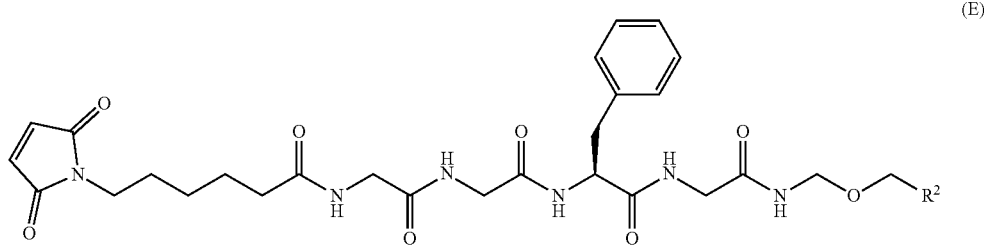

(E)

wherein R² represents the same meaning as above; then deprotecting the protecting group for the carboxy group of the compound represented by the formula (E) to convert it into the compound represented by formula (10):

[Chem. 14]

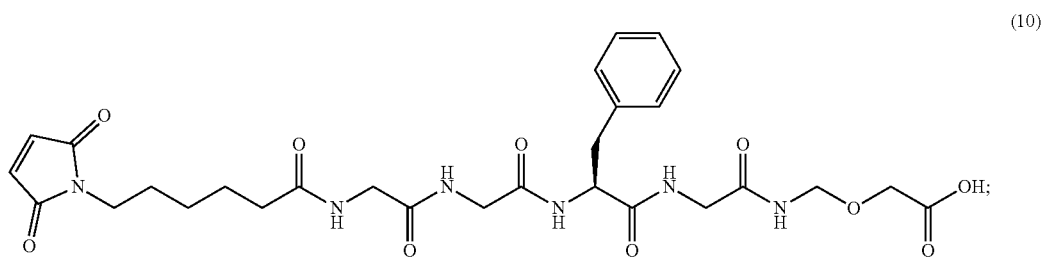 [SMILES: O=C(O)COCNC(=O)CNC(=O)[C@H](Cc1ccccc1)NC(=O)CNC(=O)CNC(=O)CCCCCN1C(=O)C=CC1=O]

(10)

and then condensing the compound represented by the formula (10) with the compound represented by formula (11):

[Chem. 15]

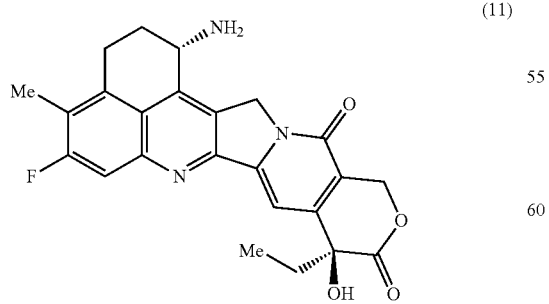

(11)

to convert it into the compound represented by the formula (1):

[Chem. 16]

(1)

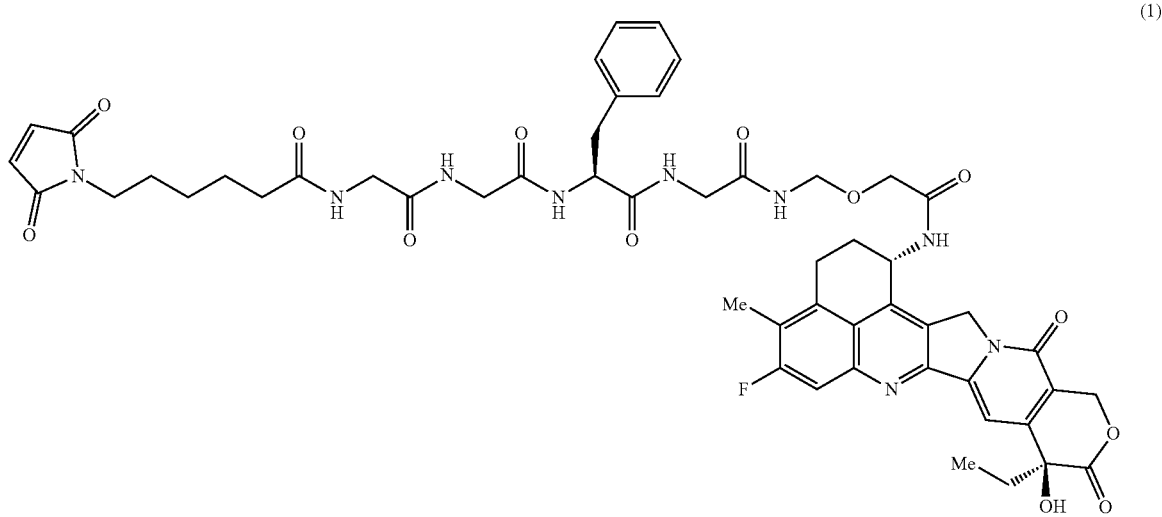 [SMILES: CC[C@@]1(O)C(=O)OCc2c1cc1n(c2=O)Cc2c-1nc1cc(F)c(C)c3c1c2[C@@H](NC(=O)COCNC(=O)CNC(=O)[C@H](Cc1ccccc1)NC(=O)CNC(=O)CNC(=O)CCCCCN1C(=O)C=CC1=O)CC3]

[13] The production method according to [11] or [12], comprising the steps of: dissolving the compound represented by the formula (10) in a solvent containing 1,2-dimethoxyethane; and then precipitating crystals of a 1,2-dimethoxyethane adduct of the compound represented by the formula (10).

[14] The production method according to [13], wherein the crystals of the 1,2-dimethoxyethane adduct of the compound represented by the formula (10) show main peaks at diffraction angles (2θ) of 19.0±0.2° and 25.0±0.2° in powder X-ray diffraction obtained by irradiation with copper Kα radiation.

[15] The production method according to any one of [11] to [14], wherein the step of condensing the compound represented by the formula (10) and the compound represented by the formula (11) to convert it into the compound represented by the formula (1) is performed in a two-phase system of an aqueous sodium sulfate solution and tetrahydrofuran.

[16] The production method according to any one of [3] to [10], wherein the compound represented by the formula (1) is produced by a production method (III), wherein the production method (III) is a production method comprising the steps of:

deprotecting a protecting group for a carboxy group of a compound represented by formula (B):

[Chem. 17]

(B)

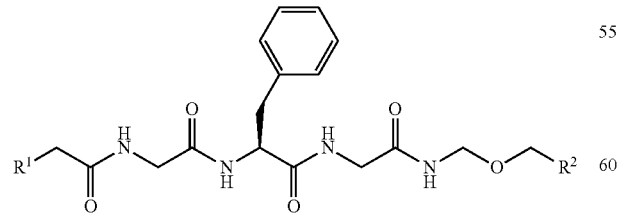

wherein $R^1$ represents an amino group protected with a protecting group, and $R^2$ represents a carboxy group protected with a protecting group, to convert it into a compound represented by formula (F):

[Chem. 18]

(F)

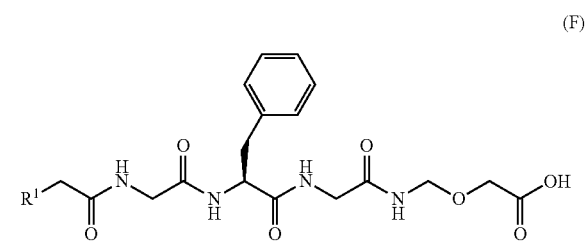

wherein $R^1$ represents the same meaning as above; then condensing the compound represented by the formula (F) with the compound represented by formula (11):

[Chem. 19]

(11)

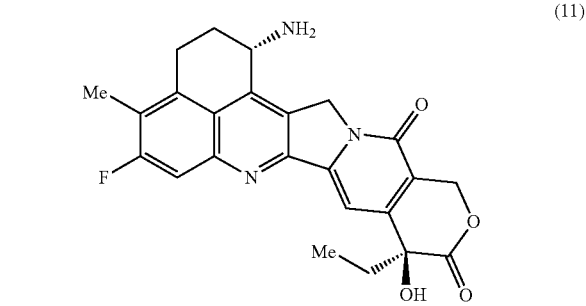 [SMILES: CC[C@@]1(O)C(=O)OCc2c1cc1n(c2=O)Cc2c-1nc1cc(F)c(C)c3c1c2[C@@H](N)CC3]

to convert it into a compound represented by formula (G):
[Chem. 20]
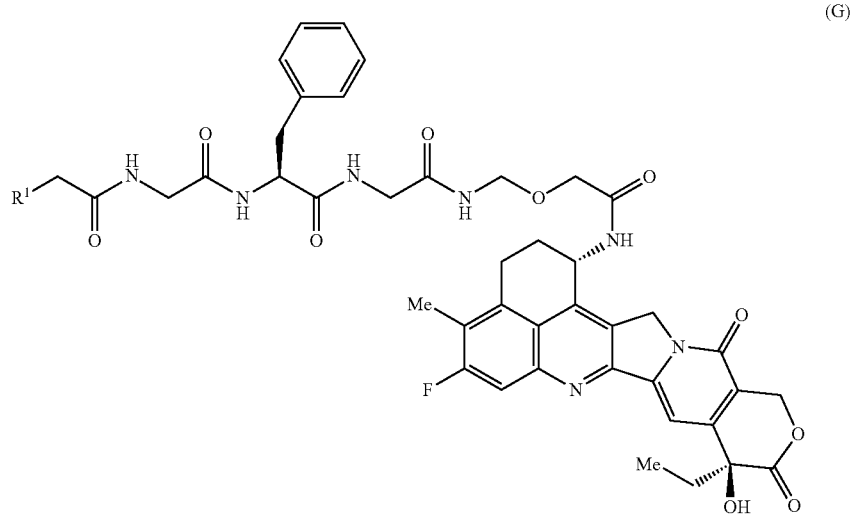
wherein R¹ represents the same meaning as above; then deprotecting the protecting group for the amino group of the compound represented by the formula (G) to convert it into the compound represented by formula (16):
[Chem. 21]
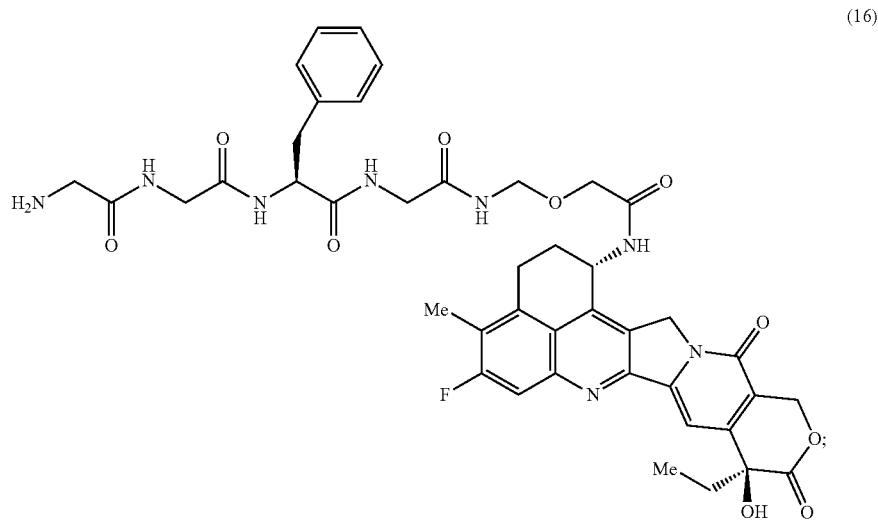 [SMILES: CC[C@@]1(O)C(=O)OCc2c1cc1n(c2=O)Cc2c-1nc1cc(F)c(C)c3c1c2[C@@H](NC(=O)COCNC(=O)CNC(=O)[C@H](Cc1ccccc1)NC(=O)CNC(=O)CN)CC3]

and then
condensing the compound represented by the formula (16) with a compound represented by formula (C):

[Chem. 22]

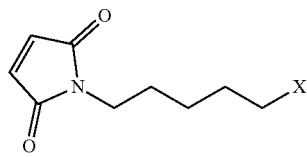
(C)

wherein X represents an active ester group or a carboxy group, to convert it into the compound represented by the formula (1):

[Chem. 23]

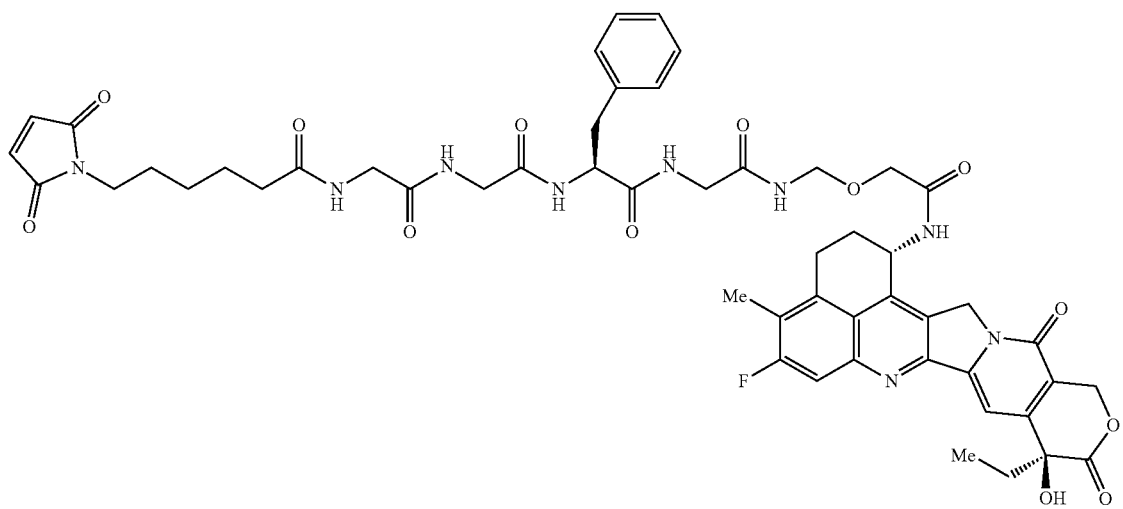
(1)

reacting a compound represented by formula (H):

[Chem. 24]

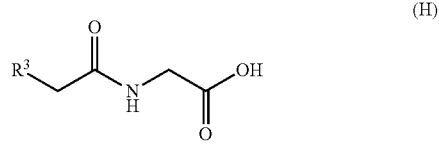
(H)

wherein $R^3$ represents an amino group protected with a protecting group, with lead tetraacetate to convert it into a compound represented by formula (J):

[Chem. 25]

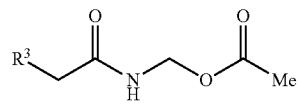
(J)

wherein $R^3$ represents the same meaning as above; then reacting the compound represented by the formula (J) with a compound represented by formula (K):

[Chem. 26]

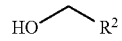
(K)

wherein $R^2$ represents the same meaning as the $R^2$ according to any one of claims 11 to 22, in the presence of an acid or a base to convert it into a compound represented by formula (L):

[17] The production method according to any one of [11] to [16], wherein the compound represented by the formula (11) is in the form of a methanesulfonic acid salt.
[18] The production method according to any one of [11] to [16], wherein the compound represented by the formula (11) is in the form of a methanesulfonic acid salt m-hydrate, wherein m is in the range of 0 to 3.
[19] The production method according to any one of [11] to [16], wherein the compound represented by the formula (11) is in the form of a methanesulfonic acid salt anhydride.
[20] The production method according to any one of [11] to [16], wherein the compound represented by the formula (11) is in the form of a methanesulfonic acid salt monohydrate.
[21] The production method according to any one of [11] to [16], wherein the compound represented by the formula (11) is in the form of a methanesulfonic acid salt dihydrate.
[22] The production method according to any one of [11] to [16], wherein the compound represented by the formula (11) is in the form of a methanesulfonic acid salt trihydrate.
[23] The production method according to any one of [11] to [22], wherein the compound represented by the formula (B) is produced by a production method (IV), wherein the production method (IV) is a production method comprising the steps of:

[Chem. 27]

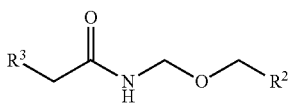
(L)

wherein R² and R³ represent the same meanings as above; then
deprotecting the protecting group for the amino group of the compound represented by the formula (L) to convert it into a compound represented by formula (M):

[Chem. 28]

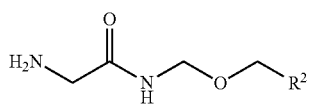
(M)

wherein R² represents the same meaning as above; and then condensing the compound represented by the formula (M) with a compound represented by formula (N):

[Chem. 29]

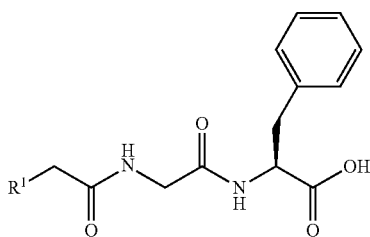
(N)

wherein R¹ represents the same meaning as the R-according to any one of [11] to [22], to convert it into the compound represented by the formula (B):

[Chem. 30]

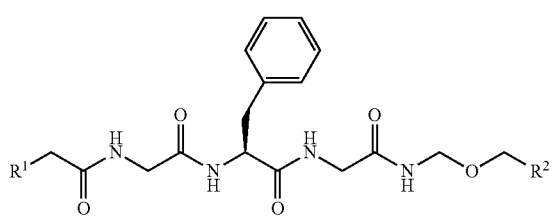
(B)

wherein R¹ and R² represent the same meanings as above.

[24] The production method according to [23], wherein the step of reacting the compound represented by the formula (H) with lead tetraacetate to convert it into the compound represented by the formula (J) is performed in the presence of acetic acid.

[25] The production method according to [23] or [24], wherein the step of reacting the compound represented by the formula (J) with the compound represented by the formula (K) to convert it into the compound represented by the formula (L) is performed in the presence of an aqueous sodium hydroxide solution.

[26] The production method according to [23] or [24], wherein the step of reacting the compound represented by the formula (J) with the compound represented by the formula (K) to convert it into the compound represented by the formula (L) is performed in the presence of tris(pentafluorophenyl)borane.

[27] The production method according to any one of [23] to [26], comprising a step of adding an acid to precipitate a salt of the compound represented by the formula (M) and the acid after the step of deprotecting the protecting group for the amino group of the compound represented by the formula (L) to convert it into the compound represented by the formula (M).

[28] The production method according to [27], wherein the acid is 1-hydroxybenzotriazole.

[29] The production method according to any one of [11] to [28], wherein R¹ is an amino group protected with a benzyloxycarbonyl group.

[30] The production method according to any one of [11] to [28], wherein R¹ is an amino group protected with a (9H-fluoren-9-ylmethoxy)carbonyl group.

[31] The production method according to any one of [11] to [30], wherein R² is a carboxy group protected with a benzyl group.

[32] The production method according to any one of [23] to [31], wherein R³ is an amino group protected with a (9H-fluoren-9-ylmethoxy)carbonyl group.

[33] The production method according to any one of [11] to [32], wherein X is a (2,5-dioxopyrrolidin-1-yl)oxycarbonyl group.

[34] The production method according to any one of [3] to [10], wherein the compound represented by the formula (1) is produced by a production method (V), wherein the production method (V) is a production method comprising the steps of:
reacting the compound represented by formula (2):

[Chem. 31]

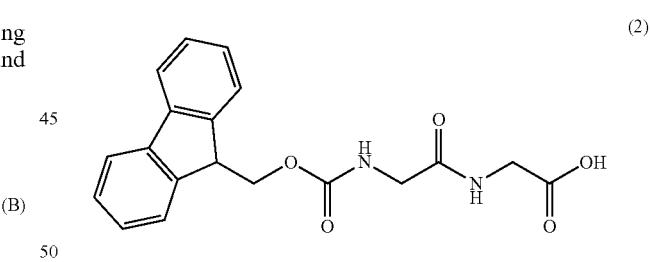
(2)

with lead tetraacetate to convert it into the compound represented by formula (3):

[Chem. 32]

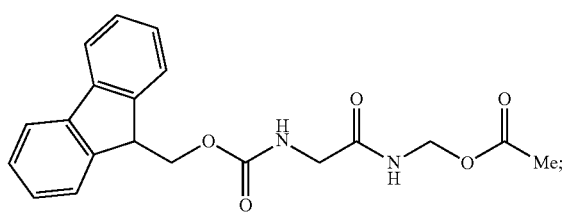
(3)

then
reacting the compound represented by the formula (3) with benzyl glycolate in the presence of an acid or a base to convert it into the compound represented by formula (4):

[Chem. 33]

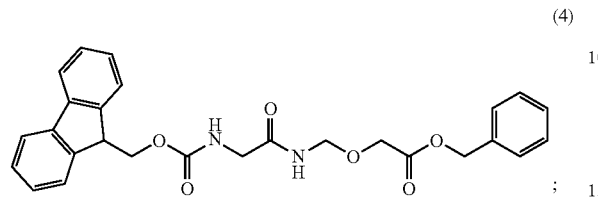
(4)

then
deprotecting a protecting group for an amino group of the compound represented by the formula (4) to convert it into the compound represented by formula (5):

[Chem. 34]

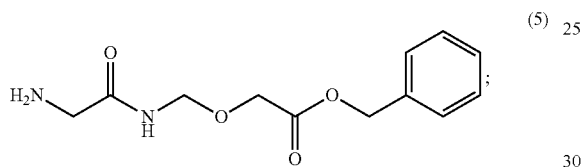
(5)

then
condensing the compound represented by the formula (5) with the compound represented by formula (6):

[Chem. 35]

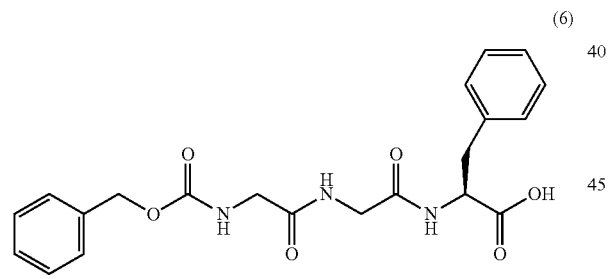
(6)

to convert it into the compound represented by formula (7):

[Chem. 36]

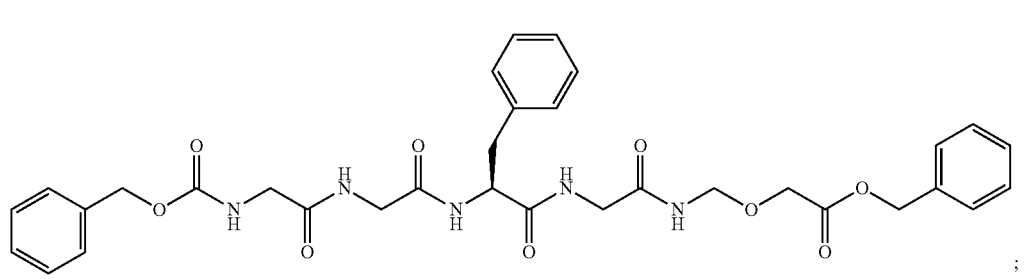
(7)

then
deprotecting protecting groups for an amino group and a carboxy group of the compound represented by the formula (7) to convert it into the compound represented by formula (8):

[Chem. 37]

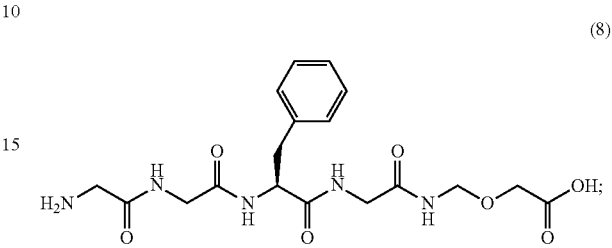
(8)

then
condensing the compound represented by the formula (8) with the compound represented by formula (9):

[Chem. 38]

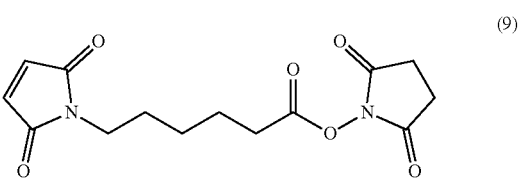 [SMILES: O=C(CCCCCN1C(=O)C=CC1=O)ON1C(=O)CCC1=O]
(9)

to convert it into the compound represented by formula (10):

[Chem. 39]

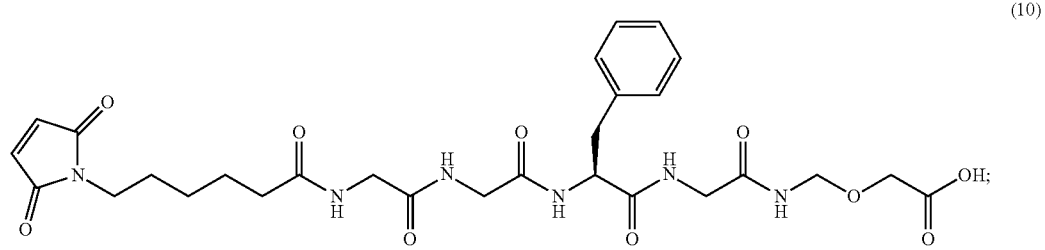

(10)

and then
condensing the compound represented by the formula (10) with the compound represented by formula (11):

[Chem. 40]

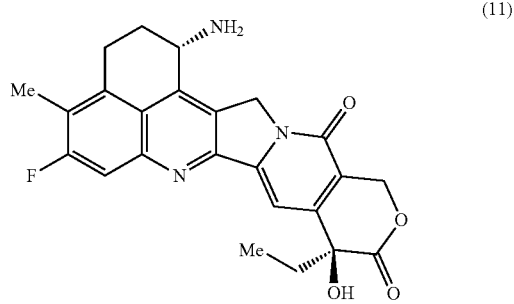 [SMILES: CC[C@@]1(O)C(=O)OCc2c1cc1n(c2=O)Cc2c-1nc1cc(F)c(C)c3c1c2[C@@H](N)CC3]

(11)

to convert it into the compound represented by the formula (1):

[Chem. 41]

[35] The production method according to [34], comprising the steps of: dissolving the compound represented by the formula (10) in a solvent containing 1,2-dimethoxyethane; and then precipitating crystals of a 1,2-dimethoxyethane adduct of the compound represented by the formula (10).

[36] The production method according to [35], wherein the crystals of the 1,2-dimethoxyethane adduct of the compound represented by the formula (10) show main peaks at diffraction angles (2θ) of 19.0±0.2° and 25.0±0.2° in powder X-ray diffraction obtained by irradiation with copper Kα radiation.

[37] The production method according to any one of [34] to [36], wherein the step of condensing the compound represented by the formula (10) with the compound represented by the formula (11) to convert it into the compound represented by the formula (1) is performed in a two-phase system of an aqueous sodium sulfate solution and tetrahydrofuran.

[38] The production method according to any one of [3] to [10], wherein the compound represented by the formula (1) is produced by a production method (VI),
wherein the production method (VI) is a production method comprising the steps of:

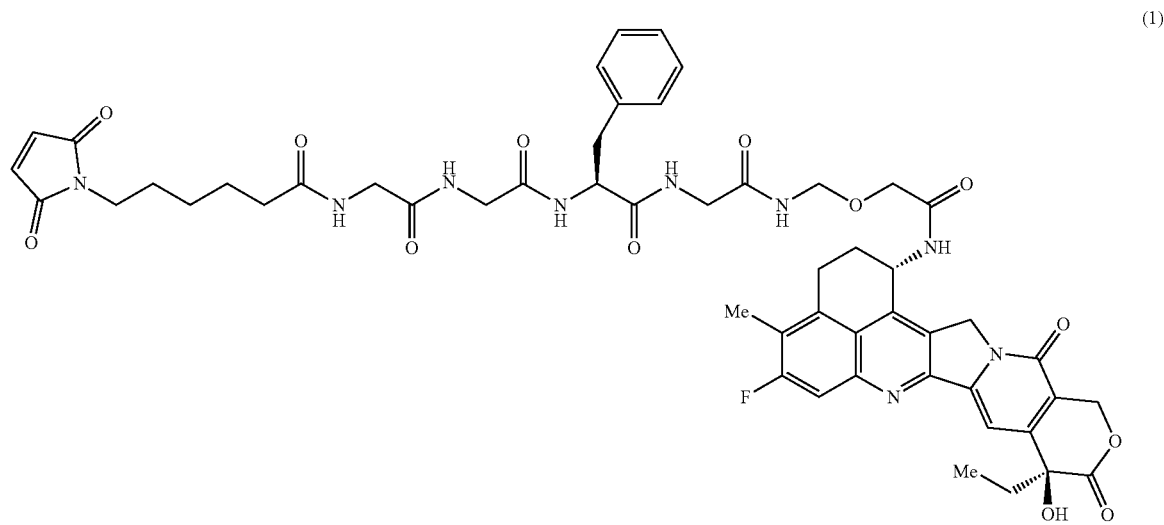 [SMILES: CC[C@@]1(O)C(=O)OCc2c1cc1n(c2=O)Cc2c-1nc1cc(F)c(C)c3c1c2[C@@H](NC(=O)COCNC(=O)CNC(=O)[C@H](Cc1ccccc1)NC(=O)CNC(=O)CNC(=O)CCCCCN1C(=O)C=CC1=O)CC3]

(1)

reacting the compound represented by formula (2):

[Chem. 42]

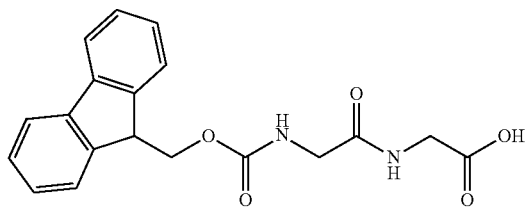
(2)

with lead tetraacetate to convert it into the compound represented by formula (3):

[Chem. 43]

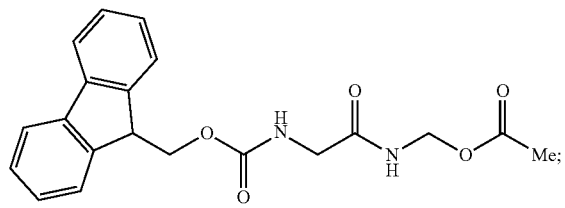
(3)

then
reacting the compound represented by the formula (3) with benzyl glycolate in the presence of an acid or a base to convert it into the compound represented by formula (4):

[Chem. 44]

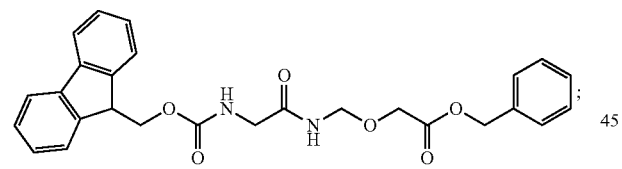
(4)

then
deprotecting a protecting group for an amino group of the compound represented by the formula (4) to convert it into the compound represented by formula (5):

[Chem. 45]

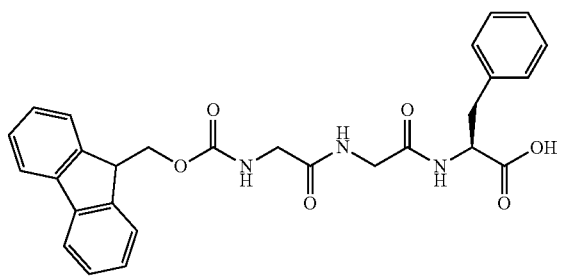
(5)

then
condensing the compound represented by the formula (5) with the compound represented by formula (12):

[Chem. 46]

(12)

to convert it into the compound represented by formula (13):

[Chem. 47]

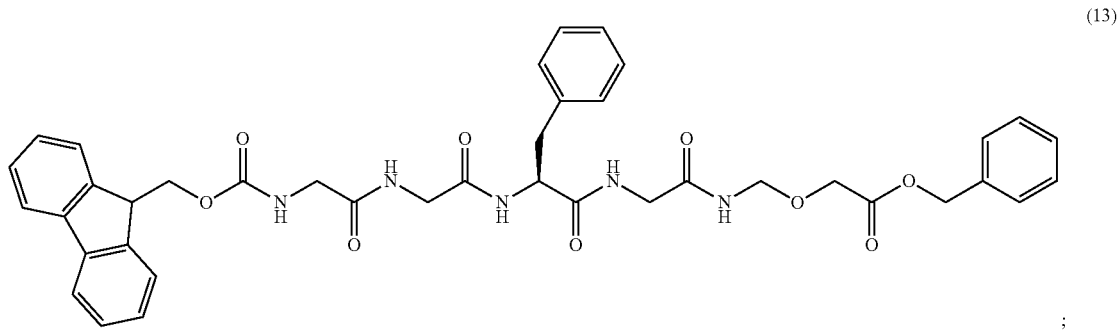 [SMILES: O=C(CNC(=O)OCC1c2ccccc2-c2ccccc21)NCC(=O)N[C@@H](Cc1ccccc1)C(=O)NCC(=O)NCOCC(=O)OCc1ccccc1]
(13)

then
deprotecting a protecting group for a carboxy group of the compound represented by the formula (13) to convert it into the compound represented by formula (14):
[Chem. 48]
(14)
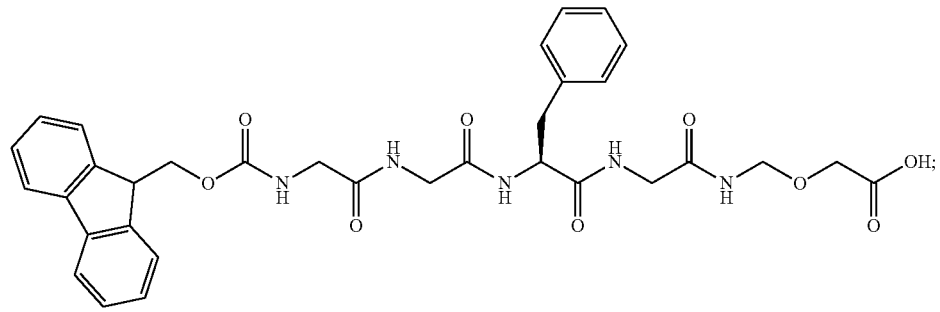
then
condensing the compound represented by the formula (14) with the compound represented by formula (11):
[Chem. 49]
(11)
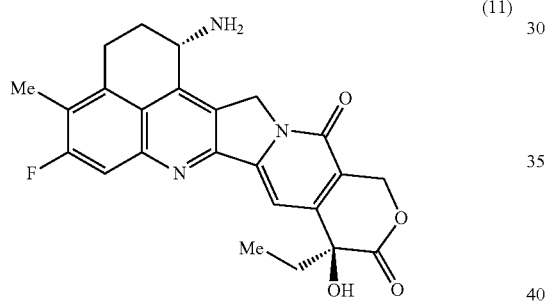
to convert it into the compound represented by formula (15):
[Chem. 50]
(15)
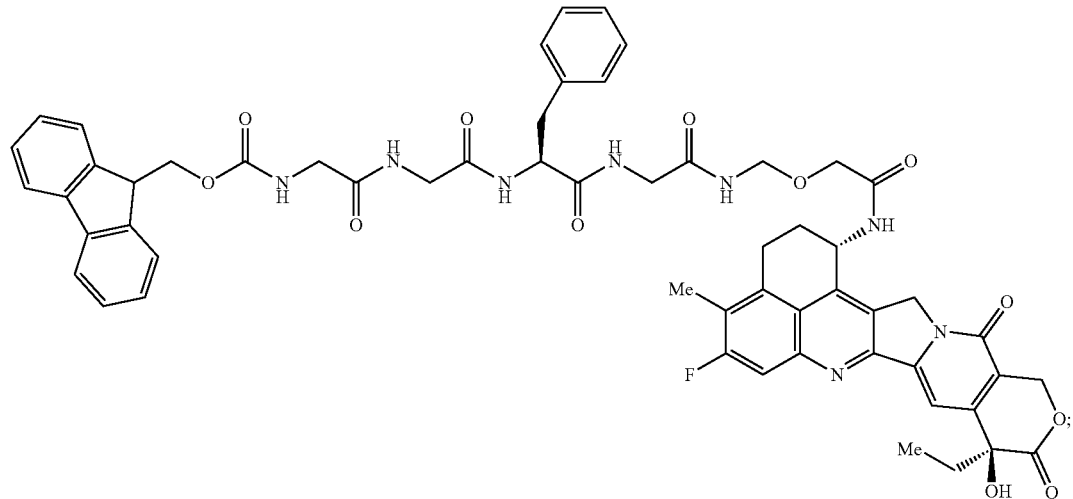

then
deprotecting a protecting group for an amino group of the compound represented by the formula (15) to convert it into the compound represented by formula (16):
[Chem. 51]
(16)
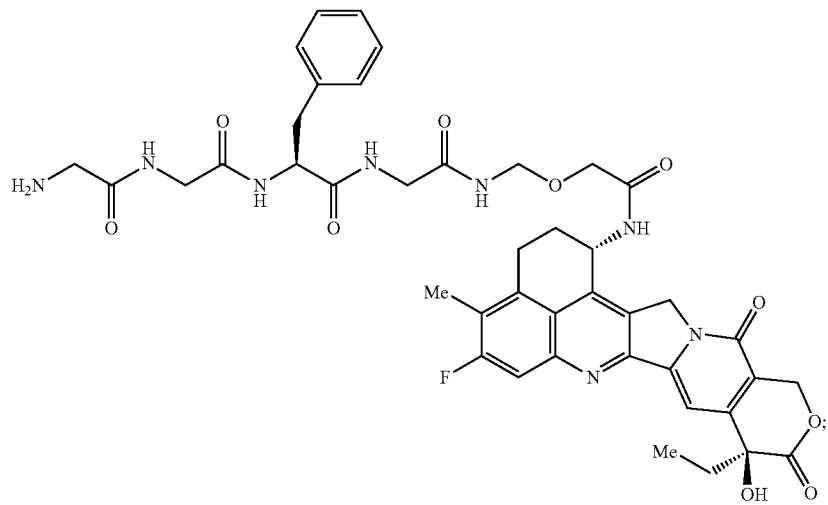
and then
condensing the compound represented by the formula (16) with the compound represented by formula (9):
[Chem. 52]
(9)
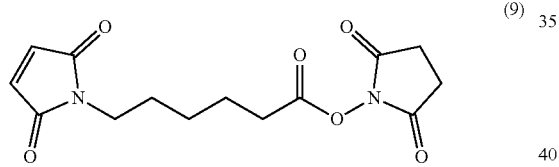
to convert it into the compound represented by the formula (1):
[Chem. 53]
(1)
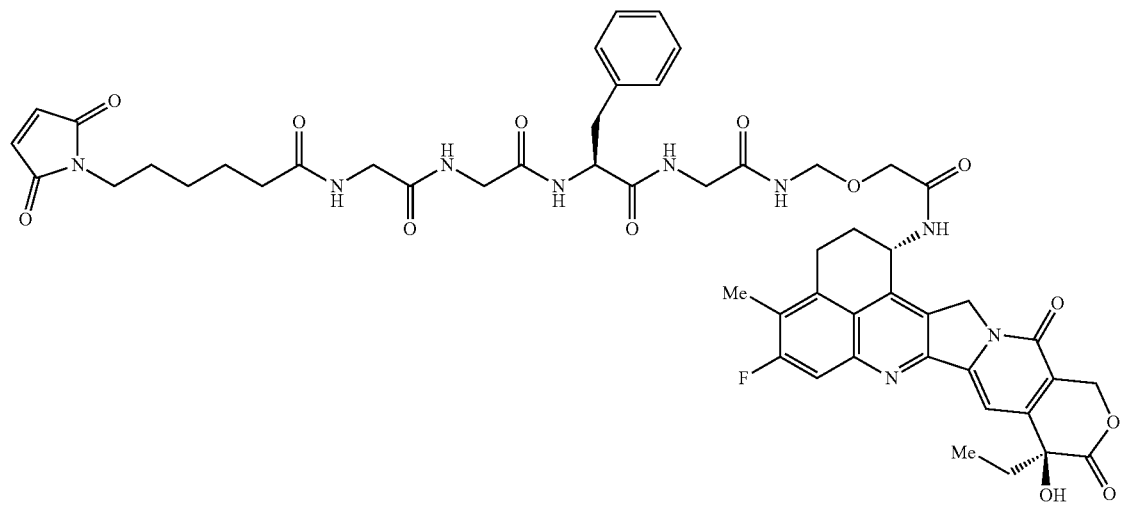

[39] The production method according to any one of [34] to [38], wherein the step of reacting the compound represented by the formula (2) with lead tetraacetate to convert it into the compound represented by the formula (3) is performed in the presence of acetic acid.

[40] The production method according to any one of [34] to [39], wherein the step of converting the compound represented by the formula (3) into the compound represented by the formula (4) is performed in the presence of an aqueous sodium hydroxide solution.

[41] The production method according to any one of [34] to [39], wherein the step of converting the compound represented by the formula (3) into the compound represented by the formula (4) is performed in the presence of tris(pentafluorophenyl)borane.

[42] The production method according to any one of [34] to [41], comprising a step of adding an acid to precipitate a salt of the compound represented by the formula (5) and the acid after the step of deprotecting the protecting group for the amino group of the compound represented by the formula (4) to convert it into the compound represented by the formula (5).

[43] The production method according to [42], wherein the acid is 1-hydroxybenzotriazole.

[44] The production method according to any one of [34] to [43], wherein the compound represented by the formula (6) is produced by a method comprising the steps of: condensing the compound represented by formula (23):

[Chem. 54]

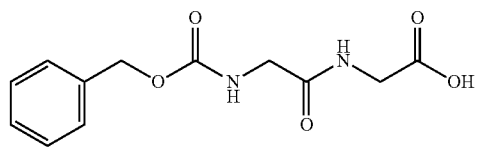

(23)

with N-hydroxysuccinimide to convert it into the compound represented by formula (24):

[Chem. 55]

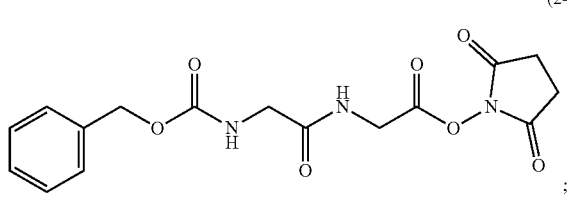

(24)

;

and then
condensing the compound represented by the formula (24) with L-phenylalanine to convert it into the compound represented by the formula (6).

[45] The production method according to any one of [34] to [44], wherein the compound represented by the formula (9) is produced by a method comprising the steps of: reacting the compound represented by formula (17):

[Chem. 56]

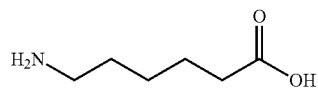

(17)

with maleic anhydride to convert it into the compound represented by formula (18):

[Chem. 57]

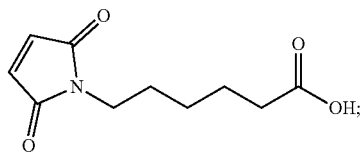

(18)

and then
adding thionyl chloride to the compound represented by the formula (18) and a mixed solution containing N-hydroxysuccinimide and 2,6-lutidine to convert it into the compound represented by the formula (9).

[46] The production method according to any one of [34] to [45], wherein the compound represented by the formula (11) is in the form of a methanesulfonic acid salt.

[47] The production method according to any one of [34] to [45], wherein the compound represented by the formula (11) is in the form of a methanesulfonic acid salt m-hydrate, wherein m is in the range of 0 to 3.

[48] The production method according to any one of [34] to [45], wherein the compound represented by the formula (11) is in the form of a methanesulfonic acid salt anhydride.

[49] The production method according to any one of [34] to [45], wherein the compound represented by the formula (11) is in the form of a methanesulfonic acid salt monohydrate.

[50] The production method according to any one of [34] to [45], wherein the compound represented by the formula (11) is in the form of a methanesulfonic acid salt dihydrate.

[51] The production method according to any one of [34] to [45], wherein the compound represented by the formula (11) is in the form of a methanesulfonic acid salt trihydrate.

[52] A method for producing a compound represented by formula (J), comprising the step of:
reacting a compound represented by formula (H):

[Chem. 58]

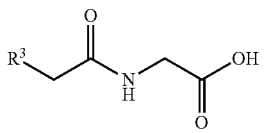

(H)

wherein $R^3$ represents an amino group protected with a protecting group, with lead tetraacetate in the presence of acetic acid to convert it into the compound represented by the formula (J):

[Chem. 59]

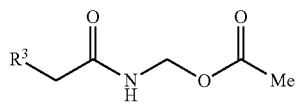

wherein R³ represents the same meaning as above.

[53] The production method according to [52], wherein R³ is an amino group protected with a (9H-fluoren-9-ylmethoxy)carbonyl group.

[54] A method for producing a compound represented by formula (L), comprising the step of:
reacting a compound represented by formula (J):

[Chem. 60]

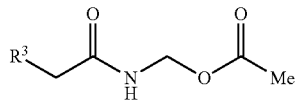

wherein R³ represents an amino group protected with a protecting group, with a compound represented by formula (K):

[Chem. 61]

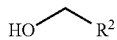

wherein R² represents a carboxy group protected with a protecting group, in the presence of an aqueous sodium hydroxide solution or tris(pentafluorophenyl)borane to convert it into the compound represented by the formula (L):

[Chem. 62]

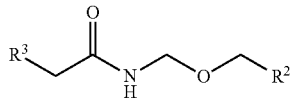

wherein R² and R³ represent the same meanings as above.

[55] The production method according to [54], wherein the reaction is performed in the presence of an aqueous sodium hydroxide solution.

[56] The production method according to [54], wherein the reaction is performed in the presence of tris(pentafluorophenyl)borane.

[57] The production method according to any one of [54] to [56], wherein R² is a carboxy group protected with a benzyl group.

[58] The production method according to any one of [54] to [57], wherein R³ is an amino group protected with a (9H-fluoren-9-ylmethoxy)carbonyl group.

[59] A method for producing a salt of a compound represented by formula (M) and an acid, comprising the steps of:
deprotecting a protecting group for an amino group of a compound represented by formula (L):

[Chem. 63]

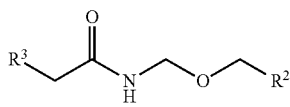

wherein R² represents a carboxy group protected with a protecting group, and R³ represents an amino group protected with a protecting group, to convert it into the compound represented by the formula (M):

[Chem. 64]

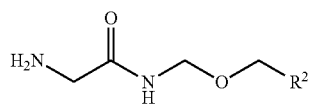

wherein R² represents the same meaning as above; and then adding an acid to precipitate the salt of the compound represented by the formula (M) and the acid.

[60] The production method according to [59], wherein the acid is 1-hydroxybenzotriazole.

[61] The production method according to [59] or [60], wherein R² is a carboxy group protected with a benzyl group.

[62] The production method according to any one of [59] to [61], wherein R³ is an amino group protected with a (9H-fluoren-9-ylmethoxy)carbonyl group.

[63] A method for producing the compound represented by formula (9), comprising the step of:
adding thionyl chloride to the compound represented by formula (18):

[Chem. 65]

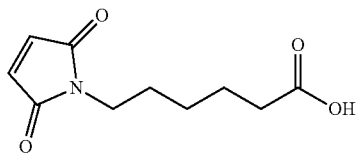

and a mixed solution containing N-hydroxysuccinimide and 2,6-lutidine to convert it into the compound represented by the formula (9):

[Chem. 66]

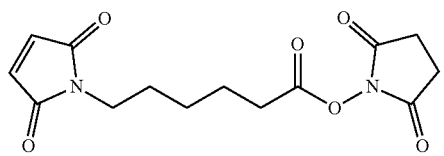

[64] The production method according to [63], wherein the compound represented by the formula (18) is produced by a method comprising the step of:

reacting the compound represented by formula (17):

[Chem. 67]

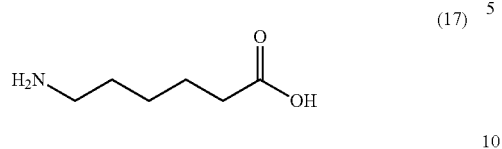
(17)

with maleic anhydride.

[65] A method for producing crystals of a 1,2-dimethoxyethane adduct of the compound represented by formula (10), comprising the steps of: dissolving the compound represented by the formula (10):

[Chem. 68]

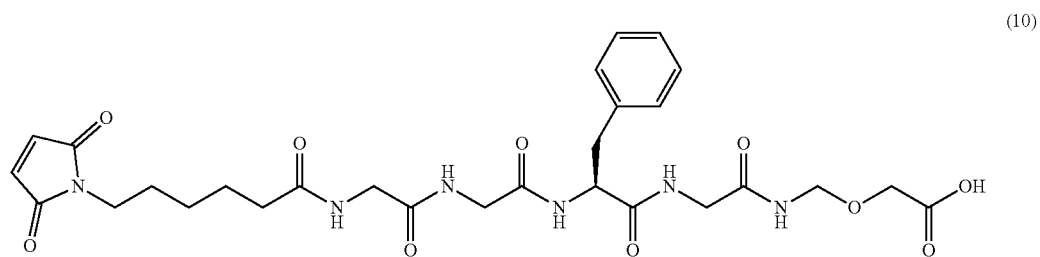
(10)

in a solvent containing 1,2-dimethoxyethane; and then precipitating crystals of the 1,2-dimethoxyethane adduct of the compound represented by the formula (10).

[66] The production method according to [65], wherein the crystals of the 1,2-dimethoxyethane adduct of the compound represented by the formula (10) show peaks at diffraction angles (2θ) of 19.0±0.2° and 25.0±0.2° in powder X-ray diffraction obtained by irradiation with copper Kα radiation.

[67] A method for producing the compound represented by formula (1), comprising the step of: condensing the compound represented by formula (10):

[Chem. 69]

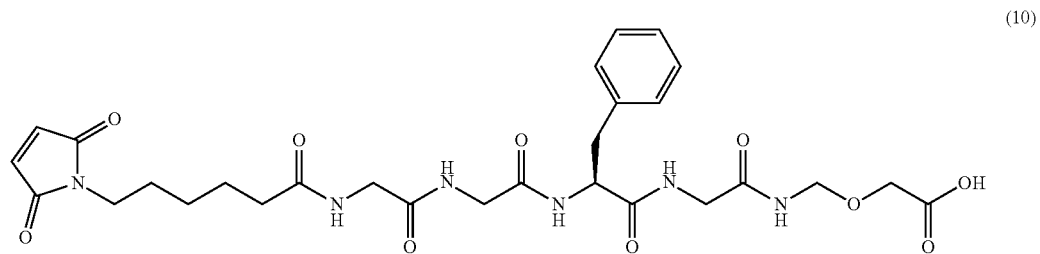
(10)

and the compound represented by formula (11):

[Chem. 70]

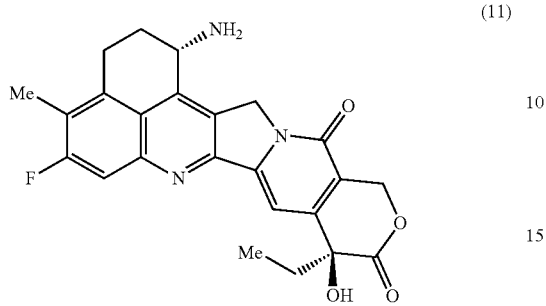

(11)

in a two-phase system of an aqueous sodium sulfate solution and tetrahydrofuran to convert it into the compound represented by the formula (1):

[Chem. 71]

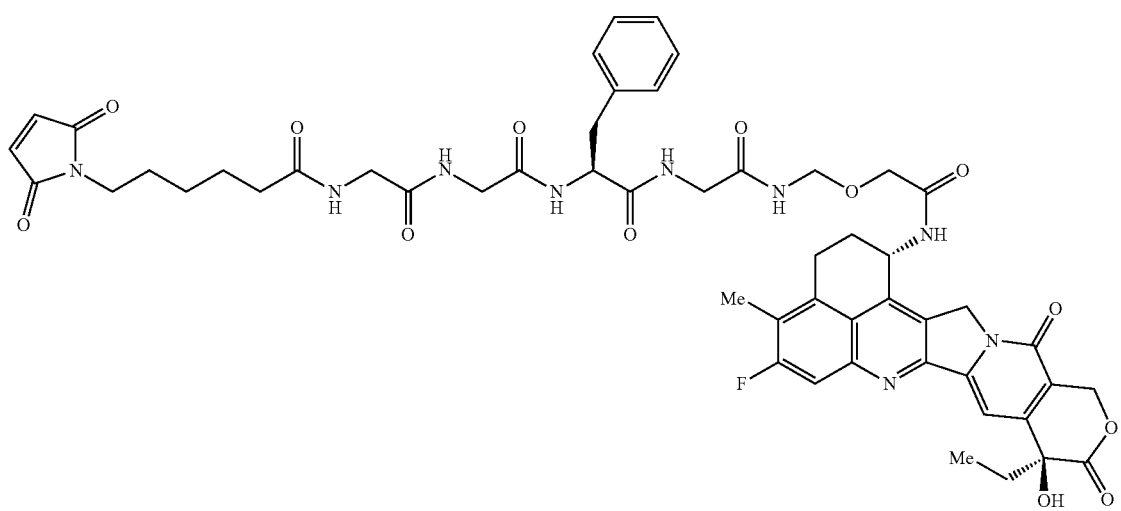

(1)

[69] The production method according to [67], wherein the compound represented by the formula (11) is in the form of a methanesulfonic acid salt m-hydrate, wherein m is in the range of 0 to 3.
[70] The production method according to [67], wherein the compound represented by the formula (11) is in the form of a methanesulfonic acid salt anhydride.
[71] The production method according to [67], wherein the compound represented by the formula (11) is in the form of a methanesulfonic acid salt monohydrate.
[72] The production method according to [67], wherein the compound represented by the formula (11) is in the form of a methanesulfonic acid salt dihydrate.
[73] The production method according to [67], wherein the compound represented by the formula (11) is in the form of a methanesulfonic acid salt trihydrate.
[74] The production method according to any one of [3] to [73], wherein no chromatography is used.
[75] Crystals of a 1,2-dimethoxyethane adduct of the compound represented by formula (10):

[Chem. 72]

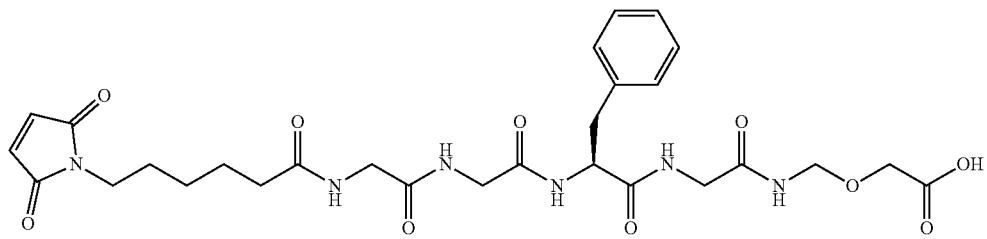

(10)

[76] The crystals according to [75], wherein the crystals show main peaks at diffraction angles (2θ) of 19.0±0.2° and 25.0±0.2° in powder X-ray diffraction obtained by irradiation with copper Kα radiation.

[77] A salt of the compound represented by formula (5):

[Chem. 73]

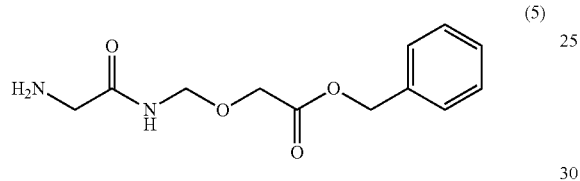

(5)

and an acid.

[78] The salt according to [77], wherein the acid is 1-hydroxybenzotriazole.

[79] A method for producing an antibody-drug conjugate, in which a drug-linker represented by formula (19):

[Chem. 75]

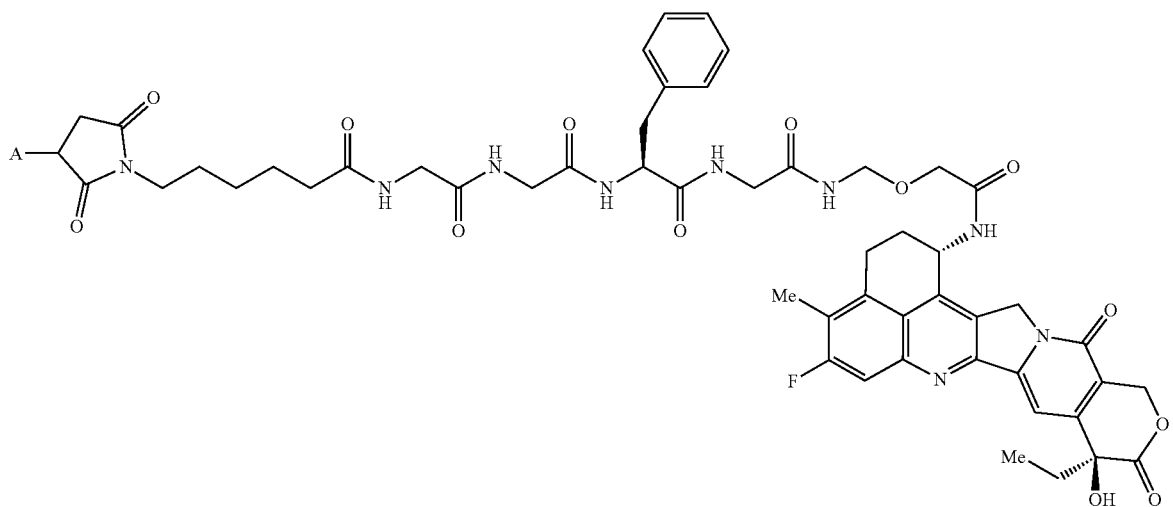

(19)

wherein A represents the connecting position to an antibody, is conjugated to the antibody via a thioether bond, wherein crystals of the compound represented by formula (1):

[Chem. 74]

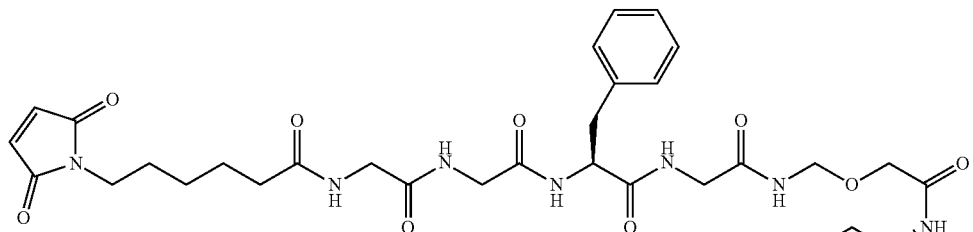
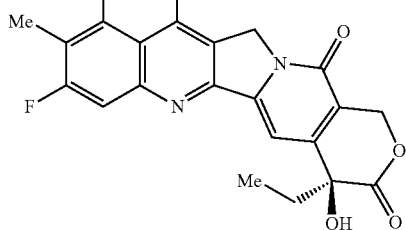

(1)

produced by the method according to any one of [3] to [51] are used as a starting material, and the method comprises the steps of:
  i) reducing an antibody; and then
  ii) adding a solution in which the crystals of the compound represented by the formula (1) produced in the above-mentioned method are dissolved, to react the solution with the reduced antibody.

[80] The production method according to [79], wherein the antibody is an anti-HER2 antibody, an anti-HER3 antibody, an anti-TROP2 antibody, an anti-B7-H3 antibody, or an anti-GPR20 antibody.

[81] The production method according to [80], wherein the antibody is an anti-HER2 antibody.

[82] The production method according to [81], wherein the anti-HER2 antibody is an antibody comprising a heavy chain consisting of an amino acid sequence consisting of amino acid residues 1 to 449 of SEQ ID NO: 1 and a light chain consisting of an amino acid sequence consisting of amino acid residues 1 to 214 of SEQ ID NO: 2, or an antibody comprising a heavy chain consisting of the amino acid sequence represented by SEQ ID NO: 1 and a light chain consisting of the amino acid sequence represented by SEQ ID NO: 2.

[83] The production method according to [81] or [82], wherein the average number of units of the drug-linker conjugated per antibody molecule in the antibody-drug conjugate is in the range of from 7 to 8.

[84] The production method according to [80], wherein the antibody is an anti-HER3 antibody.

[85] The production method according to [84], wherein the anti-HER3 antibody is an antibody comprising a heavy chain consisting of the amino acid sequence represented by SEQ ID NO: 3 and a light chain consisting of the amino acid sequence represented by SEQ ID NO: 4, or a variant of the antibody in which a lysine residue at the carboxyl terminus of the heavy chain of the antibody is deleted.

[86] The production method according to [84] or [85], wherein the average number of units of the drug-linker conjugated per antibody molecule in the antibody-drug conjugate is in the range of from 7 to 8.

[87] The production method according to [80], wherein the antibody is an anti-TROP2 antibody.

[88] The production method according to [87], wherein the anti-TROP2 antibody is an antibody comprising a heavy chain consisting of an amino acid sequence consisting of amino acid residues 20 to 470 of SEQ ID NO: 5 and a light chain consisting of an amino acid sequence consisting of amino acid residues 21 to 234 of SEQ ID NO: 6, or a variant of the antibody in which a lysine residue at the carboxyl terminus of the heavy chain of the antibody is deleted.

[89] The production method according to [87] or [88], wherein the average number of units of the drug-linker conjugated per antibody molecule in the antibody-drug conjugate is in the range of from 3 to 5.

[90] The production method according to [80], wherein the antibody is an anti-B7-H3 antibody.

[91] The production method according to [90], wherein the anti-B7-H3 antibody is an antibody comprising a heavy chain consisting of an amino acid sequence consisting of amino acid residues 20 to 471 of SEQ ID NO: 7 and a light chain consisting of an amino acid sequence consisting of amino acid residues 21 to 233 of SEQ ID NO: 8, or a variant of the antibody in which a lysine residue at the carboxyl terminus of the heavy chain of the antibody is deleted.

[92] The production method according to [90] or [91], wherein the average number of units of the drug-linker conjugated per antibody molecule in the antibody-drug conjugate is in the range of from 3 to 5.

[93] The production method according to [80], wherein the antibody is an anti-GPR20 antibody.

[94] The production method according to [93], wherein the anti-GPR20 antibody is an antibody comprising a heavy chain consisting of an amino acid sequence consisting of amino acid residues 20 to 472 of SEQ ID NO: 9 and a light chain consisting of an amino acid sequence consisting of amino acid residues 21 to 234 of SEQ ID NO: 10, or a variant of the antibody in which a lysine residue at the carboxyl terminus of the heavy chain of the antibody is deleted.

[95] The production method according to [93] or [94], wherein the average number of units of the drug-linker conjugated per antibody molecule in the antibody-drug conjugate is in the range of from 7 to 8.

Advantageous Effects of Invention

The present invention enables obtainment of the compound represented by formula (1) as crystals and can provide the compound represented by the formula (1) with given quality. The present invention can also provide an industrially excellent method for producing the compound represented by the formula (1) without the need for purification by chromatography. The present invention can further provide an improved method for producing an antibody-drug conjugate wherein the aforementioned method is used.

BRIEF DESCRIPTION OF DRAWINGS

FIG. 1 shows an amino acid sequence of a heavy chain of an anti-HER2 antibody (SEQ ID NO: 1).

FIG. 2 shows an amino acid sequence of a light chain of an anti-HER2 antibody (SEQ ID NO: 2).

FIG. 3 shows powder X-ray diffraction of a crystals of a 1,2-dimethoxyethane adduct of the compound represented by formula (10).

FIG. 4 shows powder X-ray diffraction of a crystals of the compound represented by formula (1).

FIG. 5 shows an amino acid sequence of a heavy chain of an anti-HER3 antibody (SEQ ID NO: 3).

FIG. 6 shows an amino acid sequence of a light chain of an anti-HER3 antibody (SEQ ID NO: 4).

FIG. 7 shows an amino acid sequence of a heavy chain of an anti-TROP2 antibody (SEQ ID NO: 5).

FIG. 8 shows an amino acid sequence of a light chain of an anti-TROP2 antibody (SEQ ID NO: 6).

FIG. 9 shows an amino acid sequence of a heavy chain of an anti-B7-H3 antibody (SEQ ID NO: 7).

FIG. 10 shows an amino acid sequence of a light chain of an anti-B7-H3 antibody (SEQ ID NO: 8).

FIG. 11 shows an amino acid sequence of a heavy chain of an anti-GPR20 antibody (SEQ ID NO: 9).

FIG. 12 shows an amino acid sequence of a light chain of an anti-GPR20 antibody (SEQ ID NO: 10).

DESCRIPTION OF EMBODIMENTS

Hereinafter, preferred modes for carrying out the present invention are described with reference to the drawings. The embodiments described below are given merely for illustrating one example of a typical embodiment of the present invention and are not intended to limit the scope of the present invention.

[Antibody-Drug Conjugate]

The antibody-drug conjugate produced by the present invention is an antibody-drug conjugate in which a drug-linker represented by formula (19):

[Chem. 76]

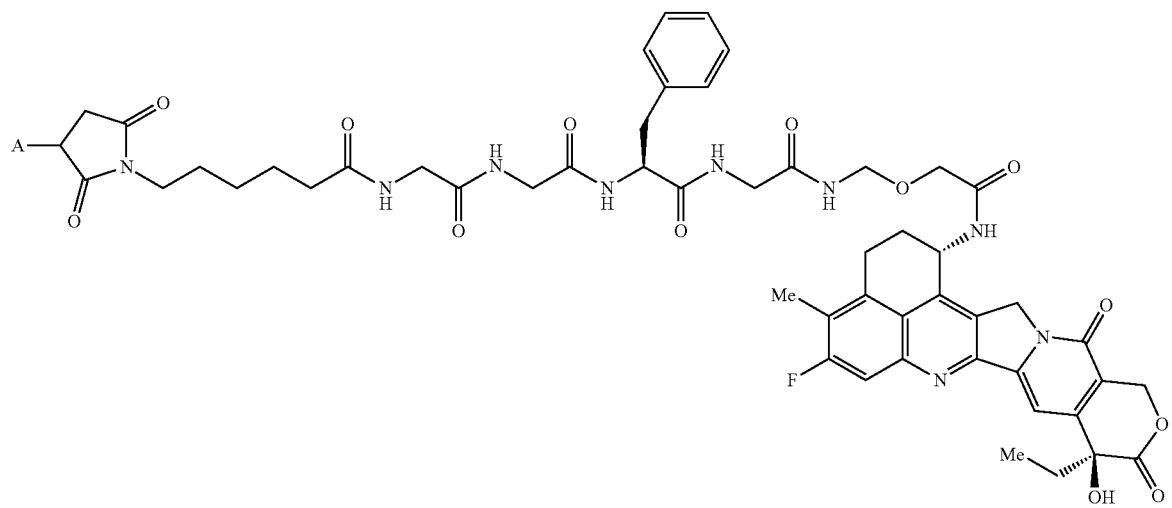

(19)

wherein A represents the connecting position to an antibody, is conjugated to the antibody via a thioether bond.

In the present invention, the partial structure consisting of a linker and a drug in the antibody-drug conjugate is referred to as a "drug-linker". The drug-linker is connected to a thiol group (in other words, the sulfur atom of a cysteine residue) formed at an interchain disulfide bond site (two sites between heavy chains, and two sites between a heavy chain and a light chain) in the antibody.

The drug-linker of the present invention includes exatecan, which is a topoisomerase I inhibitor, as a component. Exatecan is the compound represented by formula (11):

[Chem. 77]

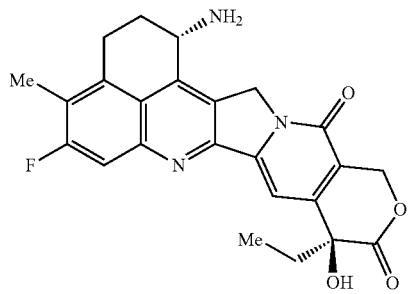

(11)

and is a camptothecin derivative having an antitumor effect.

The antibody-drug conjugate used in the present invention can also be represented by formula (20):

[Chem. 78]

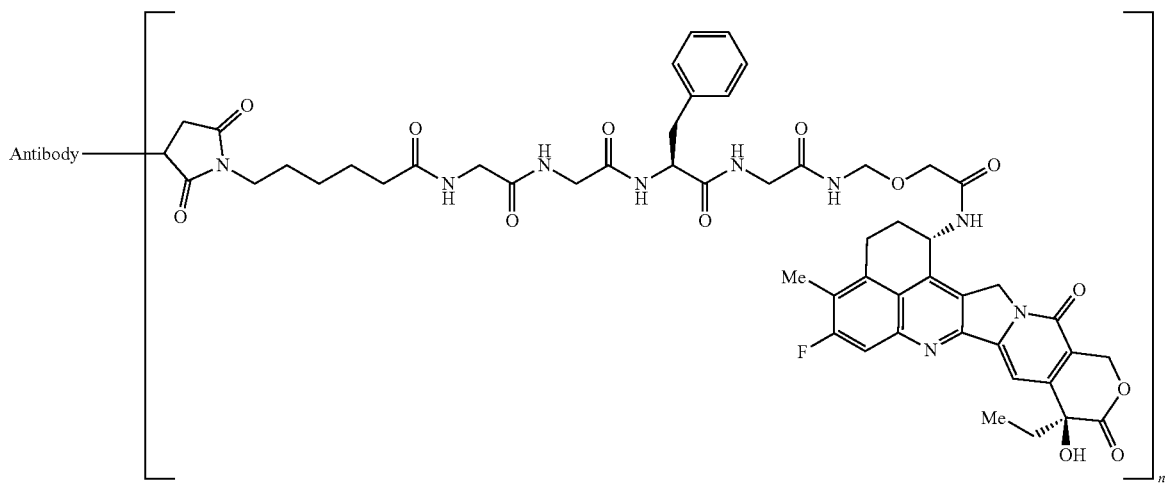

(20)

wherein, the drug-linker is conjugated to an antibody via a thioether bond. The meaning of n is the same as that of what is called the average number of conjugated drug molecules (DAR; Drug-to-Antibody Ratio), and indicates the average number of units of the drug-linker conjugated per antibody molecule.

After migrating into cancer cells, the antibody-drug conjugate used in the present invention releases the compound represented by formula (22):

[Chem. 79]

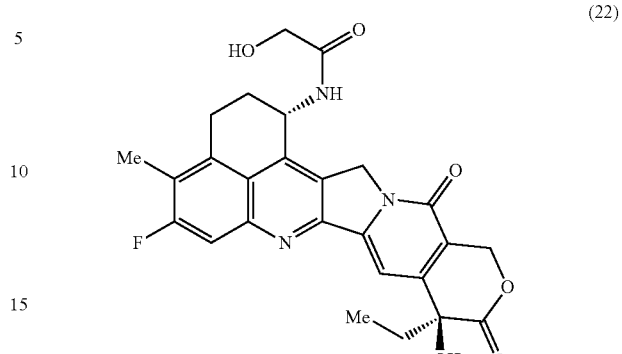

(22)

and thereby exerts an antitumor effect.

The compound represented by the formula (22) is inferred to be the original source of the antitumor activity of the antibody-drug conjugate produced by the present invention, and has been confirmed to have a topoisomerase I inhibitory effect (Ogitani Y. et al., Clinical Cancer Research, 2016, Oct. 15; 22 (20): 5097-5108, Epub 2016 Mar. 29).

The compound represented by the formula (22) is inferred to be formed by decomposition of an aminal structure of the compound represented by formula (21):

[Chem. 80]

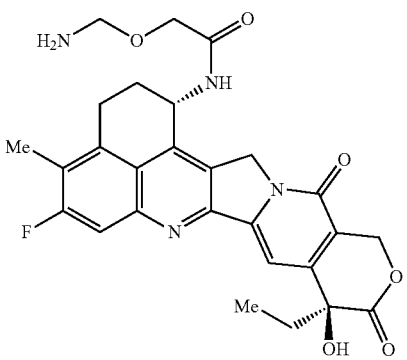

(21)

which is inferred to be formed by cleavage at the linker part of the antibody-drug conjugate produced by the present invention.

The antibody-drug conjugate produced by the present invention is known to have a bystander effect (Ogitani Y. et al., Cancer Science (2016) 107, 1039-1046).

The bystander effect is exerted through a process in which the antibody-drug conjugate produced according to the present invention is internalized in cancer cells expressing a target and the compound represented by the formula (22) released then exerts an antitumor effect also on cancer cells which are present therearound and not expressing the target.

[Drug-Linker Intermediate for Use in the Production of Antibody-Drug Conjugate]

A drug-linker intermediate for use in the production of the antibody-drug conjugate of the present invention is the compound represented by formula (1):

residual solvent, and appearance. Also, it can be evaluated by using, as an index, preservation stability for 3 months, 6 months, 12 months, 24 months, and 36 months in an environment of 25° C./60% RH or 40° C./75% RH, for example.

By such quality evaluation, superiority over an amorphous compound represented by the formula (1) can also be confirmed.

The production method of the present invention comprises precipitating a crystals of the compound represented by the formula (1) from a solution in which the compound represented by the formula (1) is dissolved, to produce crystals of the compound represented by the formula (1). As a result, highly pure crystals of the compound represented by the formula (1) having given quality can be produced.

The crystals of the compound represented by the formula (1) preferably show main peaks at diffraction angles (2θ) of 5.6°, 15.5° and 22.0° in powder X-ray diffraction obtained by irradiation with copper Kα radiation. Since diffraction angles (2θ) in powder X-ray diffraction may generally cause an error within the range of ±0.2°, it should be understood that the above-described values of the diffraction angles include numeric values within the range of ±0.2° (for technical common sense regarding measurement and evaluation by powder X-ray diffraction, see, for example, the Japanese Pharmacopoeia, 16th edition, p. 64-68 (2.58 X-Ray Powder Diffraction Method) or the Japanese Pharmacopoeia, 17th edition, p. 71-74 (2.58 X-Ray Powder Diffraction Method)).

Accordingly, crystals having diffraction angles that agree completely with the above-described diffraction angles is identical to crystals having main peaks at diffraction angles (2θ) of 5.6±0.2°, 15.5±0.2° and 22.0±0.2°, and both of them are included in the present invention. In the present invention, the term "±0.2°" refers to a numeric value in the range

[Chem. 81]

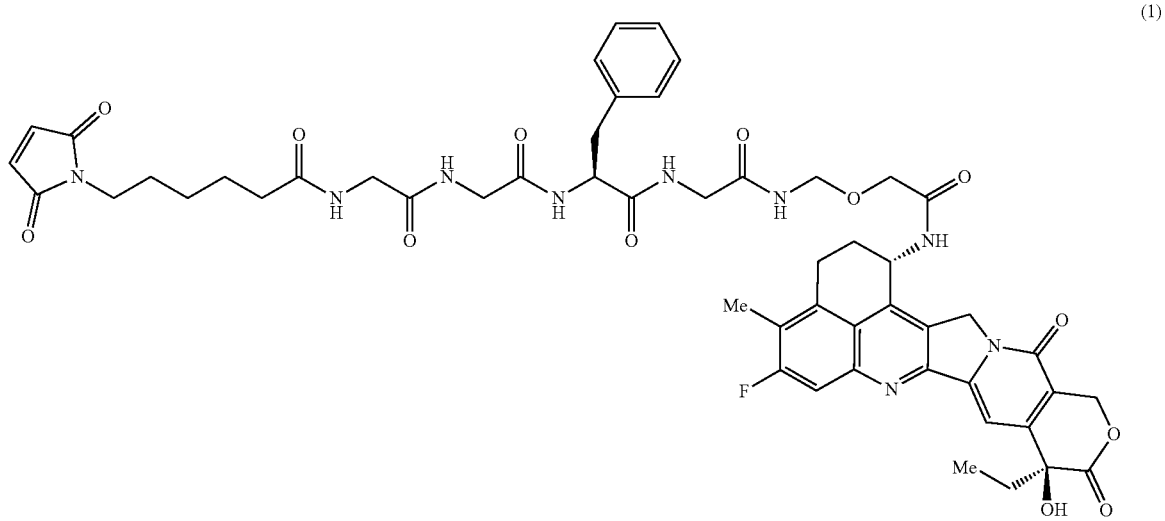

(1)

According to the present invention, the compound represented by the formula (1) can be obtained as crystals, and the crystals can be preferably used for production of the antibody-drug conjugate of the present invention.

The quality of the crystals of the compound represented by the formula (1) can be evaluated, for example, on the basis of indexes such as impurity content, the amount of a of −0.2° to +0.2° with respect to a specific numeric value. For example, the term "5.6±0.2°" refers to a numeric value in the range of 5.4° to 5.8°.

The solution for precipitating the crystals of the compound represented by the formula (1) is preferably a solution containing acetone and a lower alcohol as a solvent. Likewise, a solution containing a lower ketone and a lower alcohol as a solvent can also be preferably used as the solution for precipitating the crystals of the compound represented by the formula (1).

In the present invention, the term "lower ketone" refers to a ketone having 3 to 6 carbon atoms. Examples thereof can include acetone, methyl ethyl ketone, methyl propyl ketone, methyl isopropyl ketone, methyl butyl ketone, methyl isobutyl ketone, methyl tert-butyl ketone, ethyl ethyl ketone, ethyl propyl ketone, and ethyl isopropyl ketone, and acetone and methyl ethyl ketone can be preferably exemplified, and acetone can be more preferably exemplified.

In the present invention, the term "lower alcohol" refers to an alcohol having 1 to 4 carbon atoms. Examples thereof can include methanol, ethanol, 1-propanol, 2-propanol, 1-butanol, 2-methyl-1-propanol, 2-butanol, and tert-butanol, and 1-propanol and 2-butanol can be preferably exemplified, and 1-propanol can be more preferably exemplified.

Accordingly, the solution for precipitating the crystals of the compound represented by the formula (1) is preferably a solution containing acetone and 1-propanol or a solution containing acetone and 2-butanol, and more preferably a solution containing acetone and 1-propanol.

Precipitation of the crystals of the compound represented by the formula (1) can also be performed by adding a seed crystal of the crystals of the compound represented by the formula (1) to a solution containing the compound represented by the formula (1).

The seed crystal of the crystals of the compound represented by the formula (1) can be obtained by directly performing the above-described method, but can be preferably obtained by purifying a small amount of the compound represented by the formula (1) by chromatography, then dissolving it in a solvent containing acetone and 1-propanol or a solvent containing acetone and 2-butanol, and crystallizing from the solution.

The compound represented by the formula (1) can be produced with reference to the descriptions in International Publication No. WO 2014/057687, International Publication No. WO 2015/098099, International Publication No. WO 2015/115091, International Publication No. WO 2015/155998, and so on, but compounds produced by production methods (I), (II), (III), (V), (VI), and (IX) described below can be preferably used. As a result, the crystals of the compound represented by the formula (1) can be produced at a high yield without the use of chromatography in all steps.

[Production Method (I)]

The production method (I) is a method of converting a compound represented by formula (B) into the compound represented by the formula (1) through steps 1 to 3. Hereinafter, the steps 1 to 3 will be described in detail.

[Chem. 82]

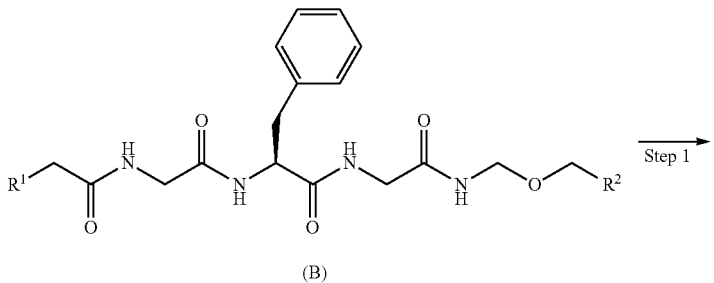

(B)

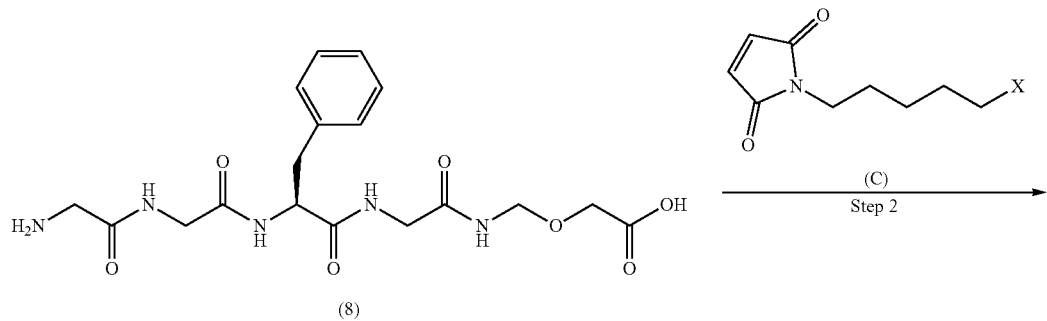

(8)

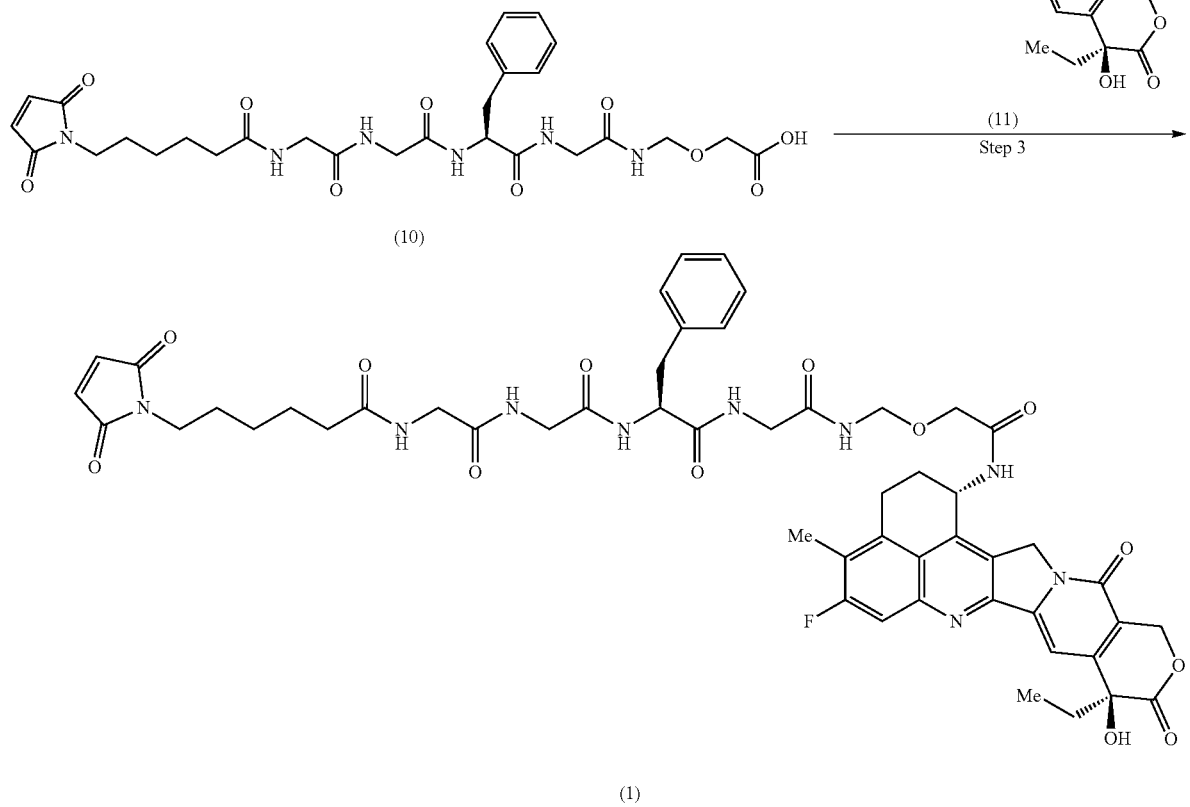

In the scheme, $R^1$ represents an amino group protected with a protecting group, and preferably represents an amino group protected with a benzyloxycarbonyl group, $R^2$ represents a carboxy group protected with a protecting group, and preferably represents a carboxy group protected with a benzyl group, and X represents an active ester group or a carboxy group, and preferably represents a (2,5-dioxopyrrolidin-1-yl)oxycarbonyl group.

Step 1:

This step is a step of deprotecting protecting groups for an amino group and a carboxy group of a compound represented by formula (B) to convert it into the compound represented by formula (8).

Deprotection of the protecting groups for the amino group and the carboxy group of the compound represented by the formula (B) can be performed by a method well known in the art (see, for example, Peter G. M. Wuts, Theodora W. Greene, Greene's Protective Groups in Organic Synthesis 4th Edition (2007), Wiley-Interscience).

In the case that $R^1$ is an amino group protected with a benzyloxycarbonyl group, and $R^2$ is a carboxy group protected with a benzyl group, this step can be preferably performed by the following method.

Deprotection of the protecting groups for the amino group and the carboxy group of the compound represented by the formula (B) is not limited by its method as long as the reaction proceeds. It can be preferably performed using a palladium catalyst, a platinum catalyst, a nickel catalyst, a ruthenium catalyst, or a rhodium catalyst under a hydrogen atmosphere, can be more preferably performed using a palladium catalyst, and can be even more preferably performed using palladium carbon, and 5% palladium carbon can be even more preferably used. The amount of the 5% palladium carbon used in this step is not limited as long as the reaction proceeds. It is preferably 5 to 40% by weight with respect to the compound represented by the formula (B).

The solvent used in this step is not particularly limited as long as the reaction is not inhibited. Examples thereof can include acetonitrile, dichloromethane, chloroform, methanol, ethanol, diethyl ether, 1,2-dimethoxyethane, tetrahydrofuran, 2-methyltetrahydrofuran, 1,4-dioxane, ethyl acetate, hexane, pentane, heptane, cyclohexane, ethylcyclohexane, benzene, toluene, chlorobenzene, acetone, 2-butanone, N,N-dimethylformamide, N,N-dimethylacetamide, 1-methyl-2-pyrrolidone, dimethyl sulfoxide, and water, and mixed solvents thereof, and a mixed solvent of tetrahydrofuran and water can be preferably exemplified.

The reaction temperature of this step is not limited as long as the reaction proceeds. It is preferably 10 to 40° C. The reaction time of this step is not limited as long as the reaction proceeds. It is preferably 1 to 5 hours.

Step 2:

This step is a step of condensing the compound represented by the formula (8) with a compound represented by formula (C) to convert it into the compound represented by formula (10). As the compound represented by the formula (C), a commercially available product or a compound produced by a known method, or a compound produced by a method conforming to the production method (VII) described below can be used. In the case that X is a (2,5-dioxopyrrolidin-1-yl)oxycarbonyl group, this step can be preferably performed by the following method.

The amount of the compound represented by the formula (C) used in this step is not limited as long as the reaction proceeds. It is preferably 1 to 4 equivalents with respect to the compound represented by the formula (8).

This step preferably employs a base. The base used in this step is not particularly limited as long as the reaction proceeds. Examples thereof can include triethylamine, tributylamine, diisopropylethylamine, N-methylmorpholine, N-methylpyrrolidine, and N-methylpiperidine, and N,N-diisopropylethylamine can be preferably exemplified. The amount of the N,N-diisopropylethylamine used in this step is not limited as long as the reaction proceeds. It is preferably 0.5 to 2 equivalents with respect to the compound represented by the formula (8).

The solvent used in this step is not particularly limited as long as the reaction is not inhibited. Examples thereof can include acetonitrile, dichloromethane, chloroform, methanol, ethanol, diethyl ether, 1,2-dimethoxyethane, tetrahydrofuran, 2-methyltetrahydrofuran, 1,4-dioxane, ethyl acetate, hexane, pentane, heptane, cyclohexane, ethylcyclohexane, benzene, toluene, chlorobenzene, acetone, 2-butanone, N,N-dimethylformamide, N,N-dimethylacetamide, 1-methyl-2-pyrrolidone, dimethyl sulfoxide, and water, and mixed solvents thereof, and a mixed solvent of acetonitrile and water can be preferably exemplified.

The reaction temperature of this step is not limited as long as the reaction proceeds. It is preferably 10 to 40° C. The reaction time of this step is not limited as long as the reaction proceeds. It is preferably 7 to 30 hours.

The compound represented by the formula (10) can be preferably obtained as a crystals of a 1,2-dimethoxyethane adduct.

The quality of the crystals of the 1,2-dimethoxyethane adduct of the compound represented by the formula (10) can be evaluated, for example, on the basis of indexes such as an impurity content, an amount of a residual solvent, and appearance. Also, it can be evaluated by using, as an index, preservation stability for 3 months, 6 months, 12 months, 24 months, and 36 months in an environment of 25° C./60% RH or 40° C./75% RH, for example. By such quality evaluation, superiority over an amorphous compound represented by the formula (10) can also be confirmed.

The crystals of the 1,2-dimethoxyethane adduct of the compound represented by the formula (10) preferably show main peaks at diffraction angles (2θ) of 19.0° and 25.0° in powder X-ray diffraction obtained by irradiation with copper Kα radiation. Since diffraction angles (2θ) in powder X-ray diffraction may generally cause an error within the range of ±0.2°, it should be understood that the above-described values of the diffraction angles include numeric values within the range of ±0.2° (for technical common sense regarding measurement and evaluation by powder X-ray diffraction, see, for example, the Japanese Pharmacopoeia, 16th edition, p. 64-68 (2.58 X-Ray Powder Diffraction Method) or the Japanese Pharmacopoeia, 17th edition, p. 71-74 (2.58 X-Ray Powder Diffraction Method)). Accordingly, crystals having diffraction angles that agree completely with the above-described diffraction angles are identical to crystals having main peaks at diffraction angles (2θ) of 19.0±0.2° and 25.0±0.2°, and both of them are included in the present invention.

Step 3:

This step is a step of condensing the compound represented by the formula (10) with the compound represented by formula (11) to convert it into the compound represented by the formula (1). The compound represented by the formula (11) can be preferably used in the form of a methanesulfonic acid salt, can be more preferably used in the form of a methanesulfonic acid salt m-hydrate, wherein m is 0 to 3, can be even more preferably used in the form of a methanesulfonic acid salt anhydride, a methanesulfonic acid salt monohydrate, a methanesulfonic acid salt dihydrate, or a methanesulfonic acid salt trihydrate, and can be even more preferably used in the form of a methanesulfonic acid salt dihydrate, but all of them can be used in the production method of the present invention. The number of water molecules in the above-described hydrate can be controlled by adjusting the humidity at the time of obtaining or drying of the crystals.

The amount of the compound represented by the formula (11) used in this step is not limited as long as the reaction proceeds. It is preferably 0.5 to 2 equivalents with respect to the compound represented by the formula (10).

The compound represented by the formula (10) can be preferably derivatized into an active ester and condensed with the compound represented by the formula (11). Derivatization into the active ester in this step is not limited by its method as long as the reaction proceeds. It can be performed, for example, by using a condensing agent such as 1-ethyl-3-(3-dimethylaminopropyl)carbodiimide hydrochloride (WSCD-HCl) or N,N'-dicyclohexylcarbodiimide (DCC), and reacting with an additive such as 1-hydroxybenzotriazole (HOBt), 1-hydroxy-7-azabenzotriazole (HOAt), N-hydroxysuccinimide, ethyl cyano(hydroxyimino)acetate, or p-nitrophenol, and can be preferably performed using 3-(3-dimethylaminopropyl)carbodiimide hydrochloride and ethyl cyano(hydroxyimino)acetate. The amount of the 3-(3-dimethylaminopropyl)carbodiimide hydrochloride used in this step is not limited as long as the reaction proceeds. It is preferably 0.5 to 2 equivalents with respect to the compound represented by the formula (10). The amount of the ethyl cyano(hydroxyimino)acetate used in this step is not limited as long as the reaction proceeds. It is preferably 0.02 to 0.2 equivalents with respect to the compound represented by the formula (10).

This step preferably employs a base. The base used in this step is not particularly limited as long as the reaction proceeds. Examples thereof can include triethylamine, tributylamine, diisopropylethylamine, N-methylmorpholine, N-methylpyrrolidine, and N-methylpiperidine, and N-methylmorpholine can be preferably exemplified. The amount of the N-methylmorpholine used in this step is not limited as long as the reaction proceeds. It is preferably 0.5 to 2 equivalents with respect to the compound represented by the formula (10).

The solvent used in this step is not particularly limited as long as the reaction is not inhibited. Examples thereof can include acetonitrile, dichloromethane, chloroform, methanol, ethanol, diethyl ether, 1,2-dimethoxyethane, tetrahydrofuran, 2-methyltetrahydrofuran, 1,4-dioxane, ethyl acetate, hexane, pentane, heptane, cyclohexane, ethylcyclohexane, benzene, toluene, chlorobenzene, acetone, 2-butanone, N,N-dimethylformamide, N,N-dimethylacetamide, 1-methyl-2-pyrrolidone, dimethyl sulfoxide, and water, and mixed solvents thereof, and a mixed solvent of tetrahydrofuran and water can be preferably exemplified.

The methanesulfonic acid salt of the compound represented by the formula (11) is neutralized with a base to prepare a free form, and then, the reaction proceeds. Here, the methanesulfonic acid salt of the compound represented by the formula (11) is hydrophilic, whereas the free form of the compound represented by the formula (11) is lipophilic. Therefore, in order to allow a series of reactions to proceed efficiently, this step can be preferably performed in a two-phase system of an aqueous layer and an organic layer. In the case that the organic layer contains tetrahydrofuran, an aqueous solution having high ionic strength, for example, an aqueous sodium sulfate solution, can be preferably used as an aqueous layer less miscible therewith.

The reaction temperature of this step is not limited as long as the reaction proceeds. It is preferably 10 to 40° C. The reaction time of this step is not limited as long as the reaction proceeds. It is preferably 0.5 to 2 hours.

[Production Method (II)]

The production method (II) is a method of converting a compound represented by formula (B) into the compound represented by the formula (1) through steps 4 to 7. Hereinafter the steps 4 to 7 will be described in detail.

[Chem. 83]

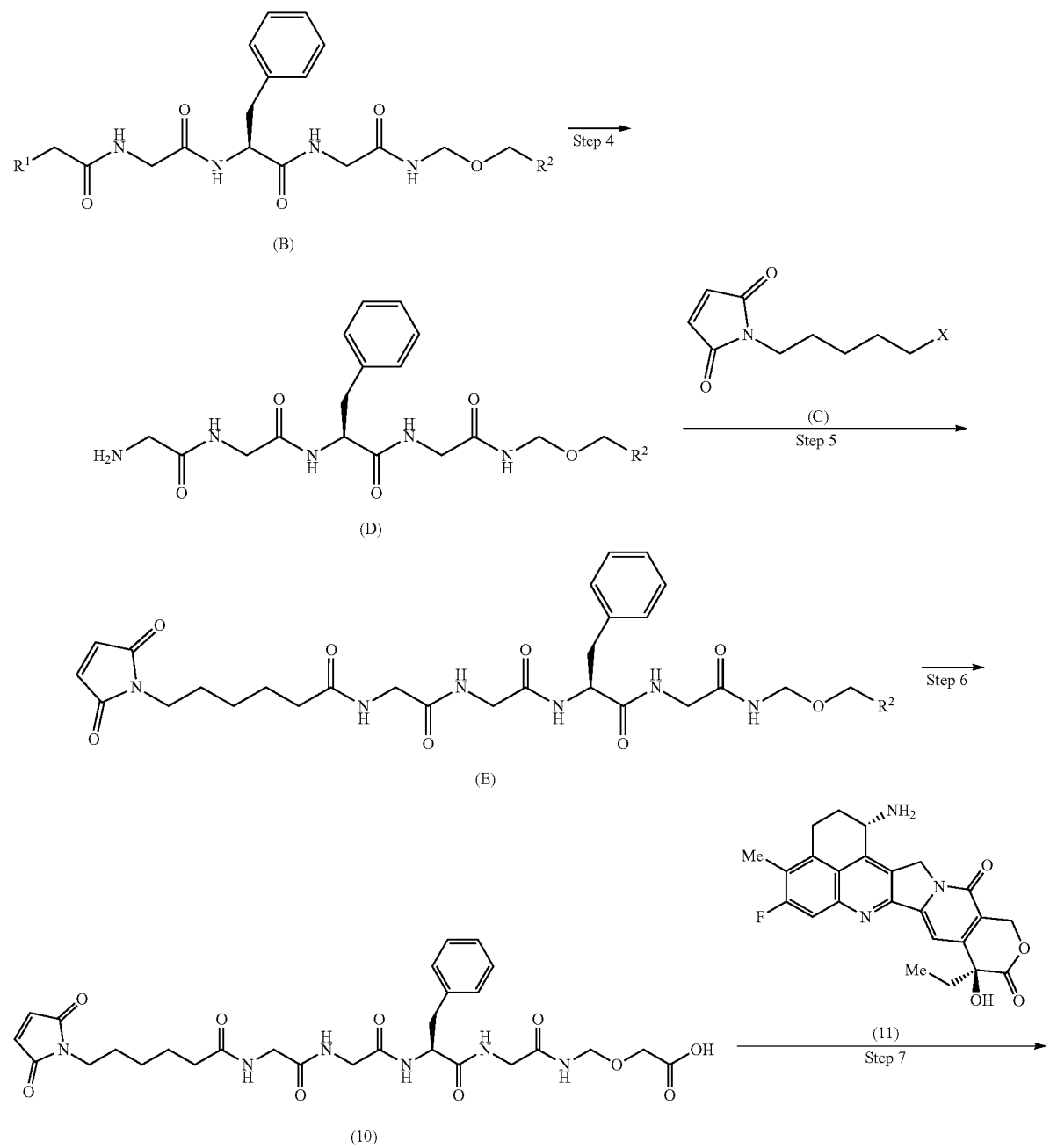

-continued

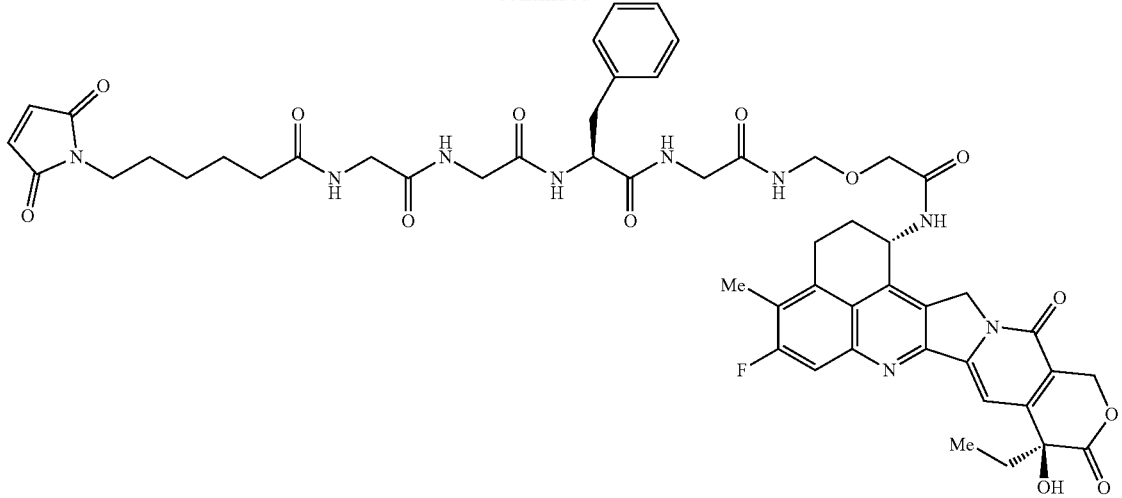

(1)

In the scheme, $R^1$ represents an amino group protected with a protecting group, $R^2$ represents a carboxy group protected with a protecting group, and X represents an active ester group or a carboxy group, and preferably represents a (2,5-dioxopyrrolidin-1-yl)oxycarbonyl group.

Step 4:

This step is a step of deprotecting a protecting group for an amino group of a compound represented by formula (B) to convert it into a compound represented by formula (D).

Deprotection of the protecting group for the amino group of the compound represented by the formula (B) can be performed by a method well known in the art (see, for example, Peter G. M. Wuts, Theodora W. Greene, Greene's Protective Groups in Organic Synthesis 4th Edition (2007), Wiley-Interscience).

Step 5:

This step is a step of condensing the compound represented by the formula (D) with a compound represented by formula (C) to convert it into a compound represented by formula (E).

This step can be performed in the same manner as in the step 2 of the production method (I).

Step 6:

This step is a step of deprotecting the protecting group for the carboxy group of the compound represented by the formula (E) to convert it into the compound represented by formula (10).

Deprotection of the protecting group for the carboxy group of the compound represented by the formula (B) can be performed by a method well known in the art (see, for example, Peter G. M. Wuts, Theodora W. Greene, Greene's Protective Groups in Organic Synthesis 4th Edition (2007), Wiley-Interscience).

The compound represented by the formula (10) can be preferably obtained as crystals of a 1,2-dimethoxyethane adduct in the same manner as in the step 2 of the production method (I).

Step 7:

This step is a step of condensing the compound represented by the formula (10) with the compound represented by formula (11) to convert it into the compound represented by the formula (1).

This step can be performed in the same manner as in the step 3 of the production method (I).

[Production Method (III)]

The production method (III) is a method of converting a compound represented by formula (B) into the compound represented by the formula (1) through steps 8 to 11. Hereinafter the steps 8 to 11 will be described in detail.

[Chem. 84]

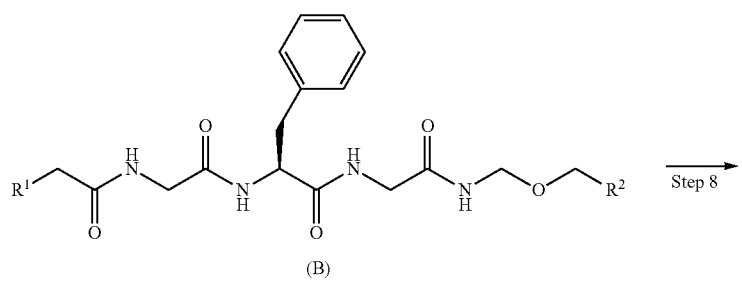

(B)

-continued
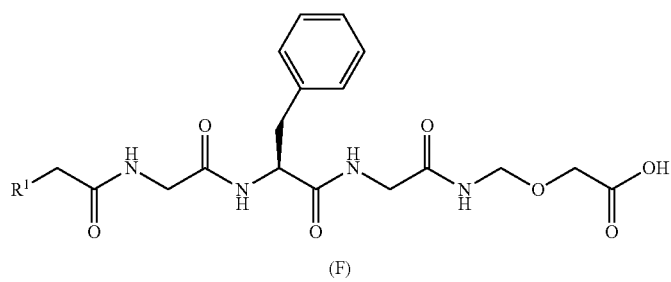
(F)
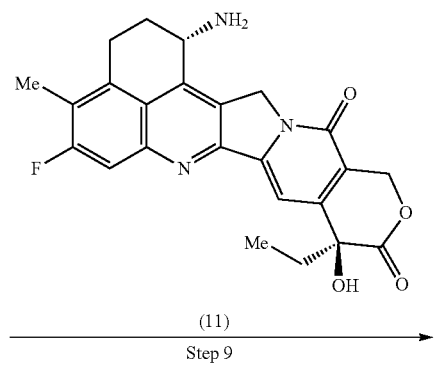
(11) Step 9
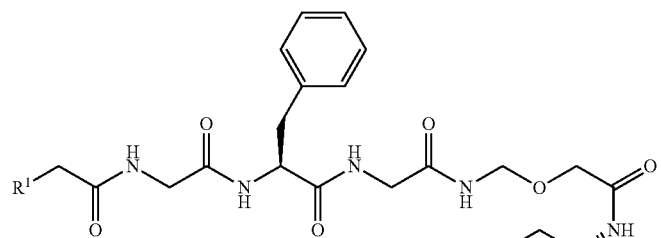
(G)
Step 10
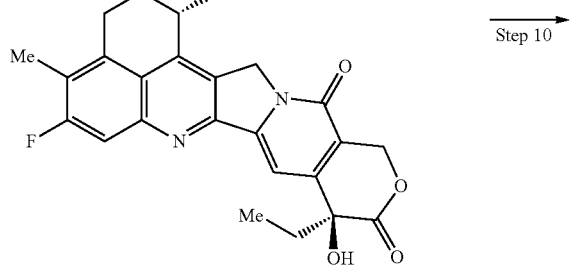
(16)
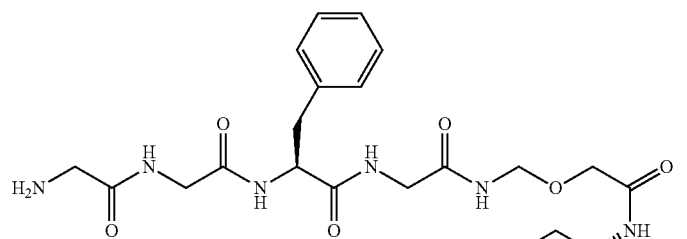
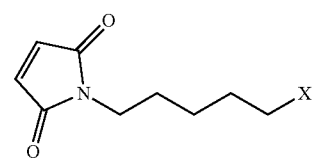
(C) Step 11

-continued

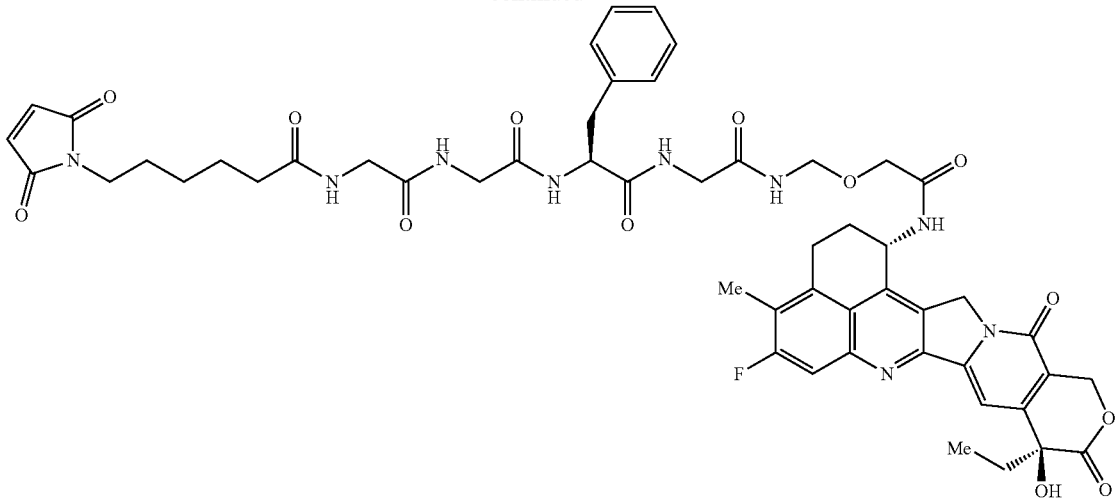

(1)

In the scheme, $R^1$ represents an amino group protected with a protecting group, and preferably represents an amino group protected with a (9H-fluoren-9-ylmethoxy)carbonyl group, $R^2$ represents a carboxy group protected with a protecting group, and preferably represents a carboxy group protected with a benzyl group, and X represents an active ester group or a carboxy group, and preferably represents a (2,5-dioxopyrrolidin-1-yl)oxycarbonyl group.

Step 8:

This step is a step of deprotecting a protecting group for a carboxy group of a compound represented by formula (B) to convert it into a compound represented by formula (F).

Deprotection of the protecting group for the carboxy group of the compound represented by the formula (B) can be performed by a method well known in the art (see, for example, Peter G. M. Wuts, Theodora W. Greene, Greene's Protective Groups in Organic Synthesis 4th Edition (2007), Wiley-Interscience).

In the case that $R^2$ is a carboxy group protected with a benzyl group, this step can be preferably performed by the following method.

Deprotection of the protecting group for the carboxy group of the compound represented by the formula (B) is not limited by its method as long as the reaction proceeds. It can be preferably performed using a palladium catalyst, a platinum catalyst, a nickel catalyst, a ruthenium catalyst, or a rhodium catalyst under a hydrogen atmosphere, can be more preferably performed using a palladium catalyst, and can be even more preferably performed using palladium carbon, and a palladium carbon-ethylenediamine complex can be even more preferably used. The amount of the palladium carbon-ethylenediamine complex used in this step is not limited as long as the reaction proceeds. It is preferably 34 to 136% by weight with respect to the compound represented by the formula (B).

The solvent used in this step is not particularly limited as long as the reaction is not inhibited. Examples thereof can include acetonitrile, dichloromethane, chloroform, methanol, ethanol, diethyl ether, 1,2-dimethoxyethane, tetrahydrofuran, 2-methyltetrahydrofuran, 1,4-dioxane, ethyl acetate, hexane, pentane, heptane, cyclohexane, ethylcyclohexane, benzene, toluene, chlorobenzene, acetone, 2-butanone, N,N-dimethylformamide, N,N-dimethylacetamide, 1-methyl-2-pyrrolidone, dimethyl sulfoxide, and water, and mixed solvents thereof, and a mixed solvent of tetrahydrofuran and water can be preferably exemplified.

The reaction temperature of this step is preferably 10 to 40° C., but is not limited thereto as long as the reaction proceeds. The reaction time of this step is preferably 1 to 54 hours, but is not limited thereto as long as the reaction proceeds.

Step 9:

This step is a step of condensing the compound represented by the formula (F) with the compound represented by formula (11) to convert it into a compound represented by formula (G).

The compound represented by the formula (F) can be preferably derivatized into an active ester and condensed with the compound represented by the formula (11). The amount of the compound represented by the formula (11) used in this step is not limited as long as the reaction proceeds. It is preferably 0.7 to 1.3 equivalents with respect to the compound represented by the formula (F). Derivatization into the active ester in this step is not limited by its method as long as the reaction proceeds. It can be performed, for example, by using a condensing agent such as 1-ethyl-3-(3-dimethylaminopropyl)carbodiimide hydrochloride (WSCD-HCl) or N,N'-dicyclohexylcarbodiimide (DCC), and reacting with an additive such as 1-hydroxybenzotriazole (HOBt), 1-hydroxy-7-azabenzotriazole (HOAt), N-hydroxysuccinimide, ethyl cyano(hydroxyimino)acetate, or p-nitrophenol, and can be preferably performed using 3-(3-dimethylaminopropyl)carbodiimide hydrochloride and 1-hydroxybenzotriazole. The amount of the 3-(3-dimethylaminopropyl)carbodiimide hydrochloride used in this step is not limited as long as the reaction proceeds. It is preferably 0.7 to 1.3 equivalents with respect to the compound represented by the formula (F). The amount of the 1-hydroxybenzotriazole used in this step is not limited as long as the reaction proceeds. It is preferably 0.7 to 1.3 equivalents with respect to the compound represented by the formula (F).

This step employs a base. The base used in this step is not particularly limited as long as the reaction proceeds. Examples thereof can include triethylamine, tributylamine, diisopropylethylamine, N-methylmorpholine, N-methylpyrrolidine, and N-methylpiperidine, and triethylamine can be preferably exemplified. The amount of the triethylamine used in this step is not limited as long as the reaction proceeds. It is preferably 0.7 to 1.3 equivalents with respect to the compound represented by the formula (F).

The solvent used in this step is not particularly limited as long as the reaction is not inhibited. Examples thereof can include acetonitrile, dichloromethane, chloroform, methanol, ethanol, diethyl ether, 1,2-dimethoxyethane, tetrahydrofuran, 2-methyltetrahydrofuran, 1,4-dioxane, ethyl acetate, hexane, pentane, heptane, cyclohexane, ethylcyclohexane, benzene, toluene, chlorobenzene, acetone, 2-butanone, N,N-dimethylformamide, N,N-dimethylacetamide, 1-methyl-2-pyrrolidone, dimethyl sulfoxide, and water, and mixed solvents thereof, and tetrahydrofuran can be preferably exemplified.

The reaction temperature of this step is not limited as long as the reaction proceeds. It is preferably 10 to 40° C. The reaction time of this step is not limited as long as the reaction proceeds. It is preferably 1 to 4 hours.

Step 10:

This step is a step of deprotecting the protecting group for the amino group of the compound represented by the formula (G) to convert it into the compound represented by formula (16).

Deprotection of the protecting group for the amino group of the compound represented by the formula (G) can be performed by a method well known in the art (see, for example, Peter G. M. Wuts, Theodora W. Greene, Greene's Protective Groups in Organic Synthesis 4th Edition (2007), Wiley-Interscience).

In the case that $R^1$ is an amino group protected with a (9H-fluoren-9-ylmethoxy)carbonyl group, this step can be preferably performed by the following method.

Deprotection of the protecting group for the amino group of the compound represented by the formula (G) is not particularly limited as long as the reaction proceeds. It can be performed using, for example, 1,8-diazabicyclo[5,4,0]-7-undecene, trimethylguanidine, 1,5,7-triazabicyclo[4,4,0]dec-5-ene, or 7-methyl-1,5,7-triazabicyclo[4,4,0]dec-5-ene 1,5-diazabicyclo[4,3,0]-5-nonene, and can be preferably performed using 1,8-diazabicyclo[5,4,0]-7-undecene. The amount of the 1,8-diazabicyclo[5,4,0]-7-undecene used in this step is not limited as long as the reaction proceeds. It is preferably 0.5 to 2 equivalents with respect to the compound represented by the formula (15).

The solvent used in this step is not particularly limited as long as the reaction is not inhibited. Examples thereof can include acetonitrile, dichloromethane, chloroform, methanol, ethanol, diethyl ether, 1,2-dimethoxyethane, tetrahydrofuran, 2-methyltetrahydrofuran, 1,4-dioxane, ethyl acetate, hexane, pentane, heptane, cyclohexane, ethylcyclohexane, benzene, toluene, chlorobenzene, acetone, 2-butanone, N,N-dimethylformamide, N,N-dimethylacetamide, 1-methyl-2-pyrrolidone, dimethyl sulfoxide, and water, and mixed solvents thereof, and tetrahydrofuran can be preferably exemplified.

The reaction temperature of this step is not limited as long as the reaction proceeds. It is preferably 10 to 40° C. The reaction time of this step is not limited as long as the reaction proceeds. It is preferably 1 to 5 hours.

Step 11:

This step is a step of condensing the compound represented by the formula (16) with a compound represented by formula (C) to convert it into the compound represented by the formula (1). As the compound represented by the formula (C), a commercially available product, a compound produced by a known method, or a compound produced by a method conforming to the production method (VII) described below can be used. In the case that X is a (2,5-dioxopyrrolidin-1-yl)oxycarbonyl group, this step can be preferably performed by the following method.

The amount of the compound represented by the formula (C) used in this step is not limited as long as the reaction proceeds. It is preferably 0.5 to 2 equivalents with respect to the compound represented by the formula (16).

This step preferably employs a base. The base used in this step is not particularly limited as long as the reaction proceeds. Examples thereof can include triethylamine, tributylamine, diisopropylethylamine, N-methylmorpholine, N-methylpyrrolidine, and N-methylpiperidine, and triethylamine can be preferably exemplified. The amount of the triethylamine used in this step is not limited as long as the reaction proceeds. It is preferably 0.75 to 6 equivalents with respect to the compound represented by the formula (16).

This step can preferably further employ pyridinium p-toluenesulfonate. The amount of the pyridinium p-toluenesulfonate used in this step is not limited as long as the reaction proceeds. It is preferably 1 to 4 equivalents with respect to the compound represented by the formula (16).

The solvent used in this step is not particularly limited as long as the reaction is not inhibited. Examples thereof can include acetonitrile, dichloromethane, chloroform, methanol, ethanol, diethyl ether, 1,2-dimethoxyethane, tetrahydrofuran, 2-methyltetrahydrofuran, 1,4-dioxane, ethyl acetate, hexane, pentane, heptane, cyclohexane, ethylcyclohexane, benzene, toluene, chlorobenzene, acetone, 2-butanone, N,N-dimethylformamide, N,N-dimethylacetamide, 1-methyl-2-pyrrolidone, dimethyl sulfoxide, pyridine, and water, and mixed solvents thereof, and a mixed solvent of pyridine, acetonitrile, and tetrahydrofuran can be preferably exemplified.

The reaction temperature of this step is not limited as long as the reaction proceeds. It is preferably 10 to 40° C. The reaction time of this step is not limited as long as the reaction proceeds. It is preferably 1.5 to 7 hours.

As the compound represented by the formula (B) in the production methods (I) to (III), a compound produced by the following production method (IV) can be preferably used.

[Production Method (IV)]

The production method (IV) is a method of converting a compound represented by formula (H) into the compound represented by the formula (B) through steps 12 to 15. Hereinafter the steps 12 to 15 will be described in detail.

[Chem. 85]

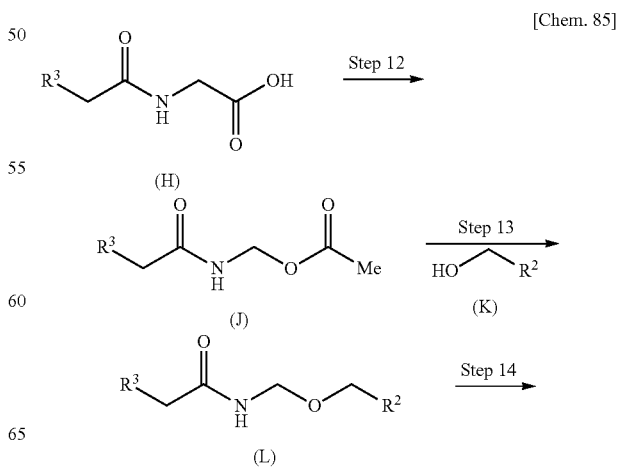

-continued

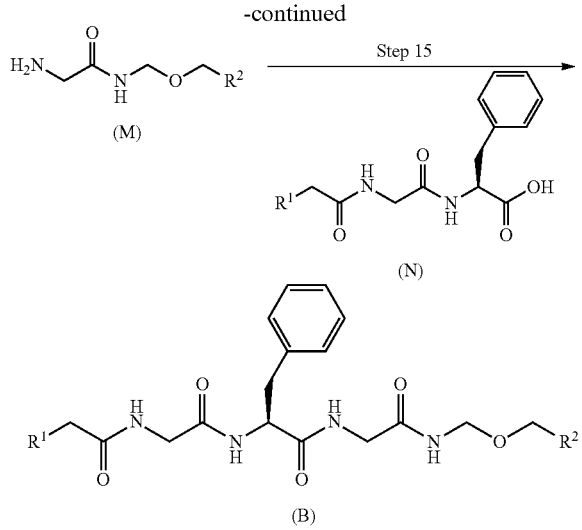

In the scheme, $R^1$ represents an amino group protected with a protecting group, and preferably represents an amino group protected with a benzyloxycarbonyl group or a (9H-fluoren-9-ylmethoxy)carbonyl group, $R^2$ represents a carboxy group protected with a protecting group, and preferably represents a carboxy group protected with a benzyl group, $R^3$ represents an amino group protected with a protecting group, and preferably represents an amino group protected with a (9H-fluoren-9-ylmethoxy)carbonyl group, and X represents an active ester group or a carboxy group, and preferably represents a (2,5-dioxopyrrolidin-1-yl)oxycarbonyl group.

Step 12:

This step is a step of reacting a compound represented by formula (H) with lead tetraacetate to convert it into a compound represented by formula (J). As the compound represented by the formula (H), a commercially available product or a compound produced with reference to a known method can be used. The amount of the lead tetraacetate used in this step is not limited as long as the reaction proceeds. It is preferably 1 to 3 equivalents with respect to the compound represented by the formula (H).

This step can be preferably performed in the presence of acetic acid or pyridine, and can be more preferably performed in the presence of acetic acid.

The solvent used in this step is not particularly limited as long as the reaction is not inhibited. Examples thereof can include acetonitrile, 1,2-dimethoxyethane, tetrahydrofuran, 2-methyltetrahydrofuran, 1,4-dioxane, ethyl acetate, N,N-dimethylformamide, N,N-dimethylacetamide, 1-methyl-2-pyrrolidone, and dimethyl sulfoxide, and mixed solvents thereof, and tetrahydrofuran can be preferably exemplified.

The reaction temperature of this step is not limited as long as the reaction proceeds. It is preferably 45 to 85° C., and more preferably a temperature that attains heating to reflux of tetrahydrofuran. The reaction time of this step is not limited as long as the reaction proceeds. It is preferably 0.5 to 3 hours.

Step 13:

This step is a step of reacting the compound represented by the formula (J) with a compound represented by formula (K) in the presence of an acid or a base to convert it into a compound represented by formula (L). The amount of the compound represented by the formula (K) used in this step is not limited as long as the reaction proceeds. It is preferably 1 to 4 equivalents with respect to the compound represented by the formula (J).

This step can be performed in the presence of a base or an acid. The base used in this step is preferably an aqueous sodium hydroxide solution. The amount of the aqueous sodium hydroxide solution used in this step is not limited as long as the reaction proceeds. It is preferably 0.5 to 2 equivalents with respect to the compound represented by the formula (J). The acid used in this step is preferably tris (pentafluorophenyl)borane. The amount of the tris(pentafluorophenyl)borane used in this step is not limited as long as the reaction proceeds. It is preferably 0.01 to 0.1 equivalents with respect to the compound represented by the formula (J).

The solvent used in this step is not particularly limited as long as the reaction is not inhibited. Examples thereof can include 1,2-dimethoxyethane, tetrahydrofuran, 2-methyltetrahydrofuran, and 1,4-dioxane, and 1,2-dimethoxyethane can be preferably exemplified.

The reaction temperature of this step is not limited as long as the reaction proceeds. It is preferably −10 to 15° C. The reaction time of this step is not limited as long as the reaction proceeds. It is preferably 0.5 to 6 hours.

Step 14:

This step is a step of deprotecting the protecting group for the amino group of the compound represented by the formula (L) to convert it into a compound represented by formula (M).

Deprotection of the protecting group for the amino group of the compound represented by the formula (L) can be performed by a method well known in the art (see, for example, Peter G. M. Wuts, Theodora W. Greene, Greene's Protective Groups in Organic Synthesis 4th Edition (2007), Wiley-Interscience).

In the case that $R^3$ is an amino group protected with a (9H-fluoren-9-ylmethoxy)carbonyl group, this step can be preferably performed by the following method.

Deprotection of the protecting group for the amino group of the compound represented by the formula (L) is not particularly limited as long as the reaction proceeds. It can be performed using, for example, 1,8-diazabicyclo[5,4,0]-7-undecene, trimethylguanidine, 1,5,7-triazabicyclo[4,4,0]dec-5-ene, or 7-methyl-1,5,7-triazabicyclo[4,4,0]dec-5-ene 1,5-diazabicyclo[4,3,0]-5-nonene, and can be preferably performed using 1,8-diazabicyclo[5,4,0]-7-undecene. The amount of the 1,8-diazabicyclo[5,4,0]-7-undecene used in this step is not limited as long as the reaction proceeds. It is preferably 0.25 to 1 equivalents with respect to the compound represented by the formula (L).

The solvent used in this step is not particularly limited as long as the reaction is not inhibited. Examples thereof can include acetonitrile, dichloromethane, chloroform, methanol, ethanol, diethyl ether, 1,2-dimethoxyethane, tetrahydrofuran, 2-methyltetrahydrofuran, 1,4-dioxane, ethyl acetate, hexane, pentane, heptane, cyclohexane, ethylcyclohexane, benzene, toluene, chlorobenzene, acetone, 2-butanone, N,N-dimethylformamide, N,N-dimethylacetamide, 1-methyl-2-pyrrolidone, dimethyl sulfoxide, and water, and mixed solvents thereof, and acetonitrile and N,N-dimethylacetamide can be preferably exemplified.

The reaction temperature of this step is not limited as long as the reaction proceeds. It is preferably 10 to 40° C. The reaction time of this step is not limited as long as the reaction proceeds. It is preferably 2 to 8 hours.

The compound represented by the formula (M) can be precipitated from the reaction solution by forming a salt with an acid, and preferably isolated and purified. As a result, by-products, which can be a factor inhibiting reactions in the subsequent steps, can be removed.

The above-described acid is preferably 1-hydroxybenzotriazole. The 1-hydroxybenzotriazole used in this step can also function as one of the condensing agents in the next step 15. Likewise, an acid other than 1-hydroxybenzotriazole can be preferably used in this step as long as it functions as one of the condensing agents.

Step 15:

This step is a step of condensing the compound represented by the formula (M) with a compound represented by formula (N) to convert it into the compound represented by the formula (B). As the compound represented by the formula (N), a commercially available product, a compound produced by a known method, or a compound produced by a method conforming to the production method (VIII) described below can be used. The amount of the compound represented by the formula (N) used in this step is not limited as long as the reaction proceeds. It is preferably 0.7 to 1.3 equivalents with respect to the compound represented by the formula (M).

The compound represented by the formula (M) can be preferably derivatized into an active ester and condensed with the compound represented by the formula (N). Derivatization into the active ester can be performed, for example, by using a condensing agent such as 1-ethyl-3-(3-dimethylaminopropyl)carbodiimide hydrochloride (WSCD-HCl) or N,N'-dicyclohexylcarbodiimide (DCC), and reacting with an additive such as 1-hydroxybenzotriazole (HOBt), 1-hydroxy-7-azabenzotriazole (HOAt), N-hydroxysuccinimide, ethyl cyano(hydroxyimino)acetate, or p-nitrophenol, and can be preferably performed using 3-(3-dimethylaminopropyl)carbodiimide hydrochloride and 1-hydroxybenzotriazole. The amount of the 3-(3-dimethylaminopropyl)carbodiimide hydrochloride used in this step is not limited as long as the reaction proceeds. It is preferably 0.7 to 1.3 equivalents with respect to the compound represented by the formula (5). The amount of the 1-hydroxybenzotriazole used in this step is not limited as long as the reaction proceeds. It is preferably 0.7 to 1.3 equivalents with respect to the compound represented by the formula (M).

In the case that the compound represented by the formula (M) is in the form of a 1-hydroxybenzotriazole salt, this step can be preferably performed without the addition of fresh 1-hydroxybenzotriazole.

The solvent used in this step is not particularly limited as long as the reaction is not inhibited. Examples thereof can include acetonitrile, dichloromethane, chloroform, methanol, ethanol, diethyl ether, 1,2-dimethoxyethane, tetrahydrofuran, 2-methyltetrahydrofuran, 1,4-dioxane, ethyl acetate, hexane, pentane, heptane, cyclohexane, ethylcyclohexane, benzene, toluene, chlorobenzene, acetone, 2-butanone, N,N-dimethylformamide, N,N-dimethylacetamide, 1-methyl-2-pyrrolidone, dimethyl sulfoxide, and water, and mixed solvents thereof, and a mixed solvent of acetonitrile and water can be preferably exemplified.

In the case that the compound represented by the formula (M) is not isolated in the step 14, and this step is performed continuously therefrom, the solvent used in the step 14 can be used as it is as the solvent of this step.

The reaction temperature of this step is not limited as long as the reaction proceeds. It is preferably −10 to 15° C. The reaction time of this step is not limited as long as the reaction proceeds. It is preferably 1.5 to 7 hours.

In a more specific aspect, the compound represented by the formula (1) can be preferably produced by the following production method (V) or (VI), and used.

[Production Method (V)]

The production method (V) is a method of converting the compound represented by formula (2) into the compound represented by the formula (1) through steps 16 to 22. Hereinafter the steps 16 to 22 will be described in detail.

[Chem. 86]

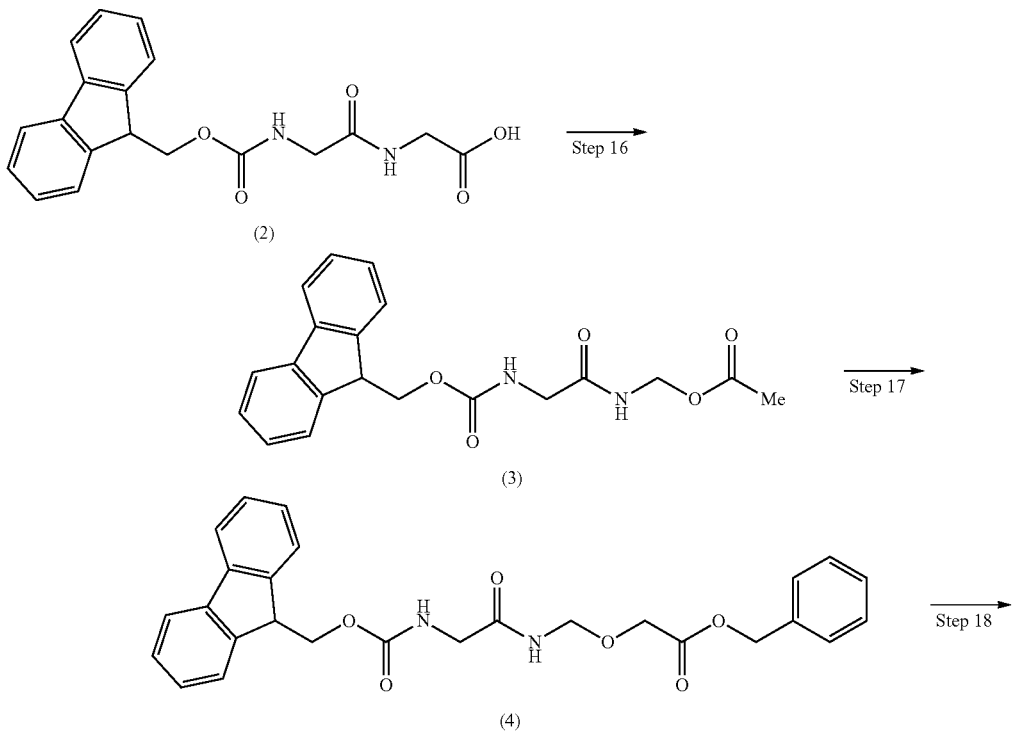

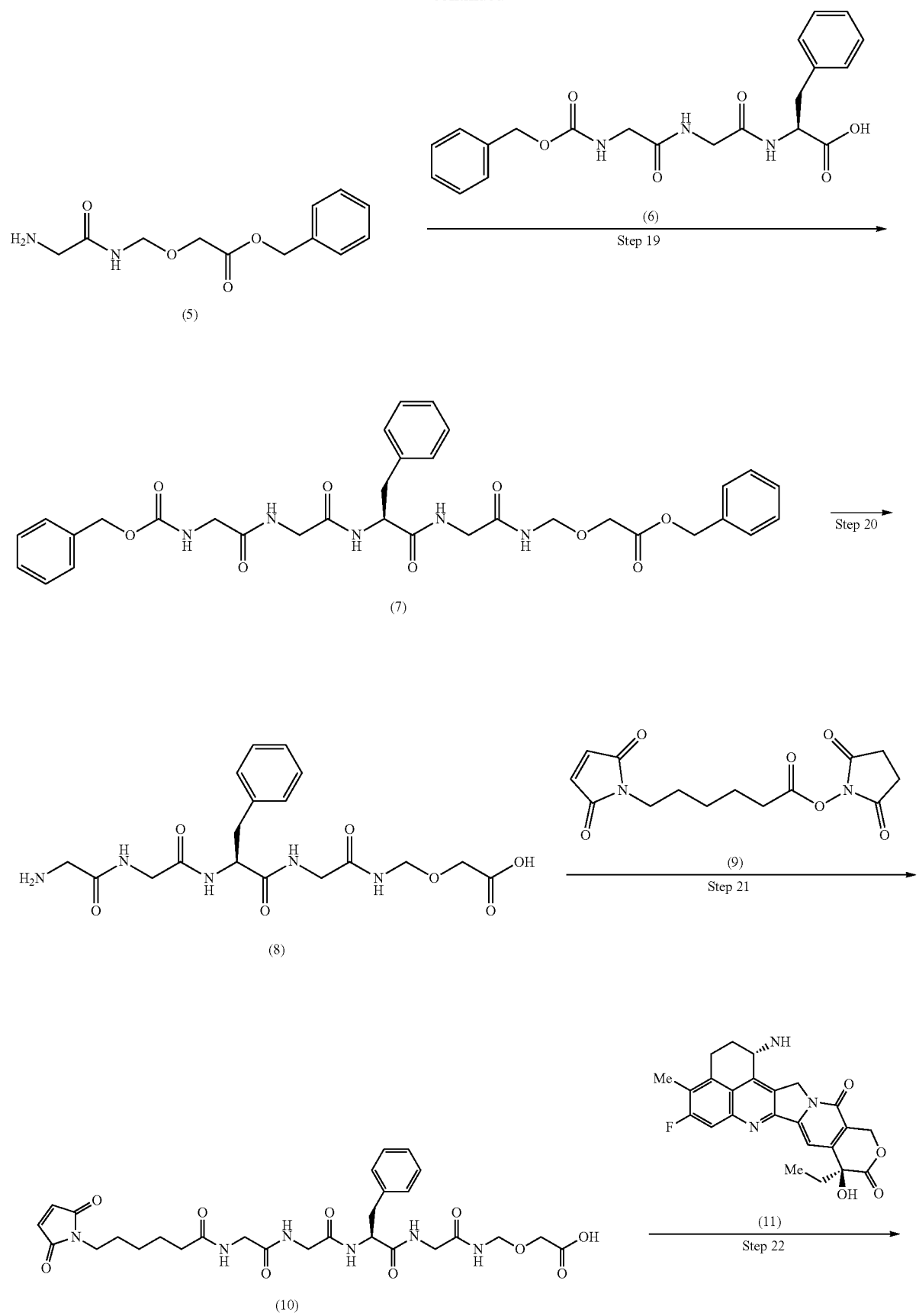

-continued

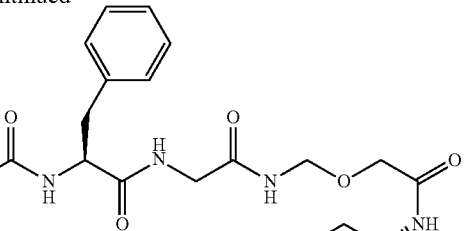
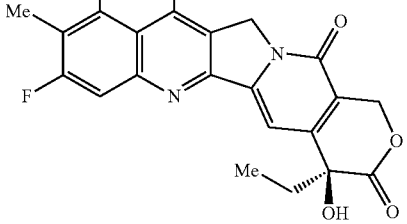

(1)

Step 16:
This step is a step of reacting the compound represented by formula (2) with lead tetraacetate to convert it into the compound represented by formula (3). As the compound represented by the formula (2), a commercially available product or a compound produced with reference to a known method can be used. This step can be performed in the same manner as in the step 12 of the production method (IV).

Step 17:
This step is a step of reacting the compound represented by the formula (3) with benzyl glycolate in the presence of an acid or a base to convert it into the compound represented by formula (4). This step can be performed in the same manner as in the step 13 of the production method (IV).

Step 18:
This step is a step of deprotecting the protecting group for the amino group of the compound represented by the formula (4) to convert it into the compound represented by formula (5). This step can be performed in the same manner as in the step 14 of the production method (IV).

Step 19:
This step is a step of condensing the compound represented by the formula (5) with the compound represented by formula (6) to convert it into the compound represented by formula (7). As the compound represented by the formula (6), a commercially available product, a compound produced by a known method, or a compound produced by the production method (VIII) described below can be used. This step can be performed in the same manner as in the step 15 of the production method (IV).

Step 20:
This step is a step of deprotecting the protecting groups for the amino group and the carboxy group of the compound represented by the formula (7) to convert it into the compound represented by formula (8). This step can be performed in the same manner as in the step 1 of the production method (I).

Step 21:
This step is a step of condensing the compound represented by the formula (8) with the compound represented by formula (9) to convert it into the compound represented by formula (10). This step can be performed in the same manner as in the step 2 of the production method (I).

Step 22:
This step is a step of condensing the compound represented by the formula (10) with the compound represented by formula (11) to convert it into the compound represented by the formula (1). This step can be performed in the same manner as in the step 3 of the production method (I).

[Production Method (VI)]
The production method (VI) is a method of converting the compound represented by formula (2) into the compound represented by the formula (1) through steps 23 to 30. Hereinafter the steps 23 to 30 will be described in detail.

[Chem. 87]

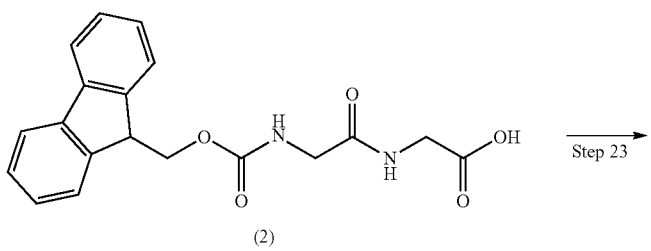

(2)  Step 23

-continued
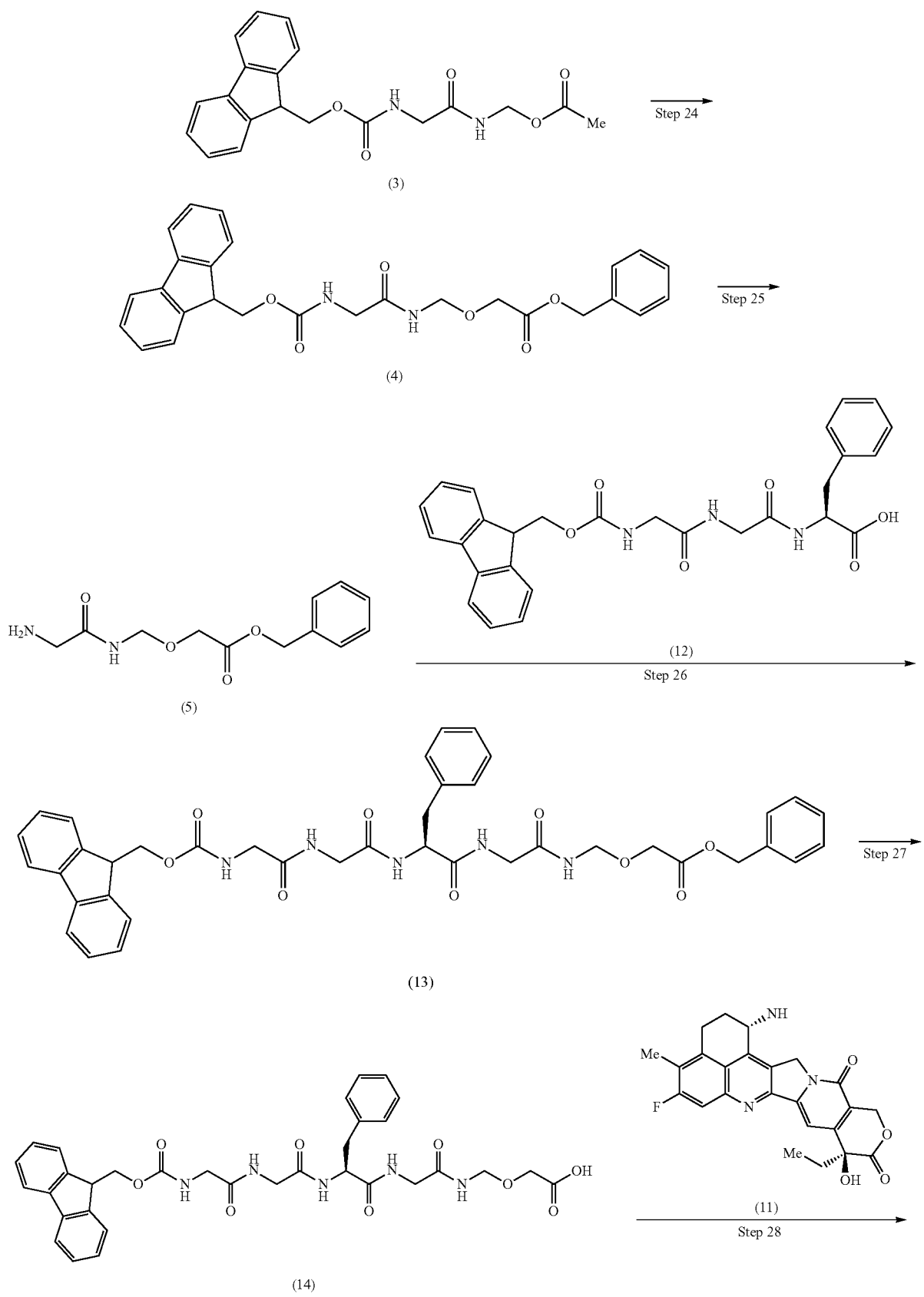

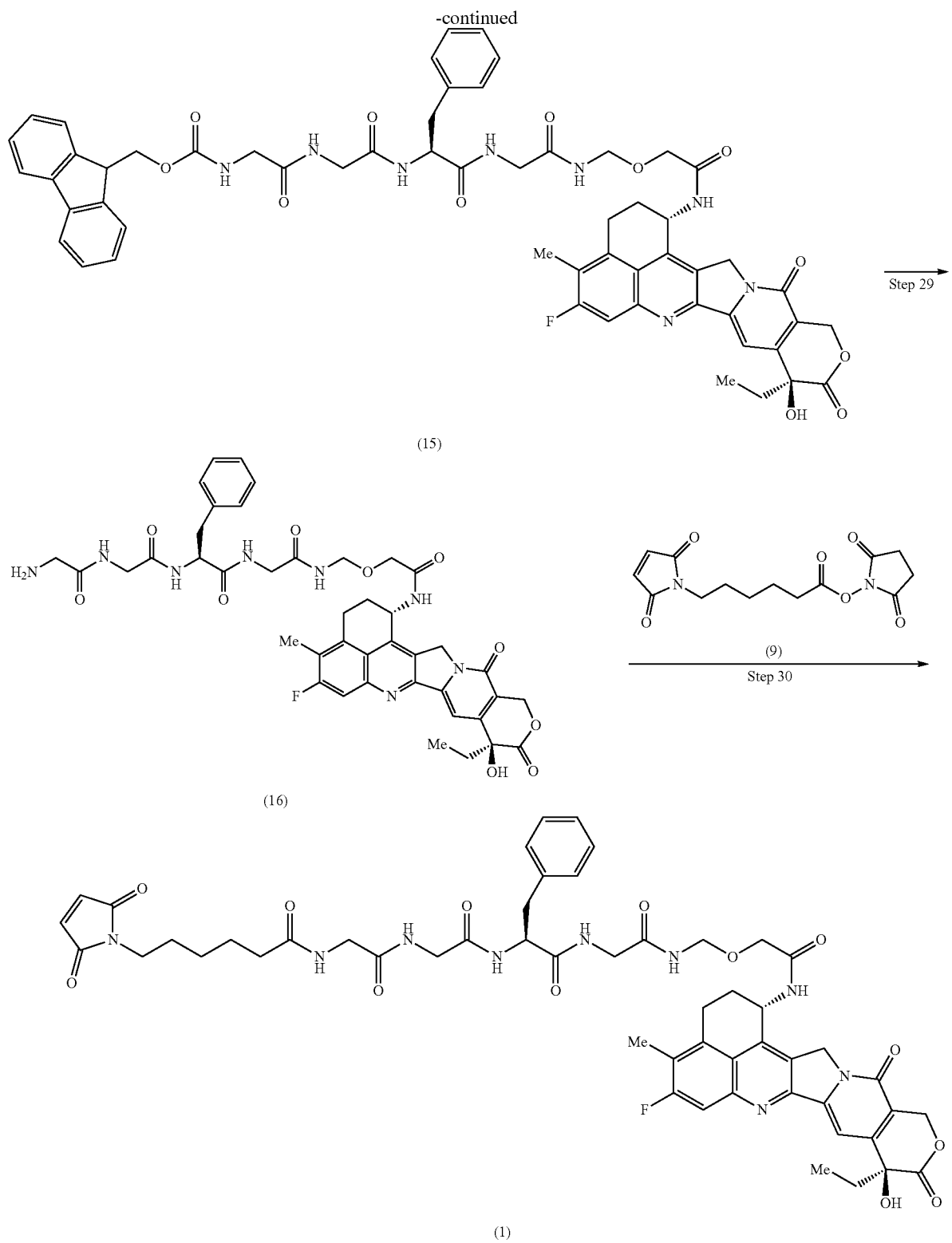

Step 23:

This step is a step of reacting the compound represented by formula (2) with lead tetraacetate to convert it into the compound represented by formula (3). As the compound represented by the formula (2), a commercially available product or a compound produced with reference to a known method can be used. This step can be performed in the same manner as in the step 12 of the production method (IV).

Step 24:

This step is a step of reacting the compound represented by the formula (3) with benzyl glycolate in the presence of an acid or a base to convert it into the compound represented by formula (4). This step can be performed in the same manner as in the step 13 of the production method (IV).

Step 25:

This step is a step of deprotecting the protecting group for the amino group of the compound represented by the formula (4) to convert it into the compound represented by formula (5). This step can be performed in the same manner as in the step 14 of the production method (IV).

Step 26:

This step is a step of condensing the compound represented by the formula (5) with the compound represented by formula (12) to convert it into the compound represented by formula (13). As the compound represented by the formula (13), a commercially available product or a compound produced by a known method can be used. This step can be performed in the same manner as in the step 15 of the production method (IV).

Step 27:

This step is a step of deprotecting the protecting group for the carboxy group of the compound represented by the formula (13) to convert it into the compound represented by formula (14). This step can be performed in the same manner as in the step 8 of the production method (III).

Step 28:

This step is a step of condensing the compound represented by the formula (14) with the compound represented by formula (11) to convert it into the compound represented by formula (15). This step can be performed in the same manner as in the step 9 of the production method (III).

Step 29:

This step is a step of deprotecting the protecting group for the amino group of the compound represented by the formula (15) to convert it into the compound represented by formula (16). This step can be performed in the same manner as in the step 10 of the production method (III).

Step 30:

This step is a step of condensing the compound represented by the formula (16) with the compound represented by formula (9) to convert it into the compound represented by the formula (1). This step can be performed in the same manner as in the step 11 of the production method (III).

[Production Method (VII)]

The compound represented by the formula (9) can be preferably produced by the production method (VII) described below, and used. As a result, impurities that might influence the quality of compounds produced in the subsequent steps can be suppressed, and this can contribute to obtainment of the compound represented by the formula (1) with high quality.

[Chem. 88]

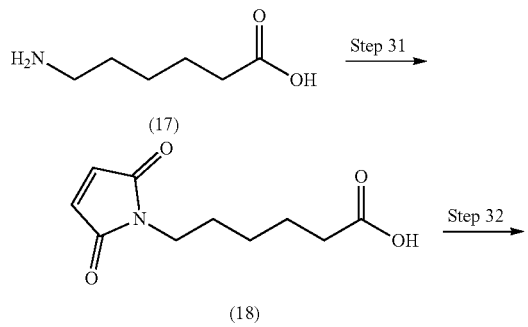

-continued

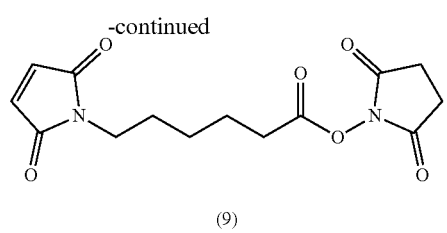

(9)

Step 31:

This step is a step of condensing the compound represented by formula (17) with maleic anhydride to convert it into the compound represented by formula (18). The amount of the maleic anhydride used in this step is not limited as long as the reaction proceeds. It is preferably 0.7 to 1.3 equivalents with respect to the compound represented by the formula (17).

This step is preferably performed in acetic acid.

The reaction temperature of this step is not limited as long as the reaction proceeds. It is preferably 80 to 120° C. The reaction time of this step is not limited as long as the reaction proceeds. It is preferably 8 to 32 hours.

Step 32:

This step is a step of condensing the compound represented by the formula (18) with N-hydroxysuccinimide to convert it into the compound represented by the formula (9). The amount of the N-hydroxysuccinimide used in this step is not limited as long as the reaction proceeds. It is preferably 0.7 to 1.3 equivalents with respect to the compound represented by the formula (17).

The compound represented by the formula (18) can be derivatized into an active ester, a mixed acid anhydride, or an acid halide, etc. and condensed with the N-hydroxysuccinimide, or can be preferably derivatized into an acid halide and condensed with the N-hydroxysuccinimide.

Derivatization into the acid halide can be preferably performed by using thionyl chloride. The amount of the thionyl chloride used in this step is not limited as long as the reaction proceeds. It is preferably 0.5 to 1.5 equivalents with respect to the compound represented by the formula (18). In this step, a base is preferably used. The base used in this step is preferably 2,6-lutidine. The amount of the 2,6-lutidine used in this step is not limited as long as the reaction proceeds. It is preferably 1 to 3 equivalents with respect to the compound represented by the formula (18).

The solvent used in this step is not particularly limited as long as the reaction is not inhibited. Examples thereof can include acetonitrile, dichloromethane, chloroform, diethyl ether, 1,2-dimethoxyethane, tetrahydrofuran, 2-methyltetrahydrofuran, ethyl acetate, hexane, pentane, heptane, cyclohexane, ethylcyclohexane, benzene, toluene, and chlorobenzene, and mixed solvents thereof, and acetonitrile can be preferably exemplified.

The reaction temperature of this step is not limited as long as the reaction proceeds. It is preferably −25° C. to 0° C. The reaction time of this step is not limited as long as the reaction proceeds. It is preferably 0.5 to 2 hours.

[Production Method (VIII)]

The compound represented by the formula (6) can be produced by the following production method (VIII), and used.

[Chem. 89]

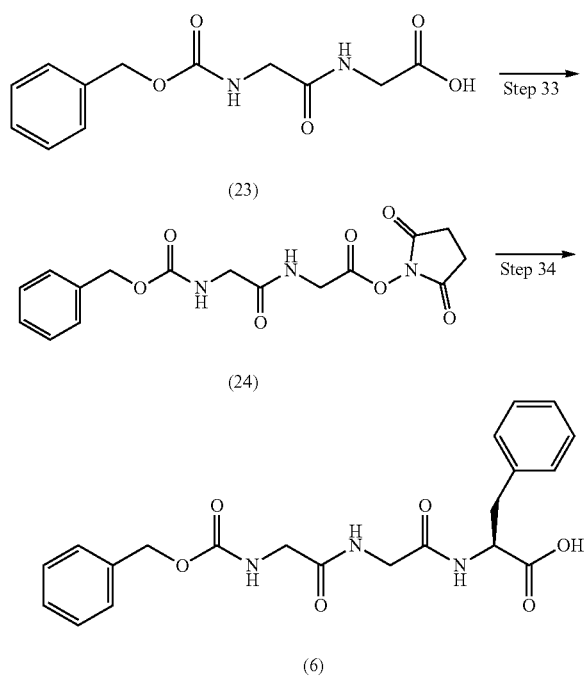

Step 33:

This step is a step of condensing the compound represented by formula (23) with N-hydroxysuccinimide to convert it into the compound represented by formula (24). The amount of the compound represented by the formula (23) used in this step is not limited as long as the reaction proceeds. It is preferably 0.7 to 1.5 equivalents with respect to the compound represented by the formula (23).

The compound represented by the formula (23) can be derivatized into an active ester, a mixed acid anhydride, or an acid halide, etc. and condensed with the N-hydroxysuccinimide, and can be preferably derivatized into an active esterified form and condensed with the N-hydroxysuccinimide.

Active esterification can be preferably performed by using 3-(3-dimethylaminopropyl)carbodiimide hydrochloride. The amount of the 3-(3-dimethylaminopropyl)carbodiimide hydrochloride used in this step is not limited as long as the reaction proceeds. It is preferably 0.7 to 1.5 equivalents with respect to the compound represented by the formula (23).

The solvent used in this step is not particularly limited as long as the reaction is not inhibited. Examples thereof can include acetonitrile, dichloromethane, chloroform, methanol, ethanol, diethyl ether, 1,2-dimethoxyethane, tetrahydrofuran, 2-methyltetrahydrofuran, 1,4-dioxane, ethyl acetate, hexane, pentane, heptane, cyclohexane, ethylcyclohexane, benzene, toluene, chlorobenzene, acetone, 2-butanone, N,N-dimethylformamide, N,N-dimethylacetamide, 1-methyl-2-pyrrolidone, dimethyl sulfoxide, and water, and mixed solvents thereof, and acetonitrile can be preferably exemplified.

The reaction temperature of this step is not limited as long as the reaction proceeds. It is preferably 10 to 40° C. The reaction time of this step is not limited as long as the reaction proceeds. It is preferably 2 to 8 hours.

Step 34:

This step is a step of condensing the compound represented by the formula (24) with L-phenylalanine to convert it into the compound represented by the formula (6). The amount of the L-phenylalanine used in this step is not limited as long as the reaction proceeds. It is preferably 0.7 to 1.3 equivalents with respect to the compound represented by the formula (24).

This step preferably employs a base. The base used in this step is not particularly limited as long as the reaction proceeds. Examples thereof can include triethylamine, tributylamine, diisopropylethylamine, N-methylmorpholine, N-methylpyrrolidine, and N-methylpiperidine, and triethylamine can be preferably exemplified. The amount of the triethylamine used in this step is not limited as long as the reaction proceeds. It is preferably 0.7 to 1.3 equivalents with respect to the compound represented by the formula (24).

The solvent used in this step is not particularly limited as long as the reaction is not inhibited. Examples thereof can include acetonitrile, dichloromethane, chloroform, methanol, ethanol, diethyl ether, 1,2-dimethoxyethane, tetrahydrofuran, 2-methyltetrahydrofuran, 1,4-dioxane, ethyl acetate, hexane, pentane, heptane, cyclohexane, ethylcyclohexane, benzene, toluene, chlorobenzene, acetone, 2-butanone, N,N-dimethylformamide, N,N-dimethylacetamide, 1-methyl-2-pyrrolidone, dimethyl sulfoxide, and water, and mixed solvents thereof, and a mixed solvent of acetonitrile and water can be preferably exemplified.

The reaction temperature of this step is not limited as long as the reaction proceeds. It is preferably the compound represented by formula (23). The reaction time of this step is not limited as long as the reaction proceeds. It is preferably 1 to 4 hours.

[Production Method (IX)]

The compound represented by the formula (1) can also be produced by the following production method (IX), and used.

[Chem. 90]

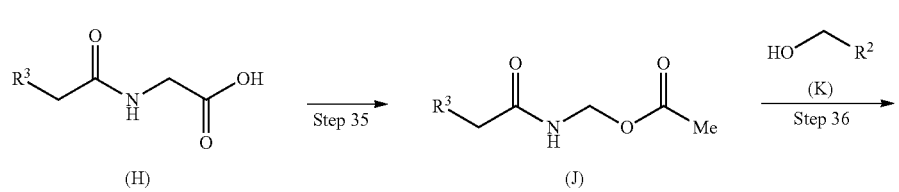

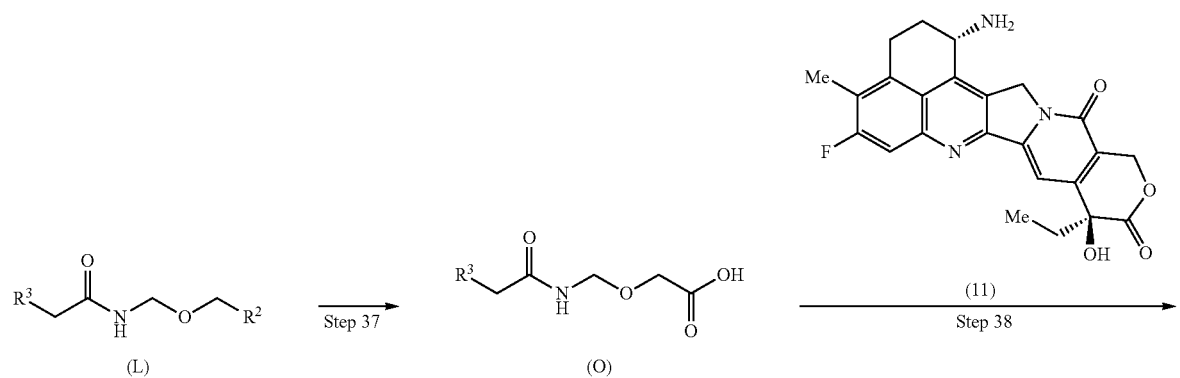
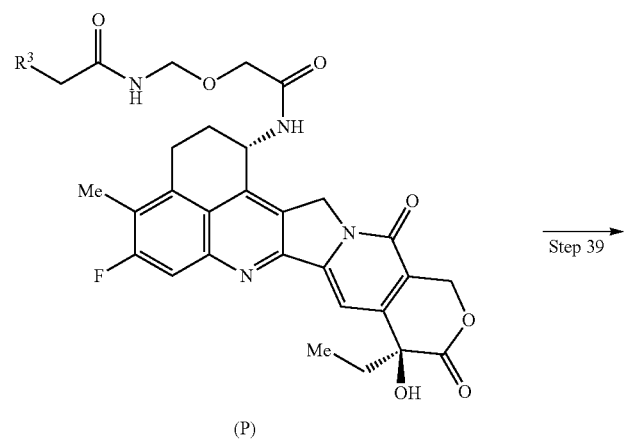
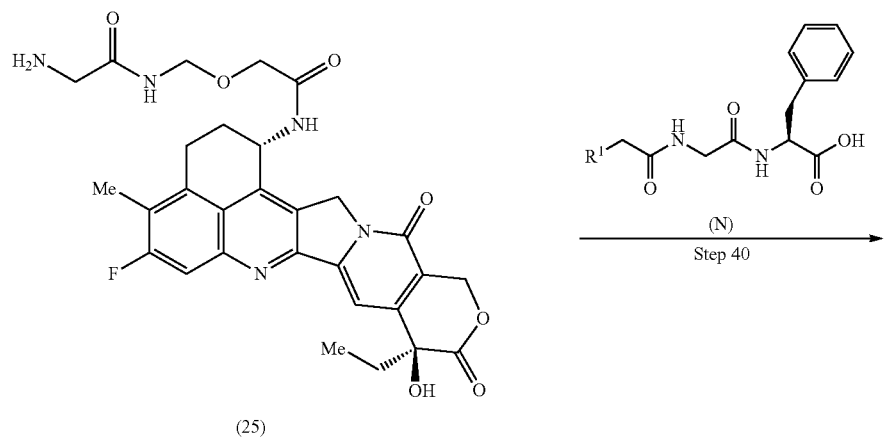

-continued
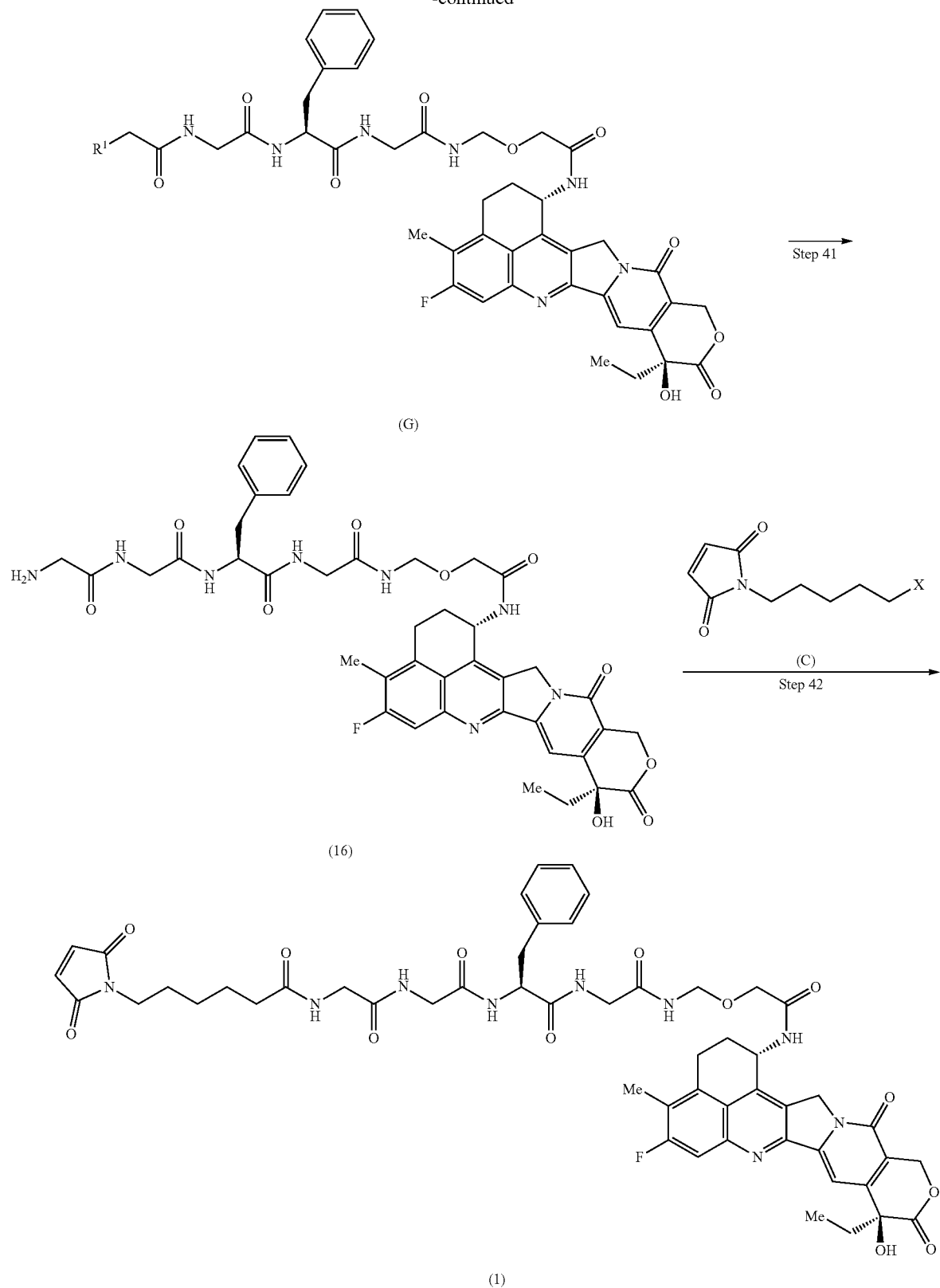
In the scheme, R¹ represents an amino group protected with a protecting group, R² represents a carboxy group protected with a protecting group, R³ represents an amino group protected with a protecting group, and X represents an active ester group or a carboxy group, and preferably represents a (2,5-dioxopyrrolidin-1-yl)oxycarbonyl group.

Step 35:

This step is a step of reacting a compound represented by formula (H) with lead tetraacetate to convert it into a compound represented by formula (J). As the compound represented by the formula (H), a commercially available product or a compound produced with reference to a known method can be used. This step can be performed in the same manner as in the step 12 of the production method (IV).

Step 36:

This step is a step of reacting the compound represented by the formula (J) with a compound represented by formula (K) in the presence of an acid or a base to convert it into a compound represented by formula (L). This step can be performed in the same manner as in the step 13 of the production method (IV).

Step 37:

This step is a step of deprotecting the protecting group for the carboxy group of the compound represented by the formula (L) to convert it into a compound represented by formula (O).

Deprotection of the protecting group for the carboxy group of the compound represented by the formula (L) can be performed by a method well known in the art (see, for example, Peter G. M. Wuts, Theodora W. Greene, Greene's Protective Groups in Organic Synthesis 4th Edition (2007), Wiley-Interscience).

Step 38:

This step is a step of condensing the compound represented by the formula (O) with the compound represented by formula (11) to convert it into a compound represented by formula (P).

The compound represented by the formula (O) can be preferably derivatized into an active ester and condensed with the compound represented by the formula (11).

Step 39:

This step is a step of deprotecting the protecting group for the amino group of the compound represented by the formula (P) to convert it into the compound represented by formula (25).

Deprotection of the protecting group for the carboxy group of the compound represented by the formula (P) can be performed by a method well known in the art (see, for example, Peter G. M. Wuts, Theodora W. Greene, Greene's Protective Groups in Organic Synthesis 4th Edition (2007), Wiley-Interscience).

Step 40:

This step is a step of condensing the compound represented by the formula (25) with a compound represented by formula (N) to convert it into a compound represented by formula (G).

The compound represented by the formula (N) can be preferably derivatized into an active ester and condensed with the compound represented by the formula (25).

Step 41:

This step is a step of deprotecting the protecting group for the amino group of the compound represented by the formula (G) to convert it into the compound represented by formula (16). This step can be performed in the same manner as in the step 10 of the production method (III).

Step 42:

This step is a step of condensing the compound represented by the formula (16) with a compound represented by formula (C) to convert it into the compound represented by the formula (1). This step can be performed in the same manner as in the step 11 of the production method (III).

[Antibody for Use in the Production of an Antibody-Drug Conjugate]

The antibody for use in the production of the antibody-drug conjugate of the present invention may be derived from any species, and is preferably an antibody derived from a human, a rat, a mouse, or a rabbit. In cases where the antibody is derived from species other than human species, it is preferably chimerized or humanized using a well-known technique. The antibody of the present invention may be a polyclonal antibody or a monoclonal antibody and is preferably a monoclonal antibody.

The antibody for use in the production of the antibody-drug conjugate of the present invention is an antibody preferably having a characteristic of being capable of targeting cancer cells, and is preferably an antibody possessing, for example, the property of recognizing a cancer cell, the property of binding to a cancer cell, the property of internalizing in a cancer cell, and/or cytocidal activity against cancer cells.

The binding activity of the antibody against cancer cells can be confirmed using flow cytometry. The internalization of the antibody into tumor cells can be confirmed using (1) an assay of visualizing an antibody incorporated in cells under a fluorescence microscope using a secondary antibody (fluorescently labeled) binding to the therapeutic antibody (Cell Death and Differentiation (2008) 15, 751-761), (2) an assay of measuring a fluorescence intensity incorporated in cells using a secondary antibody (fluorescently labeled) binding to the therapeutic antibody (Molecular Biology of the Cell, Vol. 15, 5268-5282, December 2004), or (3) a Mab-ZAP assay using an immunotoxin binding to the therapeutic antibody wherein the toxin is released upon incorporation into cells to inhibit cell growth (Bio Techniques 28: 162-165, January 2000). As the immunotoxin, a recombinant complex protein of a diphtheria toxin catalytic domain and protein G may be used.

The antitumor activity of the antibody can be confirmed in vitro by determining inhibitory activity against cell growth. For example, a cancer cell line overexpressing a target protein for the antibody is cultured, and the antibody is added into the culture system at varying concentrations to determine inhibitory activity against focus formation, colony formation, and spheroid growth. The antitumor activity can be confirmed in vivo, for example, by administering the antibody to a nude mouse with a transplanted cancer cell line highly expressing the target protein, and determining change in the cancer cell.

Since the compound conjugated in the antibody-drug conjugate exerts an antitumor effect, it is preferred but not essential that the antibody itself should have an antitumor effect. For the purpose of specifically and selectively exerting the cytotoxic activity of the antitumor compound against cancer cells, it is important and also preferred that the antibody should have the property of internalizing to migrate into cancer cells.

The antibody for use in the production of the antibody-drug conjugate of the present invention can be obtained by a procedure known in the art. For example, the antibody of the present invention can be obtained using a method usually carried out in the art, which involves immunizing animals with an antigenic polypeptide and collecting and purifying antibodies produced in vivo. The origin of the antigen is not limited to humans, and the animals may be immunized with an antigen derived from a non-human animal such as a mouse, a rat and the like. In this case, the cross-reactivity of antibodies binding to the obtained heterologous antigen with human antigens can be tested to screen for an antibody applicable to a human disease.

Alternatively, antibody-producing cells which produce antibodies against the antigen are fused with myeloma cells according to a method known in the art (e.g., Kohler and Milstein, Nature (1975) 256, p. 495-497; and Kennet, R. ed., Monoclonal Antibodies, p. 365-367, Plenum Press, N.Y. (1980)) to establish hybridomas, from which monoclonal antibodies can in turn be obtained.

The antigen can be obtained by genetically engineering host cells to produce a gene encoding the antigenic protein. Specifically, vectors that permit expression of the antigen gene are prepared and transferred to host cells so that the gene is expressed. The antigen thus expressed can be purified. The antibody can also be obtained by a method of immunizing animals with the above-described genetically engineered antigen-expressing cells or a cell line expressing the antigen.

The antibody for use in the production of the antibody-drug conjugate of the present invention is preferably a recombinant antibody obtained by artificial modification for the purpose of decreasing heterologous antigenicity to humans such as a chimeric antibody or a humanized antibody, or is preferably an antibody having only the gene sequence of an antibody derived from a human, that is, a human antibody. These antibodies can be produced using a known method.

As the chimeric antibody, an antibody in which antibody variable and constant regions are derived from different species, for example, a chimeric antibody in which a mouse- or rat-derived antibody variable region is connected to a human-derived antibody constant region can be exemplified (Proc. Natl. Acad. Sci. USA, 81, 6851-6855, (1984)).

As the humanized antibody, an antibody obtained by integrating only the complementarity determining region (CDR) of a heterologous antibody into a human-derived antibody (Nature (1986) 321, pp. 522-525), and an antibody obtained by grafting a part of the amino acid residues of the framework of a heterologous antibody as well as the CDR sequence of the heterologous antibody to a human antibody by a CDR-grafting method (WO 90/07861), and an antibody humanized using a gene conversion mutagenesis strategy (U.S. Pat. No. 5,821,337) can be exemplified.

As the human antibody, an antibody generated by using a human antibody-producing mouse having a human chromosome fragment including genes of a heavy chain and light chain of a human antibody (see Tomizuka, K. et al., Nature Genetics (1997) 16, p. 133-143; Kuroiwa, Y. et. al., Nucl. Acids Res. (1998) 26, p. 3447-3448; Yoshida, H. et. al., Animal Cell Technology: Basic and Applied Aspects vol. 10, p. 69-73 (Kitagawa, Y., Matsuda, T. and Iijima, S. eds.), Kluwer Academic Publishers, 1999; Tomizuka, K. et. al., Proc. Natl. Acad. Sci. USA (2000) 97, p. 722-727, etc.) can be exemplified. As an alternative, an antibody obtained by phage display, the antibody being selected from a human antibody library (see Wormstone, I. M. et. al, Investigative Ophthalmology & Visual Science. (2002) 43 (7), p. 2301-2308; Carmen, S. et. al., Briefings in Functional Genomics and Proteomics (2002), 1 (2), p. 189-203; Siriwardena, D. et. al., Ophthalmology (2002) 109 (3), p. 427-431, etc.) can be exemplified.

In the present invention, modified variants of the antibody for use in the production of the antibody-drug conjugate of the present invention are also included. The modified variant refers to a variant obtained by subjecting the antibody according to the present invention to chemical or biological modification. Examples of the chemically modified variant include variants including a linkage of a chemical moiety to an amino acid skeleton, variants including a linkage of a chemical moiety to an N-linked or O-linked carbohydrate chain, etc. Examples of the biologically modified variant include variants obtained by post-translational modification (such as N-linked or O-linked glycosylation, N- or C-terminal processing, deamidation, isomerization of aspartic acid, or oxidation of methionine), and variants in which a methionine residue has been added to the N terminus by being expressed in a prokaryotic host cell. Further, an antibody labeled so as to enable the detection or isolation of the antibody or an antigen according to the present invention, for example, an enzyme-labeled antibody, a fluorescence-labeled antibody, and an affinity-labeled antibody are also included in the meaning of the modified variant. Such a modified variant of the antibody according to the present invention is useful for improving the stability and blood retention of the antibody, reducing the antigenicity thereof, detecting or isolating an antibody or an antigen, and so on.

Further, by regulating the modification of a glycan which is linked to the antibody according to the present invention (glycosylation, defucosylation, etc.), it is possible to enhance antibody-dependent cellular cytotoxic activity. As the technique for regulating the modification of a glycan of antibodies, WO 99/54342, WO 00/61739, WO 02/31140, etc. are known. However, the technique is not limited thereto. In the antibody according to the present invention, antibodies in which the modification of a glycan is regulated are also included.

It is known that a lysine residue at the carboxyl terminus of the heavy chain of an antibody produced in a cultured mammalian cell is deleted (Journal of Chromatography A, 705: 129-134 (1995)), and it is also known that two amino acid residues (glycine and lysine) at the carboxyl terminus of the heavy chain of an antibody produced in a cultured mammalian cell are deleted and a proline residue newly located at the carboxyl terminus is amidated (Analytical Biochemistry, 360: 75-83 (2007)). However, such deletion and modification of the heavy chain sequence do not affect the antigen-binding affinity and the effector function (the activation of complement, antibody-dependent cellular cytotoxicity, etc.) of the antibody. Therefore, in the antibody according to the present invention, antibodies subjected to such modification and functional fragments of the antibody are also included, and deletion variants in which one or two amino acids have been deleted at the carboxyl terminus of the heavy chain, variants obtained by amidation of deletion variants (for example, a heavy chain in which the carboxyl terminal proline residue has been amidated), and the like are also included. The type of deletion variant having a deletion at the carboxyl terminus of the heavy chain of the antibody according to the present invention is not limited to the above variants as long as the antigen-binding affinity and the effector function are conserved. The two heavy chains constituting the antibody according to the present invention may be of one type selected from the group consisting of a full-length heavy chain and the above-described deletion variant, or may be of two types in combination selected therefrom. The ratio of the amount of each deletion variant can be affected by the type of cultured mammalian cells which produce the antibody according to the present invention and the culture conditions; however, an antibody in which one amino acid residue at the carboxyl terminus has been deleted in both of the two heavy chains in the antibody according to the present invention can be preferably exemplified.

As isotypes of the antibody according to the present invention, for example, IgG (IgG1, IgG2, IgG3, IgG4) can be exemplified, and IgG1 or IgG2 can be exemplified preferably.

Examples of antibodies applicable to the production of the antibody-drug conjugate of the present invention can include, but are not particularly limited to, an anti-HER2 antibody, an anti-HER3 antibody, an anti-TROP2 antibody, an anti-B7-H3 antibody, an anti-CD3 antibody, an anti-CD30 antibody, an anti-CD33 antibody, an anti-CD37 antibody, an anti-CD56 antibody, an anti-CD98 antibody, an anti-DR5 antibody, an anti-EGFR antibody, an anti-EPHA2 antibody, an anti-FGFR2 antibody, an anti-FGFR4 antibody, an anti-FOLR1 antibody, an anti-VEGF antibody, and an anti-GPR20 antibody, and preferably an anti-HER2 antibody, an anti-HER3 antibody, an anti-TROP2 antibody, an anti-B7-H3 antibody, and an anti-GPR20 antibody can be exemplified.

In the present invention, the term "anti-HER2 antibody" refers to an antibody which specifically binds to HER2 (Human Epidermal Growth Factor Receptor Type 2; ErbB-2), and preferably has an activity of internalizing in HER2-expressing cells by binding to HER2.

Examples of the anti-HER2 antibody can include trastuzumab (U.S. Pat. No. 5,821,337) and pertuzumab (International Publication No. WO 01/00245), and trastuzumab can be preferably exemplified.

In the present invention, the term "trastuzumab" is a humanized anti-HER2 monoclonal antibody comprising a heavy chain consisting of an amino acid sequence consisting of amino acid residues 1 to 449 of SEQ ID NO: 1 (FIG. 1) and a light chain consisting of an amino acid sequence consisting of amino acid residues 1 to 214 of SEQ ID NO: 2 (FIG. 2).

In the present invention, the term "anti-HER3 antibody" refers to an antibody which specifically binds to HER3 (Human Epidermal Growth Factor Receptor Type 3; ErbB-3), and preferably has an activity of internalizing in HER3-expressing cells by binding to HER3 on HER3-expressing cell surface.

Examples of the anti-HER3 antibody can include patritumab (U3-1287), U1-59 (International Publication No. WO 2007/077028), MM-121 (seribantumab), an anti-ERBB3 antibody described in International Publication No. WO 2008/100624, RG-7116 (lumretuzumab), and LJM-716 (elgemtumab), and patritumab and U1-59 can be preferably exemplified.

In the present invention, the term "anti-TROP2 antibody" refers to an antibody which specifically binds to TROP2 (TACSTD2: Tumor-associated calcium signal transducer 2; EGP-1), and preferably has an activity of internalizing in TROP2-expressing cells by binding to TROP2.

Examples of the anti-TROP2 antibody can include hTINA1-H1L1 (International Publication No. WO 2015/098099).

In the present invention, the term "anti-B7-H3 antibody" refers to an antibody which specifically binds to B7-H3 (B cell antigen #7 homolog 3; PD-L3; CD276), and preferably has an activity of internalizing in B7-H3-expressing cells by binding to B7-H3.

Examples of the anti-B7-H3 antibody can include M30-H1-L4 (International Publication No. WO 2014/057687).

In the present invention, the term "anti-GPR20 antibody" refers to an antibody which specifically binds to GPR20 (G protein-coupled receptor 20), and preferably has an activity of internalizing in GPR20-expressing cells by binding to GPR20.

Examples of the anti-GPR20 antibody can include h046-H4e/L7 (International Publication No. WO 2018/135501).

[Conjugation Between the Antibody and the Drug-Linker Intermediate]

The antibody-drug conjugate of the present invention can be produced by reacting the compound represented by the formula (1) and an antibody having a thiol group (alternatively referred to as a sulfhydryl group).

The crystals of the compound represented by the formula (1) of the present invention is preferably dissolved in a solvent to prepare a solution containing the compound represented by the formula (1), which can then be used in reaction. The solvent for use in this step is not particularly limited as long as the reaction is not inhibited. Preferably, a solvent containing dimethyl sulfoxide, dimethylformamide, dimethylacetamide, or N-methylpyrrolidone can be used, and a solvent containing dimethyl sulfoxide can be more preferably used.

The antibody having a sulfhydryl group can be obtained by a method well known in the art (Hermanson, G. T, Bioconjugate Techniques, pp. 56-136, pp. 456-493, Academic Press (1996)). For example, by using 0.3 to 3 molar equivalents of a reducing agent such as tris(2-carboxyethyl) phosphine hydrochloride (TCEP) per interchain disulfide within the antibody and reacting with the antibody in a buffer solution containing a chelating agent such as ethylenediamine tetraacetic acid (EDTA), an antibody having a sulfhydryl group with partially or completely reduced interchain disulfides within the antibody can be obtained.

Further, by using 2 to 20 molar equivalents of the compound represented by the formula (1) per antibody having a sulfhydryl group, an antibody-drug conjugate in which 2 to 8 drug molecules are conjugated per antibody molecule can be produced.

The average number of conjugated drug molecules per antibody molecule of the antibody-drug conjugate produced can be determined, for example, by a method of calculation based on measurement of UV absorbance for the antibody-drug conjugate and the conjugation precursor thereof at two wavelengths of 280 nm and 370 nm (UV method), or a method of calculation based on quantification through HPLC measurement for fragments obtained by treating the antibody-drug conjugate with a reducing agent (HPLC method).

Conjugation between the antibody and the drug-linker intermediate (compound represented by the formula (1)) and calculation of the average number of conjugated drug molecules per antibody molecule of the antibody-drug conjugate can be performed with reference to descriptions in International Publication No. WO 2014/057687, International Publication No. WO 2015/098099, International Publication No. WO 2015/115091, International Publication No. WO 2015/155998, and International Publication No. WO 2018/135501, and so on.

In the present invention, the term "anti-HER2 antibody-drug conjugate" refers to an antibody-drug conjugate in which the antibody in the antibody-drug conjugate is an anti-HER2 antibody.

The anti-HER2 antibody is preferably an antibody comprising a heavy chain consisting of an amino acid sequence consisting of amino acid residues 1 to 449 of SEQ ID NO: 1 and a light chain consisting of an amino acid sequence consisting of amino acid residues 1 to 214 of SEQ ID NO: 2, or an antibody comprising a heavy chain consisting of the amino acid sequence represented by SEQ ID NO: 1 and a light chain consisting of the amino acid sequence represented by SEQ ID NO: 2.

The average number of units of the drug-linker conjugated per antibody molecule in the anti-HER2 antibody-drug conjugate produced according to the present invention is preferably 2 to 8, more preferably 3 to 8, even more preferably 7 to 8, even more preferably 7.5 to 8, and even more preferably about 8.

The anti-HER2 antibody-drug conjugate can be produced with reference to descriptions in International Publication No. WO 2015/115091 and so on by using the crystals of the compound represented by the formula (1) produced by the production method of the present invention.

In the present invention, the term "anti-HER3 antibody-drug conjugate" refers to an antibody-drug conjugate such that the antibody in the antibody-drug conjugate is an anti-HER3 antibody.

The anti-HER3 antibody is preferably an antibody comprising a heavy chain consisting of the amino acid sequence represented by SEQ ID NO: 3 and a light chain consisting of the amino acid sequence represented by SEQ ID NO: 4, or a variant of the antibody in which a lysine residue at the carboxyl terminus of the heavy chain of the antibody is deleted.

The average number of units of the drug-linker conjugated per antibody molecule in the anti-HER3 antibody-drug conjugate produced according to the present invention is preferably 2 to 8, more preferably 3 to 8, even more preferably 7 to 8, even more preferably 7.5 to 8, and even more preferably about 8.

The anti-HER3 antibody-drug conjugate can be produced with reference to descriptions in International Publication No. WO 2015/155998 and so on by using the crystals of the compound represented by the formula (1) produced by the production method of the present invention.

In the present invention, the term "anti-TROP2 antibody-drug conjugate" refers to an antibody-drug conjugate such that the antibody in the antibody-drug conjugate is an anti-TROP2 antibody.

The anti-TROP2 antibody is preferably an antibody comprising a heavy chain consisting of an amino acid sequence consisting of amino acid residues 20 to 470 of SEQ ID NO: 5 and a light chain consisting of an amino acid sequence consisting of amino acid residues 21 to 234 of SEQ ID NO: 6, or a variant of the antibody in which a lysine residue at the carboxyl terminus of the heavy chain of the antibody is deleted.

The average number of units of the drug-linker conjugated per antibody molecule in the anti-TROP2 antibody-drug conjugate produced according to the present invention is preferably 2 to 8, more preferably 3 to 5, even more preferably 3.5 to 4.5, and even more preferably about 4.

The anti-TROP2 antibody-drug conjugate can be produced with reference to descriptions in International Publication No. WO 2015/098099 and so on by using the crystals of the compound represented by the formula (1) produced by the production method of the present invention.

In the present invention, the term "anti-B7-H3 antibody-drug conjugate" refers to an antibody-drug conjugate such that the antibody in the antibody-drug conjugate is an anti-B7-H3 antibody.

The anti-B7-H3 antibody is preferably an antibody comprising a heavy chain consisting of an amino acid sequence consisting of amino acid residues 20 to 471 of SEQ ID NO: 7 and a light chain consisting of an amino acid sequence consisting of amino acid residues 21 to 233 of SEQ ID NO: 8, or a variant of the antibody in which a lysine residue at the carboxyl terminus of the heavy chain of the antibody is deleted.

The average number of units of the drug-linker conjugated per antibody molecule in the anti-B7-H3 antibody-drug conjugate produced according to the present invention is preferably 2 to 8, more preferably 3 to 5, even more preferably 3.5 to 4.5, and even more preferably about 4.

The anti-B7-H3 antibody-drug conjugate can be produced with reference to descriptions in International Publication No. WO 2014/057687 and so on by using the crystals of the compound represented by the formula (1) produced by the production method of the present invention.

In the present invention, the term "anti-GPR20 antibody-drug conjugate" refers to an antibody-drug conjugate such that the antibody in the antibody-drug conjugate is an anti-GPR20 antibody.

The anti-GPR20 antibody is preferably an antibody comprising a heavy chain consisting of an amino acid sequence consisting of amino acid residues 20 to 472 of SEQ ID NO: 9 and a light chain consisting of an amino acid sequence consisting of amino acid residues 21 to 234 of SEQ ID NO: 10, or a variant of the antibody in which a lysine residue at the carboxyl terminus of the heavy chain of the antibody is deleted.

The average number of units of the drug-linker conjugated per antibody molecule in the anti-GPR20 antibody-drug conjugate produced according to the present invention is preferably 2 to 8, more preferably 3 to 8, even more preferably 7 to 8, even more preferably 7.5 to 8, and even more preferably about 8.

The anti-GPR20 antibody-drug conjugate can be produced with reference to descriptions in International Publication No. WO 2018/135501 and so on by using the crystals of the compound represented by the formula (1) produced by the production method of the present invention.

[Pharmaceutical Compositions]

The antibody-drug conjugate produced by the present invention can contain at least one pharmaceutically suitable ingredient and be administered. The pharmaceutically suitable ingredient can be suitably selected and applied from formulation additives or the like that are generally used in the art, according to the dosage, administration concentration, and so on of the antibody-drug conjugate produced by the present invention. For example, the antibody-drug conjugate produced by the present invention can be administered as a pharmaceutical composition containing a buffer such as a histidine buffer, an excipient such as sucrose or trehalose, and a surfactant such as polysorbate 80 or polysorbate 20.

The pharmaceutical composition containing the antibody-drug conjugate produced by the present invention can be expected to exert a therapeutic effect by application as a systemic therapy to patients, and additionally, by local application to cancer tissues.

The pharmaceutical composition containing the antibody-drug conjugate produced by the present invention can be preferably used for a mammal, and can be more preferably used for a human.

The pharmaceutical composition containing the antibody-drug conjugate produced by the present invention can be preferably used as an injection, can be more preferably used as an aqueous injection or a lyophilized injection, and can be even more preferably used as a lyophilized injection.

In the case that the pharmaceutical composition containing the antibody-drug conjugate produced by the present invention is an aqueous injection, preferably, it can be diluted with a suitable diluent and then intravenously administered by drip infusion. Examples of the diluent can include glucose solution (preferably a 5% glucose solution) and physiological saline.

In the case that the pharmaceutical composition containing the antibody-drug conjugate produced by the present invention is a lyophilized injection, preferably, it can be dissolved in water for injection, and then, a necessary amount can be diluted with a suitable diluent and then intravenously administered by drip infusion. Examples of the diluent can include a glucose solution (preferably a 5% glucose solution) and physiological saline.

Examples of administration routes that can be used for administering the pharmaceutical composition containing the antibody-drug conjugate produced by the present invention can include intravenous, intradermal, subcutaneous, intramuscular, and intraperitoneal routes, and an intravenous route can be preferably exemplified.

The antibody-drug conjugate produced by the present invention can be administered to a human at intervals of once a day to every 180 days, preferably can be administered at intervals of once a week, every 2 weeks, every 3 weeks, or every 4 weeks, and even more preferably can be administered at intervals of once every 3 weeks. Also, the antibody-drug conjugate produced by the present invention can be administered at a dosage of about 0.001 to 100 mg/kg per dose, and preferably can be administered at a dosage of 0.8 to 12.4 mg/kg per dose. In the case that the antibody-drug conjugate produced by the present invention is an anti-HER2 antibody-drug conjugate, it can be preferably administered at a dosage of 5.4, 6.4, or 7.4 mg/kg per dose, and more preferably can be administered at a dosage of 5.4 mg/kg or 6.4 mg/kg per dose.

The pharmaceutical composition containing the antibody-drug conjugate produced by the present invention can be used for treating cancer, and can be preferably used for treating at least one type of cancer selected from the group consisting of breast cancer, gastric cancer (also called gastric adenocarcinoma), colorectal cancer (also called colon and rectal cancer, and including colon cancer and rectal cancer), lung cancer (including small cell lung cancer and non-small cell lung cancer), esophageal cancer, salivary gland cancer, esophagogastric junction adenocarcinoma, bile duct cancer, Paget's disease, pancreatic cancer, ovarian cancer, uterine carcinosarcoma, urothelial cancer, prostate cancer, bladder cancer, gastrointestinal stromal tumor, digestive stromal tumor, uterine cervix cancer, squamous cell carcinoma, peritoneal cancer, liver cancer, hepatocellular cancer, colon cancer, rectal cancer, endometrial cancer, uterine cancer, kidney cancer, vulval cancer, thyroid cancer, penile cancer, leukemia, malignant lymphoma, plasmacytoma, myeloma, neuroepithelial tissue tumor, nerve sheath tumor, head-and-neck cancer, skin cancer, pharyngeal cancer, gallbladder cancer, bile duct cancer, mesothelioma, and sarcoma, and in the case that the antibody-drug conjugate produced by the present invention is an anti-HER2 antibody-drug conjugate, for example, it can be more preferably used for treating at least one type of cancer selected from the group consisting of breast cancer, gastric cancer, colorectal cancer, non-small cell lung cancer, esophageal cancer, salivary gland cancer, esophagogastric junction adenocarcinoma, bile duct cancer, Paget's disease, pancreatic cancer, ovarian cancer, and uterine carcinosarcoma, and can be even more preferably used for treating at least one type of cancer selected from the group consisting of breast cancer, gastric cancer, colorectal cancer, non-small cell lung cancer, esophageal cancer, salivary gland cancer, esophagogastric junction adenocarcinoma, bile duct cancer, and Paget's disease, and can be even more preferably used for treating breast cancer, gastric cancer, colorectal cancer, or non-small cell lung cancer.

The pharmaceutical composition containing the antibody-drug conjugate produced by the present invention can be selectively used as an agent for drug therapy, which is a main method for treating cancer, and as a result, can delay development of cancer cells, inhibit growth thereof, and further kill cancer cells. These effects can allow cancer patients to be free from symptoms caused by cancer or achieve improvement in QOL of cancer patients and attain a therapeutic effect by sustaining the lives of the cancer patients. Even if the pharmaceutical composition and therapeutic method of the present invention do not accomplish killing cancer cells, it can achieve higher QOL of cancer patients while achieving longer-term survival, by inhibiting or controlling the growth of cancer cells.

In such drug therapy, the pharmaceutical composition containing the antibody-drug conjugate produced by the present invention can be used as an agent alone and in addition, it can be used in combination with an additional therapy in adjuvant therapy and can be combined with surgery, radiotherapy, hormone therapy, or the like. Furthermore, it can also be used as an agent for drug therapy in neoadjuvant therapy.

In addition to the therapeutic use as described above, for example, a prophylactic effect such as suppressing the growth of small metastatic cancer cells and further killing them can also be expected for the pharmaceutical composition containing the antibody-drug conjugate produced by the present invention. For example, an effect of inhibiting and killing cancer cells in a body fluid in the course of metastasis or an effect of, for example, inhibiting and killing small cancer cells immediately after implantation in any tissue can be expected. Accordingly, inhibition of cancer metastasis or a prophylactic effect can be expected, particularly, after surgical removal of cancer.

The pharmaceutical composition containing the antibody-drug conjugate produced by the present invention can be administered in combination with other cancer treating agents. The anti-cancer effect may be enhanced accordingly. Examples of other cancer treating agents used for such purpose can include 5-fluorouracil (5-FU), pertuzumab, trastuzumab, paclitaxel, carboplatin, cisplatin, gemcitabine, capecitabine, irinotecan (CPT-11), docetaxel, pemetrexed, sorafenib, vinblastin, vinorelbine, everolims, tanespimycin, bevacizumab, oxaliplatin, lapatinib, trastuzumab emtansine (T-DM1) or agents described in International Publication No. WO 2003/038043, LH-RH analogues (leuprorelin, goserelin, or the like), estramustine phosphate, estrogen antagonists (tamoxifen, raloxifene, or the like), and aromatase inhibitors (anastrozole, letrozole, exemestane, or the like), but are not limited as long as they are agents having an antitumor activity.

EXAMPLES

The present invention is described in more detail below by way of examples. However, the present invention is not limited to these.

In the Examples, the terms "$^1$H-NMR" and "$^{13}$C-NMR" mean "nuclear magnetic resonance spectrum". Within parentheses, CDCl$_3$ means deuterated chloroform which is a measuring solvent, DMSO-d$_6$ means deuterated dimethyl sulfoxide which is a measuring solvent, D$_2$O means deuterium oxide which is a measuring solvent, and MeOH-d$_4$ means deuterated methanol which is a measuring solvent. TMS (tetramethylsilane) was used as an internal standard.

The meanings of multiplicity in $^1$H-NMR are s=singlet, d=doublet, t=triplet, q=quartet, m=multiplet, and brs=broad singlet.

Example 1

2,5-Dioxopyrrolidin-1-yl N-[(benzyloxy)carbonyl]glycylglycinate

[Chem. 91]

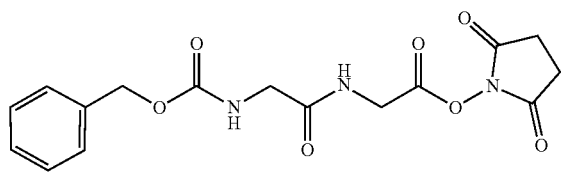

(24)

To a mixture of N-[(benzyloxy)carbonyl]glycylglycine (200.00 g, 0.751 mol) and acetonitrile (2.0 L), N-hydroxysuccinimide (95.10 g, 0.826 mol) and 1-(3-dimethylaminopropyl)-3-ethylcarbodiimide hydrochloride (172.80 g, 0.901 mol) were added, and the resulting mixture was stirred at room temperature for about 4 hours. The reaction solution was cooled to 1° C. and stirred for about 3 hours. Precipitates were filtered, and a powder separated by the filtration was washed with acetonitrile (400 mL). The obtained powder was dried under reduced pressure at 40° C. to obtain 2,5-dioxopyrrolidin-1-yl N-[(benzyloxy)carbonyl] glycylglycinate (221.6 g, 0.610 mol, yield: 81.2%).

$^1$H-NMR (400 MHz, DMSO-$d_6$) δ 2.81 (4H, s), δ 3.69 (2H, d, 6.7 Hz), δ 4.28 (2H, d, 6.1 Hz), δ 5.04 (2H, s), δ 7.29-7.39 (5H, m), δ 7.56 (1H, t, 6.4 Hz), δ 8.55 (1H, t, 5.8 Hz).

$^{13}$C-NMR (100 MHz, DMSO-$d_6$) δ 25.4, 38.2, 43.3, 65.6, 127.7, 127.8, 128.3, 137.0, 156.5, 166.3, 170.0, 170.0.

MS (ESI) (m/z): 364 ([M+H]$^+$).

Example 2

N-[(Benzyloxy)carbonyl]glycylglycyl-L-phenylalanine

[Chem. 92]

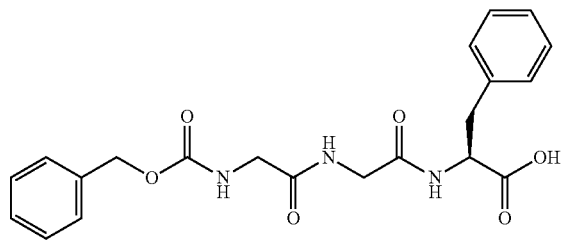

(6)

To a mixture of L-phenylalanine (80.0 g, 0.487 mol), acetonitrile (400 mL), and water (400 mL), triethylamine (74.7 mL, 0.536 mol) and 2,5-dioxopyrrolidin-1-yl N-[(benzyloxy)carbonyl]glycylglycinate (212.4 g, 0.585 mol) were added, and the resulting mixture was stirred at room temperature for about 2 hours. Water (800 mL) and concentrated hydrochloric acid (40.6 mL) were added to the reaction solution, then N-[(benzyloxy)carbonyl]glycylglycyl-L-phenylalanine (80 mg) was added, and the resulting mixture was stirred at room temperature for about 6 hours. Precipitates were filtered, and a powder separated by the filtration was washed with water (160 mL). The obtained powder was dried under reduced pressure at 40° C. to obtain N-[(benzyloxy)carbonyl]glycylglycyl-L-phenylalanine (157.2 g, 0.380 mol, yield: 78.0%).

$^1$H-NMR (400 MHz, DMSO-$d_6$) δ 2.86-2.91 (1H, m), δ 3.03-3.08 (1H, m), δ 3.64-3.78 (4H, m), δ 4.41-4.47 (1H, m), δ 5.04 (2H, s), δ 7.18-7.40 (10H, m), δ 7.50 (1H, t, 6.1 Hz), δ 8.05 (1H, t, 5.8 Hz), δ 8.17 (1H, d, 7.9 Hz), δ 12.77 (1H, s).

$^{13}$C-NMR (100 MHz, DMSO-$d_6$) δ 36.8, 41.6, 43.5, 53.5, 65.5, 126.5, 127.7, 127.8, 128.2, 128.3, 129.1, 137.0, 137.4, 156.5, 168.6, 169.3, 172.7.

MS (ESI) (m/z): 412 ([M−H]$^−$).

Example 3

({N-[(9H-Fluoren-9-ylmethoxy) carbonyl] glycyl}amino)methyl acetate

[Chem. 93]

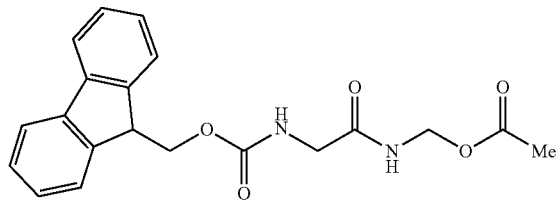

(3)

To N-[(9H-fluoren-ylmethoxy)carbonyl]glycylglycine (650.0 g, 1.834 mol), tetrahydrofuran (9.75 L) and acetic acid (1.95 L) were added, and the resulting mixture was dissolved by warming to 40° C. Lead tetraacetate (1301.3 g, 2.935 mol) was added thereto, and the resulting mixture was refluxed for about 1.5 hours. After cooling to room temperature, insoluble matter was filtered off, then the insoluble matter separated by the filtration was washed with ethyl acetate (3.25 L), and the washes were combined with the filtrate. A 20 (w/v )% aqueous trisodium citrate dihydrate solution (3.25 L) was added to the obtained solution, and the resulting mixture was stirred and separated into organic and aqueous layers. The aqueous layer was removed. The obtained organic layer was washed twice with a 20 (w/v )% aqueous trisodium citrate dihydrate solution (3.25 L), and then, the organic layer was concentrated to 6.5 L under reduced pressure. Water (1.95 L) was added to the residue, then ({N-[(9H-fluoren-9-ylmethoxy)carbonyl] glycyl}amino)methyl acetate (0.65 g) was added, and the resulting mixture was stirred at room temperature for about 1 hour. Water (6.5 L) was added dropwise thereto, and the resulting mixture was cooled to 0 to 5° C. and stirred for about 3 hours. Precipitates were filtered, and a powder separated by the filtration was washed with a cold 30 (v/v )% aqueous tetrahydrofuran solution (2.6 L). The obtained powder was dried under reduced pressure at 40° C. to obtain ({N-[(9H-fluoren-9-ylmethoxy)carbonyl]glycyl}amino) methyl acetate (617.1 g, 1.675 mol, yield: 91.3%).

$^1$H-NMR (400 MHz, CDCl$_3$) δ 2.06 (3H, s), δ 3.90 (2H, d, 4.9 Hz), δ 4.23 (1H, t, 6.7 Hz), δ 4.45 (2H, d, 6.7 Hz), δ 5.25 (2H, d, 7.3 Hz), δ 5.39 (1H, brs), δ 7.05 (1H, brs), δ 7.30-7.34 (2H, m), δ 7.41 (2H, t, 7.3 Hz), δ 7.59 (2H, d, 7.3 Hz), δ 7.77 (2H, d, 7.3 Hz).

$^{13}$C-NMR (100 MHz, CDCl$_3$) δ 20.8, 44.4, 47.0, 63.9, 67.2, 120.0, 125.0, 127.1, 127.7, 141.3, 143.6, 156.6, 169.8, 171.7.

MS (ESI) (m/z): 369 ([M+H]$^+$).

Example 4

Benzyl [({N-[(9H-fluoren-9-ylmethoxy)carbonyl] glycyl}amino)methoxy]acetate

[Chem. 94]

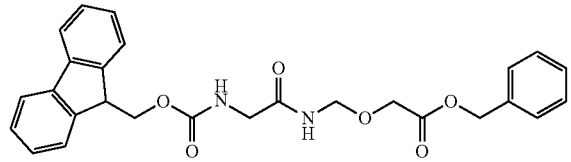

(4)

To a mixture of ({N-[(9H-fluoren-9-ylmethoxy)carbonyl] glycyl}amino)methyl acetate (610.0 g, 1.656 mol) and 1,2-dimethoxyethane (9.15 L), benzyl glycolate (470 mL, 3.312 mol) was added, and the resulting mixture was cooled to 0 to 5° C. A 10 mol/L sodium hydroxide solution (162.6 mL, 1.626 mol) was added thereto, and the resulting mixture was stirred for about 1 hour. Acetic acid (47.4 mL) was added thereto, and the resulting mixture was stirred at 1° C. for about 1 hour. Then, water (2.0 L) was added dropwise thereto, then benzyl [({N-[(9H-fluoren-9-ylmethoxy)carbonyl]glycyl}amino)methoxy]acetate (0.61 g) was added, and the resulting mixture was stirred at 0 to 5° C. for about 1 hour. Water (4.7 L) was added dropwise thereto, and the resulting mixture was stirred at 0 to 5° C. for about 2.5 hours. Precipitates were filtered, and a powder separated by the filtration was washed with a cold 50 (v/v)% aqueous 1,2-dimethoxyethane solution (2.44 L). To the obtained wet powder, 1,2-dimethoxyethane (9.15 L) was added, and the resulting mixture was dissolved by stirring at room temperature for about 30 minutes. Water (3.66 L) was added thereto, then benzyl [({N-[(9H-fluoren-9-ylmethoxy)carbonyl]glycyl}amino)methoxy]acetate (0.61 g) was added, and the resulting mixture was stirred at room temperature for about 1 hour. Water (3.05 L) was added dropwise thereto, and the resulting mixture was stirred at room temperature for about 1 hour. After cooling to 0 to 5° C. and stirring for about 1 hour, precipitates were filtered, and a powder separated by the filtration was washed with a cold 50 (v/v)% aqueous 1,2-dimethoxyethane solution (2.44 L). To the obtained wet powder, 1,2-dimethoxyethane (9.0 L) was added, and the resulting mixture was dissolved by stirring at room temperature for about 30 minutes. Water (3.6 L) was added thereto, then benzyl [({N-[(9H-fluoren-9-ylmethoxy)carbonyl]glycyl}amino)methoxy]acetate (0.01 g) was added, and the resulting mixture was stirred at room temperature for about 1 hour. Water (3.0 L) was added dropwise thereto, and the resulting mixture was stirred at room temperature for about 1 hour. After cooling to 0 to 5° C. and stirring for about 1 hour, precipitates were filtered, and a powder separated by the filtration was washed with a cold 50% (v/v) aqueous 1,2-dimethoxyethane solution (2.4 L). To the obtained wet powder, 1,2-dimethoxyethane (9.0 L) was added, and the resulting mixture was dissolved by stirring at room temperature for about 20 minutes. Water (3.6 L) was added thereto, then benzyl [({N-[(9H-fluoren-9-ylmethoxy)carbonyl]glycyl}amino)methoxy]acetate (0.15 g) was added, and the resulting mixture was stirred at room temperature for about 2 hours. Water (3.0 L) was added dropwise thereto, and the resulting mixture was stirred at room temperature for about 1 hour. After cooling to 0 to 5° C. and stirring for about 2 hours, precipitates were filtered, and a powder separated by the filtration was washed with a cold 50 (v/v)% aqueous 1,2-dimethoxyethane solution (2.4 L). The obtained powder was dried under reduced pressure at 40° C. to obtain crude benzyl [({N-[(9H-fluoren-9-ylmethoxy)carbonyl] glycyl}amino)methoxy] acetate. To the obtained crude benzyl [({N-[(9H-fluoren-9-ylmethoxy)carbonyl] glycyl}amino)methoxy]acetate, toluene (12 L) was added, and the resulting mixture was dissolved by heating to 70° C. After cooling to 0 to 5° C. and stirring for about 2 hours, precipitates were filtered, and a powder separated by the filtration was washed with cold toluene (2.4 L). The obtained powder was dried under reduced pressure at 40° C. to obtain benzyl [({N-[(9H-fluoren-9-ylmethoxy)carbonyl] glycyl}amino)methoxy]acetate (575.5 g, 1.213 mol, yield: 73.2%).

$^1$H-NMR (400 MHz, CDCl$_3$) δ 3.82 (2H, d, 4.9 Hz), δ 4.19-4.22 (3H, m), δ 4.45 (2H, d, 6.7 Hz), δ 4.83 (2H, d, 6.7 Hz), δ 5.15 (2H, s), δ 5.34 (1H, brs), δ 6.95 (1H, brs), δ 7.29-7.37 (7H, m), δ 7.40 (2H, t, 7.3 Hz), δ 7.58 (2H, d, 7.3 Hz), δ 7.76 (2H, d, 7.9 Hz).

$^{13}$C-NMR (100 MHz, CDCl$_3$) δ 44.5, 47.1, 66.6, 66.8, 67.1, 70.6, 120.0, 124.9, 127.1, 127.8, 128.4, 128.5, 128.6, 135.2, 141.3, 143.6, 170.2, 170.2, 170.4.

MS (ESI) (m/z): 475 ([M+H]$^+$).

Example 5

Glycylglycyl-L-phenylalanyl-N-[(carboxymethoxy) methyl]glycinamide ("glycylglycyl-phenylalanyl-glycinamide" disclosed as SEQ ID NO: 11)

[Chem. 95]

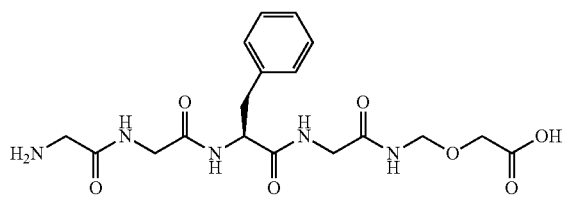

(8)

To a mixture of benzyl [({N-[(9H-fluoren-9-ylmethoxy) carbonyl]glycyl}amino)methoxy]acetate (340.0 g, 0.717 mol) and acetonitrile (10.2 L), 1,8-diazabicyclo[5,4,0]-7-undecene (53.6 mL, 0.358 mol) was added, and the resulting mixture was stirred at room temperature for about 2 hours. After cooling to 0 to 5° C., 1-hydroxybenzotriazole monohydrate (132.0 g, 0.862 mol) and N-[(benzyloxy)carbonyl] glycylglycyl-L-phenylalanine (311.0 g, 0.752 mol) were added thereto, then 1-(3-dimethylaminopropyl)-3-ethylcarbodiimide hydrochloride (158.0 g, 0.824 mol) was added in divided portions, and the resulting mixture was stirred at 0 to 5° C. for about 1 hour. A 10 (w/v)% phosphate buffer solution (pH 3, 3.4 L) was added thereto, and the resulting mixture was warmed to room temperature. After separation into organic and aqueous layers and removal of the aqueous layer, the organic layer was concentrated to 3.7 L under reduced pressure. Ethyl acetate (3.4 L) and water (1.7 L) were added to the residue, and the resulting mixture was separated into organic and aqueous layers. The aqueous layer was removed. A 10 (w/v )% aqueous potassium bicarbonate solution (3.4 L) was added thereto, and the resulting mixture was separated into organic and aqueous layers. The aqueous layer was removed. A 10 (w/v )% aqueous potassium bicarbonate solution (3.4 L) was added thereto, and the resulting mixture was stirred and separated into organic and aqueous layers. The aqueous layer was removed. Water (3.4 L) was added thereto, and the resulting mixture was stirred. After separation into organic and aqueous layers and removal of the aqueous layer, the organic layer was concentrated to 1.5 L under reduced pressure. 2-Methoxyethanol (3.74 L) was added to the residue, and the resulting mixture was concentrated to 3.06 L under reduced pressure. The residue was transferred to a 20 L autoclave, then tetrahydrofuran (1.36 L), water (3.4 L), and 5% palladium carbon (72.6 g, water content: 53.2%) were added thereto, and the atmosphere was exchanged to hydrogen. After stirring at room temperature for about 19 hours, the atmosphere was exchanged to nitrogen, then water (360 mL) was added thereto, and the resulting mixture was stirred at room temperature for about 30 minutes. The palladium carbon was separated by filtration, then the palladium carbon was washed with water (1.36 L), and the washes were combined with the filtrate. Ethyl acetate (0.85 L) and n-heptane (2.55 L) were added thereto, and the resulting mixture was stirred and then separated into organic and aqueous layers. The organic layer was removed and concentrated to 1.6 L under reduced pressure. Water (221 mL) and 2-methoxyethanol (126 mL) were added to the residue, then glycylglycyl-L-phenylalanyl-N-[(carboxymethoxy)methyl]glycinamide ("glycylglycyl-phenylalanyl-glycinamide" disclosed as SEQ ID NO: 11) (0.34 g) was added, and the resulting mixture was heated to 40° C. and stirred for about 19 hours. Ethanol (3.4 L) was added dropwise thereto, and the resulting mixture was stirred at room temperature for about 18 hours. Precipitates were filtered, and a powder separated by the filtration was washed with ethanol (1.02 L). The obtained powder was dried under reduced pressure at 40° C. to obtain glycylglycyl-L-phenylalanyl-N-[(carboxymethoxy)methyl]glycinamide ("glycylglycyl-phenylalanyl-glycinamide" disclosed as SEQ ID NO: 11) (243.7 g, 0.576 mol, yield: 80.3%).

$^1$H-NMR (400 MHz, D$_2$O) δ 3.03-3.20 (2H, m), δ 3.79-3.96 (6H, m), δ 3.97 (2H, s), δ 4.64 (1H, t, 7.9 Hz), δ 4.67-4.75 (2H, m), δ 7.29-7.42 (5H, m).

$^{13}$C-NMR (100 MHz, D$_2$O) δ 37.3, 41.0, 42.7, 43.2, 56.0, 67.3, 70.0, 127.8, 129.4, 129.8, 136.9, 168.4, 171.7, 172.9, 174.4, 178.1.
MS (ESI) (m/z): 422 ([M−H]$^−$).

Example 6

Benzyl [(glycylamino)methoxy]acetate 1H-benzotriazol-1-ol

[Chem. 96]

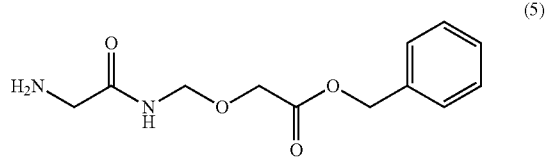

(5)

To a mixture of benzyl [({N-[(9H-fluoren-9-ylmethoxy)carbonyl]glycyl}amino)methoxy]acetate (50.00 g, 105.4 mmol) and acetonitrile (1.5 L), 1,8-diazabicyclo[5,4,0]-7-undecene (8.02 g, 52.7 mmol) was added, and the resulting mixture was stirred at room temperature for about 4 hours. 1-Hydroxybenzotriazole monohydrate (35.51 g, 231.9 mmol) was added thereto in divided portions at room temperature, and the resulting mixture was stirred for about 30 minutes. The reaction mixture was cooled to 1° C. and stirred for about 11 hours. Precipitates were filtered, and a powder separated by the filtration was washed with acetonitrile (250 mL). The obtained powder was dried under reduced pressure at 40° C. to obtain benzyl [(glycylamino)methoxy]acetate 1H-benzotriazol-1-ol (38.98 g, 100.6 mol, yield: 95.4%).

$^1$H-NMR (500 MHz, MeOH-d4) δ 3.63-3.68 (2H, brs), δ 4.19-4.23 (2H, brs), δ 4.79 (2H, s), δ 5.16-5.20 (2H, brs), δ 7.25-7.38 (7H, m), δ 7.64-7.72 (2H, dd, 17.3 Hz, 7.8 Hz).

$^{13}$C-NMR (125 MHz, MeOH-d$_4$) δ 41.9, 66.3, 67.6, 71.0, 112.3, 118.7, 125.24, 125.27, 128.8, 129.25, 129.30, 129.5, 136.9, 144.4, 169.5, 171.8

Example 7

N-[(Benzyloxy)carboxyl]glycylglycyl-L-phenylalanyl-N-{[2-(benzyloxy)-2-oxoethoxy]methyl}glycinamide ("glycylglycyl-phenylalanyl-glycinamide" disclosed as SEQ ID NO: 11)

[Chem. 97]

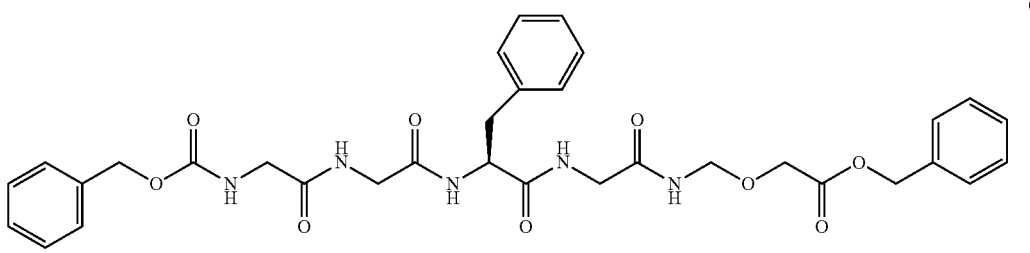

(7)

To a mixture of N-[(benzyloxy)carbonyl]glycylglycyl-L-phenylalanine (10.99 g, 26.58 mmol), acetonitrile (120 mL), and water (20 mL), benzyl [(glycylamino)methoxy]acetate 1H-benzotriazol-1-ol (10.00 g, 25.81 mmol) was added, and the resulting mixture was cooled to 2° C. 1-(3-Dimethylaminopropyl)-3-ethylcarbodiimide hydrochloride (5.70 g, 29.73 mmol) was added thereto, and the resulting mixture was stirred at 0 to 5° C. for about 3.5 hours. Ethanol (100 mL) and water (150 mL) were added to the reaction solution, and the resulting mixture was stirred at room temperature for 14 hours. Water (130 mlL) was added thereto in divided portions, and the resulting mixture was stirred for 2 hours, then cooled to 1° C., and stirred for about 1 hour. Precipitates were filtered, and a powder separated by the filtration was washed with acetonitrile:water=1:2 (60 mL). The obtained powder was dried under reduced pressure at 40° C. to obtain N-[(benzyloxy)carboxyl]glycylglycyl-L-phenylalanyl-N-{[2-(benzyloxy)-2-oxoethoxy]methyl}glycinamide ("glycylglycyl-phenylalanyl-glycinamide" disclosed as SEQ ID NO: 11) (15.34 g, 23.68 mmol, yield: 91.7%).

$^1$H-NMR (500 MHz, DMSO-d$_6$) δ 2.79 (1H, dd, 14 Hz, 9.2 Hz), δ 3.06 (1H, dd, 14 Hz, 4.5 Hz), δ 3.55-3.80 (6H, m), δ 4.15 (2H, s), δ 4.51 (1H, ddd, Hz, 9.2 Hz, 8.6 Hz, 4.5 Hz), δ 4.63 (2H, d, 6.5 Hz), δ 5.03 (2H, s), δ 5.15 (2H, s), δ 7.15-7.40 (15H, m), δ 7.15-7.40 (15H, m), δ 7.50 (1H, t, 6 Hz), δ 8.02 (1H, t, 5.8 Hz), δ 8.15 (1H, d, 8.6 Hz), δ 8.33 (1H, t, 5.8 Hz), δ 8.60 (1H, t, 7 Hz)

$^{13}$C-NMR (125 MHz, DMSO-d$_6$) δ 37.4, 41.9, 42.2, 43.6, 54.2, 64.5, 65.6, 65.7, 69.1, 126.3, 127.77, 127.85, 128.10, 128.14, 128.2, 128.4, 128.5, 129.2, 135.8, 137.0, 137.9, 156.6, 168.9, 169.5, 169.9, 170.2, 171.5.

Example 8

Glycylglycyl-L-phenylalanyl-N-[(carboxymethoxy)methyl] glycinamide ("glycylglycyl-phenylalanyl-glycinamide" disclosed as SEQ ID NO: 11)

[Chem. 98]

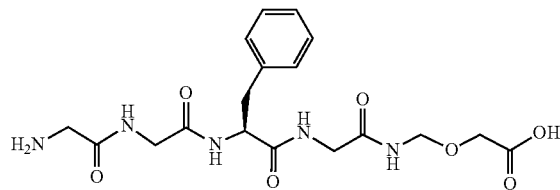

(8)

To a mixture of N-[(benzyloxy)carboxyl]glycylglycyl-L-phenylalanyl-N-{[2-(benzyloxy)-2-oxoethoxy]methyl}glycinamide ("glycylglycyl-phenylalanyl-glycinamide" disclosed as SEQ ID NO: 11) (15.0 g, 23.16 mmol), tetrahydrofuran (315 mL), and water (210 mL), 5% palladium carbon (3.31 g, water content: 54.7%) was added, and the atmosphere was exchanged to hydrogen. After stirring at room temperature for about 2.5 hours, the atmosphere was exchanged to nitrogen. The palladium carbon was separated by filtration, then the palladium carbon was washed with water (60 mL), and the washes were combined with the filtrate. The resulting filtrate was concentrated to 240 mL under reduced pressure. Ethanol (150 mL) was added to the residue, and the resulting mixture was concentrated to 180 mL under reduced pressure. Ethanol (150 mL) was added to the residue, and the resulting mixture was concentrated to 135 mL under reduced pressure. Ethanol (150 mL) was added to the residue, and the resulting mixture was concentrated to 90 mL under reduced pressure. Ethanol (300 mL) was added to the residue, and the resulting mixture was stirred for 17 hours. Precipitates were filtered, and a powder separated by the filtration was washed with ethanol (75 mL). The obtained powder was dried under reduced pressure at 40° C. to obtain glycylglycyl-L-phenylalanyl-N-[(carboxymethoxy)methyl]glycinamide ("glycylglycyl-phenylalanyl-glycinamide" disclosed as SEQ ID NO: 11) (8.95 g, 21.14 mmol, yield: 91.3%).

$^1$H-NMR (400 MHz, D$_2$O) δ 3.03-3.20 (2H, m), δ 3.79-3.96 (6H, m), δ 3.97 (2H, s), δ 4.64 (1H, t, 7.9 Hz), δ 4.67-4.75 (2H, m), δ 7.29-7.42 (5H, m).

$^{13}$C-NMR (100 MHz, D$_2$O) δ 37.3, 41.0, 42.7, 43.2, 56.0, 67.3, 70.0, 127.8, 129.4, 129.8, 136.9, 168.4, 171.7, 172.9, 174.4, 178.1.

MS (ESI) (m/z): 422 ([M–H]$^-$).

Example 9

6-(2,5-Dioxo-2,5-dihydro-1H-pyrrol-1-yl)hexanoic acid

[Chem. 99]

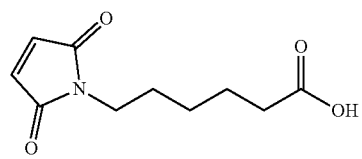

(18)

To a solution of 6-aminohexanoic acid (2.5 kg, 19.1 mol) in acetic acid (10 L), a solution of maleic anhydride (1.87 kg, 19.1 mol) in acetic acid (10 L) was added dropwise at 25 to 30° C. over 1 hour, and the resulting mixture was stirred at the same temperature as the above for 2 hours. To the obtained slurry, sulfuric acid (0.93 kg, 9.55 mol) was added dropwise, and the resulting mixture was heated to 100° C. and then stirred for 16 hours. The reaction solution was cooled to 30° C. and then concentrated to 7.0 L under reduced pressure. The obtained concentrate (about 7.0 L) was added dropwise to cold water (20 L) of 0 to 5° C. over 1 hour under stirring conditions, and the resulting mixture was stirred at the same temperature as the above for 1 hour. Precipitates were filtered, and a powder separated by the filtration was washed with cold water (5.0 L). The obtained powder was dried under reduced pressure at 40° C. to obtain 6-(2,5-dioxo-2,5-dihydro-1H-pyrrol-1-yl)hexanoic acid (1.46 kg, 6.95 mol, yield: 36.4%).

The obtained 6-(2,5-dioxo-2,5-dihydro-1H-pyrrol-1-yl)hexanoic acid (1.40 kg, 6.66 mol) was dissolved in a mixed solution of acetic acid (2.1 L) and purified water (1.4 L) at 25 to 30° C. To the solution, purified water (0.7 L) was added, and then, the resulting mixture was cooled to 20 to 25° C. and then stirred for 2 hours. To the obtained suspension, purified water (7.0 L) was added dropwise over 1 hour, and the resulting mixture was cooled to 0 to 5° C. and then stirred for 1 hour. Precipitates were filtered, and a powder separated by the filtration was washed with cold water (2.1 L). The obtained powder was dried under reduced pressure at 40° C. to obtain 6-(2,5-dioxo-2,5-dihydro-1H-pyrrol-1-yl)hexanoic acid (1.27 kg, 6.02 mol, yield: 90.4%).

$^1$H-NMR (400 MHz, DMSO-d$_6$) δ 1.18-1.24 (2H, m), δ 1.45-1.52 (4H, m), δ 2.18 (2H, t, 7.5 Hz), δ 3.38 (2H, t, 7.5 Hz), δ 7.01 (2H, s), δ 11.98 (1H, s).

Example 10

1-{6-[(2,5-Dioxopyrrolidin-1-yl)oxy]-6-oxohexyl}-1H-pyrrole-2,5-dione

[Chem. 100]

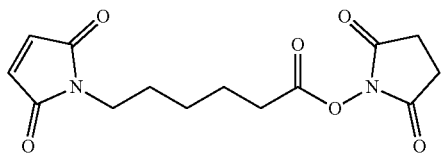

(9)

To a mixture of 6-(2,5-dioxo-2,5-dihydro-1H-pyrrol-1-yl)hexanoic acid (5.0 g, 23.6 mmol), N-hydroxysuccinimide (3.0 g, 26.0 mmol), and acetonitrile (50 mL), 1-(3-dimethylaminopropyl)-3-ethylcarbodiimide hydrochloride (5.45 g, 28.4 mmol) was added, and the resulting mixture was stirred at room temperature for about 3.5 hours. Water (100 mL) and toluene (100 mL) were added thereto, and the resulting mixture was stirred and then separated into organic and aqueous layers. The aqueous layer was removed. The organic layer was washed twice with water (50 mL), and the organic layer was concentrated to 25 mL under reduced pressure. A silica gel cartridge (KP-sil 10 g) was charged with the residue, then toluene:acetone=9:1 (100 mL) was passed therethrough, and an eluate was recovered and concentrated to 25 mL under reduced pressure. 1-Butanol (50 mL) was added to the residue, then 1-{6-[(2,5-dioxopyrrolidin-1-yl)oxy]-6-oxohexyl}-1H-pyrrole-2,5-dione (10 mg) was added, and the resulting mixture was stirred at room temperature for 1 hour. 1-Butanol (50 mL) was added dropwise thereto, and the resulting mixture was cooled to −10° C. and stirred. Precipitates were filtered, and a powder separated by the filtration was washed with cold 1-butanol (20 mL). The obtained powder was dried under reduced pressure at 40° C. to obtain 1-{6-[(2,5-dioxopyrrolidin-1-yl)oxy]-6-oxohexyl}-1H-pyrrole-2,5-dione (6.52 g, 21.1 mmol, yield: 89.4%).

$^1$H-NMR (400 MHz, DMSO-d$_6$) δ 1.27-1.35 (2H, m), δ 1.48-1.56 (2H, m), δ 1.59-1.67 (2H, m), δ 2.65 (2H, t, 7.3 Hz), δ 2.81 (4H, s), δ 3.39 (2H, t, 7.0 Hz), δ 7.00 (2H, s).

$^{13}$C-NMR (100 MHz, DMSO-d$_6$) δ 23.7, 25.1, 25.4, 27.4, 30.0, 36.8, 134.4, 168.9, 170.2, 171.1.

MS (ESI) (m/z): 309 ([M+H]$^+$).

Example 11

1-{6-[(2,5-Dioxopyrrolidin-1-yl)oxy]-6-oxohexyl}-1H-pyrrole-2,5-dione

[Chem. 101]

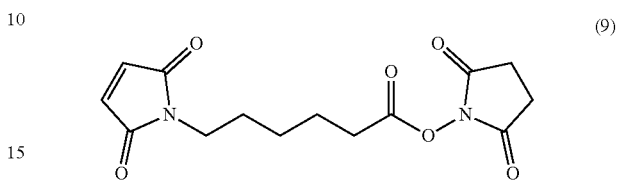

(9)

A mixed solution of 6-(2,5-dioxo-2,5-dihydro-1H-pyrrol-1-yl)hexanoic acid (1.1 kg, 5.21 mol), N-hydroxysuccinimide (0.72 kg, 6.25 mol), and acetonitrile (11 L) was cooled to −15° C. 2,6-Lutidine (1.34 kg, 12.50 mol) was added thereto, and then, thionyl chloride (0.74 kg, 6.25 mol) was added dropwise at −15° C. to −10° C. over 1 hour. Water (11 L) and toluene (11 L) were added thereto, and the resulting mixture was stirred and then separated into organic and aqueous layers. The aqueous layer was removed. The organic layer was washed twice with cold water (11 L) of 0 to 5° C. and washed with 20% saline (11 L) of 0 to 5° C., and the organic layer was concentrated to 5.5 L under reduced pressure. Then, toluene (5.5 L) was added to the residue, and the resulting mixture was concentrated again to 5.5 L under reduced pressure. A funnel was packed with neutral silica gel (Silica gel 60N, 3.3 kg) wetted with toluene, then the concentrate was passed therethrough, and the funnel was washed with toluene:acetone=9:1 (29 L) to obtain a filtrate. The obtained filtrate was concentrated to 5.5 L under reduced pressure, then 1-butanol (8.8 L) was added to the residue, and then, the resulting mixture was stirred at 20 to 25° C. for 16 hours. 1-Butanol (13.2 L) was added dropwise thereto, and the resulting mixture was cooled to −15° C. and stirred for 1 hour. Precipitates were filtered, and a powder separated by the filtration was washed with cold 1-butanol (4.4 L). The obtained powder was dried under reduced pressure at 40° C. to obtain 1-{6-[(2,5-dioxopyrrolidin-1-yl)oxy]-6-oxohexyl}-1H-pyrrole-2,5-dione (1.45 kg, 4.72 mol, yield: 90.5%).

$^1$H-NMR (400 MHz, DMSO-d$_6$) δ 1.27-1.35 (2H, m), δ 1.48-1.56 (2H, m), δ 1.59-1.67 (2H, m), δ 2.65 (2H, t, 7.3 Hz), δ 2.81 (4H, s), δ 3.39 (2H, t, 7.0 Hz), δ 7.00 (2H, s).

$^{13}$C-NMR (100 MHz, DMSO-d$_6$) δ 23.7, 25.1, 25.4, 27.4, 30.0, 36.8, 134.4, 168.9, 170.2, 171.1.

MS (ESI) (m/z): 309 ([M+H]$^+$).

Example 12

N-[6-(2,5-Dioxo-2,5-dihydro-1H-pyrrol-1-yl)hexanoyl]glycylglycyl-L-phenylalanyl-N-[(carboxymethoxy)methyl] glycinamide ("glycylglycyl-phenylalanyl-glycinamide" disclosed as SEQ ID NO: 11)

[Chem. 102]

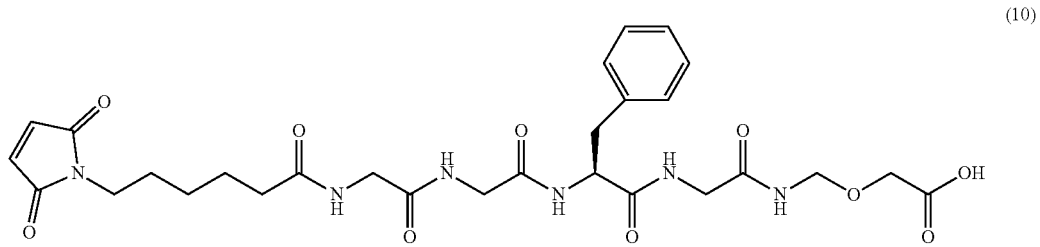

(10)

To a solution of 1-{6-[(2,5-dioxopyrrolidin-1-yl)oxy]-6-oxohexyl}-1H-pyrrole-2,5-dione (291.3 g, 0.945 mol) in acetonitrile (1.8 L), glycylglycyl-L-phenylalanyl-N-[(carboxymethoxy)methyl]glycinamide ("glycylglycyl-phenylalanyl-glycinamide" disclosed as SEQ ID NO: 11) (200.0 g, 0.472 mol), water (4.2 L), and N,N-diisopropylethylamine (48.8 g, 0.378 mol) were added, and the resulting mixture was stirred at room temperature for about 9 hours. Isopropyl acetate (2.0 L), anhydrous sodium dihydrogen phosphate (400.0 g), and anhydrous disodium hydrogen phosphate (26.0 g) were added thereto, and the resulting mixture was stirred and then separated into organic and aqueous layers. The organic layer was removed. Tetrahydrofuran (1.0 L), ethyl acetate (1.0 L), and anhydrous sodium dihydrogen phosphate (160.0 g) were added thereto, and the resulting mixture was stirred and then separated into organic and aqueous layers. The aqueous layer was removed. A 10 (w/v)% phosphate buffer solution (pH 3.4, 0.6 L) was added thereto, and the resulting mixture was stirred. After separation into organic and aqueous layers and removal of the aqueous layer, the organic layer was concentrated to 1.0 L under reduced pressure. 1,2-Dimethoxyethane (4.0 L) was added to the residue, and the resulting mixture was concentrated to 1.0 L under reduced pressure. 1,2-Dimethoxyethane (4.0 L) and acetonitrile (0.4 L) were added to the residue, and the resulting mixture was concentrated to 1.0 L under reduced pressure. Acetonitrile (20 mL) was added to the residue, and the water content of the solution was measured and was consequently 6.1% (corresponding to 18.8 mL of water). Water (19 mL) was added thereto, then N-[6-(2,5-dioxo-2,5-dihydro-1H-pyrrol-1-yl)hexanoyl]glycylglycyl-L-phenylalanyl-N-[(carboxymethoxy)methyl]glycinamide ("glycylglycyl-phenylalanyl-glycinamide" disclosed as SEQ ID NO: 11) (0.2 g) was added, then 1,2-dimethoxyethane (0.8 L) was added dropwise, and the resulting mixture was stirred at room temperature for about 16 hours. 1,2-Dimethoxyethane (3.2 L) was added dropwise thereto, and the resulting mixture was concentrated to 4.0 L under reduced pressure. 1,2-Dimethoxyethane (1.0 L) was added to the residue, and the resulting mixture was cooled to 0 to 5° C. and stirred for about 19.5 hours. Precipitates were filtered, and a powder separated by the filtration was washed with 1,2-dimethoxyethane (0.8 L). The obtained powder was dried under reduced pressure at 40° C. to obtain N-[6-(2,5-dioxo-2,5-dihydro-1H-pyrrol-1-yl)hexanoyl]glycylglycyl-L-phenylalanyl-N-[(carboxymethoxy)methyl]glycinamide ("glycylglycyl-phenylalanyl-glycinamide" disclosed as SEQ ID NO: 11) (268.3 g, 0.435 mol, yield: 92.1%).

$^1$H-NMR (400 MHz, DMSO-$d_6$) δ 1.15-1.23 (2H, m), δ 1.43-1.52 (4H, m), δ 2.11 (2H, t, 7.3 Hz), δ 2.78-2.84 (1H, m), δ 3.04-3.09 (1H, m), δ 3.37 (2H, t, 7.0 Hz) δ 3.61-3.79 (6H, m), δ 3.94 (2H, s), δ 4.47-4.52 (1H, m), δ 4.61 (2H, d, 6.7 Hz), δ 6.99 (2H, s), δ 7.15-7.27 (5H, m), δ 8.11-8.15 (2H, m), δ 8.22 (1H, d, 8.5 Hz), δ 8.31 (1H, t, 5.8 Hz), δ 8.63 (1H, t, 6.4 Hz).

$^{13}$C-NMR (100 MHz, DMSO-$d_6$) δ 24.6, 25.8, 27.8, 34.9, 37.0, 37.2, 41.9, 42.1, 42.1, 54.2, 65.1, 69.2, 126.2, 128.1, 129.1, 134.4, 137.9, 168.9, 169.5, 169.8, 171.1, 171.4, 171.9, 172.6.

MS (ESI) (m/z): 615 ([M−H]$^-$).

Example 13

1,2-Dimethoxyethane adduct of N-[6-(2,5-dioxo-2,5-dihydro-1H-pyrrol-1-yl)hexanoyl]glycylglycyl-L-phenylalanyl-N-[(carboxymethoxy)methyl]glycinamide ("glycylglycyl-phenylalanyl-glycinamide" disclosed as SEQ ID NO: 11)

[Chem. 103]

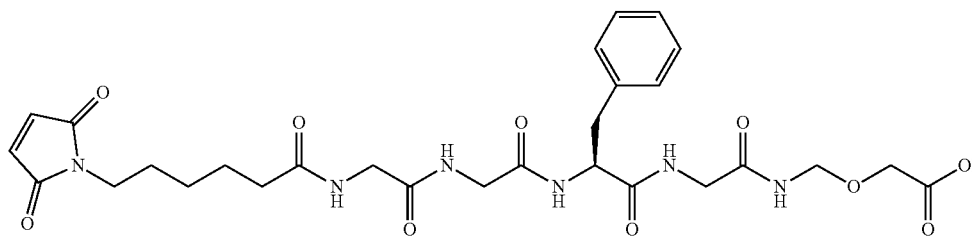

(10)

To a solution of 1-{6-[(2,5-dioxopyrrolidin-1-yl)oxy]-6-oxohexyl}-1H-pyrrole-2,5-dione (72.8 g, 0.236 mol) in acetonitrile (450.0 mL), glycylglycyl-L-phenylalanyl-N-[(carboxymethoxy)methyl]glycinamide ("glycylglycyl-phenylalanyl-glycinamide" disclosed as SEQ ID NO: 11) (50.0 g, 0.118 mol), water (1050.0 mL), and N,N-diisopropylethylamine (16.5 mL, 0.095 mol) were added, and the resulting mixture was stirred at room temperature for about 15 hours. Isopropyl acetate (500.0 mL), anhydrous sodium dihydrogen phosphate (100.0 g), and anhydrous disodium hydrogen phosphate (6.5 g) were added thereto, and the resulting mixture was stirred and then separated into organic and aqueous layers. The organic layer was removed. Isopropyl acetate (500.0 mL) was added thereto, and the resulting mixture was stirred and then separated into organic and aqueous layers. The organic layer was removed. 1,2-Dimethoxyethane (250.0 mL), ethyl acetate (250.0 mL), acetonitrile (25.0 mL), and anhydrous sodium dihydrogen phosphate (400.0 g) were added thereto, and the resulting mixture was stirred and then separated into organic and aqueous layers. The aqueous layer was removed. Acetonitrile (750.0 mL), water (113.0 mL), sodium chloride (30.0 g), anhydrous sodium dihydrogen phosphate (7.5 g), and phosphoric acid (85%, 1.5 g, 0.012 mol) were added thereto, and the resulting mixture was stirred and separated into organic and aqueous layers. The aqueous layer was removed. Water (113.0 mL), sodium chloride (30.0 g), and anhydrous sodium dihydrogen phosphate (7.5 g) were added thereto, and the resulting mixture was stirred and separated into organic and aqueous layers. The aqueous layer was removed. Water (113 mL), sodium chloride (30.0 g), and anhydrous sodium dihydrogen phosphate (7.5 g) were added thereto, and the resulting mixture was stirred. After separation into organic and aqueous layers and removal of the aqueous layer, the organic layer was concentrated to 500.0 mL under reduced pressure. 1,2-Dimethoxyethane (750.0 mL) was added to the residue, and then, the resulting mixture was concentrated to 500.0 mL under reduced pressure. The water content of the solution was measured and was consequently 6.9% (corresponding to 31.3 g of water). Water (9.5 mL) and 1,2-dimethoxyethane (1.0 L) were added thereto, and then, the resulting mixture was stirred at room temperature for about 13 hours. 1,2-Dimethoxyethane (250.0 mL) was added dropwise thereto, and the resulting mixture was stirred at room temperature for about 5 hours and then concentrated to 1.0 L under reduced pressure. 1,2-Dimethoxyethane (1.0 L) was added dropwise to the residue, and the resulting mixture was stirred at room temperature for about 1 hour and then concentrated to 1.0 L under reduced pressure. 1,2-Dimethoxyethane (250.0 mL) was added dropwise to the residue, and the resulting mixture was stirred at room temperature for about 16 hours. Then, precipitates were filtered, and a powder separated by the filtration was washed with 1,2-dimethoxyethane (250.0 L). To the obtained wet powder, 1,2-dimethoxyethane (2.0 L) and water (65.0 mL) were added, and the resulting mixture was heated to 45° C. After stirring for 30 minutes, the sodium chloride was separated by filtration, then the sodium chloride was washed with 1,2-dimethoxyethane/water (97/3, 150 mL), and the washes were combined with the filtrate. The resulting mixture was concentrated to 1.0 L under reduced pressure. 1,2-Dimethoxyethane (1.0 L) was added to the residue, and the resulting mixture was stirred at room temperature for about 3 hours and then concentrated to 1.0 L under reduced pressure. 1,2-Dimethoxyethane (1.0 L) was added dropwise to the residue, and the resulting mixture was concentrated to 1.0 L under reduced pressure. 1,2-Dimethoxyethane (250.0 mL) was added dropwise to the residue, and the resulting mixture was stirred at room temperature for about 16 hours. Then, precipitates were filtered, and a powder separated by the filtration was washed with 1,2-dimethoxyethane (250 mL). The obtained powder was dried under reduced pressure (4 kPa) at 25° C. to obtain a 1,2-dimethoxyethane adduct of N-[6-(2,5-dioxo-2,5-dihydro-1H-pyrrol-1-yl)hexanoyl]glycylglycyl-L-phenylalanyl-N-[(carboxymethoxy)methyl]glycinamide ("glycylglycyl-phenylalanyl-glycinamide" disclosed as SEQ ID NO: 11) (65.7 g, 0.107 mol, yield: 90.3%) in the form of crystals.

$^1$H-NMR (500 MHz, DMSO-$d_6$) δ 1.16-1.23 (2H, m), δ 1.44-1.52 (4H, m), δ 2.11 (2H, t, 7.5 Hz), δ 2.79-2.84 (1H, m), δ 3.05-3.09 (1H, m), δ 3.24 (6H, s), δ 3.37 (2H, t, 7.3 Hz), δ 3.43 (4H, s), δ 3.56-3.78 (6H, m), δ 3.99 (2H, s), δ 4.48-4.52 (1H, m), δ 4.61 (2H, d, 6.5 Hz), δ 7.00 (2H, s), δ 7.16-7.27 (5H, m), δ 8.02-8.10 (2H, m), δ 8.15 (1H, d, 8.0 Hz), δ 8.32 (1H, t, 6.0 Hz), δ 8.58 (1H, t, 6.8 Hz). δ 12.61 (1H, brs)

$^{13}$C-NMR (100 MHz, DMSO-d$_6$) δ 25.5, 26.8, 28.7, 35.9, 37.9, 38.2, 42.8, 43.0, 43.1, 55.1, 59.0, 65.2, 69.8, 72.0, 127.2, 129.0, 130.1, 135.4, 138.8, 169.8, 170.4, 170.9, 172.0, 172.3, 172.4, 173.6.

MS (ESI) (m/z): 615 ([M−H]$^-$).

Powder X-ray diffraction:

The crystals of the title compound were subjected to powder X-ray diffraction obtained by irradiation with copper Kα radiation. The results are shown in Table 1 and FIG. 3. Main peaks were observed at diffraction angles (2θ) of 19.0° and 25.0°.

TABLE 1

| Diffraction angle 2θ (°) | Interplanar spacing d (Å) | Relative intensity (%) |
|---|---|---|
| 7.0 | 12.6 | 32.0 |
| 12.4 | 7.1 | 40.9 |
| 19.0 | 4.7 | 82.9 |
| 25.0 | 3.6 | 100.0 |
| 25.2 | 3.5 | 59.5 |

Example 14

N-[6-(2,5-Dioxo-2,5-dihydro-1H-pyrrol-1-yl) hexanoyl]glycylglycyl-L-phenylalanyl-N-[(2-{[(1S, 9S)-9-ethyl-5-fluoro-9-hydroxy-4-methyl-10,13-dioxo-2,3,9,10,13,15-hexahydro-1H,12H-benzo[de] pyrano[3',4':6,7]indolizino[1,2-b]quinolin-1-yl] amino}-2-oxoethoxy)methyl] glycinamide ("glycylglycyl-phenylalanyl-glycinamide" disclosed as SEQ ID NO: 11)

To a suspension of (1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-aminium methanesulfonate dihydrate (gross amount: 154.6 g, internal content after correction with a water content value of 2.95%: 150.0 g, 0.282 mol) in tetrahydrofuran (1.8 L), a 5 (w/v )% aqueous sodium sulfate solution (1.5 L) and N-methylmorpholine (28.5 g, 0.282 mol) were added, and the resulting mixture was stirred at 32° C. for about 1 hour.

Ethyl cyano(hydroxyimino)acetate (8.0 g, 56.3 mmol), N-[6-(2,5-dioxo-2,5-dihydro-1H-pyrrol-1-yl)hexanoyl] glycylglycyl-L-phenylalanyl-N-[(carboxymethoxy)methyl] glycinamide ("glycylglycyl-phenylalanyl-glycinamide" disclosed as SEQ ID NO: 11) (gross amount: 232.0 g, internal content after conversion into 2.50% 1,2-dimethoxyethane: 226.2 g, 0.367 mol), and 1-(3-dimethylaminopropyl)-3-ethylcarbodiimide hydrochloride (108.2 g, 0.564 mol) were added thereto, and the resulting mixture was stirred at 29 to 32° C. for about 1 hour and then separated into organic and aqueous layers. The aqueous layer was removed. Ethyl acetate (1.8 L) and a 5 (v/v )% aqueous acetic acid solution (0.45 L) were added thereto, and the resulting mixture was stirred and separated into organic and aqueous layers. The aqueous layer was removed. Activated carbon (15.0 g, Kyoryoku Shirasagi (manufactured by Osaka Gas Chemicals Co., Ltd.)) was added thereto, and the resulting mixture was stirred at room temperature for about 30 minutes. Then, the activated carbon was separated by filtration, then the activated carbon was washed with tetrahydrofuran (0.45 L), and the washes were combined with the filtrate. The resulting mixture was concentrated to 0.75 L under reduced pressure. 1-Propanol (1.5 L) was added to the residue, and the resulting mixture was concentrated to 0.75 L under reduced pressure. Acetone:1-propanol=1:1 (3.0 L) was added to the residue. N-[6-(2,5-Dioxo-2,5-dihydro-1H-pyrrol-1-yl)hexanoyl]glycylglycyl-L-phenylalanyl-N-[(2-{[(1S,9S)-9-ethyl-5-fluoro-9-hydroxy-4-methyl-10,13-dioxo-2,3,9,10,13,15-hexahydro-1H,12H-benzo[de]pyrano [3',4':6,7]indolizino[1,2-b]quinolin-1-yl]amino}-2-oxoethoxy)methyl]glycinamide ("glycylglycyl-phenylalanyl-glycinamide" disclosed as SEQ ID NO: 11) (0.15 g) was added thereto, and the resulting mixture was stirred at room temperature for about 45 hours. Precipitates were filtered, and a powder separated by the filtration was washed with acetone:1-propanol=1:1 (0.6 L). The obtained wet powder was dissolved by the addition of tetrahydrofuran (1.5 L) and water (0.3 L), and the solution was concentrated to 0.75 L under reduced pressure. 1-Propanol (1.5 L) was added to the residue, and the resulting mixture was concentrated to 0.75 L under reduced pressure. Acetone:1-propanol=1:1 (3.0 L) was added to the residue. N-[6-(2,5-Dioxo-

[Chem. 104]

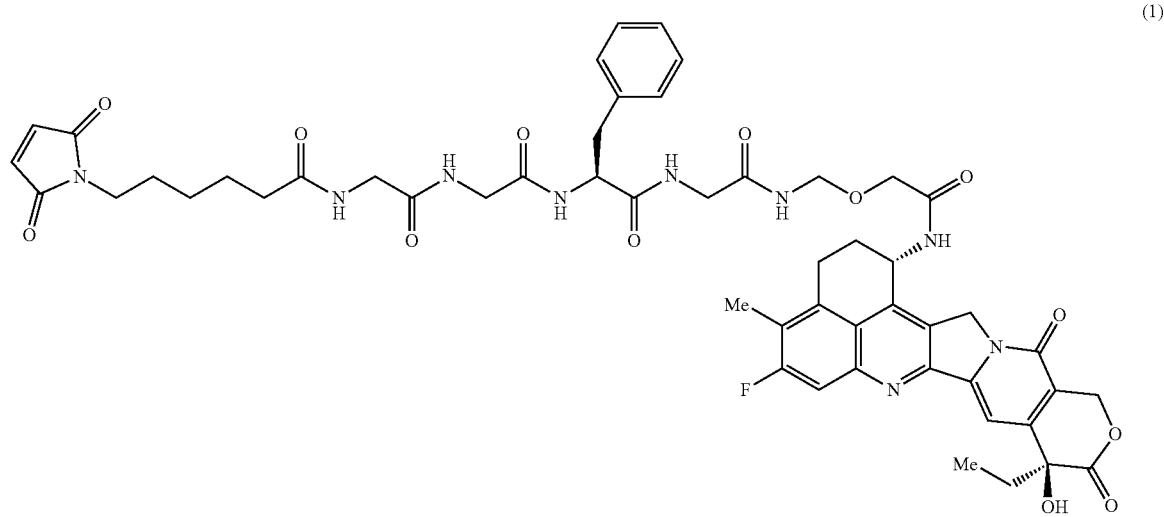

(1)

2,5-dihydro-1H-pyrrol-1-yl)hexanoyl]glycylglycyl-L-phenylalanyl-N-[(2-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-2-oxoethoxy)methyl]glycinamide ("glycylglycyl-phenylalanyl-glycinamide" disclosed as SEQ ID NO: 11) (0.15 g) was added thereto, and the resulting mixture was stirred at room temperature for about 24 hours. Precipitates were filtered, and crystals separated by the filtration were washed with acetone:1-propanol=1:1 (0.6 L). The obtained crystals were dried under reduced pressure at 40° C. to obtain N-[6-(2,5-dioxo-2,5-dihydro-1H-pyrrol-1-yl)hexanoyl]glycylglycyl-L-phenylalanyl-N-[(2-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-2-oxoethoxy)methyl]glycinamide ("glycylglycyl-phenylalanyl-glycinamide" disclosed as SEQ ID NO: 11) (254.6 g, yield: 87.3%) in the form of crystals.

$^1$H-NMR (400 MHz, DMSO-$d_6$) δ 0.87 (3H, t, 7.3 Hz), δ 1.14-1.21 (2H, m), δ 1.41-1.50 (4H, m), δ 1.78-1.93 (2H, m), δ 2.09 (2H, t, 7.3 Hz), δ 2.13-2.23 (2H, m), δ 2.36 (3H, s), δ 2.74-2.80 (1H, m), δ 3.00-3.04 (1H, m), δ 3.08-3.25 (2H, m), δ 3.32-3.37 (2H, m), δ 3.56-3.77 (6H, m), δ 4.02 (2H, s), δ 4.44-4.50 (1H, m), δ 4.64 (2H, d, 6.7 Hz), δ 5.17 (2H, d, 5.5 Hz), δ 5.41 (2H, s), δ 5.57-5.62 (1H, m), δ 6.51 (1H, s), δ 6.99 (2H, s), δ 7.14-7.26 (5H, m), δ 7.30 (1H, s), δ 7.75 (1H, d, 11.0 Hz), δ 8.00 (1H, t, 5.8 Hz), δ 8.06 (1H, t, 5.3 Hz), δ 8.12 (1H, d, 7.9 Hz), δ 8.29 (1H, t, 5.8 Hz), δ 8.49 (1H, d, 8.5 Hz), δ 8.62 (1H, t, 6.7 Hz).

$^{13}$C-NMR (100 MHz, DMSO-$d_6$) δ 7.6, 10.8, 10.9, 23.5, 24.6, 25.7, 27.7, 30.2, 30.6, 34.8, 36.9, 37.1, 41.7, 42.0, 44.4, 49.5, 54.1, 65.1, 66.9, 69.7, 72.2, 96.6, 109.6, 109.8, 119.0, 121.5, 123.4, 123.6, 125.3, 126.2, 128.0, 129.0, 134.3, 136.2, 136.3, 137.7, 140.4, 145.0, 147.7, 147.8, 149.9, 152.2, 156.6, 160.2, 162.7, 168.8, 169.1, 169.3, 170.0, 171.0, 171.3, 172.3, 172.5.

MS (ESI) (m/z): 1034 ([M+H]$^+$).

Powder X-Ray Diffraction:

The crystals of the title compound were subjected to powder X-ray diffraction obtained by irradiation with copper Kα radiation. The results are shown in Table 2 and FIG. 4. Main peaks were observed at diffraction angles (2θ) of 5.6°, 15.5°, and 22.0°.

TABLE 2

| Diffraction angle 2θ (°) | Interplanar spacing d (Å) | Relative intensity (%) |
|---|---|---|
| 5.6 | 15.9 | 100.0 |
| 5.8 | 15.3 | 41.6 |
| 15.5 | 5.7 | 73.6 |
| 17.9 | 5.0 | 35.0 |
| 20.5 | 4.3 | 35.1 |
| 21.4 | 4.2 | 31.4 |
| 22.0 | 4.0 | 74.5 |

Example 15

({N-[(9H-Fluoren-9-ylmethoxy) carbonyl]glycyl}amino)methyl acetate

[Chem. 105]

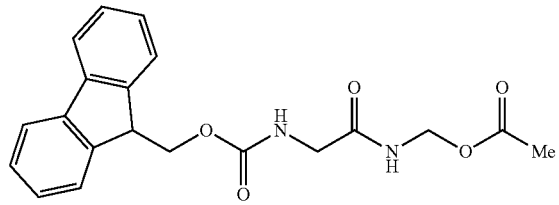

(3)

To a suspension of N-9-fluorenylmethoxycarbonylglycylglycine (2.85 kg, 8.04 mol) in anhydrous tetrahydrofuran (38.0 kg), acetic acid (2.41 kg, 40.1 mol) and lead(IV) tetraacetate (5.35 kg, 12.0 mol) were added under a nitrogen atmosphere, and the resulting mixture was refluxed for 1.5 hours. After cooling to room temperature, the precipitated solid was separated by filtration, and the solid thus separated by filtration was washed with tetrahydrofuran (10.1 kg). The obtained filtrate and washes were concentrated under reduced pressure until the amount of the liquid became about 16 L. To the obtained concentrate, ethyl acetate (26 kg), a 10% aqueous citric acid solution (17.1 L), and 20% saline (5.7 L) were added, and the resulting mixture was stirred and then separated into organic and aqueous layers. The obtained organic layer was separated into organic and aqueous layers and washed with a 10% aqueous citric acid solution (17.1 L), a 9% aqueous sodium bicarbonate solution (28.5 L), and 20% saline (14.3 L) in this order. To the obtained organic layer, silica gel 60 (5.7 kg) and ethyl acetate (10.3 kg) were added, and the resulting mixture was stirred for 1 hour. Then, a solid was separated by filtration, and the solid thus separated by filtration was washed with ethyl acetate (7.7 kg). The obtained filtrate and washes were concentrated under reduced pressure until the amount of the liquid became about 5 L. Cyclopentyl methyl ether (24.5 kg) was added to the residue. The resulting mixture was concentrated again under reduced pressure until the amount of the liquid became about 5 L. To the obtained concentrate, cyclopentyl methyl ether (14.7 kg) was added, and the resulting mixture was stirred at about 5° C. for 1 hour. The precipitated solid was filtered, and the obtained crystals were washed with cyclopentyl methyl ether (4.9 kg) cooled to about 5° C. The obtained crystals were dried under reduced pressure at 40° C. to obtain the title compound (2.01 kg, yield: 68%) as a colorless solid.

Example 16

Benzyl [({N-[(9H-fluoren-9-ylmethoxy)carbonyl]glycyl}amino)methoxy]acetate

[Chem. 106]

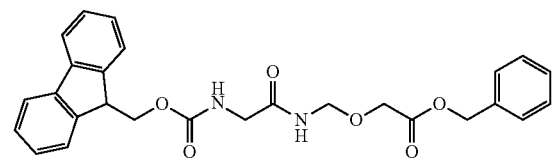

(4)

To a suspension of ({N-[(9H-fluoren-9-ylmethoxy)carbonyl]glycyl}amino)methyl acetate (2.01 kg, 5.46 mol) in anhydrous 1,2-dimethoxyethane (21 kg), benzyl glycolate (1.81 kg, 10.9 mol) was added under a nitrogen atmosphere, and the resulting mixture was cooled to about 0° C. Tris (pentafluorophenyl)borane (142 g, 0.27 mol) was added thereto, and the resulting mixture was stirred at the same temperature as the above for 3 hours. Then, ethyl acetate (27.1 kg) and a 10% aqueous potassium bicarbonate solution were added thereto, and the resulting mixture was heated to room temperature and separated into organic and aqueous layers. The obtained organic layer was separated into organic and aqueous layers and washed by the addition of 10% saline (20.1 L). The obtained organic layer was concentrated under reduced pressure until the amount of the liquid became about 4 L. Methanol (15.7 kg) was added to the residue. The resulting mixture was concentrated under reduced pressure until the amount of the liquid became about 4 L. To the obtained concentrate, methanol (7.8 kg) was added. The resulting mixture was concentrated under reduced pressure until the amount of the liquid became about 4 L. To the obtained concentrate, methanol (12.5 kg) was added, and the resulting mixture was cooled to about 5° C. and stirred for 1 hour. The precipitated crystals were filtered, and the obtained crystals were washed with methanol (4.7 kg) cooled to about 5° C. The obtained solid was dried under reduced pressure at 40° C. to obtain the title compound (2.28 kg, yield: 88%).

Example 17

Benzyl [({N-[(9H-fluoren-9-ylmethoxy)carbonyl]glycylglycyl-L-phenylalanyl}amino)methoxy]acetate

[Chem. 107]

the resulting mixture was stirred at room temperature for 3 hours. Ethyl acetate (21.0 kg) and 10% saline (34 L) were added thereto, and the resulting mixture was stirred and then separated into organic and aqueous layers. The obtained organic layer was separated into organic and aqueous layers and washed with a 10% aqueous citric acid solution (11.4 L). To the obtained organic layer, tetrahydrofuran (20 kg) and a 15% aqueous potassium bicarbonate solution (22.8 L) were added, and the resulting mixture was stirred and separated into organic and aqueous layers. The obtained organic layer was separated into organic and aqueous layers and washed with 10% saline (22.8 L). The obtained organic layer was concentrated under reduced pressure until the amount of the liquid became about 6.8 L. 2-Propanol (12.4 kg) was added to the residue. The resulting mixture was concentrated again under reduced pressure until the amount of the liquid became about 6.8 L. To the obtained concentrate, 2-propanol (30.2 kg) was added under warming at about 50° C. The resulting mixture was stirred at the same temperature as the above for 1 hour, then cooled to about 5° C., and further stirred for 2 hours. The precipitated solid was filtered, and the solid separated by the filtration was washed with 2-propanol (14.2 kg) cooled to about 5° C. The obtained crystals 2 were suspended in 2-propanol (36 kg), and the suspension was stirred at about 5° C. for 1 hour. Then, the precipitated solid was filtered, and the solid separated by the filtration was washed with 2-propanol (28.5 kg) cooled to about 5° C. The obtained crystals were dried under reduced pressure at 50° C. to obtain the title compound (3.34 kg, yield: 94%).

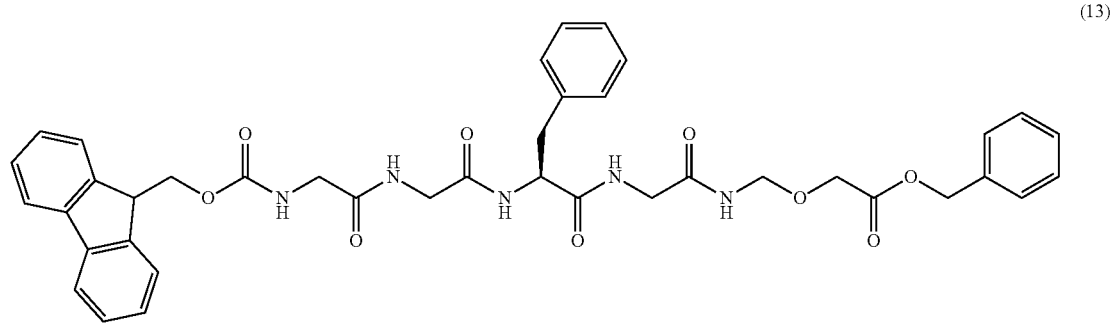

(13)

To a solution of benzyl [({N-[(9H-fluoren-9-ylmethoxy)carbonyl]glycyl}amino)methoxy]acetate (2.28 kg, 4.81 mol) in N,N-dimethylacetamide (15.0 kg), 1,8-diazabicyclo[5.4.0]undec-7-ene (0.37 kg, 2.4 mol) was added under a nitrogen atmosphere, and the resulting mixture was stirred at room temperature for 30 minutes. Pyridinium p-toluenesulfonate (0.60 kg, 2.4 mol),1-hydroxybenzotriazole monohydrate (0.74 kg, 4.8 mol), N-[(9H-fluoren-9-ylmethoxy)carbonyl]glycylglycyl-L-phenylalanine (2.19 kg, 4.37 mol), and 1-ethyl-3-(3-dimethylaminopropyl)-carbodiimide hydrochloride (0.84 kg, 4.37 mol) were added thereto, and $^1$H-NMR (400 MHz, DMSO-d$_6$) δ 2.79 (1H, dd, J=14.0, 9.8 Hz), 3.05 (1H, dd, J=14.0, 4.3 Hz), 3.58-3.79 (6H, m), 4.15 (2H, s), 4.20-4.24 (1H, m), 4.28-4.30 (2H, m), 4.48-4.53 (1H, m), 4.63 (2H, d, J=6.7 Hz), 5.14 (2H, s), 7.15-7.43 (13H, m), 7.58 (1H, t, J=6.1 Hz), 7.71 (2H, d, J=7.3 Hz), 7.89 (2H, d, J=7.9 Hz), 8.01 (1H, t, J=5.5 Hz), 8.15 (1H, d, J=7.9 Hz), 8.33 (1H, t, J=5.8 Hz), 8.59 (1H, t, J=6.4 Hz).
$^{13}$C-NMR (100 MHz, DMSO-d$_6$) δ 37.3, 41.8, 42.1, 43.5, 46.6, 54.1, 64.4, 65.6, 65.7, 69.0, 120.1, 125.2, 126.3, 127.1, 127.6, 128.0, 128.1, 128.1, 128.4, 129.1, 135.8, 137.8, 140.7, 143.8, 156.5, 168.8, 169.4, 169.9, 170.1, 171.4. MS (ESI) (m/z): 736 ([M+H]$^+$).

Example 18

N-[(9H-Fluoren-9-ylmethoxy)carbonyl]glycylglycyl-L-phenylalanyl-N-[(carboxymethoxy)methyl]glycinamide ("glycylglycyl-phenylalanyl-glycinamide" disclosed as SEQ ID NO: 11)

[Chem. 108]

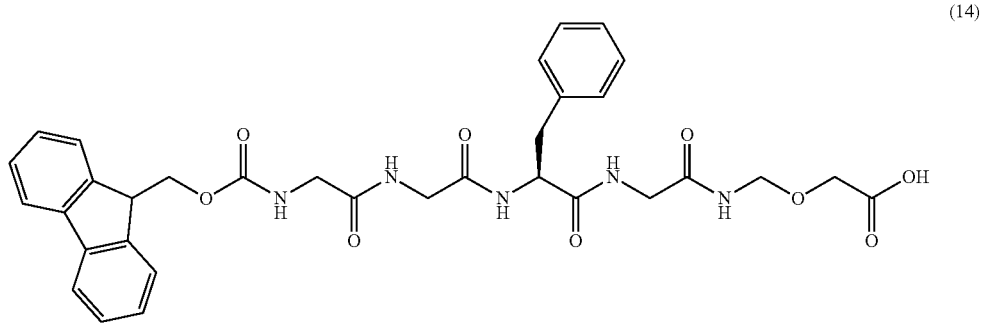 [SMILES: O=C(O)COCNC(=O)CNC(=O)[C@H](Cc1ccccc1)NC(=O)CNC(=O)CNC(=O)OCC1c2ccccc2-c2ccccc21]

(14)

To a suspension of benzyl [({N-[(9H-fluoren-9-ylmethoxy)carbonyl]glycylglycyl-L-phenylalanyl}amino)methoxy]acetate (367 g, 0.499 mol) in tetrahydrofuran (5.88 kg) and water (1.61 L), a palladium carbon-ethylenediamine complex (28 g) was added, and the resulting mixture was stirred at room temperature for 1 hour to 3 hours under a hydrogen gas atmosphere at ordinary pressure. The catalyst was separated by filtration, and the catalyst thus separated by filtration was washed with tetrahydrofuran (1.63 kg) to obtain a filtrate and washes. The above-described operation of reaction and separation of a catalyst by filtration was repetitively performed 9 times, and the obtained 9 portions of filtrates and washes were combined. The resulting mixture was concentrated under reduced pressure until the amount of the liquid became about 17 L. To the obtained concentrate, 2-propanol (39 kg) was added, and the operation of concentration under reduced pressure until the amount of the liquid became about 17 L was repetitively performed three times. To the obtained concentrate, ethyl acetate (45 kg) was added, and the resulting mixture was stirred at room temperature for 6 hours. This suspension was further stirred at about 5° C. for 1 hour. The precipitated solid was filtered, and the solid separated by the filtration was washed with a 1:3 mixed solution of 2-propanol and ethyl acetate (23.1 L) cooled to about 5° C. The obtained crystals were dried under reduced pressure at 40° C. to obtain a crude form of the title compound (2.18 kg, yield: 75%). The obtained crude form (400 g, 0.62 mol) was suspended in tetrahydrofuran (2.4 L) and ethyl acetate (5.6 L). To the suspension, a 1% aqueous potassium bisulfate solution (4 L) was added, and the resulting mixture was dissolved by warming to about 32° C. and stirring. After separation into organic and aqueous layers, the obtained organic layer was separated into organic and aqueous layers and washed with water (2 L). The obtained organic layer was concentrated under reduced pressure until the amount of the liquid became about 2 L. To the obtained concentrate, acetonitrile (6 L) was added, and the resulting mixture was concentrated under reduced pressure until the amount of the liquid became about 2.8 L. As a result, a solid was precipitated. Ethyl acetate (6 L) was added thereto, and the resulting mixture was stirred at room temperature for 18 hours, then cooled to about 5° C., and stirred for 3 hours. The precipitated solid was filtered, and the crystals separated by the filtration were washed with a 1:2 mixed solution of acetonitrile and ethyl acetate (7 L). The obtained solid was dried under reduced pressure at 40° C. to obtain the title compound (356 g, yield: 89%).

$^1$H-NMR (400 MHz, DMSO-$d_6$) δ 2.79 (1H, dd, J=14.0, 9.8 Hz), 3.06 (1H, dd, J=13.7, 4.6 Hz), 3.58-3.79 (6H, m), 3.98 (2H, s), 4.21-4.25 (1H, m), 4.28-4.30 (2H, m), 4.48-4.54 (1H, m), 4.61 (2H, d, J=6.7 Hz), 7.16-7.20 (1H, m), 7.22-7.27 (4H, m), 7.33 (2H, t, J=7.3 Hz), 7.42 (2H, t, J=7.3 Hz), 7.59 (1H, t, J=6.1 Hz), 7.71 (2H, d, J=7.3 Hz), 7.89 (2H, d, J=7.3 Hz), 8.03 (1H, t, J=5.5 Hz), 8.16 (1H, d, J=7.9 Hz), 8.33 (1H, t, J=5.8 Hz), 8.57 (1H, t, J=6.7 Hz).

$^{13}$C-NMR (100 MHz, CDCl$_3$) δ 37.4, 41.8, 42.1, 43.5, 46.6, 54.1, 64.2, 65.7, 68.8, 120.1, 125.2, 126.3, 127.1, 127.6, 128.1, 129.1, 137.8, 140.7, 143.8, 156.5, 168.8, 169.2, 170.0, 171.4, 171.4.

MS (ESI) (m/z): 646 ([M+H]$^+$).

Example 19

N-[(9H-Fluoren-9-ylmethoxy)carbonyl]glycylglycyl-L-phenylalanyl-N-[(2-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-2-oxoethoxy)methyl]glycinamide ("glycylglycyl-phenylalanyl-glycinamide" disclosed as SEQ ID NO: 11)

[Chem. 109]

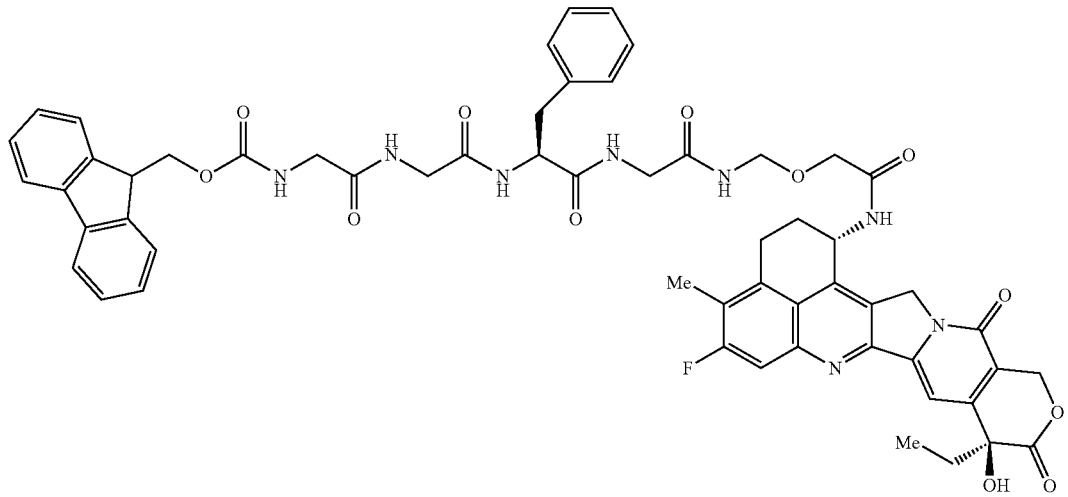

(15)

To a suspension of (1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-aminium methanesulfonate dihydrate (260 g, 0.458 mol) in dimethyl sulfoxide (1.8 L) and tetrahydrofuran (1.3 L), triethylamine (55.6 g, 0.549 mol), 1-hydroxybenzotriazole monohydrate (84.2 g, 0.549 mol), N-[(9H-fluoren-9-ylmethoxy)carbonyl]glycylglycyl-L-phenylalanyl-N-[(carboxymethoxy)methyl]glycinamide ("glycylglycyl-phenylalanyl-glycinamide" disclosed as SEQ ID NO: 11) (325 g, 0.503 mol), and 1-ethyl-3-(3-dimethylaminopropyl)-carbodiimide hydrochloride (114 g, 0.595 mol) were added under a nitrogen atmosphere, and the resulting mixture was stirred at room temperature for 2 hours. Tetrahydrofuran (3.9 L), ethyl acetate (2.6 L), and a 11% aqueous potassium bicarbonate solution (5.2 L) were added thereto, and the resulting mixture was stirred and separated into organic and aqueous layers. The obtained organic layer was washed with a 19% aqueous citric acid solution (3.9 L), a 22% aqueous potassium bicarbonate solution (2.6 L), and 18% saline (0.78 L) in this order. To the obtained organic layer, activated carbon (52 g) was added, and the resulting mixture was stirred for 30 minutes. Then, tetrahydrofuran (0.78 L) and anhydrous magnesium sulfate (0.78 g) were added thereto, and the resulting mixture was stirred for 30 minutes. A solid was separated by filtration, and the solid thus separated by filtration was washed with tetrahydrofuran (0.78 L). The obtained filtrate and washes were concentrated under reduced pressure until the amount of the liquid became about 200 mL. To the obtained concentrate, ethyl acetate (1.3 L) was added, and the resulting mixture was concentrated under reduced pressure until the amount of the liquid became about 200 mL. To the obtained concentrate, tetrahydrofuran (1.8 L) was added. The obtained solution was added dropwise over 12 minutes to a mixed solution of ethyl acetate (1.3 L) and cyclopentyl methyl ether (1.3 L) prepared in another container. To this suspension, cyclopentyl methyl ether (2.6 L) was added, and the resulting mixture was stirred for 18 hours, then cooled to about 5° C., and further stirred for 1 hour. The precipitated solid was filtered, and the solid separated by the filtration was washed with a 1:3 mixed solution of tetrahydrofuran and cyclopentyl methyl ether (1.3 L). The obtained solid was dried under reduced pressure at 40° C. to obtain the title compound (408 g, yield: 84%).

$^1$H-NMR (400 MHz, DMSO-$d_6$) δ 0.86 (3H, t, J=7.3), 1.79-1.90 (2H, m), 2.11-2.22 (2H, m), 2.37 (3H, s), 2.77 (1H, dd, J=14.0, 9.8 Hz), 3.02 (1H, dd, J=13.7, 4.6 Hz), 3.07-3.25 (2H, m), 3.58-3.79 (6H, m), 4.02 (2H, s), 4.18-4.23 (1H, m), 4.26-4.30 (2H, m), 4.45-4.54 (1H, m), 4.64 (2H, d, J=6.7 Hz), 5.17 (2H, dd, J=23.5, J=19.2 Hz), 5.40 (2H, s), 5.56-5.61 (1H, m), 6.52 (1H, s), 7.14-7.43 (10H, m), 7.58 (1H, t, J=6.1 Hz), 7.68 (2H, d, J=7.3 Hz), 7.76 (1H, d, J=11.0 Hz), 7.86 (2H, d, J=7.3 Hz), 8.02 (1H, t, J=5.5 Hz), 8.15 (1H, d, J=7.9 Hz), 8.32 (1H, t, J=5.8 Hz), 8.50 (1H, d, J=8.5 Hz), 8.63 (1H, t, J=6.4 Hz).

$^{13}$C-NMR (100 MHz, DMSO-$d_6$) δ 7.7, 10.9, 11.0, 23.1, 23.7, 27.8, 30.3, 31.4, 37.3, 41.8, 42.1, 43.5, 44.6, 46.6, 49.6, 54.2, 55.6, 65.2, 65.8, 67.0, 69.8, 72.3, 82.0, 96.7, 109.7, 109.9, 119.1, 120.0, 121.6, 123.5, 123.7, 125.2, 125.3, 126.3, 127.0, 127.6, 128.1, 129.1, 136.3, 136.4, 137.8, 140.5, 140.7, 143.8, 143.8, 145.1, 147.8, 147.9, 150.0, 152.3, 156.5, 156.7, 160.3, 162.8, 168.9, 169.2, 169.4, 170.2, 171.4, 172.4.

MS (ESI) 1063: (M+H)$^+$

Example 20

Glycylglycyl-L-phenylalanyl-N-[(2-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-2-oxoethoxy)methyl]glycinamide ("glycylglycyl-phenylalanyl-glycinamide" disclosed as SEQ ID NO: 11) [0486]

[Chem. 110]

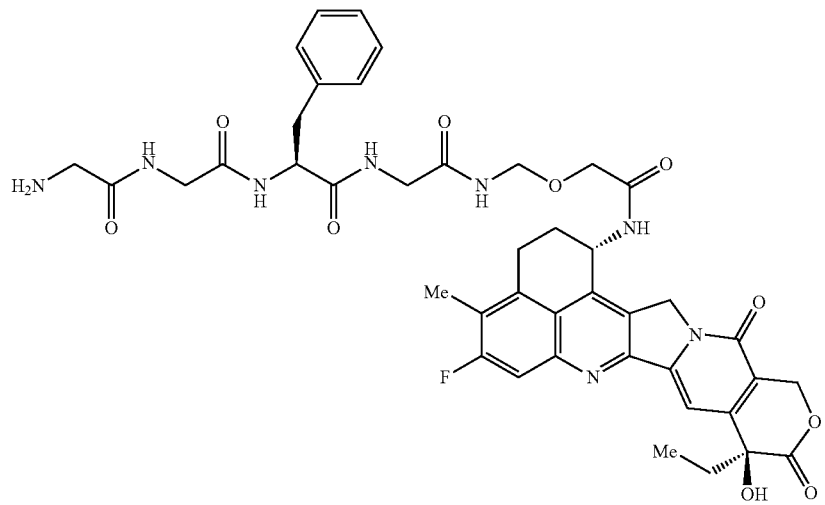

(16)

To a suspension of N-[(9H-fluoren-9-ylmethoxy)carbonyl]glycylglycyl-L-phenylalanyl-N-[(2-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl] amino}-2-oxoethoxy)methyl] glycinamide ("glycylglycyl-phenylalanyl-glycinamide" disclosed as SEQ ID NO: 11) (400 g, 0.376 mol) in dehydrated tetrahydrofuran (8 L), 1,8-diazabicyclo[5.4.0]undec-7-ene (51.6 g, 0.339 mol) was added every 5 minutes in 8 divided portions under a stream of nitrogen gas, and the resulting mixture was stirred for 2.5 hours. The precipitated solid was filtered under the stream of nitrogen gas, and the solid separated by the filtration was washed with tetrahydrofuran (2.4 L). The obtained solid was dried under reduced pressure at 40° C. to obtain a mixture containing the title compound (363 g, yield: 115%).

$^1$H-NMR (400 MHz, DMSO-$d_6$) δ 0.87 (3H, t, J=7.3), 1.57-1.67 (6H, m), 1.80-1.92 (2H, m), 2.06-2.25 (2H, m), 2.35-2.38 (3H, m), 2.61-2.63 (2H, m), 2.73-2.89 (1H, m), 3.00-3.79 (29H, m), 3.80 (1H, dd, J=16.2, 7.0 Hz), 3.99-4.10 (2H, m), 4.30-4.51 (1H, m), 4.58 (1H, dd, J=9.8, 6.1 Hz), 4.63-4.69 (1H, m), 5.01 (0.5H, br), 5.15 (1H, t, J=18.3 Hz), 5.24 (1H, t, J=18.3 Hz), 5.41 (2H, s), 5.54-5.62 (1H, m), 6.52 (0.6H, br), 7.11-7.31 (6H, m), 7.75-7.79 (1H, m), 8.12-8.15 (0.6H, m), 8.22 (0.2H, d, J=8.5 Hz), 8.36 (0.2H, t, J=5.8 Hz), 8.52 (0.2H, t, J=5.5 Hz), 8.66 (0.2H, t, J=6.4 Hz), 8.93 (0.6H, t, J=5.5 Hz), 9.10 (1H, dd, J=20.1, 9.2 Hz), 9.82 (0.6H, br).

MS (ESI) 841: (M+H)$^+$

Example 21

Preparation of seed crystals of N-[6-(2,5-dioxo-2,5-dihydro-1H-pyrrol-1-yl)hexanoyl]glycylglycyl-L-phenylalanyl-N-[(2-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl] amino}-2-oxoethoxy)methyl] glycinamide ("glycylglycyl-phenylalanyl-glycinamide" disclosed as SEQ ID NO: 11)

[Chem. 111]

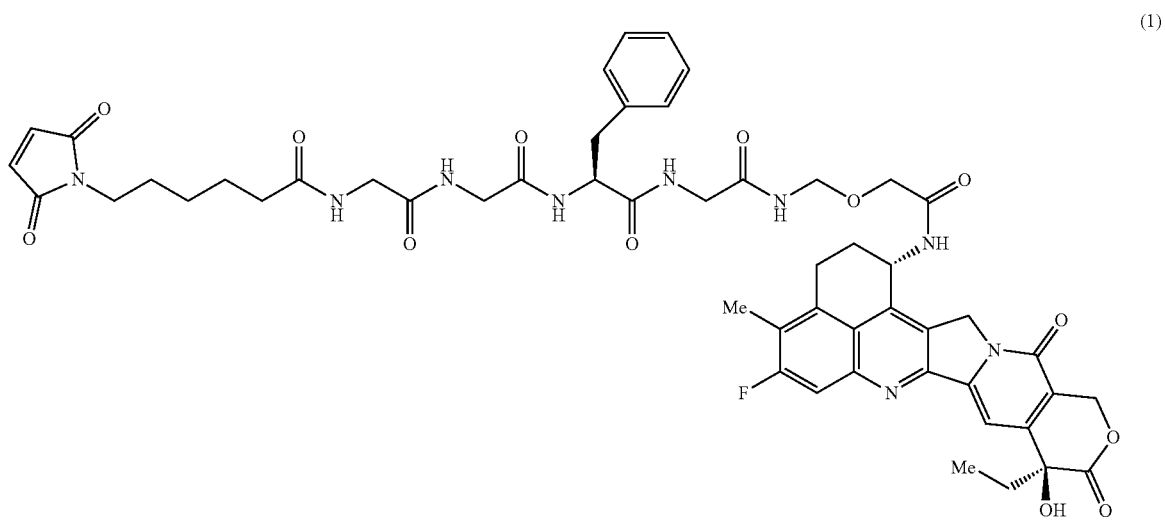

(1)

To a suspension of glycylglycyl-L-phenylalanyl-N-[(2-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl] amino}-2-oxoethoxy)methyl] glycinamide ("glycylglycyl-phenylalanyl-glycinamide" disclosed as SEQ ID NO: 11) (200 mg, 0.24 mmol) in pyridine (0.2 mL), tetrahydrofuran (2.0 mL) and acetonitrile (0.6 mL), pyridinium p-toluenesulfonate (120 mg, 0.48 mmol), triethylamine (100 μL, 0.72 mmol), and N-succinimidyl 6-maleimidohexanoate (73 mg, 0.24 mmol) were added, and the resulting mixture was stirred at room temperature for 3 hours. The reaction solution was purified by silica gel flash column chromatography (Biotage AB) [tetrahydrofuran:acetone=3:7 to 7:3 (v/v)] to obtain the title compound as an oil. To 19.5 mg of the obtained oil, acetone (0.4 mL) and 2-butanol (0.2 mL) were added, and the resulting mixture was warmed to about 60° C. The precipitated solid was filtered at room temperature, and the solid separated by the filtration was washed with 2-butanol (about 0.2 mL) to obtain the title compound (14.3 mg) as a colorless powder. The obtained powder was used as a seed crystal in the next reaction.

Example 22

N-[6-(2,5-Dioxo-2,5-dihydro-1H-pyrrol-1-yl)hexanoyl]glycylglycyl-L-phenylalanyl-N-[(2-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-2-oxoethoxy)methyl]glycinamide ("glycylglycyl-phenylalanyl-glycinamide" disclosed as SEQ ID NO: 11)

[Chem. 112]

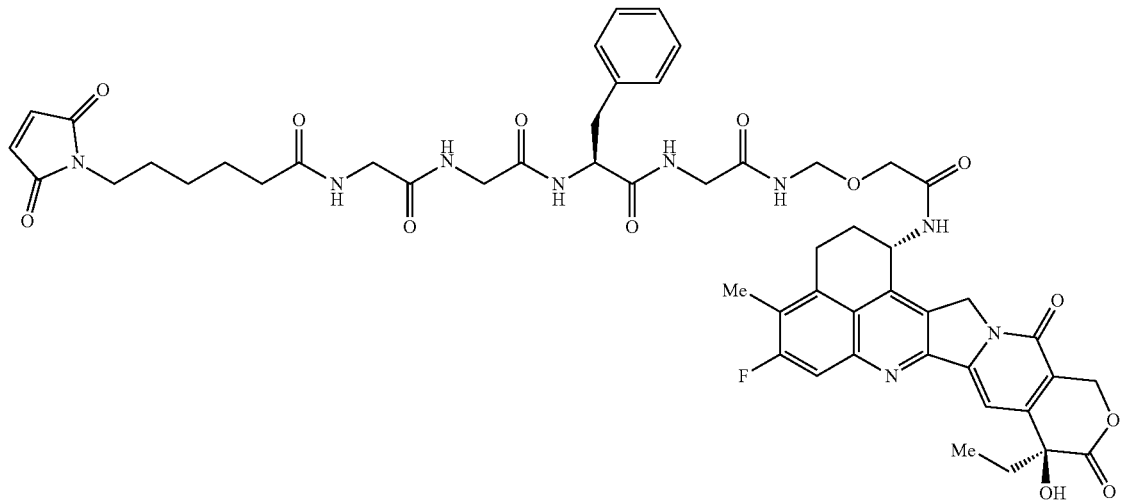

(1)

In pyridine (0.35 L), acetonitrile (1.1 L), and tetrahydrofuran (3.5 L), pyridinium p-toluenesulfonate (209 g, 0.832 mol), N-succinimidyl 6-maleimidohexanoate (128 g, 0.415 mol), and glycylglycyl-L-phenylalanyl-N-[(2-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl] amino}-2-oxoethoxy)methyl]glycinamide ("glycylglycyl-phenylalanyl-glycinamide" disclosed as SEQ ID NO: 11) (350 g, 0.416 mol) were dissolved under a nitrogen atmosphere. To the solution, triethylamine (63.2 g, 0.625 mol) was then added, and the resulting mixture was stirred at room temperature for 3.5 hours. Tetrahydrofuran (3.5 L), a 19% aqueous citric acid solution (3.5 L), ethyl acetate (2.5 L), and 18% saline (2.5 L) were added thereto, and the resulting mixture was stirred and then separated into organic and aqueous layers. To the obtained organic layer, a 19% aqueous citric acid solution (2.5 L) and 18% saline (2.5 L) were added, and the resulting mixture was stirred and then separated into organic and aqueous layers. The obtained organic layer was separated into organic and aqueous layers and washed with a 22% aqueous potassium bicarbonate solution (2.1 L) and subsequently with 18% saline (1.8 L). The obtained organic layer was added dropwise to a suspension of activated carbon (35 g) in acetonitrile (35 L) prepared in another container, and the resulting mixture was stirred for 30 minutes. Then, the activated carbon was separated by filtration, and the activated carbon thus separated by filtration was washed with acetonitrile (1.8 L). The obtained filtrate and washes were concentrated under reduced pressure at an external temperature of about 40° C. until the solvent was no longer distilled off. To the obtained concentrated residue, acetone (1.8 L) and 1-propanol (3.5 L) were added in this order, and the resulting mixture was dissolved by warming to 55° C. Then, the solution was cooled to room temperature. The powder (0.2 g) obtained in Example 21 was added thereto as a seed crystal, and the resulting mixture was stirred for 86 hours. Then, the precipitated solid was filtered, and the solid separated by the filtration was washed with acetone (1.1 L). The obtained solid was dried under reduced pressure at 40° C. to obtain the title compound (191 g, yield: 44%) in the form of crystals.

Example 23

N-[6-(2,5-Dioxo-2,5-dihydro-1H-pyrrol-1-yl)
hexanoyl]glycylglycyl-L-phenylalanyl-N-[(2-{[(1S,
9S)-9-ethyl-5-fluoro-9-hydroxy-4-methyl-10,13-
dioxo-2,3,9,10,13,15-hexahydro-1H,12H-benzo[de]
pyrano[3',4':6,7]indolizino[1,2-b]quinolin-1-yl]
amino}-2-oxoethoxy)methyl] glycinamide
("glycylglycyl-phenylalanyl-glycinamide" disclosed
as SEQ ID NO: 11)

[Chem. 113]

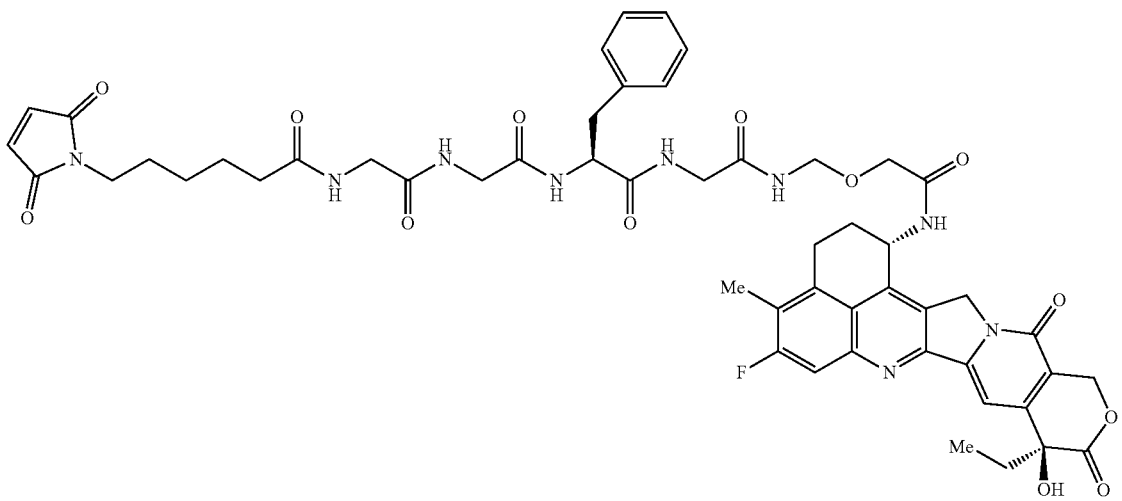

(1)

To anhydrous sodium sulfate (1.8 g), ethyl cyano(hydroxyimino)acetate (0.16 g, 1.13 mmol), and a mixed solution of purified water and tetrahydrofuran (24 mL and 18 mL) containing N-[6-(2,5-dioxo-2,5-dihydro-1H-pyrrol-1-yl)hexanoyl]glycylglycyl-L-phenylalanyl-N-[(carboxymethoxy)methyl] glycinamide ("glycylglycyl-phenylalanyl-glycinamide" disclosed as SEQ ID NO: 11) (gross amount: 5.76 g, internal content after conversion into 12.40% 1,2-dimethoxyethane: 5.05 g, 8.18 mmol), a mixed suspension of purified water and tetrahydrofuran (9 mL and 15 mL) containing (1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-aminium methanesulfonate (3.0 g, 5.64 mmol) was added at 20 to 30° C. To the mixed solution, tetrahydrofuran (9 mL) and a solution of tetrahydrofuran (7.5 mL) containing N-methylmorpholine (0.63 g, 6.23 mmol) were added, and the resulting mixture was stirred at the same temperature as the above for 15 minutes. Then, 1-(3-dimethylaminopropyl)-3-ethylcarbodiimide hydrochloride (2.16 g, 11.27 mmol) and a mixed solution of purified water and tetrahydrofuran (1.5 mL and 1.5 mL) were added thereto. The mixed solution was stirred at 20 to 30° C. for 30 minutes or longer. After confirmation of termination of the reaction, the reaction mixture was separated into organic and aqueous layers, and the aqueous layer was removed. The temperature of the organic layer was adjusted to 15 to 25° C., then ethyl acetate (36 mL), anhydrous sodium sulfate (1.26 g), and purified water (24 mL) containing N-methylmorpholine (0.14 g, 1.38 mmol) were added thereto, and the resulting mixture was stirred and separated into organic and aqueous layers. The aqueous layer was removed. Purified water (9 mL) was added to the organic layer, and the resulting mixture was stirred and separated into organic and aqueous layers. Purified water (9 mL) containing acetic acid (0.45 mL) was further added thereto, and the resulting mixture was stirred and separated into organic and aqueous layers to obtain an organic layer. Activated carbon (0.30 g, Kyoryoku Shirasagi (manufactured by Osaka Gas Chemicals Co., Ltd.)) was added thereto, and the resulting mixture was stirred at room temperature for about 15 minutes. Then, the activated carbon was separated by filtration, then the activated carbon was washed with tetrahydrofuran (9 mL), and the washes were combined with the filtrate. The resulting mixture was concentrated to 30 mL under reduced pressure. Tetrahydrofuran (75 mL) was added to the concentrate, and the resulting mixture was concentrated to 30 mL under reduced pressure. Tetrahydrofuran (45 mL) was further added to the residue, and the resulting mixture was concentrated to 30 mL under reduced pressure. After confirmation that the water content of the concentrate was 8.0% (v/v) or less, a mixed solution of acetone and 1-propanol (30 mL and 71 mL) was added thereto. N-[6-(2,5-Dioxo-2,5-dihydro-1H-pyrrol-1-yl)hexanoyl]glycylglycyl-L-phenylalanyl-N-[(2-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-2-oxoethoxy)methyl]glycinamide ("glycylglycyl-phenylalanyl-glycinamide" disclosed as SEQ ID NO: 11) (30 mg) was added thereto, and the resulting mixture was stirred at 20 to 30° C. for 12 hours or longer. The suspension was cooled to 0 to 5° C. and then further stirred for 24 hours or longer. Precipitates were filtered, and a powder separated by the filtration was washed with a 1:1 mixed solution of acetone and 1-propanol (30 mL) at 0 to 5° C. The obtained crystals were dried under reduced pressure at 35° C. to obtain crude crystals of N-[6-(2,5-dioxo-2,5-dihydro-1H-pyrrol-1-yl)hexanoyl]glycylglycyl-L-phenylalanyl-N-[(2-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-2-oxoethoxy)methyl]glycinamide ("glycylglycyl-phenylalanyl-glycinamide" disclosed as SEQ ID NO: 11) (5.23 g, yield: 89.6%).

To the crude crystals of N-[6-(2,5-dioxo-2,5-dihydro-1H-pyrrol-1-yl)hexanoyl]glycylglycyl-L-phenylalanyl-N-[(2-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-2-oxoethoxy)methyl]glycinamide ("glycylglycyl-phenylalanyl-glycinamide" disclosed as SEQ ID NO: 11) (4.50 g, 4.35 mmol), a mixed solution of acetone and purified water (10.6 mL and 2.9 mL) containing acetic acid (15 µL) was added, and the resulting mixture was stirred at 34 to 38° C. for 1 hour or longer. After confirmation of dissolution, the solution was cooled to 20 to 25° C. A mixed solution of acetone and 1-propanol (31.5 mL and 64.8 mL) was added thereto, then N-[6-(2,5-dioxo-2,5-dihydro-1H-pyrrol-1-yl)hexanoyl]glycylglycyl-L-phenylalanyl-N-[(2-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-2-oxoethoxy)methyl]glycinamide ("glycylglycyl-phenylalanyl-glycinamide" disclosed as SEQ ID NO: 11) (27 mg) was added, and the resulting mixture was stirred at 20 to 25° C. for 24 hours or longer. The suspension was cooled to 0 to 5° C. and then further stirred for 12 hours or longer. Precipitates were filtered, and a powder separated by the filtration was washed with a 1:1 mixed solution of acetone and 1-propanol (27 mL) at 0 to 5° C. The obtained crystals were dried under reduced pressure at 35° C. to obtain purified crystals of N-[6-(2,5-dioxo-2,5-dihydro-1H-pyrrol-1-yl)hexanoyl]glycylglycyl-L-phenylalanyl-N-[(2-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-2-oxoethoxy)methyl]glycinamide ("glycylglycyl-phenylalanyl-glycinamide" disclosed as SEQ ID NO: 11) (4.37 g, yield: 93.0%).

The instrumental data was similar to that of the compound described in Example 14.

Example 24

N-[6-(2,5-Dioxo-2,5-dihydro-1H-pyrrol-1-yl)hexanoyl]glycylglycyl-L-phenylalanyl-N-[(2-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-2-oxoethoxy)methyl] glycinamide ("glycylglycyl-phenylalanyl-glycinamide" disclosed as SEQ ID NO: 11)

[Chem. 114]

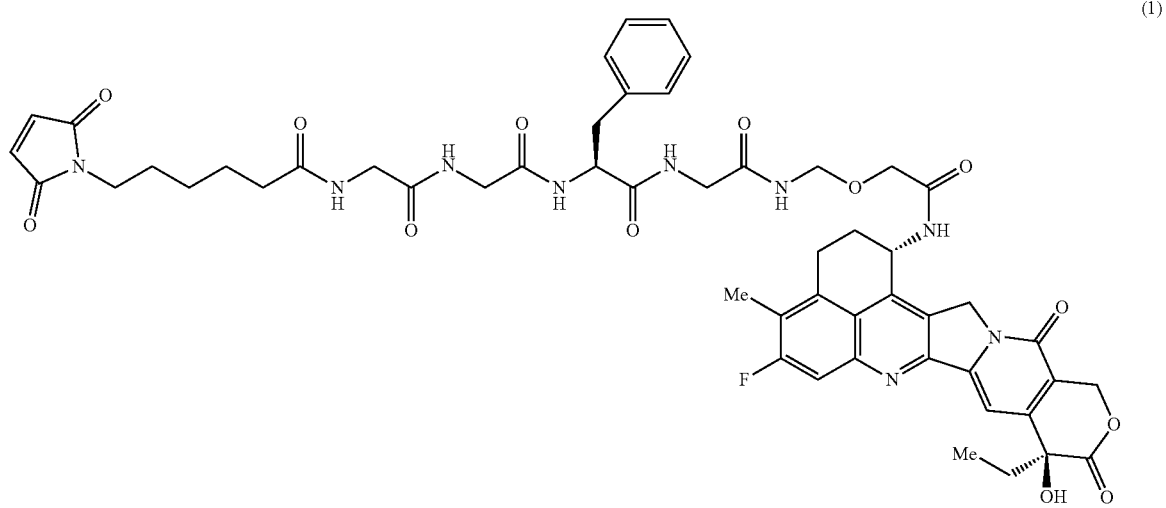

(1)

To anhydrous sodium sulfate (1.8 g), ethyl cyano(hydroxyimino)acetate (0.16 g, 1.13 mmol), and a mixed solution of purified water and tetrahydrofuran (24 mL and 18 mL) containing N-[6-(2,5-dioxo-2,5-dihydro-1H-pyrrol-1-yl)hexanoyl]glycylglycyl-L-phenylalanyl-N-[(carboxymethoxy)methyl]glycinamide ("glycylglycyl-phenylalanyl-glycinamide" disclosed as SEQ ID NO: 11) (gross amount: 5.76 g, internal content after conversion into 12.40% 1,2-dimethoxyethane: 5.05 g, 8.18 mmol), a mixed suspension of purified water and tetrahydrofuran (9 mL and 15 mL) containing (1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-aminium methanesulfonate (3.0 g, 5.64 mmol) was added at 20 to 30° C. To the mixed solution, tetrahydrofuran (9 mL) and a solution of tetrahydrofuran (7.5 mL) containing N-methylmorpholine (0.63 g, 6.23 mmol) were added, and the resulting mixture was stirred at the same temperature as the above for 15 minutes. Then, 1-(3-dimethylaminopropyl)-3-ethylcarbodiimide hydrochloride (2.16 g, 11.27 mmol) and a mixed solution of purified water and tetrahydrofuran (1.5 mL and 1.5 mL) were added thereto. The mixed solution was stirred at 20 to 30° C. for 30 minutes or longer. After confirmation of termination of the reaction, the reaction mixture was separated into organic and aqueous layers, and the aqueous layer was removed. The temperature of the organic layer was adjusted to 15 to 25° C., then ethyl acetate (36 mL), anhydrous sodium sulfate (1.26 g), and purified water (24 mL) containing N-methylmorpholine (0.14 g, 1.38 mmol) were added thereto, and the resulting mixture was stirred and separated into organic and aqueous layers. The aqueous layer was removed. Purified water (9 mL) was added to the organic layer, and the resulting mixture was stirred and separated into organic and aqueous layers. Purified water (9 mL) containing acetic acid (0.45 mL) was further added thereto, and the resulting mixture was stirred and separated into organic and aqueous layers to obtain an organic layer. Activated carbon (0.30 g, Kyoryoku Shirasagi (manufactured by Osaka Gas Chemicals Co., Ltd.)) was added thereto, and the resulting mixture was stirred at room temperature for about 15 minutes or longer. Then, the activated carbon was separated by filtration, then the activated carbon was washed with tetrahydrofuran (9 mL), and the washes were combined with the filtrate. The resulting mixture was concentrated to 30 mL under reduced pressure. Tetrahydrofuran (75 mL) was added to the concentrate, and the resulting mixture was concentrated to 30 mL under reduced pressure. Tetrahydrofuran (45 mL) was further added to the residue, and the resulting mixture was concentrated to 30 mL under reduced pressure. After confirmation that the water content of the concentrate was 8.0% (v/v) or less, a mixed solution of acetone and 1-propanol (30 mL and 71 mL) was added thereto, and the resulting mixture was stirred at 20 to 30° C. for 22 hours. The suspension was cooled to 0 to 5° C. and then further stirred for 24 hours or longer. Precipitates were filtered, and a powder separated by the filtration was washed with a 1:1 mixed solution of acetone and 1-propanol (30 mL) at 0 to 5° C. The obtained crystals were dried under reduced pressure at 35° C. to obtain crystals of N-[6-(2,5-dioxo-2,5-dihydro-1H-pyrrol-1-yl)hexanoyl]glycylglycyl-L-phenylalanyl-N-[(2-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-2-oxoethoxy)methyl]glycinamide ("glycylglycyl-phenylalanyl-glycinamide" disclosed as SEQ ID NO: 11) (5.08 g, yield: 87.0%).

The instrumental data was similar to that of the compound described in Example 14.

Free Text of Sequence Listing

SEQ ID NO: 1—Amino acid sequence of a heavy chain of the anti-HER2 antibody

SEQ ID NO: 2—Amino acid sequence of a light chain of the anti-HER2 antibody

SEQ ID NO: 3—Amino acid sequence of a heavy chain of the anti-HER3 antibody

SEQ ID NO: 4—Amino acid sequence of a light chain of the anti-HER3 antibody

SEQ ID NO: 5—Amino acid sequence of a heavy chain of the anti-TROP2 antibody

SEQ ID NO: 6—Amino acid sequence of a light chain of the anti-TROP2 antibody

SEQ ID NO: 7—Amino acid sequence of a heavy chain of the anti-B7-H3 antibody

SEQ ID NO: 8—Amino acid sequence of a light chain of the anti-B7-H3 antibody

SEQ ID NO: 9—Amino acid sequence of a heavy chain of the anti-GPR20 antibody

SEQ ID NO: 10—Amino acid sequence of a light chain of the anti-GPR20 antibody

The invention claimed is:
1. Crystals of the compound represented by formula (1):

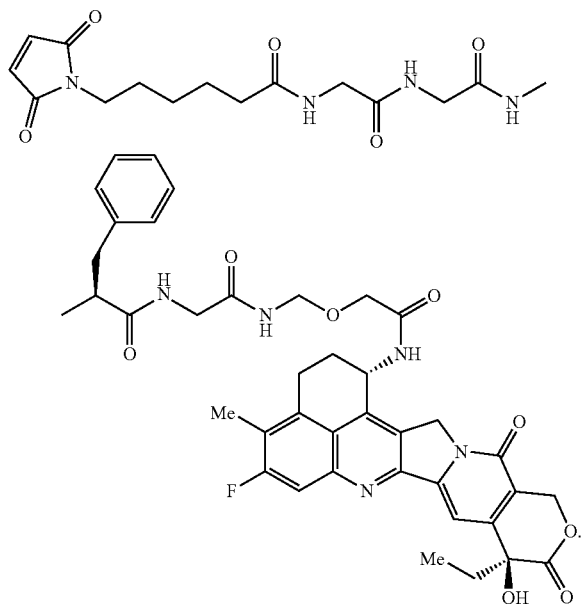

(1)

(SEQ ID NO: 11)

2. The crystals according to claim 1, wherein the crystals show main peaks at diffraction angles (2θ) of 5.6±0.2°, 15.5±0.2° and 22.0±0.2° in powder X-ray diffraction obtained by irradiation with copper Kα radiation.

3. A method for producing crystals of the compound represented by formula (1):

comprising the steps of: preparing a solution in which the compound represented by the formula (1) is dissolved, wherein the solution comprises a lower ketone and a lower alcohol as solvents, wherein the lower ketone is acetone and the lower alcohol is 1-propanol or 2-butanol; and then precipitating crystals of the compound represented by the formula (1) from the solution.

4. The production method according to claim 3, wherein the crystals of the compound represented by the formula (1) show main peaks at diffraction angles (2θ) of 5.6±0.2°, 15.5±0.2° and 22.0±0.2° in powder X-ray diffraction obtained by irradiation with a copper Kα radiation.

5. The production method according to claim 3, wherein the lower alcohol is 1-propanol.

6. The production method according to claim 3, wherein the lower alcohol is 2-butanol.

7. The production method according to claim 3, comprising a step of adding a seed crystal of the crystals of the compound represented by the formula (1).

8. The production method according to claim 3, wherein the compound represented by the formula (1) is produced by a production method (I), wherein the production method (I) is a production method comprising the steps of:

deprotecting protecting groups for an amino group and a carboxy group of a compound represented by formula (B):

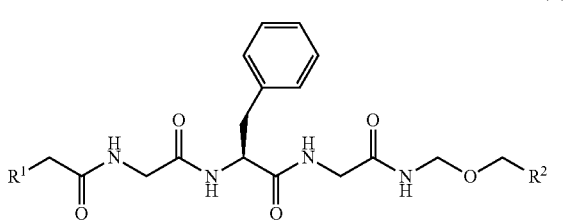

(B)

wherein $R^1$ represents an amino group protected with a protecting group, and $R^2$ represents a carboxy group protected with a protecting group, to convert it into the compound represented by formula (8):

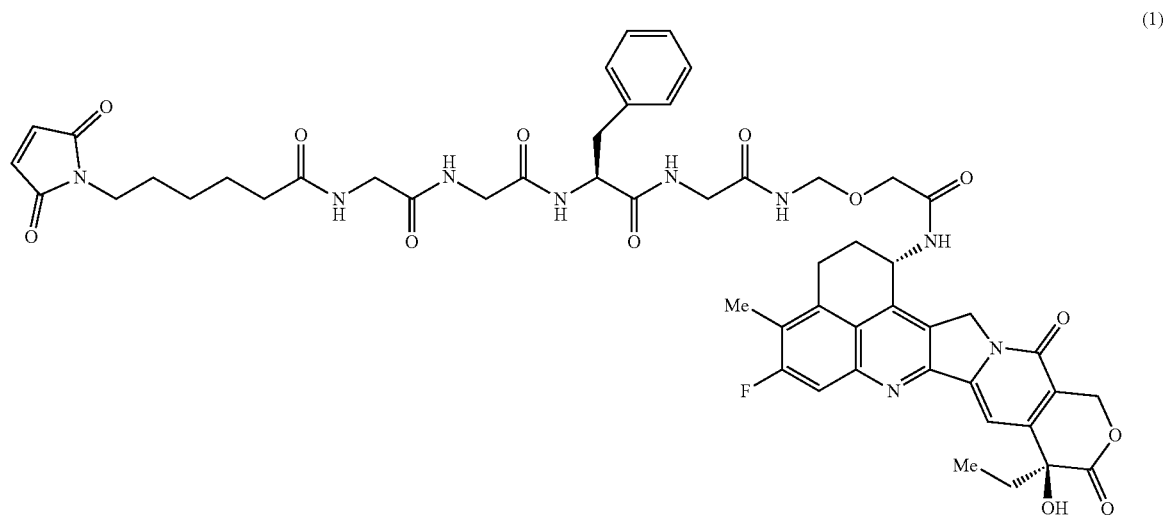

(8)

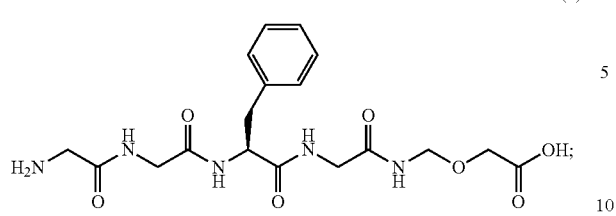

then
condensing the compound represented by the formula (8) with a compound represented by formula (C):

(C)

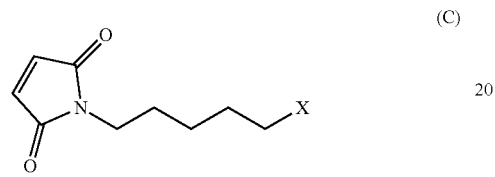

wherein X represents an active ester group or a carboxy group, to convert it into the compound represented by formula (10):

(10)

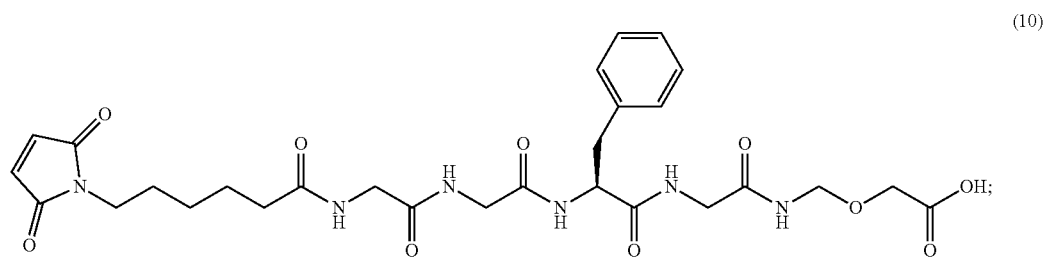

and then
condensing the compound represented by the formula (10) with the compound represented by formula (11):

(11)

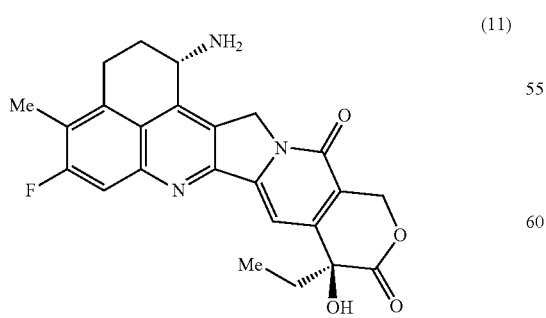

to convert it into the compound represented by the formula (1):

(1)

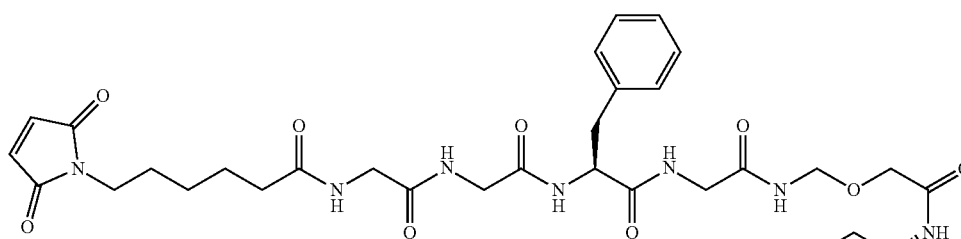
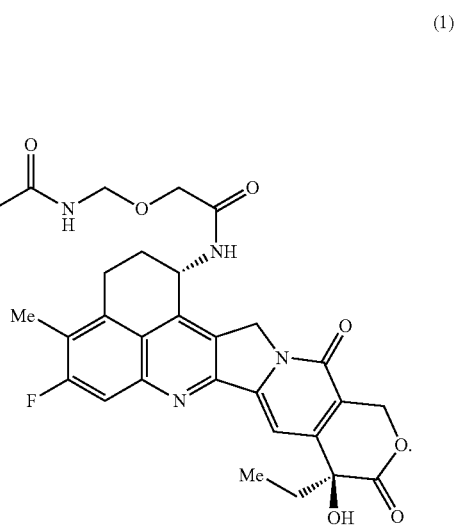

9. The production method according to claim 3, wherein the compound represented by the formula (1) is produced by a production method (II), wherein the production method (II) is a production method comprising the steps of:

deprotecting a protecting group for an amino group of a compound represented by formula (B):

(B)

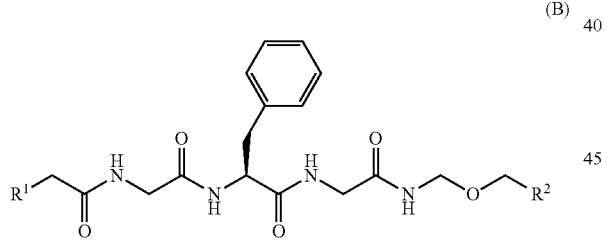

wherein $R^1$ represents an amino group protected with a protecting group, and $R^2$ represents a carboxy group protected with a protecting group, to convert it into a compound represented by formula (D):

(D)

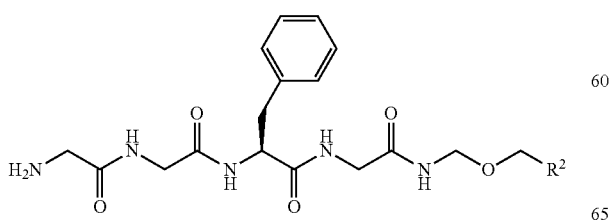

wherein $R^2$ represents the same meaning as above; then condensing the compound represented by the formula (D) with a compound represented by formula (C):

(C)

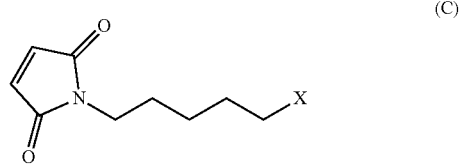

wherein X represents an active ester group or a carboxy group, to convert it into a compound represented by formula (E):

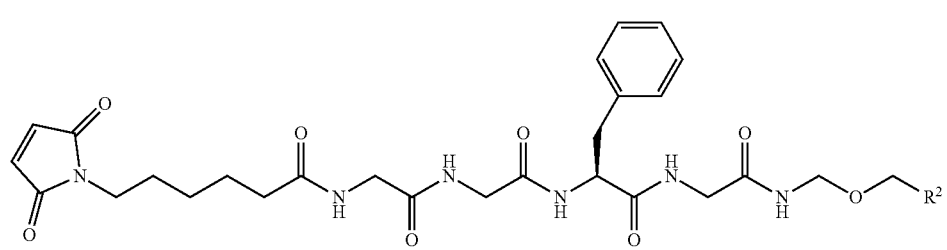
(E)

wherein R² represents the same meaning as above; then deprotecting the protecting group for the carboxy group of the compound represented by the formula (E) to convert it into the compound represented by formula (10):

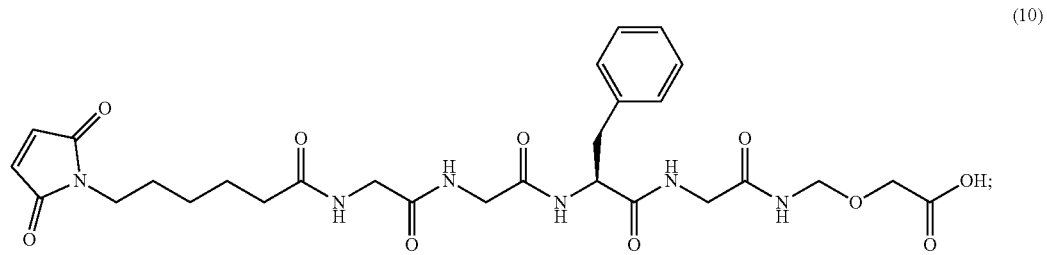
(10)

and then
condensing the compound represented by the formula (10) with the compound represented by formula (11):

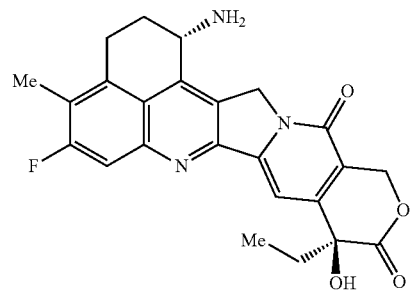
(11)

to convert it into the compound represented by the formula (1):

(1)

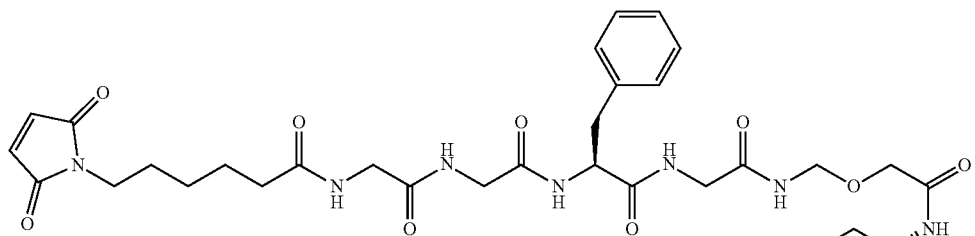
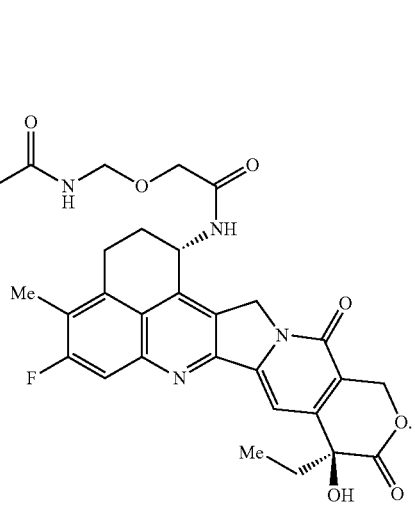

10. The production method according to claim 8, comprising the steps of: dissolving the compound represented by the formula (10) in a solvent containing 1,2-dimethoxyethane; and then precipitating crystals of a 1,2-dimethoxyethane adduct of the compound represented by the formula (10).

11. The production method according to claim 10, wherein the crystals of the 1,2-dimethoxyethane adduct of the compound represented by the formula (10) show main peaks at diffraction angles (2θ) of 19.0±0.2° and 25.0±0.2° in powder X-ray diffraction obtained by irradiation with a copper Kα radiation.

12. The production method according to claim 8, wherein the step of condensing the compound represented by the formula (10) and the compound represented by the formula (11) to convert it into the compound represented by the formula (1) is performed in a two-phase system of an aqueous sodium sulfate solution and tetrahydrofuran.

13. The production method according to claim 3, wherein the compound represented by the formula (1) is produced by a production method (III), wherein the production method (III) is a production method comprising the steps of:

deprotecting a protecting group for a carboxy group of a compound represented by formula (B):

(B)

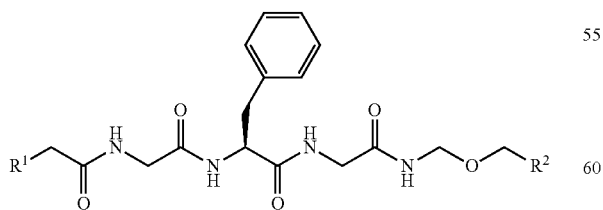

wherein $R^1$ represents an amino group protected with a protecting group, and $R^2$ represents a carboxy group protected with a protecting group, to convert it into a compound represented by formula (F):

(F)

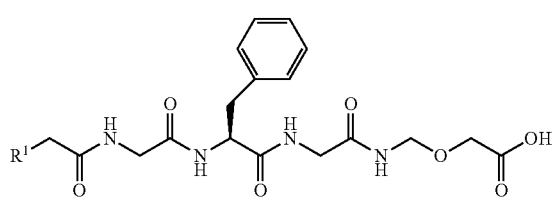

wherein $R^1$ represents the same meaning as above; then condensing the compound represented by the formula (F) with the compound represented by formula (11):

(11)

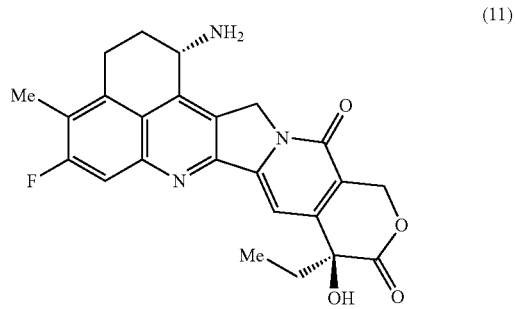 [SMILES: CC[C@@]1(O)C(=O)OCc2c1cc1n(c2=O)Cc2c-1nc1cc(F)c(C)c3c1c2[C@@H](N)CC3]

to convert it into a compound represented by formula (G):

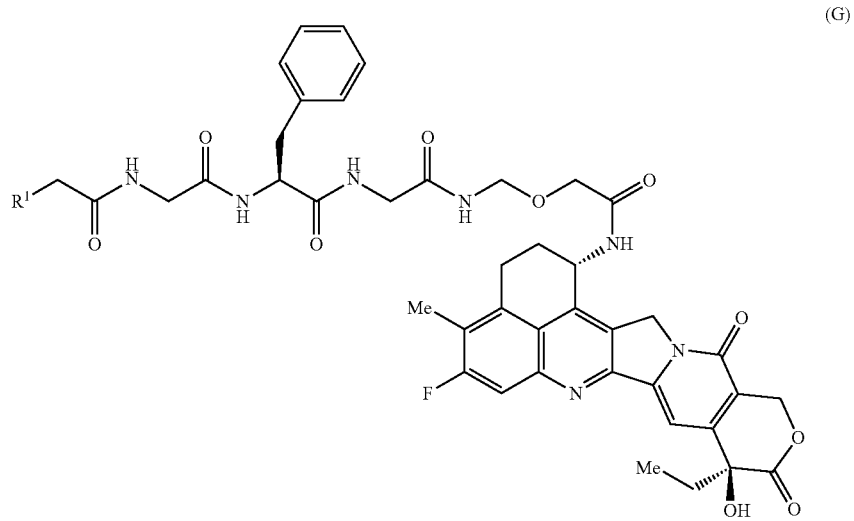

wherein R¹ represents the same meaning as above; then deprotecting the protecting group for the amino group of the compound represented by the formula (G) to convert it into the compound represented by formula (16):

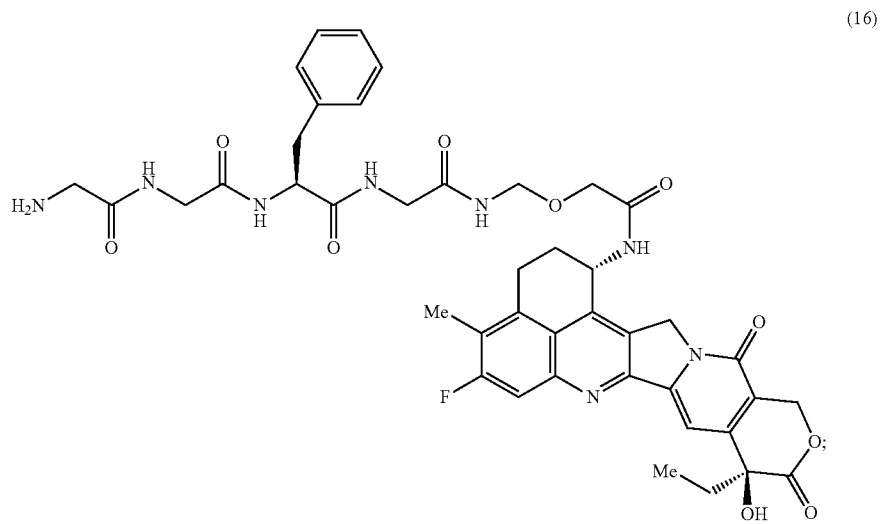 [SMILES: CC[C@@]1(O)C(=O)OCc2c1cc1n(c2=O)Cc2c-1nc1cc(F)c(C)c3c1c2[C@@H](NC(=O)COCNC(=O)CNC(=O)[C@H](Cc1ccccc1)NC(=O)CNC(=O)CN)CC3]

and then
condensing the compound represented by the formula (16) with a compound represented by formula (C):

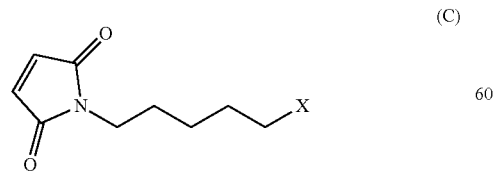

wherein X represents an active ester group or a carboxy group, to convert it into the compound represented by the formula (1):

(1)

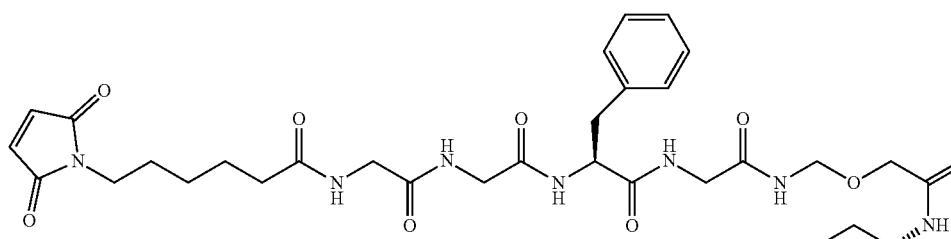
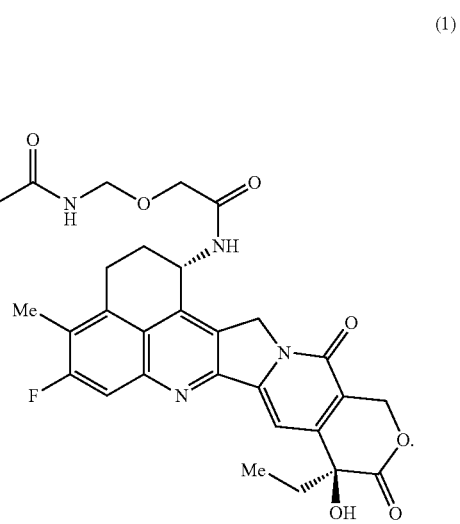

14. The production method according to claim 8, wherein the compound represented by the formula (11) is in the form of a methanesulfonic acid salt.

15. The production method according to claim 8, wherein the compound represented by the formula (11) is in the form of a methanesulfonic acid salt m-hydrate, wherein m is in the range of 0 to 3.

16. The production method according to claim 8, wherein the compound represented by the formula (11) is in the form of a methanesulfonic acid salt dihydrate.

17. The production method according to claim 8, wherein the compound represented by the formula (B) is produced by a production method (IV),
wherein the production method (IV) is a production method comprising the steps of:
reacting a compound represented by formula (H):

(H)

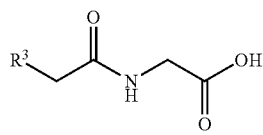

wherein $R^3$ represents an amino group protected with a protecting group, with lead tetraacetate to convert it into a compound represented by formula (J):

(J)

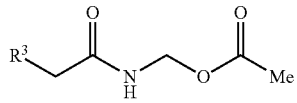

wherein $R^3$ represents the same meaning as above; then reacting the compound represented by the formula (J) with a compound represented by formula (K):

(K)

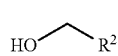

wherein $R^2$ represents the same meaning as the $R^2$ according to claim 8, in the presence of an acid or a base to convert it into a compound represented by formula (L):

(L)

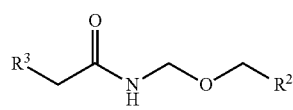

wherein $R^2$ and $R^3$ represent the same meanings as above; then
deprotecting the protecting group for the amino group of the compound represented by the formula (L) to convert it into a compound represented by formula (M):

(M)

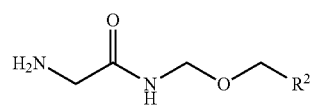

wherein $R^2$ represents the same meaning as above; and then
condensing the compound represented by the formula (M) with a compound represented by formula (N):

(N)

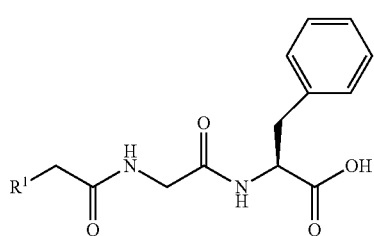

wherein $R^1$ represents the same meaning as the $R^1$ according to claim 8, to convert it into the compound represented by the formula (B):

(B)

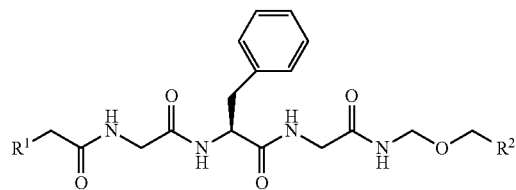

wherein R¹ and R² represent the same meanings as above.

18. The production method according to claim 17, wherein the step of reacting the compound represented by the formula (H) with lead tetraacetate to convert it into the compound represented by the formula (J) is performed in the presence of acetic acid.

19. The production method according to claim 17, wherein the step of reacting the compound represented by the formula (J) with the compound represented by the formula (K) to convert it into the compound represented by the formula (L) is performed in the presence of an aqueous sodium hydroxide solution.

20. The production method according to claim 17, wherein the step of reacting the compound represented by the formula (J) with the compound represented by the formula (K) to convert it into the compound represented by the formula (L) is performed in the presence of tris(pentafluorophenyl)borane.

21. The production method according to claim 17, comprising a step of adding an acid to precipitate a salt of the compound represented by the formula (M) and the acid after the step of deprotecting the protecting group for the amino group of the compound represented by the formula (L) to convert it into the compound represented by the formula (M).

22. The production method according to claim 21, wherein the acid is 1-hydroxybenzotriazole.

23. The production method according to claim 8, wherein R¹ is an amino group protected with a benzyloxycarbonyl group.

24. The production method according to claim 8, wherein R¹ is an amino group protected with a (9H-fluoren-9-ylmethoxy)carbonyl group.

25. The production method according to claim 8, wherein R² is a carboxy group protected with a benzyl group.

26. The production method according to claim 17, wherein R³ is an amino group protected with a (9H-fluoren-9-ylmethoxy)carbonyl group.

27. The production method according to claim 8, wherein X is a (2,5-dioxopyrrolidin-1-yl)oxycarbonyl group.

28. The production method according to claim 3, wherein the compound represented by the formula (1) is produced by a production method (V),
wherein the production method (V) is a production method comprising the steps of:
reacting the compound represented by formula (2):

(2)

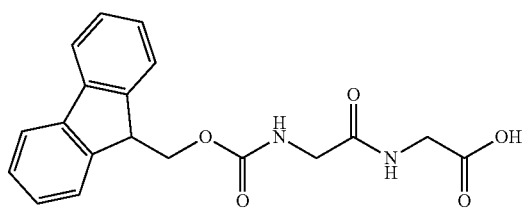

with lead tetraacetate to convert it into the compound represented by formula (3):

(3)

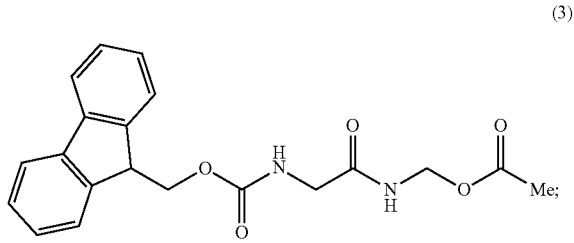

then reacting the compound represented by the formula (3) with benzyl glycolate in the presence of an acid or a base to convert it into the compound represented by formula (4):

(4)

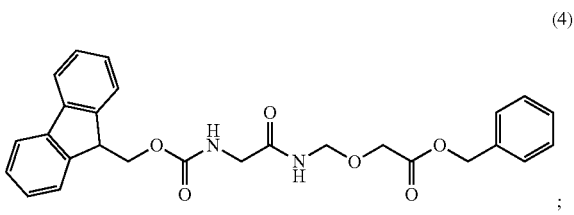

then deprotecting a protecting group for an amino group of the compound represented by the formula (4) to convert it into the compound represented by formula (5):

(5)

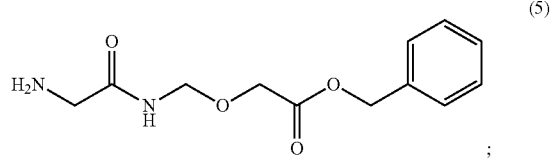

then condensing the compound represented by the formula (5) with the compound represented by formula (6):

(6)

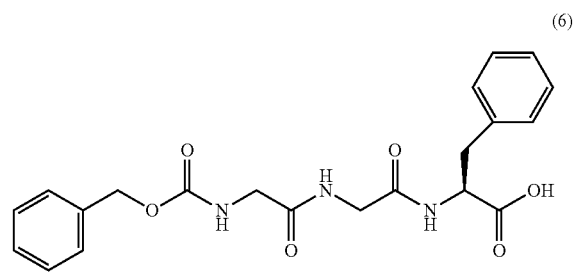

to convert it into the compound represented by formula (7):

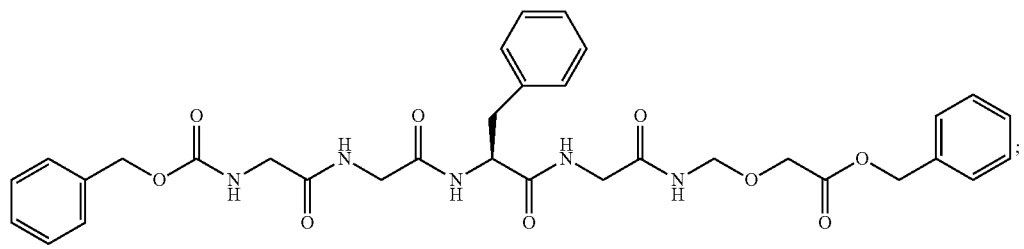
(7)

then deprotecting protecting groups for an amino group and a carboxy group of the compound represented by the formula (7) to convert it into the compound represented by formula (8):

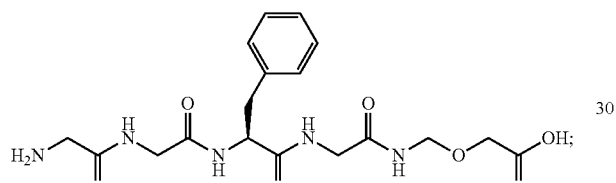
(8)

then condensing the compound represented by the formula (8) with the compound represented by formula (9):

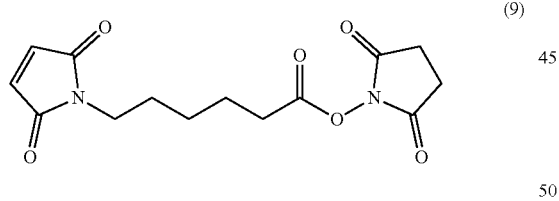
(9)

to convert it into the compound represented by formula (10):

and then condensing the compound represented by the formula (10) with the compound represented by formula (11):

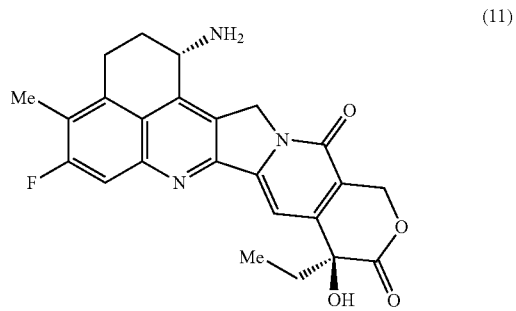
(11)

to convert it into the compound represented by formula (1):

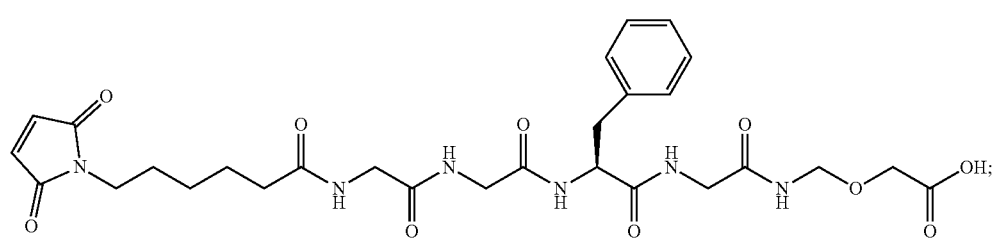
(10)

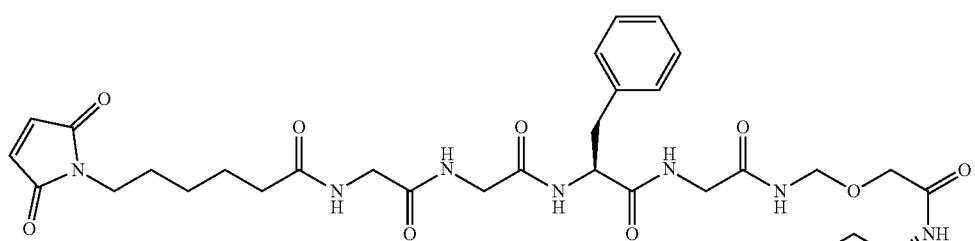
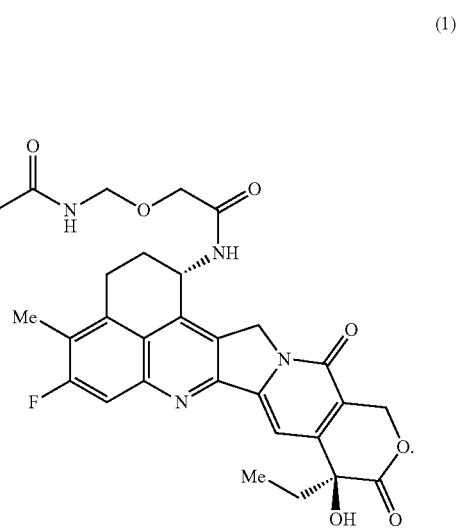

(1)

29. The production method according to claim 28, comprising the steps of: dissolving the compound represented by the formula (10) in a solvent containing 1,2-dimethoxyethane; and then precipitating crystals of a 1,2-dimethoxyethane adduct of the compound represented by the formula (10).

30. The production method according to claim 29, wherein the crystals of the 1,2-dimethoxyethane adduct of the compound represented by the formula (10) show main peaks at diffraction angles (2θ) of 19.0±0.2° and 25.0±0.2° in powder X-ray diffraction obtained by irradiation with a copper Kα radiation.

31. The production method according to claim 28, wherein the step of condensing the compound represented by the formula (10) with the compound represented by the formula (11) to convert it into the compound represented by the formula (1) is performed in a two-phase system of an aqueous sodium sulfate solution and tetrahydrofuran.

32. The production method according to claim 3, wherein the compound represented by the formula (1) is produced by a production method (VI), wherein the production method (VI) is a production method comprising the steps of:

reacting the compound represented by formula (2):

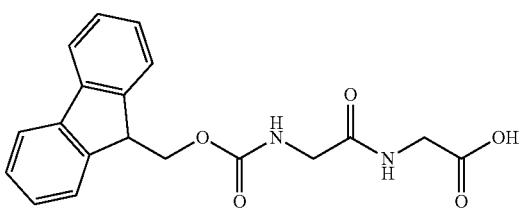

(2)

with lead tetraacetate to convert it into the compound represented by formula (3):

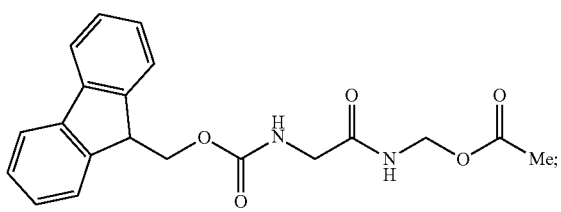

(3)

then
reacting the compound represented by the formula (3) with benzyl glycolate in the presence of an acid or a base to convert it into the compound represented by formula (4):

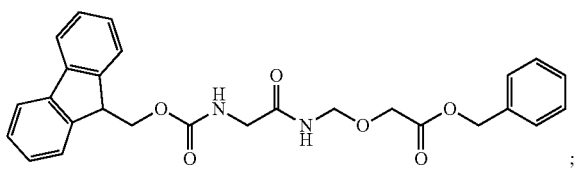

(4)

then
deprotecting a protecting group for an amino group of the compound represented by the formula (4) to convert it into the compound represented by formula (5):

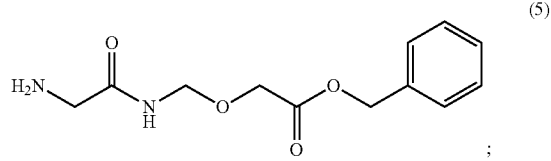

(5)

then
condensing the compound represented by the formula (5) with the compound represented by formula (12):

(12)
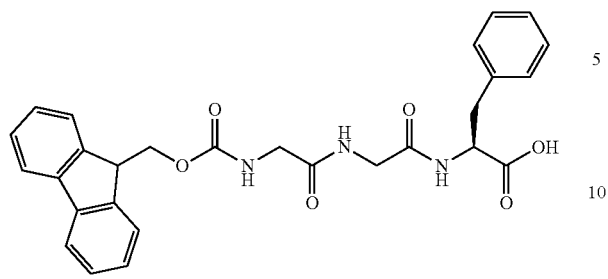
to convert it into the compound represented by formula (13):
(13)
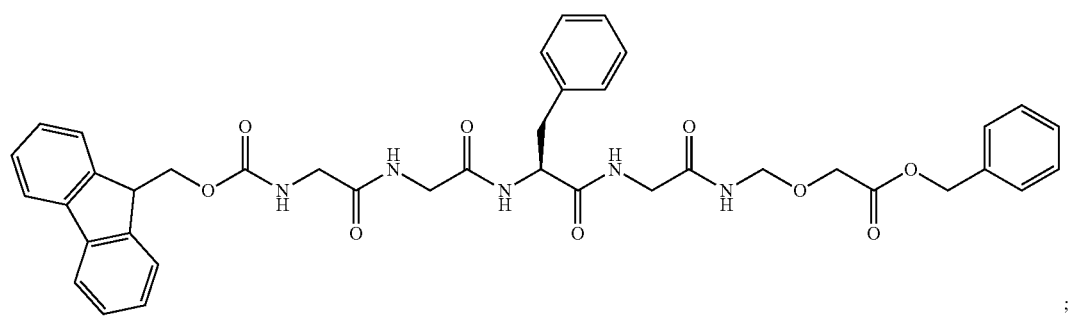
then
deprotecting a protecting group for a carboxy group of the compound represented by the formula (13) to convert it into the compound represented by formula (14):
(14)
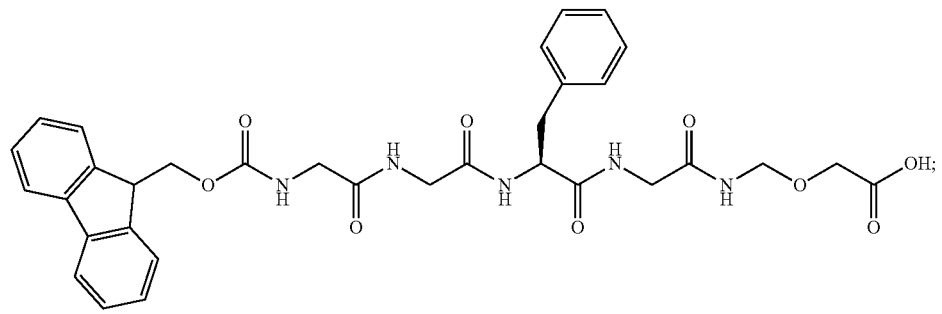
then
condensing the compound represented by the formula (14) with the compound represented by formula (11):
(11)
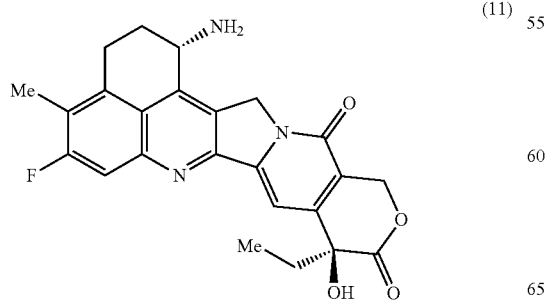

to convert it into the compound represented by formula (15):
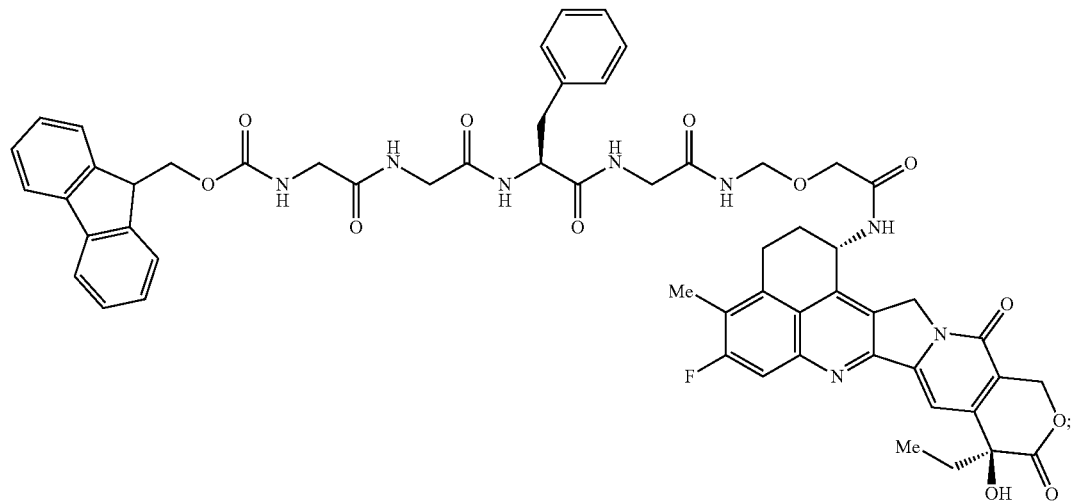
(15)
then
deprotecting a protecting group for an amino group of the compound represented by the formula (15) to convert it into the compound represented by formula (16):
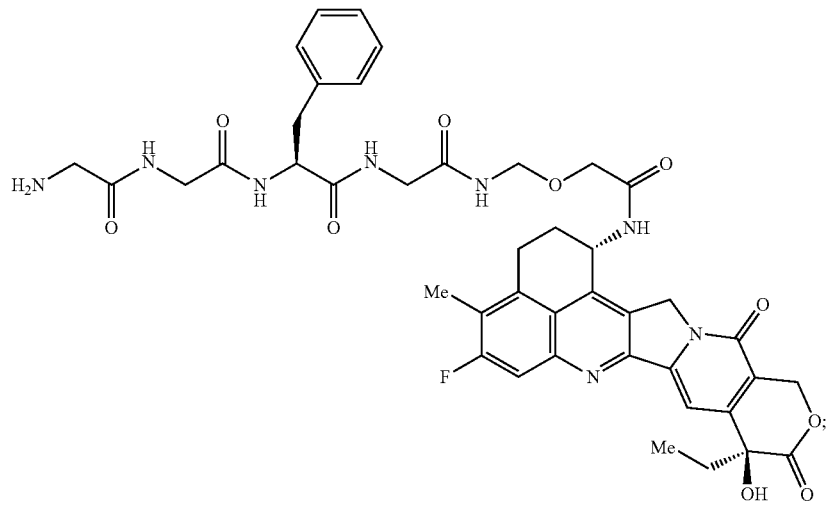
(16)
and then
condensing the compound represented by the formula (16) with the compound represented by formula (9):
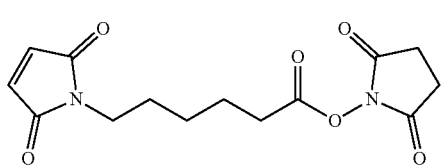
(9)

to convert it into the compound represented by the formula (1):

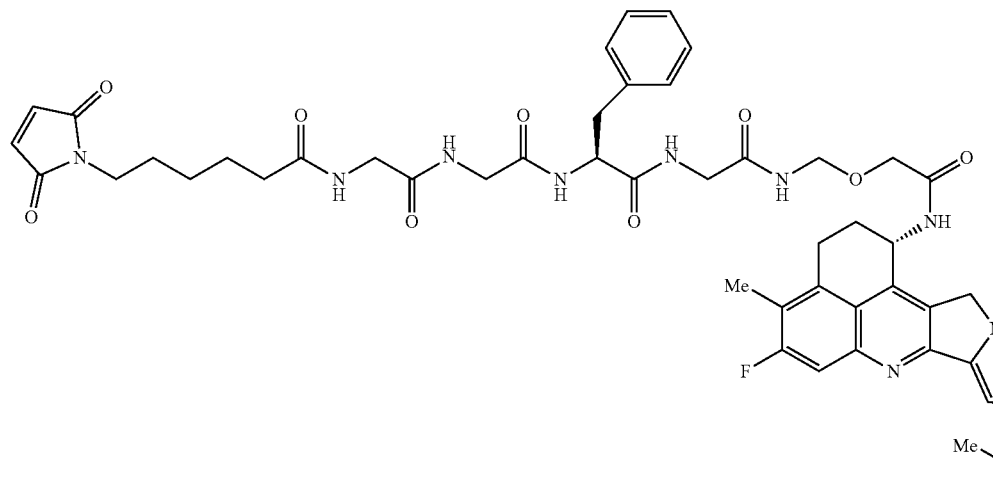

33. The production method according to claim 28, wherein the step of reacting the compound represented by the formula (2) with lead tetraacetate to convert it into the compound represented by the formula (3) is performed in the presence of acetic acid.

34. The production method according to claim 28, wherein the step of converting the compound represented by the formula (3) into the compound represented by the formula (4) is performed in the presence of an aqueous sodium hydroxide solution.

35. The production method according to claim 28, wherein the step of converting the compound represented by the formula (3) into the compound represented by the formula (4) is performed in the presence of tris(pentafluorophenyl)borane.

36. The production method according to claim 28, comprising a step of adding an acid to precipitate a salt of the compound represented by the formula (5) and the acid after the step of deprotecting the protecting group for the amino group of the compound represented by the formula (4) to convert it into the compound represented by the formula (5).

37. The production method according to claim 36, wherein the acid is 1-hydroxybenzotriazole.

38. The production method according to claim 28, wherein the compound represented by the formula (6) is produced by a method comprising the steps of:
condensing the compound represented by formula (23):

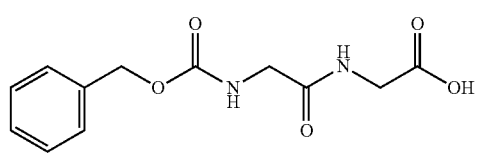

with N-hydroxysuccinimide to convert it into the compound represented by formula (24):

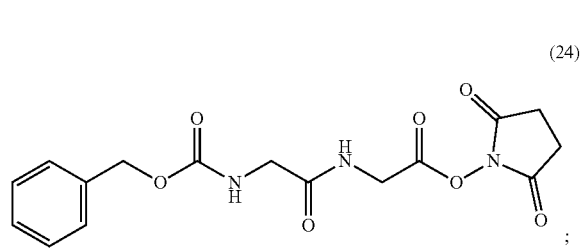 [SMILES: O=C(CNC(=O)OCc1ccccc1)NCC(=O)ON1C(=O)CCC1=O]

and then
condensing the compound represented by the formula (24) with L-phenylalanine to convert it into the compound represented by the formula (6).

39. The production method according to claim 28, wherein the compound represented by the formula (9) is produced by a method comprising the steps of:
reacting the compound represented by formula (17):

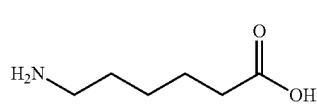

with maleic anhydride to convert it into the compound represented by formula (18):

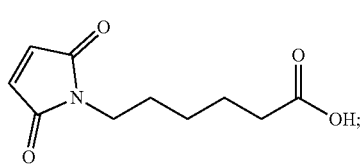

and then
adding thionyl chloride to the compound represented by the formula (18) and a mixed solution containing N-hydroxysuccinimide and 2,6-lutidine to convert it into the compound represented by the formula (9).

40. The production method according to claim 28, wherein the compound represented by the formula (11) is in the form of a methanesulfonic acid salt.

41. The production method according to claim 28, wherein the compound represented by the formula (11) is in the form of a methanesulfonic acid salt m-hydrate, wherein m is in the range of 0 to 3.

42. The production method according to claim 28, wherein the compound represented by the formula (11) is in the form of a methanesulfonic acid salt dihydrate.

43. A method for producing an antibody-drug conjugate in which a drug-linker represented by formula (19) is conjugated to an antibody via a thioether bond:

by preparing a solution in which the compound represented by the formula (1) is dissolved, wherein the solution comprises a lower ketone and a lower alcohol as solvents, wherein the lower ketone is acetone and the lower alcohol is 1-propanol or 2-butanol; and then precipitating crystals of the compound represented by the formula (1) from the solution;

ii) reducing an antibody; and then iii) adding a solution in which the crystals of the compound represented by the formula (1) produced in step i) are dissolved, to react the solution with the reduced antibody.

44. The production method according to claim 43, wherein the antibody is an anti-HER2 antibody, an anti-HER3 antibody, an anti-TROP2 antibody, an anti-B7-H3 antibody, or an anti-GPR20 antibody.

45. The production method according to claim 44, wherein the antibody is an anti-HER2 antibody.

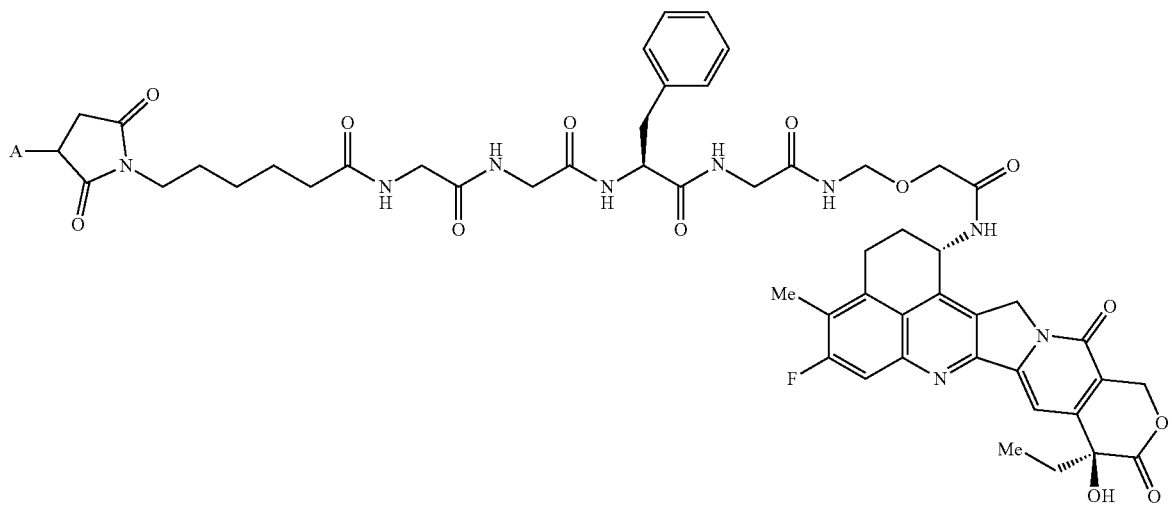

(19)

wherein A represents a connecting position to the antibody, wherein the method comprises the steps of:

i) producing crystals of a compound represented by formula (1):

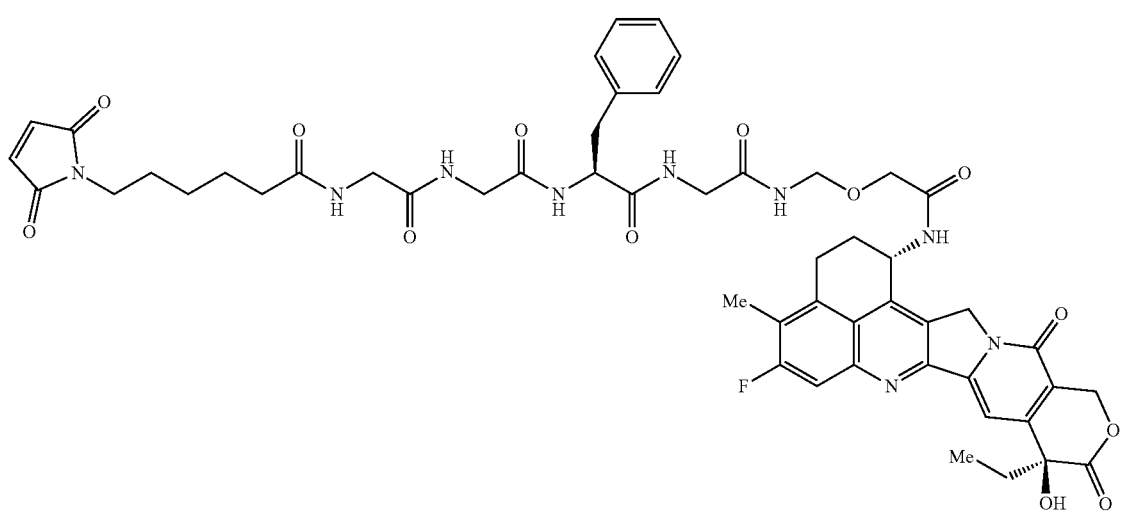

(1)

46. The production method according to claim 45, wherein the anti-HER2 antibody is an antibody comprising a heavy chain consisting of an amino acid sequence consisting of amino acid residues 1 to 449 of SEQ ID NO: 1 and a light chain consisting of an amino acid sequence consisting of amino acid residues 1 to 214 of SEQ ID NO: 2, or an antibody comprising a heavy chain consisting of the amino acid sequence represented by SEQ ID NO: 1 and a light chain consisting of the amino acid sequence represented by SEQ ID NO: 2.

47. The production method according to claim 46, wherein the anti-HER2 antibody is an antibody comprising a heavy chain consisting of an amino acid sequence consisting of amino acid residues 1 to 449 of SEQ ID NO: 1 and a light chain consisting of an amino acid sequence consisting of amino acid residues 1 to 214 of SEQ ID NO: 2.

48. The production method according to claim 46, wherein the anti-HER2 antibody is an antibody comprising a heavy chain consisting of the amino acid sequence represented by SEQ ID NO: 1 and a light chain consisting of the amino acid sequence represented by SEQ ID NO: 2.

49. The production method according to claim 44, wherein the antibody is an anti-HER3 antibody.

50. The production method according to claim 49, wherein the anti-HER3 antibody is an antibody comprising a heavy chain consisting of the amino acid sequence represented by SEQ ID NO: 3 and a light chain consisting of the amino acid sequence represented by SEQ ID NO: 4, or is an antibody comprising a heavy chain consisting of an amino acid sequence consisting of amino acid residues 1 to 446 of SEQ ID NO: 3 and a light chain consisting of the amino acid sequence represented by SEQ ID NO: 4.

51. The production method according to claim 50, wherein the anti-HER3 antibody is an antibody comprising a heavy chain consisting of the amino acid sequence represented by SEQ ID NO: 3 and a light chain consisting of the amino acid sequence represented by SEQ ID NO: 4.

52. The production method according to claim 50, wherein the anti-HER3 antibody is an antibody comprising a heavy chain consisting of an amino acid sequence consisting of amino acid residues 1 to 446 of SEQ ID NO: 3 and a light chain consisting of the amino acid sequence represented by SEQ ID NO: 4.

53. The production method according to Current claim 44, wherein the antibody is an anti-TROP2 antibody.

54. The production method according to claim 53, wherein the anti-TROP2 antibody is an antibody comprising a heavy chain consisting of an amino acid sequence consisting of amino acid residues 20 to 470 of SEQ ID NO: 5 and a light chain consisting of an amino acid sequence consisting of amino acid residues 21 to 234 of SEQ ID NO: 6, or an antibody comprising a heavy chain consisting of an amino acid sequence consisting of amino acid residues 20 to 469 of SEQ ID NO: 5 and a light chain consisting of an amino acid sequence consisting of amino acid residues 21 to 234 of SEQ ID NO: 6.

55. The production method according to claim 54, wherein the anti-TROP2 antibody is an antibody comprising a heavy chain consisting of an amino acid sequence consisting of amino acid residues 20 to 470 of SEQ ID NO: 5 and a light chain consisting of an amino acid sequence consisting of amino acid residues 21 to 234 of SEQ ID NO: 6.

56. The production method according to claim 54, wherein the anti-TROP2 antibody is an antibody comprising a heavy chain consisting of an amino acid sequence consisting of amino acid residues 20 to 469 of SEQ ID NO: 5 and a light chain consisting of an amino acid sequence consisting of amino acid residues 21 to 234 of SEQ ID NO: 6.

57. The production method according to Current claim 44, wherein the antibody is an anti-B7-H3 antibody.

58. The production method according to claim 57, wherein the anti-B7-H3 antibody is an antibody comprising a heavy chain consisting of an amino acid sequence consisting of amino acid residues 20 to 471 of SEQ ID NO: 7 and a light chain consisting of an amino acid sequence consisting of amino acid residues 21 to 233 of SEQ ID NO: 8, or an antibody comprising a heavy chain consisting of an amino acid sequence consisting of amino acid residues 20 to 470 of SEQ ID NO: 7 and a light chain consisting of an amino acid sequence consisting of amino acid residues 21 to 233 of SEQ ID NO: 8.

59. The production method according to claim 58, wherein the anti-B7-H3 antibody is an antibody comprising a heavy chain consisting of an amino acid sequence consisting of amino acid residues 20 to 471 of SEQ ID NO: 7 and a light chain consisting of an amino acid sequence consisting of amino acid residues 21 to 233 of SEQ ID NO: 8.

60. The production method according to claim 58, wherein the anti-B7-H3 antibody is an antibody comprising a heavy chain consisting of an amino acid sequence consisting of amino acid residues 20 to 470 of SEQ ID NO: 7 and a light chain consisting of an amino acid sequence consisting of amino acid residues 21 to 233 of SEQ ID NO: 8.

61. A method for producing an antibody-drug conjugate in which a drug-linker represented by formula (19) is conjugated to an antibody via a thioether bond:

(19)

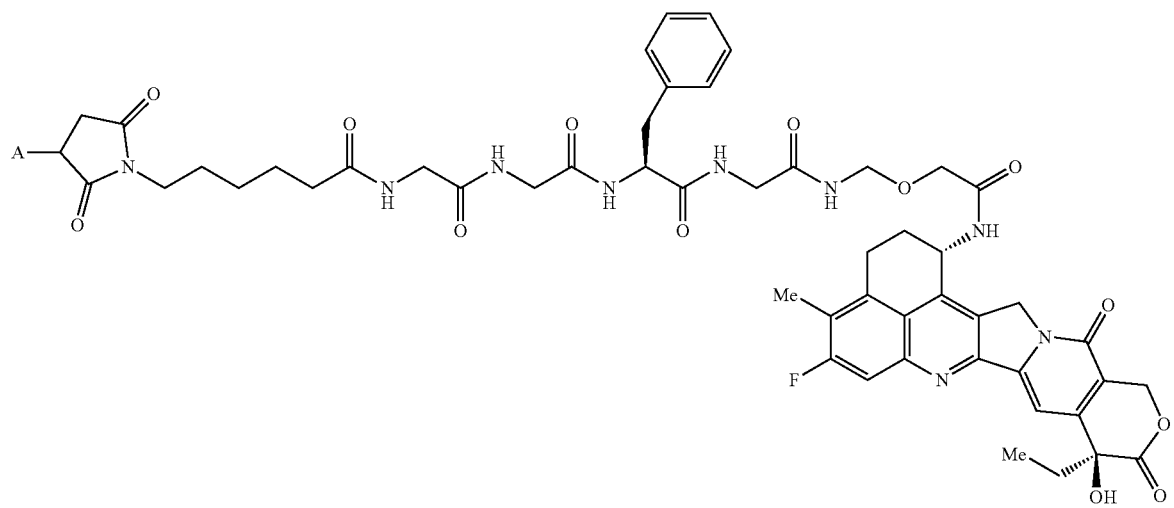

wherein A represents a connecting position to the antibody, wherein crystals of the compound represented by formula (1):

(1)

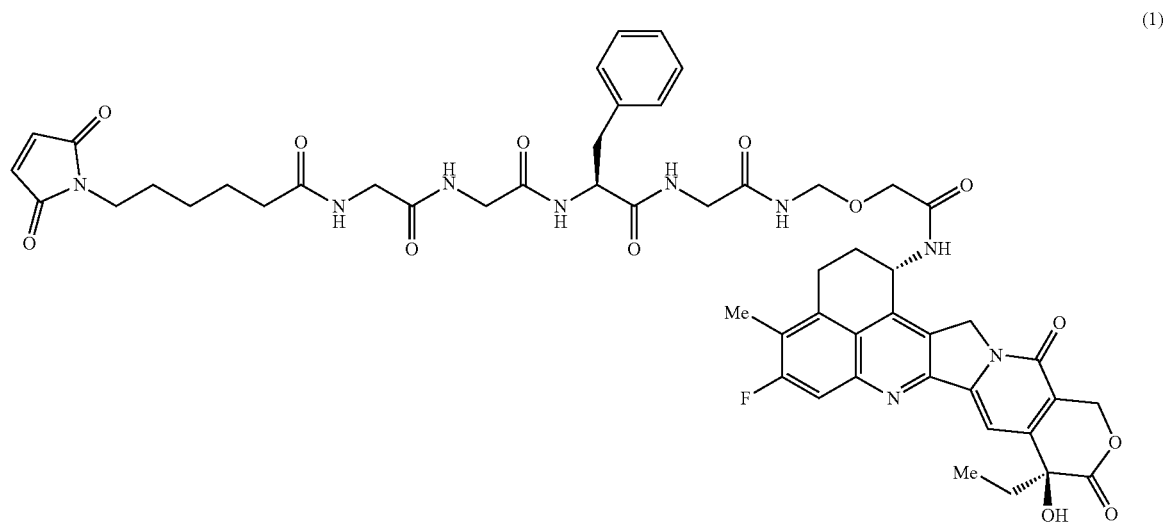 [SMILES: CC[C@@]1(O)C(=O)OCc2c1cc1n(c2=O)Cc2c-1nc1cc(F)c(C)c3c1c2[C@@H](NC(=O)COCNC(=O)CNC(=O)[C@H](Cc1ccccc1)NC(=O)CNC(=O)CNC(=O)CCCCCN1C(=O)C=CC1=O)CC3]

are used as a starting material, and the method comprises the steps of:
  i) reducing an antibody; and then
  ii) adding a solution in which the crystals of the compound represented by the formula (1) are dissolved, to react the solution with the reduced antibody.

62. The production method according to claim 61, wherein the crystals show main peaks at diffraction angles (2θ) of 5.6±0.2°, 15.5±0.2° and 22.0±0.2° in powder X-ray diffraction obtained by irradiation with copper Kα radiation.

63. The production method according to claim 61, wherein the antibody is an anti-HER2 antibody, an anti-HER3 antibody, an anti-TROP2 antibody, an anti-B7-H3 antibody, or an anti-GPR20 antibody.

* * * * *